US012590970B2

(12) United States Patent
Mao et al.

(10) Patent No.: US 12,590,970 B2
(45) Date of Patent: Mar. 31, 2026

(54) USE OF AMINO ACIDS TO ENHANCE SIGNAL IN MASS SPECTRAL ANALYSES

(71) Applicant: Regeneron Pharmaceuticals, Inc., Tarrytown, NY (US)

(72) Inventors: Yuan Mao, Hartsdale, NY (US); Andrew Kleinberg, Roslyn Heights, NY (US); Yunlong Zhao, Scarsdale, NY (US); Lili Guo, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 224 days.

(21) Appl. No.: 18/203,854

(22) Filed: May 31, 2023

(65) Prior Publication Data

US 2023/0417759 A1      Dec. 28, 2023

Related U.S. Application Data

(63) Continuation of application No. 17/143,890, filed on Jan. 7, 2021.

(Continued)

(51) Int. Cl.
*G01N 33/68*      (2006.01)
*G01N 30/34*      (2006.01)
*G01N 30/72*      (2006.01)

(52) U.S. Cl.
CPC ......... *G01N 33/6848* (2013.01); *G01N 30/34* (2013.01); *G01N 30/7233* (2013.01); *G01N 33/6857* (2013.01)

(58) Field of Classification Search
None
See application file for complete search history.

(56) References Cited

U.S. PATENT DOCUMENTS 5,851,400 A      12/1998 Frey et al.
7,241,866 B2 *   7/2007 Goklen ................. B01J 20/284
                                                          530/350

(Continued)

FOREIGN PATENT DOCUMENTS

WO      2016/069764 A1      5/2016

OTHER PUBLICATIONS

Anal. Chem. 2016, 88, 17, 8484â8494 (Year: 2016).*

(Continued)

*Primary Examiner* — Maris R Kessel
*Assistant Examiner* — Mickey Huang
(74) *Attorney, Agent, or Firm* — Schwabe, Williamson & Wyatt PC David Mellman

(57)      ABSTRACT

A method of enhancing a mass spectral signal is disclosed. The method can include contacting a sample to a separation column under conditions that permit sample components to bind to the substrate; applying a first mobile gradient to the separation column, wherein the first mobile phase gradient comprises trifluoroacetic acid (TFA) and a small molecule additive (e.g., an amino acid) or formic acid (FA) and a small molecule additive (e.g., an amino acid); applying a second mobile gradient to the separation column, wherein the second mobile phase gradient comprises TFA in acetonitrile (ACN) and a small molecule additive (e.g., an amino acid) or formic acid (FA) in ACN and a small molecule additive (e.g., an amino acid); and performing mass spectrometric analysis on eluted sample components.

17 Claims, 87 Drawing Sheets
Specification includes a Sequence Listing.

Related U.S. Application Data

(60) Provisional application No. 63/053,836, filed on Jul. 20, 2020, provisional application No. 62/958,366, filed on Jan. 8, 2020.

(56) References Cited

U.S. PATENT DOCUMENTS

| | | |
|---|---|---|
| 2012/0141497 A1 | 6/2012 | Gallo et al. |
| 2015/0162177 A1 | 6/2015 | McGivney et al. |
| 2017/0330740 A1 | 11/2017 | Fischer et al. |

OTHER PUBLICATIONS

Agilent 6200 Series TOF and 6500 Series Q-TOF LC/MS System Concept Guide, Agilent Technologies (Year: 2015).*
Journal of Pharmaceutical and Biomedical Analysis 53 (2010) 315â324 (Year: 2010).*
International Journal of Mass Spectrometry vol. 427, Apr. 2018, pp. 157-164 (Year: 2018).*
Journal of Chromatography B vol. 825, Issue 2, Oct. 25, 2005, pp. 186-192 (Year: 2005).*
Smith-et-al, human-plasma-n-glycoproteome-analysis-by-immunoaffinity-subtraction-hydrazide-chemistry-and-mass, Journal of Proteome Research, vol. 4, Issue 6 (Year: 2005).*
Majidi et al., Production and characterization of monoclonal antibodies against human IgG in Balb/c mouse, Hum Antibodies, 2005; 14(1-2):1-5 (Year: 2005).*
Liu et al., Human Plasma N-Glycoproteome Analysis by Immunoaffinity Subtraction, Hydrazide Chemistry, and Mass Spectrometry, J Proteome Res. 2005 ; 4(6): 2070-2080. (Year: 2005).
U.S. Appl. No. 17/143,890, Office Action mailed Aug. 23, 2023.
U.S. Appl. No. 17/143,890, Final Office Action mailed Jan. 30, 2024.
WIPO Application No. PCT/US2021/012523, PCT International Search Report and Written Opinion of the International Searching Authority mailed May 11, 2021.
Garcia et al., "The effect of the mobile phase additives on sensitivity in the analysis of petides and proteins by high-performance liquid chromatography-electrospray mass spectrometry," Journal of Chromatography B Elsevier, Amsterdam, NL, vol. 825 No. 2: 111-123, (Oct. 25, 2005). [XP027627025, ISSN: 1570-0232—retrieved on Oct. 25, 2005].
Mao et al., "Simple Addition of Glycine in Trifluoroacetic Acid-Containing Mobile Phases Enhances the Sensitivity of Electrospray Ionization Mass Spectrometry for Biopharmaceutical Characterization," Analytical Chemistry, vol. 92 No. 13: 8691-8696, (May 28, 2020). [XP55796110, ISSN: 0003-2700, DOI: 10.1021/acs.analchem.0c01319].
Shou et al., "Simple means to alleviate sensitivity loss by trifluoroacetic acid (TFA) mobile phases in the hydrophilic interaction chromatography-electrospray tandem mass spectrometric (HILIC-ESI/MS/MS) bioanalysis of basic compounds," Journal of Chromatography B, Elsevier, Amsterdam, NL, vol. 825 No. 2: 186-192, (Oct. 25, 2005). [XP027627033, ISSN: 1570-0232].
Zhao et al., "Glycine additive facilitates site-specific glycosylation profiling of biopharmaceuticals by ion-pairing hydrophilic interaction chromatography mass spectrometry," Analytical and Bioanalytical Chemistry, vol. 413 No. 5: 1267-1277, (Nov. 26, 2020). [XP037373229, ISSN: 1618-2642, DOI: 10.1007/S00216-020-03089-3].
U.S. Appl. No. 17/143,890, Notice of Allowance mailed Mar. 1, 2023.
U.S. Appl. No. 62/958,366, filed Jan. 8, 2020, Expired.
U.S. Appl. No. 63/053,836, filed Jul. 20, 2020, Expired.
PCT/US2021/012523, Jan. 7, 2021, WO 2021/142137, Published.
U.S. Appl. No. 17/143,890, filed Jan. 7, 2021, US-2021-0223259, Published.

* cited by examiner

SEQ ID NO: 1

QVTLRESGPALVKPTQTLTLTCTFSGFSLSTAGMSVGWIRQPPGKALEWLADIWWDDKKHYNPSLKDRLTISKDTSKNQVVLKVTMDP
ADTATYYCARDMIFNFYFDVWGQGTTVTVSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVFSCSVMHEALHNHYTQKSLSLSPGK

SEQ ID NO: 2

DIQMTQSPSTLSASVGDRVTITCSASSRVGYMHWYQQKPGKAPKLLIYDTSKLASGVPSRFSGSGSGTEFTLTISSLQPDDFATYYCFQGSG
YPFTFGGGTKVEIKRTVAAPSVFIFPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC

| Glycan Annotation* | Average Peak Area** | | Average Fold Change | Relative level | |
|---|---|---|---|---|---|
| | Peptide 1_Glycine | Peptide 1_Control | | Peptide 1_Glycine | Peptide 1_Control |
| G0F | 1.2e10±8.3e7 | 7.5e8±7.5e7 | 16.6 | 43.2%±0.1% | 46.5%±0.7% |
| G1F | 9.1e9±6.0e7 | 5.1e8±6.8e7 | 17.7 | 31.5%±0.1% | 31.7%±0.5% |
| G0 | 2.7e9±6.3e7 | 1.4e8±1.6e7 | 19.5 | 9.2%±0.1% | 8.4%±0.0% |
| G2F | 1.7e9±1.7e7 | 7.7e7±1.1e7 | 22.7 | 6.0%±0.0% | 4.7%±0.1% |
| G1 | 9.4e8±2.1e7 | 4.3e7±6.0e6 | 21.5 | 3.2%±0.0% | 2.7%±0.1% |
| Man5 | 5.3e8±2.8e6 | 2.3e7±2.8e6 | 22.8 | 1.8%±0.0% | 1.4%±0.0% |
| G0F-GlcNAc | 4.2e8±2.7e6 | 2.3e7±2.4e6 | 18.5 | 1.5%±0.0% | 1.4%±0.0% |
| G1F-GlcNAc | 2.2e8±4.7e6 | 1.0e7±1.3e6 | 21.8 | 0.77%±0.01% | 0.63%±0.01% |
| G0-GlcNAc | 1.8e8±3.8e5 | 1.0e7±1.3e6 | 17.6 | 0.63%±0.00% | 0.64%±0.00% |
| Man3 | 1.1e8±3.1e5 | 6.0e6±6.7e5 | 18.8 | 0.39%±0.00% | 0.37%±0.00% |
| G1-GlcNAc | 7.6e7±1.9e6 | 3.8e6±5.4e5 | 20.3 | 0.27%±0.00% | 0.23%±0.01% |
| G2 | 7.7e7±1.0e6 | 4.2e6±5.2e5 | 18.6 | 0.27%±0.00% | 0.26%±0.00% |
| G2FS | 5.9e7±1.9e6 | 3.0e6±4.7e5 | 19.5 | 0.20%±0.00% | 0.19%±0.01% |
| Man6 | 3.8e7±1.4e6 | 2.0e6±2.4e5 | 19.3 | 0.13%±0.00% | 0.12%±0.00% |
| Man8 | 3.4e7±1.2e6 | 2.0e6±2.6e5 | 16.9 | 0.12%±0.00% | 0.13%±0.00% |
| G0FB | 3.3e7±5.8e5 | 1.9e6±2.3e5 | 17.9 | 0.12%±0.00% | 0.11%±0.00% |
| Man4_G1 | 2.9e7±1.7e6 | 1.5e6±1.4e5 | 20.0 | 0.10%±0.01% | 0.09%±0.00% |
| Man7 | 2.7e7±7.4e5 | 1.3e6±1.6e5 | 20.9 | 0.09%±0.00% | 0.08%±0.00% |
| G1F+GlcNAc | 2.5e7±1.8e5 | 1.2e6±1.9e5 | 21.4 | 0.09%±0.00% | 0.08%±0.00% |
| G0F+GlcNAc | 2.7e7±2.7e5 | 1.3e6±1.6e5 | 20.6 | 0.09%±0.00% | 0.07%±0.00% |
| Man5_G1 | 2.1e7±5.1e5 | 1.1e6±1.8e5 | 18.8 | 0.07%±0.00% | 0.07%±0.00% |
| G1FS-GlcNAc | 1.8e7±2.4e4 | 1.1e6±1.6e5 | 16.8 | 0.06%±0.00% | 0.07%±0.00% |
| Man4 | 1.1e7±8.7e4 | 4.1e5±1.3e5 | 27.0 | 0.04%±0.00% | 0.02%±0.01% |
| Man3F | 8.2e6±2.4e5 | 4.4e5±6.6e4 | 18.9 | 0.03%±0.00% | 0.03%±0.00% |
| G0B | 5.9e6±3.7e5 | 2.5e5±5.7e4 | 23.1 | 0.02%±0.00% | 0.02%±0.00% |
| Man5F | 2.3e6±7.7e3 | ND | -- | 0.01%±0.00% | 0.00%±0.00% |
| Man4F | 1.1e7±8.8e6 | ND | -- | 0.04%±0.03% | 0.00%±0.00% |

FIG. 19

| Glycan Annotation* | Average Peak Area** | | | Fold Change*** | Relative level | | |
| | Peptide2 +Glycine | Peptide2 Control | | Peptide2 | Peptide2 +Glycine | Peptide2 Control | |
|---|---|---|---|---|---|---|---|
| G0F | 2.4e10 ±4.5e7 | 1.3e9 ±9.2e6 | | 18.4 | 70.4% ±0.1% | 72.6% ±0.7% | |
| G1F | 5.3e9 ±5.9e6 | 2.8e8 ±1.6e7 | | 19.2 | 15.4% ±0.0% | 15.2% ±0.6% | |
| G0 | 1.7e9 ±2.2e7 | 7.2e7 ±3.9e5 | | 23.7 | 5.0% ±0.0% | 4.0% ±0.0% | |
| G0F-GlcNAc | 1.1e9 ±1.2e7 | 5.3e7 ±1.8e6 | | 21.4 | 3.3% ±0.0% | 2.9% ±0.1% | |
| G2F | 6.6e8 ±1.6e7 | 3.3e7 ±1.8e6 | | 20.1 | 1.9% ±0.0% | 1.8% ±0.1% | |
| Man5 | 3.4e8 ±2.7e6 | 1.5e7 ±4.3e5 | | 22.9 | 1.0% ±0.0% | 0.80% ±0.0% | |
| G0-GlcNAc | 3.1e8 ±7.3e6 | 1.3e7 ±4.2e5 | | 23.8 | 0.89% ±0.02% | 0.71% ±0.01% | |
| Man8 | 1.9e8 ±3.3e6 | 9.3e6 ±3.1e5 | | 20.1 | 0.54% ±0.01% | 0.51% ±0.01% | |
| G1 | 1.8e8 ±9.0e5 | 9.2e6 ±2.1e5 | | 19.4 | 0.50% ±0.00% | 0.50% ±0.00% | |
| G0F+GlcNAc | 1.3e8 ±6.7e5 | 7.2e6 ±2.2e5 | | 18.1 | 0.38% ±0.00% | 0.40% ±0.01% | |
| Man6 | 4.7e7 ±1.2e5 | 2.1e6 ±9.7e4 | | 22.1 | 0.14% ±0.00% | 0.12% ±0.00% | |
| G1F+GlcNAc | 4.5e7 ±4.5e5 | 2.6e6 ±7.9e4 | | 17.6 | 0.13% ±0.00% | 0.14% ±0.00% | |
| G2FS | 3.2e7 ±3.2e4 | 1.7e6 ±2.5e4 | | 19.4 | 0.09% ±0.00% | 0.09% ±0.00% | |
| Man7 | 3.2e7 ±1.2e5 | 1.5e6 ±6.4e4 | | 22.1 | 0.09% ±0.00% | 0.08% ±0.00% | |
| G1FS | 2.8e7 ±1.3e6 | 1.6e6 ±5.2e4 | | 17.7 | 0.08% ±0.00% | 0.09% ±0.00% | |
| G2 | 2.0e7 ±5.7e5 | 1.1e6 ±1.9e4 | | 18.8 | 0.06% ±0.00% | 0.06% ±0.00% | |
| G2F+GlcNAc | 1.3e7 ±7.5e5 | 6.1e5 ±2.2e4 | | 20.7 | 0.04% ±0.00% | 0.03% ±0.00% | |
| G2FS2 | 4.4e6 ±4.6e4 | 7.9e4 ±1.1e4 | | (55.9) | 0.01% ±0.00% | 0.00% ±0.00% | |
| G3F | 2.5e6 ±1.9e5 | 5.4e4 ±7.5e3 | | (47.0) | 0.01% ±0.00% | 0.00% ±0.00% | |

FIG.20

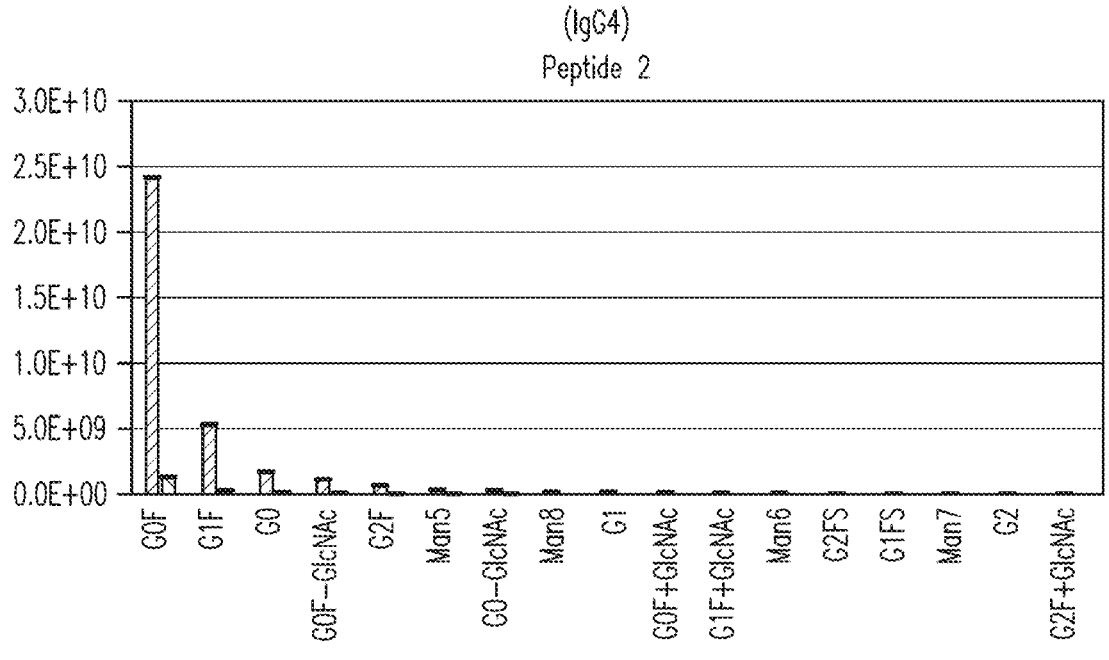
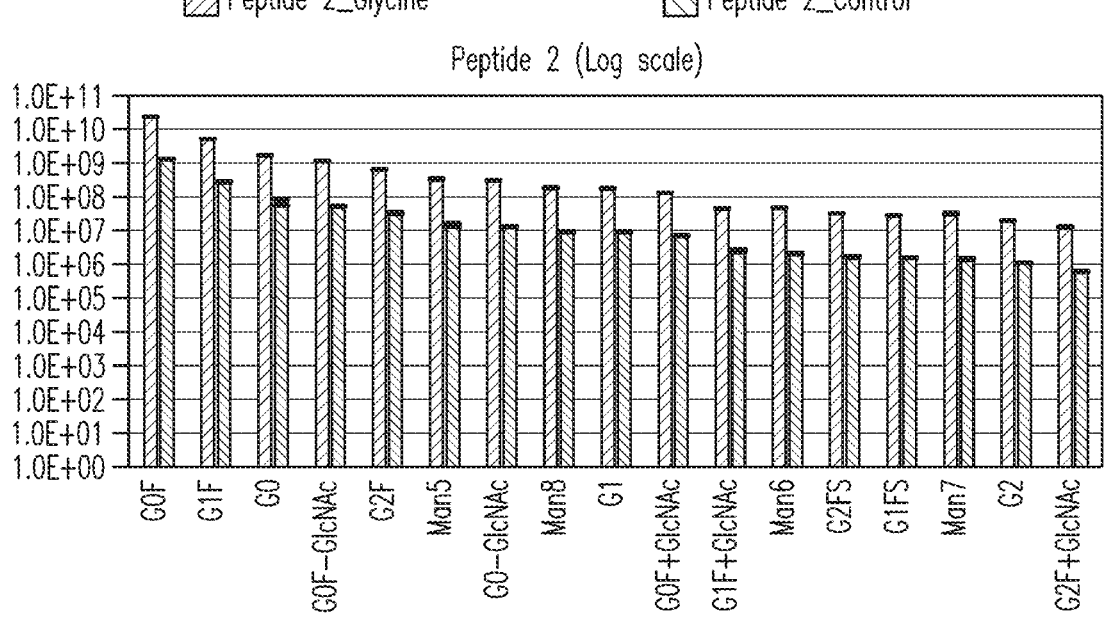
FIG.21A

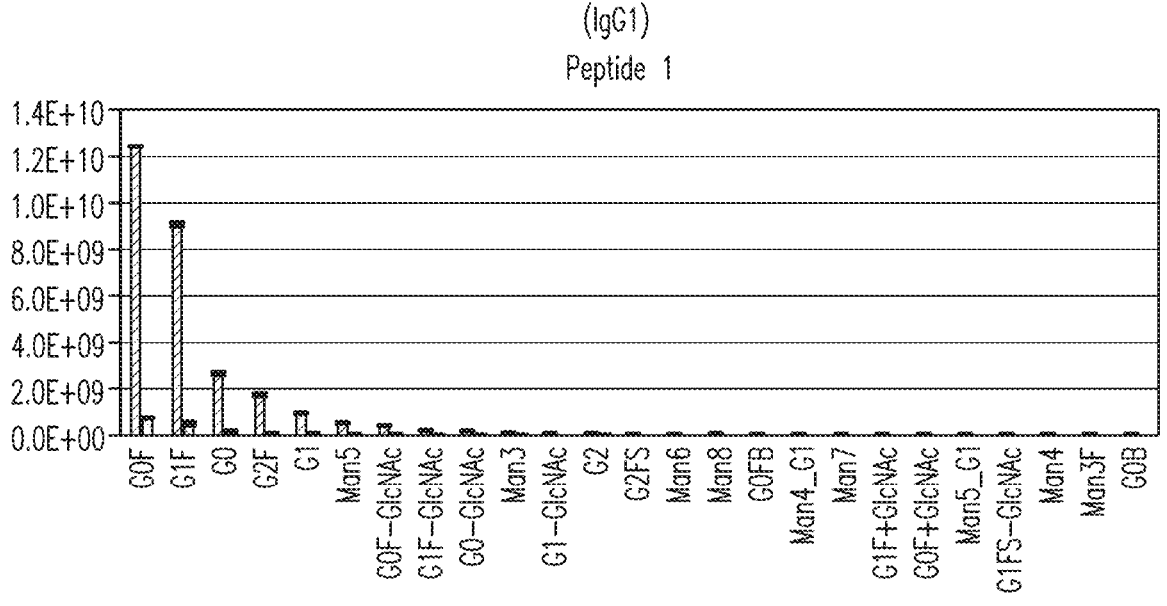
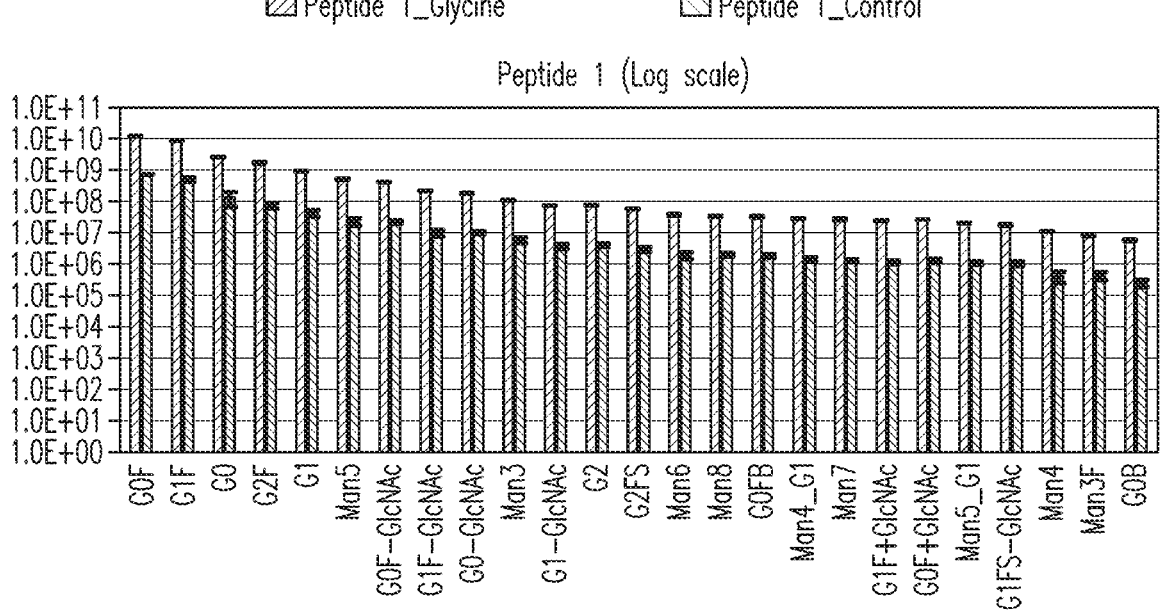
FIG.21B

| Mobile Phase | N36 | | N68 | | N123 | | N196 | | N282 | | Total | |
|---|---|---|---|---|---|---|---|---|---|---|---|---|
| | # PSM | # Glycoform | # PSM | # Glycoform | # PSM | # Glycoform | # PSM | # Glycoform | # PSM | # Glycoform | # PSM | # Glycoform |
| HILIC 0.1%TFA | 1 | 1 | 0 | 0 | 0 | 0 | 0 | 0 | 1 | 1 | 2 | 2 |
| C18 (RPLC) 0.05% TFA | 16 | 6 | 5 | 3 | 8 | 3 | 2 | 1 | 3 | 2 | 34 | 15 |
| HILIC 0.1%TFA +1mM Glycine | 15 | 9 | 45 | 12 | 112 | 23 | 139 | 31 | 29 | 12 | 340 | 87 |

HILIC 0.1% TFA + 1mM glycine: 74

C18 RPLC 0.05% TFA: 2

HILIC 0.1% TFA: 11

Glycoforms

TFA + glycine

FA 45    21    11

| Composition | Average Charge state | | Total MS signal boost by glycine |
|---|---|---|---|
| | Ctrl | Glycine | |
| M5 | 1.6 | 1.9 | 13.1 |
| M6 | 1.7 | 1.9 | 21.9 |
| M7 | 1.9 | 2.0 | 23.3 |
| M8 | 1.8 | 2.0 | 35.6 |
| M9 | 2.0 | 2.0 | 36.9 |
| A2 | 1.5 | 1.9 | 9.8 |
| A2[6]G1 | 1.8 | 2.0 | 10.6 |
| A2[3]G1 | 1.6 | 2.0 | 11.4 |
| A2G2 | 1.9 | 2.0 | 9.6 |
| FA1 | 1.5 | 1.9 | 25.1 |
| FA2 | 1.6 | 2.0 | 13.8 |
| FA2[6]G1 | 1.9 | 2.0 | 9.9 |
| FA2[3]G1 | 1.7 | 2.0 | 15.4 |
| FA2G2 | 2.0 | 2.0 | 10.1 |
| A2BG2 | 2.0 | 2.3 | 3.1 |
| FA2B | 1.8 | 2.0 | 5.1 |
| FA2[6]BG1 | 2.0 | 2.1 | 3.6 |
| FA2BG2 | 2.0 | 2.3 | 3.6 |
| M4A1G1S[6]1 | 2.0 | 2.0 | 12.2 |
| A1G1S1 | 1.9 | 2.0 | 11.4 |
| A2G1S1 | 2.0 | 2.0 | 11.8 |
| A2G2S1 | 2.0 | 2.2 | 7.9 |
| FA2G1S[6]1 | 2.0 | 2.0 | 7.3 |
| FA2G2S[6]1 | 2.0 | 2.3 | 9.0 |
| A2BG2S | 2.0 | 2.6 | 5.1 |
| FA2BG2S[6]1 | 2.0 | 2.7 | 6.6 |
| A2G2S[6,3]2 | 2.0 | 2.6 | 13.1 |
| A2G2S[6,6]2 | 2.0 | 2.6 | 6.5 |
| FA2G2S[3,3]2 | 2.0 | 2.6 | 15.0 |
| FA2G2S[3,6]2 | 2.0 | 2.7 | 16.8 |
| FA2G2S[6,6]2 | 2.0 | 2.7 | 13.8 |
| A3G3S[3,6]2 | 2.0 | 2.8 | 16.6 |
| A3G3S[6,6]2 | 2.0 | 2.8 | 18.0 |
| FA3G3S2 | 2.0 | 2.9 | 47.9 |
| FA2BG2S[6,6]2 | 2.0 | 2.8 | 10.5 |
| A3G3S[3,3,6]3 | – | 2.9 | ∞ |
| A3G3S[3,6,6]3 | 2.2 | 2.9 | 26.3 |
| A3G3S[6,6,6]3 | 2.1 | 2.9 | 33.3 |
| A3G3F1S[3,6,6]3 | – | 3.0 | ∞ |
| FA3G3S[3,6,6]3 | – | 3.0 | ∞ |
| A4G4S[3,3,6]3 | – | 3.0 | ∞ |
| A4G4S[3,3,3,6]4 | – | 3.0 | ∞ |

| Peak # | Composition | Relative levels to FA2G2 | | | |
| --- | --- | --- | --- | --- | --- |
| | | FLR | | MS | |
| | | Ctrl | Glycine | Ctrl | Glycine |
| 1 | A2 | 2.6% | 2.6% | 1.9% | 1.8% |
| 2 | FA2 | 97.2% | 97.1% | 71.4% | 98.2% |
| 3 | M5 | 16.4% | 16.4% | 12.4% | 16.1% |
| 4 | FA2B | 26.6% | 26.6% | 38.8% / 44.0% | 19.5% / 25.0% |
| | A2[6]G1 | | | 5.2% | 5.5% |
| 5 | A2[3]G1 | 2.8% | 2.9% | 2.2% | 2.5% |
| 6 | FA2[6]G1 | 109.4% | 109.3% | 116.3% | 114.2% |
| 7 | FA2[3]G1 | 40.6% | 40.5% | 26.0% | 39.8% |
| 8 | FA2[6]BG1 | 29.0% | 29.0% | 66.5% | 24.0% |
| 9 | M6 | 28.8% | 28.8% | 11.0% | 23.9% |
| 10 | A2G2 | 41.7% | 41.6% | 59.6% | 57.1% |
| 11 | A2BG2 | 7.0% | 7.2% | 11.0% | 3.4% |
| 12 | FA2G2 | 100.0% | 100.0% | 100.0% | 100.0% |
| 13 | FA2BG2 | 19.2% | 19.3% | 46.7% | 16.8% |
| 14 | M4A1G1S[6]1 | 16.3% | 16.4% | 5.8% / 19.7% | 7.1% / 18.3% |
| | A2G2S1 | | | 13.9% | 11.2% |
| 15 | A2G2S1 | 285.9% | 285.3% | 509.9% | 399.8% |
| 16 | A2BG2S1 | 105.3% | 106.8% | 25.4% / 136.6% | 12.8% / 112.2% |
| | FA2G2S[6]1 | | | 111.3% | 99.4% |
| 17 | M8 | 11.7% | 11.9% | 2.9% | 10.3% |
| 18 | FA2BG2S[6]1 | 45.3% | 45.0% | 64.7% / 69.6% | 42.3% / 49.7% |
| | FA2G2S[3,3]2 | | | 5.0% | 7.4% |
| 19 | A2G2S[6,3]2 | 54.9% | 56.3% | 57.9% | 75.4% |
| 20 | A2G2S[6,6]2 | 469.7% | 498.6% | 559.3% / 565.7% | 361.2% / 384.5% |
| | M9 | | | 6.4% | 23.3% |
| 21 | FA2G2S[6,6]2 | 46.7% | 48.3% | 35.5% | 48.6% |
| 22 | FA2BG2S[6,6]2 | 19.1% | 21.3% | 15.1% | 15.7% |
| 23 | A3G3S[3,6]2 | 29.8% | 30.1% | 25.8% | 42.6% |
| 24 | A3G3S[6,6]2 | 18.5% | 21.7% | 15.0% | 26.9% |
| 25 | A3G3S[3,3,6]3 | 5.2% | 5.3% | 0.9% / 1.2% | 5.6% / 6.9% |
| | FA3G3S2 | | | 0.3% | 1.4% |
| 26 | A3G3S[3,6,6]3 | 38.5% | 40.8% | 15.3% | 39.9% |
| 27 | A3G3S[6,6,6]3 | 17.5% | 19.7% | 3.1% / 3.1% | 10.2% / 16.4% |
| | FA3G31S[6,6,6]3 | | | 0.0% | 6.2% |

FIG.28A

| Composition | Average Charge state | | Total signal boost by glycine |
|---|---|---|---|
| | Ctrl | Glycine | |
| M5 | 2.0 | 2.0 | 6.1 |
| M6 | 2.0 | 2.0 | 5.7 |
| M7 | 2.0 | 2.0 | 6.5 |
| M8 | 2.0 | 2.0 | 11.2 |
| M9 | 2.0 | 2.0 | 16.4 |
| A2 | 2.0 | 2.0 | 2.8 |
| A2[6]G1 | 2.0 | 2.0 | 4.7 |
| A2[3]G1 | 2.0 | 2.0 | 3.7 |
| A2G2 | 2.1 | 2.1 | 7.8 |
| FA2 | 2.1 | 2.0 | 9.1 |
| FA2[6]G1 | 2.1 | 2.0 | 10.6 |
| FA2[3]G1 | 2.1 | 2.1 | 10.8 |
| FA2G2 | 2.2 | 2.1 | 11.8 |
| A2BG2 | 2.3 | 2.5 | 10.5 |
| FA2B | 2.0 | 2.0 | 11.6 |
| FA2[6]BG1 | 2.2 | 2.2 | 10.3 |
| FA2BG2 | 2.3 | 2.5 | 14.9 |
| M4A1G1S[6]1 | 2.1 | 2.1 | 10.8 |
| A2G1S1 | 2.1 | 2.0 | 13.4 |
| A2G2S[6]1 | 2.4 | 2.4 | 11.0 |
| FA2G1S[6]1 | 2.2 | 2.1 | 11.1 |
| FA2G2S[6]1 | 2.4 | 2.5 | 12.6 |
| A2BG2S | 2.5 | 2.8 | 14.5 |
| FA2BG2S[6]1 | 2.6 | 2.8 | 14.0 |
| A2G2S[6,3]2 | 2.5 | 2.7 | 30.2 |
| A2G2S[6,6]2 | 2.6 | 2.8 | 19.0 |
| FA2G2S[3,3]2 | 2.4 | 2.7 | 38.7 |
| FA2G2S[3,6]2 | 2.5 | 2.8 | 36.8 |
| FA2G2S[6,6]2 | 2.6 | 2.9 | 21.3 |

| Composition | Relative levels to FA2 | | | | | Average Charge state | | Total signal boost by glycine |
| --- | --- | --- | --- | --- | --- | --- | --- | --- |
| | FLR | MS | | | | | | |
| | Ctrl | Ctrl | | Glycine | | Ctrl | Glycine | |
| FA1 | 0.7% | – | | 0.4% | | 2.0 | 2.0 | – |
| A2 | 1.8% | 1.6% | | 2.2% | | 2.0 | 2.0 | 1.7 |
| FA2 | 102.6% | 124.1% | | 110.2% | | 2.0 | 2.0 | 1.1 |
| M5 | 48.5% | 14.8% | 49.7% | 13.9% | 41.5% | 2.0 | 2.0 | 1.2 |
| FA2B | | 34.8% | | 27.6% | | 2.0 | 2.0 | 1.0 |
| A2[6]G1 | 2.5% | 1.4% | | 2.3% | | 2.0 | 2.0 | 2.1 |
| A2[3]G1 | 1.7% | 1.1% | | 1.6% | | 2.0 | 2.0 | 1.7 |
| FA2[6]G1 | 136.3% | 140.8% | | 124.0% | | 2.0 | 2.0 | 1.1 |
| FA2[3]G1 | 56.7% | 60.5% | | 54.6% | | 2.0 | 2.1 | 1.1 |
| FA2[6]BG1 | 49.2% | 48.6% | | 46.2% | | 2.0 | 2.3 | 1.2 |
| M6 | 18.2% | 14.1% | | 14.2% | | 1.9 | 2.0 | 1.2 |
| A1G1S1 | 4.1% | 4.7% | | 5.1% | | 2.0 | 2.0 | 1.3 |
| A2G2 | 8.0% | 7.5% | | 8.7% | | 2.0 | 2.1 | 1.4 |
| FA2G2 | 100.0% | 100.0% | | 100.0% | | 2.0 | 2.1 | 1.2 |
| A2G1S1 | 27.0% | 11.6% | 24.6% | 14.4% | 31.0% | 2.0 | 2.3 | 1.5 |
| FA2BG2 | | 13.0% | | 16.7% | | 2.0 | 2.6 | 1.6 |
| M4A1G1S[6]1 | 47.1% | 5.5% | 30.1% | 6.7% | 38.9% | 2.0 | 2.1 | 1.5 |
| A2G2S1 | | 5.9% | | 6.6% | | 2.0 | 2.2 | 1.4 |
| M7 | | 1.5% | | 3.5% | | 2.0 | 2.0 | 2.8 |
| FA2G1S[6]1 | | 17.2% | | 22.2% | | 2.0 | 2.3 | 1.6 |
| A2G2S[6]1 | 266.6% | 288.0% | | 390.5% | | 2.0 | 2.4 | 1.7 |
| FA2G2S[6]1 | 131.1% | 129.7% | | 154.1% | | 2.0 | 2.6 | 2.2 |

FIG.31A (Continued on next page)

| | | | | | | | | |
|---|---|---|---|---|---|---|---|---|
| M8 | 27.0% | 2.8% | 7.9% | 4.7% | 12.0% | 2.0 | 2.0 | 2.1 |
| A2G2S[3,3]2 | | 2.3% | | 3.7% | | 2.0 | 2.7 | 2.0 |
| M5A1G1S1 | | 2.8% | | 3.6% | | 2.0 | 2.1 | 1.6 |
| FA2BG2S[6]1 | 48.0% | 37.7% | | 63.1% | | 2.0 | 2.8 | 2.1 |
| FA2G2S[3,3]2 | 18.6% | 10.5% | | 15.8% | | 2.0 | 2.7 | 1.9 |
| A2G2S[3,6]2 | 175.8% | 150.6% | | 254.5% | | 2.0 | 2.7 | 2.1 |
| FA2G2S[3,6]2 | 6.8% | 9.3% | | 19.3% | | 2.0 | 2.8 | 2.6 |
| A2G2S[6,6]2 | 1221.0% | 1010.0% | 1024.3% | 1684.0% | 1701.8% | 2.0 | 2.7 | 2.1 |
| M9 | | 14.3% | | 17.8% | | 2.0 | 2.0 | 1.5 |
| FA2G2S[6,6]2 | 100.4% | 68.6% | | 125.9% | | 2.0 | 2.8 | 2.3 |
| FA2BG2S[6,6]2 | 33.7% | 19.4% | | 41.2% | | 2.2 | 2.9 | 2.6 |
| A3G3S[3,6]2 | 24.8% | 9.6% | | 24.8% | | 2.2 | 3.0 | 3.2 |
| A3G3S[6,6]2 | 7.6% | 2.3% | | 6.4% | | 2.0 | 3.0 | 3.4 |
| A3G3S[3,3,6]3 | 34.7% | 21.0% | | 41.9% | | 2.5 | 3.0 | 2.5 |
| A3G3S[3,6,6]3 | 236.3% | 161.5% | | 294.7% | | 2.5 | 3.0 | 2.3 |
| A3G3F1S[3,6,6]3 | 94.3% | 39.7% | 67.4% | 74.4% | 142.4% | 2.6 | 3.0 | 2.3 |
| A3G3S[6,6,6]3 | | 27.6% | | 68.0% | | 2.4 | 3.0 | 3.0 |
| FA3G31S[6,6,6]3 | 30.8% | – | 8.5% | 2.4% | 17.3% | 2.7 | 3.0 | – |
| A4G4S[3,3,6]3 | | 8.5% | | 15.0% | | 3.0 | 3.0 | 2.2 |
| A4G4S[3,3,3,6]4 | 19.2% | 15.2% | | 24.5% | | 2.9 | 3.1 | 2.0 |
| A4G4S[3,6,6,6]4 | 15.7% | 9.9% | 9.9% | 17.6% | 20.2% | 3.0 | 3.0 | 2.2 |
| A4G4FS[3,3,6,6]4 | | – | | 2.6% | | 3.0 | 3.0 | – |

| Composition | Average Charge state | | Total signal boost by glycine |
|---|---|---|---|
| | Ctrl | Glycine | |
| A2 | 1.0 | 1.3 | 0.9 |
| FA2 | 1.1 | 1.5 | 2.3 |
| FA2B | 1.5 | 1.9 | 1.8 |
| M5 | 1.0 | 1.0 | 0.8 |
| FA2[6]G1 | 1.1 | 1.7 | 2.4 |
| FA2[3]G1 | 1.1 | 1.8 | 2.2 |
| FA2[6]BG1 | 1.7 | 2.0 | 1.7 |
| M6 | 1.0 | 1.0 | 0.6 |
| A2G2 | 1.2 | 1.9 | 2.9 |
| FA2G2 | 1.4 | 1.9 | 2.2 |
| FA2BG2 | 1.9 | 2.0 | 1.3 |
| FA2G1S[6]1 | 1.8 | 2.0 | 1.6 |
| A2G2S[6]1 | 1.6 | 2.0 | 2.1 |
| FA2G2S[6]1 | 1.8 | 2.0 | 1.1 |
| FA2BG2S[6]1 | 2.0 | 2.0 | 0.7 |
| A2G2S[3,6]2 | 1.9 | 2.0 | 0.8 |
| A2G2S[6,6]2 | 1.8 | 2.0 | 1.2 |
| M9 | 1.3 | 1.9 | 1.5 |
| FA2G2S[6,6]2 | 2.0 | 2.0 | 0.7 |
| FA2BG2S[6,6]2 | 2.0 | 2.0 | 0.6 |
| A3G3S[3,6,6]3 | 2.0 | 2.2 | 0.6 |
| A3G3S[6,6,6]3 | 2.0 | 2.1 | 0.5 |
| A3G3F1S[3,6,6]3 | 2.0 | 2.2 | 0.3 |
| FA3G31S[6,6,6]3 | 2.0 | 2.3 | 0.4 |

FIG.32

MS Tune Settings for N-Glycan Analysis
- Polarity: Positive
- Spray Voltage: 3.8 kV
- Capillary Temperature: 350°C
- Sheath Gas: 40
- Aux Gas: 10
- Probe Heater Temperature: 250°C
- S-Lens RF Level: 50
- Ion Source: HESI
- Range: 400 to 2000 m/z

| UPLC System | Waters Acquity UPLC I-Class | | | | |
|---|---|---|---|---|---|
| Mobile Phase | A: 50 mM ammonium formate, pH 4.4, with or without 1 mM glycine | | | | |
| | B: 15% 50 mM ammonium formate, pH 4.4/85% acetonitrile, with or without 1 mM total concentration of glycine | | | | |
| Column | ACQUITY UPLC Glycan BEH Amide Column, 130Å, 1.7 μm, 2.1x150 mm from Waters (Catalog No. 186004742) | | | | |
| Column Temperature | 60°C±1°C | | | | |
| Autosampler Temperature | 10°C±4°C | | | | |
| Gradient | Time (min) | % A | % B | Flow (mL/min) | Curve |
| | Initial | 11.8 | 88.2 | 0.45 | Initial |
| | 29 | 20.2 | 79.8 | 0.45 | Linear |
| | 65 | 25.3 | 64.7 | 0.45 | Linear |
| | 66.5 | 100.0 | 0.0 | 0.2 | Isocratic |
| | 69.5 | 100.0 | 0.0 | 0.2 | Linear |
| | 74 | 11.8 | 88.2 | 0.2 | Isocratic |
| | 77 | 11.8 | 88.2 | 0.45 | Isocratic |
| | 85 | 11.8 | 88.2 | 0.45 | Isocratic |
| Detector Wavelength for PROCA labeled glycans | Excitation wavelength at 310 nm and emission wavelength at 370 nm PMT gain set at 1.00 | | | | |

FIG.33

| Composition | Structure | Relative levels to HexNac1NeuAc1 | | | |
|---|---|---|---|---|---|
| | | FLR | | MS | |
| | | Ctrl | Glycine | Ctrl | Glycine |
| HexNAc1NeuAc1 | ⋄—▫ | 100.0% | 100.0% | 100.0% | 100.0% |
| HexNAc1NeuGc1 | ⋄—▫ | 34.9% | 34.9% | 36.4% | 37.8% |
| HexNAc2NeuAc1 | | 38.1% | 38.1% | 9.7% | 36.0% |
| HexNAc2NeuGc1 | | 17.0% | 17.0% | 3.5% | 12.7% |
| Hex1HexNAc1NeuAc2 | | 3.1% | 3.1% | 0.2% | 2.1% |

ProCA labeled BSM O-glycans

| Composition | Average charge state | | Total signal boost by glycine |
|---|---|---|---|
| | Ctrl | Glycine | |
| HexNAc | 1.0 | 1.0 | 1.8 |
| HexNAc2 | 1.0 | 1.0 | 3.2 |
| HexNAc3 | 1.0 | 1.2 | 2.1 |
| Hex1HexNAc1 | 1.0 | 1.0 | 3.7 |
| HexNAc1NeuAc1 | 1.0 | 1.0 | 2.6 |
| HexNAc1NeuGc1 | 1.0 | 1.0 | 2.7 |
| HexNAc2NeuAc1 | 1.1 | 1.5 | 8.1 |
| HexNAc2NeuGc1 | 1.1 | 1.5 | 9.0 |
| Hex1HexNAc1NeuAc1 | 1.0 | 1.2 | 8.7 |
| Hex1HexNAc1NeuAc1dHex1 | 1.1 | 1.6 | 8.8 |
| Hex1HexNAc2NeuAc1 | 1.6 | 1.9 | 18.6 |
| Hex1HexNAc2NeuGc1 | 1.6 | 1.9 | 21.7 |
| Hex1HexNAc2NeuAc1dHex1 | 1.7 | 2.0 | 21.3 |
| Hex1HexNAc2NeuGc1dHex1 | 1.7 | 2.0 | 23.7 |
| Hex1HexNAc4dHex1 | 2.0 | 2.0 | 8.3 |
| Hex3HexNac4dHex1 | 2.0 | 2.0 | 14.0 |
| Hex1HexNAc1NeuAc2 | 1.5 | 2.0 | 34.3 |
| Hex1HexNAc1NeuAc1NeuGc1 | 1.2 | 2.0 | 156.5 |
| Hex1HexNAc3NeuAc1 | 2.0 | 2.0 | 22.8 |
| Hex1HexNAc3NeuAc1dHex | 2.0 | 2.0 | 16.1 |
| Hex1HexNAc2NeuAc1dHex2 | 1.7 | 2.0 | 30.5 |
| Hex2HexNAc2NeuAc1dHex1 | – | 2.0 | ∞ |
| Hex2HexNAc2NeuGc1 | – | 2.0 | ∞ |
| Hex1HexNAc3Sulf1 | 1.0 | 1.4 | 6.3 |
| Hex2HexNAc2Sulf1 | 1.0 | 1.1 | 4.0 |
| Hex2HexNAc2dHex1Sulf1 | 1.0 | 1.2 | 4.6 |

2AB labeled BSM O-glycans

| Composition | Average charge state | | Total signal boost by glycine |
|---|---|---|---|
| | Ctrl | Glycine | |
| HexNAc2 | 1.0 | 1.0 | 2.7 |
| HexNAc3 | 1.0 | 1.0 | 2.8 |
| HexNAc1NeuAc1 | 1.0 | 1.0 | 2.2 |
| HexNAc1NeuGc1 | 1.0 | 1.0 | 1.4 |
| HexNAc2NeuAc1 | 1.0 | 1.0 | 1.3 |
| HexNAc2NeuGc1 | 1.0 | 1.0 | 1.0 |

FIG.38B

Reduced BSM O-glycans

| Composition | Average charge state | | Total signal boost by glycine |
|---|---|---|---|
| | Ctrl | Glycine | |
| HexNAc | 1.0 | 1.0 | 5.5 |
| HexNAc2 | 1.0 | 1.0 | 5.5 |
| HexNAc3 | 1.0 | 1.0 | 3.9 |
| Hex1HexNAc1 | 1.0 | 1.0 | 12.2 |
| HexNAc1NeuAc1 | 1.0 | 1.0 | 2.2 |
| HexNAc1NeuGc1 | 1.0 | 1.0 | 2.6 |
| HexNAc2NeuAc1 | 1.0 | 1.0 | 1.8 |
| HexNAc2NeuGc1 | 1.0 | 1.0 | 1.7 |
| Hex1HexNAc1NeuAc1 | 1.0 | 1.0 | 2.1 |
| Hex1HexNAc1NeuAc1dHex1 | 1.0 | 1.0 | 1.7 |
| Hex1HexNAc2NeuAc1 | 1.0 | 1.0 | 0.9 |
| Hex1HexNAc2NeuGc1 | 1.0 | 1.0 | 1.4 |
| Hex1HexNAc2NeuAc1dHex1 | 1.0 | 1.0 | 1.1 |
| Hex1HexNAc2NeuGc1dHex1 | 1.0 | 1.0 | 0.2 |
| Hex1HexNAc4dHex1 | 1.0 | 1.0 | 0.8 |
| Hex3HexNac4dHex1 | 1.0 | 1.0 | 0.3 |
| Hex1HexNAc1NeuAc2 | 1.0 | 1.0 | 0.2 |
| Hex1HexNAc1NeuAc1NeuGc1 | 1.0 | 1.0 | 0.1 |

MS Tune Settings for O—Glycan Analysis

- Polarity: Positive
- Spray Voltage: 3.8 kV
- Capillary Temperature: 350°C
- Sheath Gas: 40
- Aux Gas: 10
- Probe Heater Temperature: 250°C
- S—Lens RF Level: 50
- Ion Source: HESI
- Range: 220 to 1500 m/z

| UPLC System | Waters Acquity UPLC I—Class | | | |
|---|---|---|---|---|
| Mobile Phase | A: 50 mM ammonium formate, pH 4.4, with or without 1 mM glycine | | | |
| | B: 15% 50 mM ammonium formate, pH 4.4/85% acetonitrile, with or without 1 mM total concentration of glycine | | | |
| Column | ACQUITY UPLC Glycan BEH Amide Column, 130Å, 1.7 μm, 2.1x150 mm from Waters (Catalog No. 186004742) | | | |
| Column Temperature | 60°C ± 1°C | | | |
| Autosampler Temperature | 10°C +_4°C | | | |
| Gradient | Time (min) | % A | % B | Flow (mL/min) | Curve |
| | Initial | 0 | 100.0 | 0.45 | Initial |
| | 5 | 0 | 100.0 | 0.45 | Linear |
| | 20 | 29.5 | 70.5 | 0.45 | Linear |
| | 23.5 | 100.0 | 0.0 | 0.2 | Isocratic |
| | 26.5 | 100.0 | 0.0 | 0.2 | Linear |
| | 30 | 0 | 100 | 0.2 | Isocratic |
| | 33 | 0 | 100 | 0.45 | Isocratic |
| | 40 | 0 | 100 | 0.45 | Isocratic |
| Detector Wavelength for PROCA labeled O—glycans | Excitation wavelength at 310 nm and emission wavelength at 370 nm PMT gain set at 1.00 | | | |

FIG.39

6 min linear
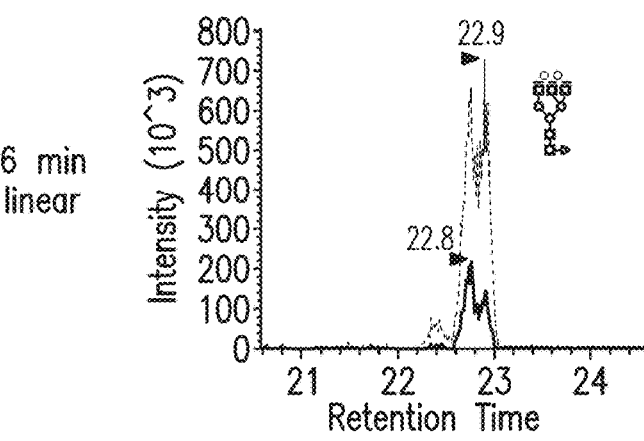
14 min linear
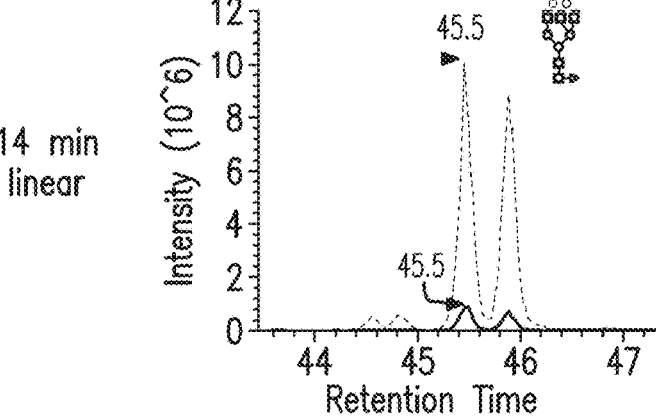
30 min linear
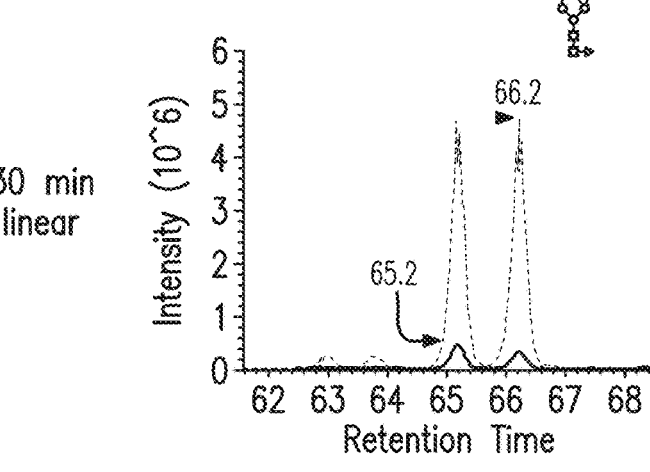
-------- +3 charge state
———— +2 charge state
FIG.42C-2

FIG.42C-3

| Glycan Name | 0.1% TFA + 1 mM Glycine | | | | 0.1% TFA | | | | Average fold change |
|---|---|---|---|---|---|---|---|---|---|
| | Replicate 1 | | Replicate 2 | | Replicate 1 | | Replicate 2 | | |
| | Peak area | Level | Peak area | Level | Peak area | Level | Peak area | Level | |
| A1 | 1.8E+08 | 0.63% | 1.8E+08 | 0.64% | 9.0E+06 | 0.63% | 1.2E+07 | 0.64% | 17.6 |
| A1G1 | 7.8E+07 | 0.27% | 7.5E+07 | 0.26% | 3.2E+06 | 0.23% | 4.3E+06 | 0.24% | 20.3 |
| FA1 | 4.3E+08 | 1.47% | 4.2E+08 | 1.47% | 2.0E+07 | 1.44% | 2.5E+07 | 1.41% | 18.5 |
| FA1G1 | 2.3E+08 | 0.78% | 2.2E+08 | 0.76% | 8.9E+06 | 0.62% | 1.1E+07 | 0.63% | 21.8 |
| FA1G1S1 | 1.8E+07 | 0.06% | 1.8E+07 | 0.06% | 9.1E+05 | 0.06% | 1.2E+06 | 0.07% | 16.8 |
| A2 | 2.7E+09 | 9.35% | 2.6E+09 | 9.08% | 1.2E+08 | 8.40% | 1.5E+08 | 8.41% | 19.5 |
| A2G1 | 9.6E+08 | 3.29% | 9.2E+08 | 3.21% | 3.7E+07 | 2.62% | 4.9E+07 | 2.74% | 21.5 |
| A2G2 | 7.8E+07 | 0.27% | 7.6E+07 | 0.27% | 3.6E+06 | 0.26% | 4.7E+06 | 0.26% | 18.6 |
| FA2 | 1.3E+10 | 43.06% | 1.2E+10 | 43.29% | 6.7E+08 | 47.20% | 8.2E+08 | 45.73% | 16.6 |
| FA2G1 | 9.1E+09 | 31.44% | 9.0E+09 | 31.60% | 4.4E+08 | 31.14% | 5.8E+08 | 32.19% | 17.7 |
| FA2G2 | 1.8E+09 | 6.05% | 1.7E+09 | 6.05% | 6.6E+07 | 4.61% | 8.7E+07 | 4.84% | 22.7 |
| FA2G2S1 | 6.1E+07 | 0.21% | 5.7E+07 | 0.20% | 2.5E+06 | 0.18% | 3.5E+06 | 0.19% | 19.5 |
| A3 | 6.2E+06 | 0.02% | 5.5E+06 | 0.02% | 2.0E+05 | 0.01% | 3.1E+05 | 0.02% | 23.1 |
| FA3 | 2.7E+07 | 0.09% | 2.7E+07 | 0.09% | 1.1E+06 | 0.08% | 1.5E+06 | 0.08% | 20.6 |
| FA3G1 | 2.5E+07 | 0.09% | 2.5E+07 | 0.09% | 9.9E+05 | 0.07% | 1.4E+06 | 0.08% | 21.4 |
| Man3 | 1.1E+08 | 0.39% | 1.1E+08 | 0.39% | 5.3E+06 | 0.37% | 6.7E+06 | 0.37% | 18.8 |
| Man3F | 8.5E+06 | 0.03% | 8.0E+06 | 0.03% | 3.7E+05 | 0.03% | 5.0E+05 | 0.03% | 18.9 |
| Man4 | 1.1E+07 | 0.04% | 1.1E+07 | 0.04% | 2.8E+05 | 0.02% | 5.4E+05 | 0.03% | 27.0 |
| Man4_A1G1 | 3.1E+07 | 0.11% | 2.8E+07 | 0.10% | 1.3E+06 | 0.09% | 1.6E+06 | 0.09% | 20.0 |
| Man4_FA1G1 | 3.4E+07 | 0.12% | 3.3E+07 | 0.11% | 1.6E+06 | 0.11% | 2.1E+06 | 0.12% | 17.9 |
| Man5 | 5.3E+08 | 1.82% | 5.2E+08 | 1.83% | 2.0E+07 | 1.42% | 2.6E+07 | 1.44% | 22.8 |
| Man5_A1G1 | 2.1E+07 | 0.07% | 2.0E+07 | 0.07% | 9.3E+05 | 0.06% | 1.3E+06 | 0.07% | 18.8 |
| Man6 | 3.9E+07 | 0.13% | 3.6E+07 | 0.13% | 1.7E+06 | 0.12% | 2.2E+06 | 0.12% | 19.3 |
| Man7 | 2.8E+07 | 0.10% | 2.7E+07 | 0.09% | 1.1E+06 | 0.08% | 1.5E+06 | 0.08% | 20.9 |
| Man8 | 3.6E+07 | 0.12% | 3.3E+07 | 0.12% | 1.8E+06 | 0.12% | 2.3E+06 | 0.13% | 16.9 |

FIG.43C

*IgG1*
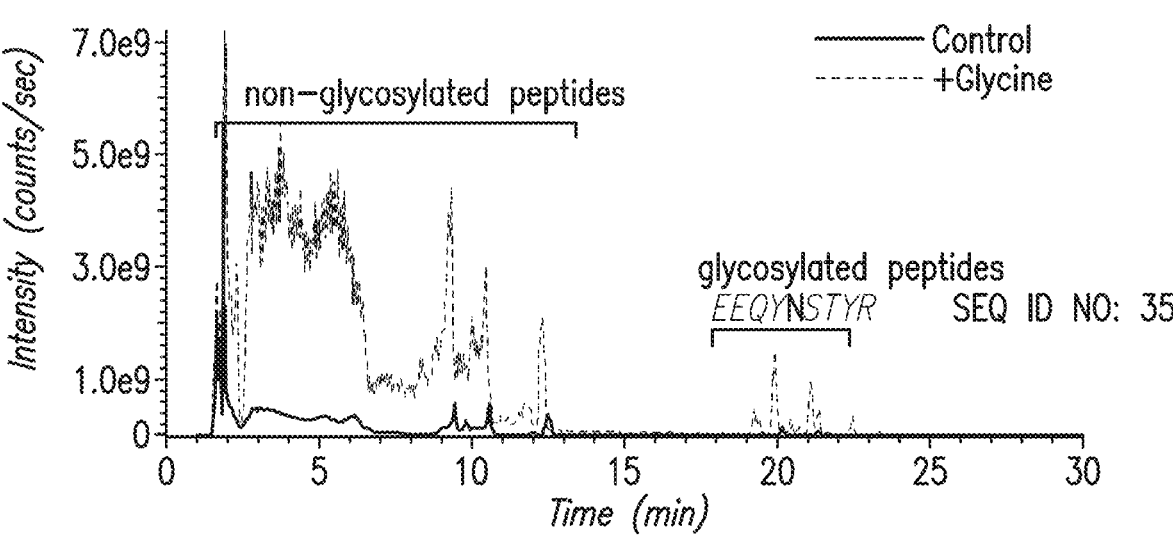
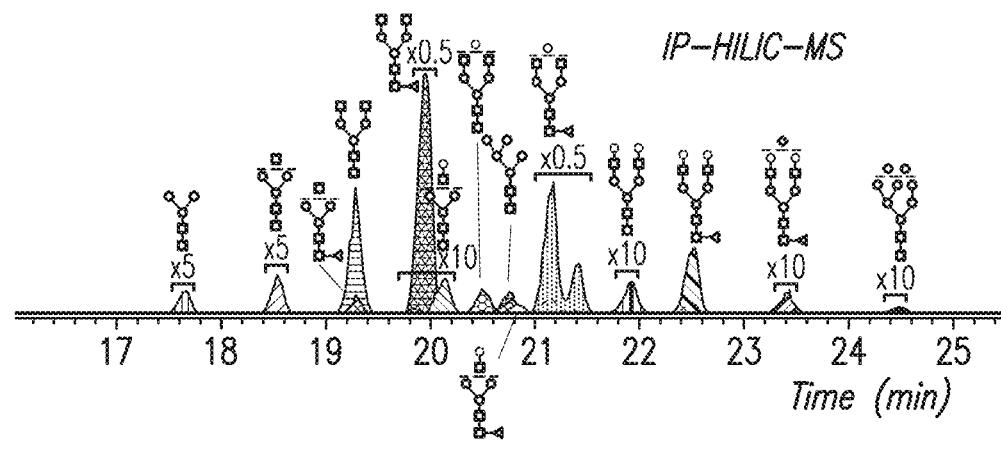
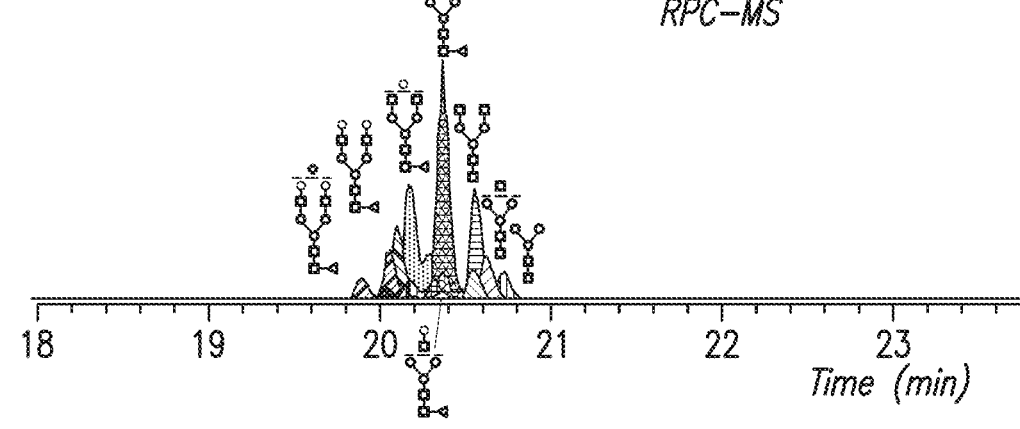
FIG.43D-1

| Glycan Name | 0.1% TFA + 1 mM Glycine | | | | 0.1% TFA | | | | Average fold change |
| | Replicate 1 | | Replicate 2 | | Replicate 1 | | Replicate 2 | | |
| | Peak area | Level | Peak area | Level | Peak area | Level | Peak area | Level | |
| A1 | 3.1E+08 | 0.91% | 3.0E+08 | 0.88% | 1.2E+07 | 0.70% | 1.3E+07 | 0.72% | 23.8 |
| FA1 | 1.1E+09 | 3.33% | 1.1E+09 | 3.28% | 5.1E+07 | 2.87% | 5.5E+07 | 2.97% | 21.4 |
| A2 | 1.7E+09 | 5.00% | 1.7E+09 | 4.91% | 7.2E+07 | 4.01% | 7.2E+07 | 3.91% | 23.7 |
| A2G1 | 1.8E+08 | 0.51% | 1.8E+08 | 0.52% | 9.0E+06 | 0.50% | 9.4E+06 | 0.51% | 19.4 |
| A2G2 | 2.0E+07 | 0.06% | 1.9E+07 | 0.06% | 1.0E+06 | 0.06% | 1.1E+06 | 0.06% | 18.8 |
| FA2 | 2.4E+10 | 70.31% | 2.4E+10 | 70.53% | 1.3E+09 | 73.32% | 1.3E+09 | 71.87% | 18.4 |
| FA2G1 | 5.3E+09 | 15.39% | 5.3E+09 | 15.46% | 2.6E+08 | 14.56% | 2.9E+08 | 15.76% | 19.2 |
| FA2G1S1 | 2.9E+07 | 0.08% | 2.6E+07 | 0.08% | 1.5E+06 | 0.08% | 1.6E+06 | 0.09% | 17.7 |
| FA2G2 | 6.8E+08 | 1.96% | 6.5E+08 | 1.89% | 3.1E+07 | 1.74% | 3.5E+07 | 1.88% | 20.1 |
| FA2G2S1 | 3.3E+07 | 0.09% | 3.2E+07 | 0.09% | 1.7E+06 | 0.09% | 1.7E+06 | 0.09% | 19.4 |
| FA2G2S2 | 4.4E+06 | 0.01% | 4.4E+06 | 0.01% | 6.8E+04 | 0.00% | 8.9E+04 | 0.00% | 55.9* |
| FA3 | 1.3E+08 | 0.38% | 1.3E+08 | 0.38% | 7.0E+06 | 0.39% | 7.4E+06 | 0.40% | 18.1 |
| FA3G1 | 4.5E+07 | 0.13% | 4.6E+07 | 0.13% | 2.5E+06 | 0.14% | 2.7E+06 | 0.14% | 17.6 |
| FA3G2 | 1.3E+07 | 0.04% | 1.2E+07 | 0.03% | 5.9E+05 | 0.03% | 6.4E+05 | 0.03% | 20.7 |
| FA3G3 | 2.7E+06 | 0.01% | 2.3E+06 | 0.01% | 4.6E+04 | 0.00% | 6.1E+04 | 0.00% | 47.0* |
| Man5 | 3.4E+08 | 0.99% | 3.3E+08 | 0.98% | 1.4E+07 | 0.80% | 1.5E+07 | 0.82% | 22.9 |
| Man6 | 4.6E+07 | 0.13% | 4.7E+07 | 0.14% | 2.0E+06 | 0.11% | 2.2E+06 | 0.12% | 22.1 |
| Man7 | 3.2E+07 | 0.09% | 3.2E+07 | 0.09% | 1.4E+06 | 0.08% | 1.5E+06 | 0.08% | 22.1 |
| Man8 | 1.9E+08 | 0.55% | 1.8E+08 | 0.53% | 8.9E+06 | 0.50% | 9.6E+06 | 0.52% | 20.1 |

FIG. 43E

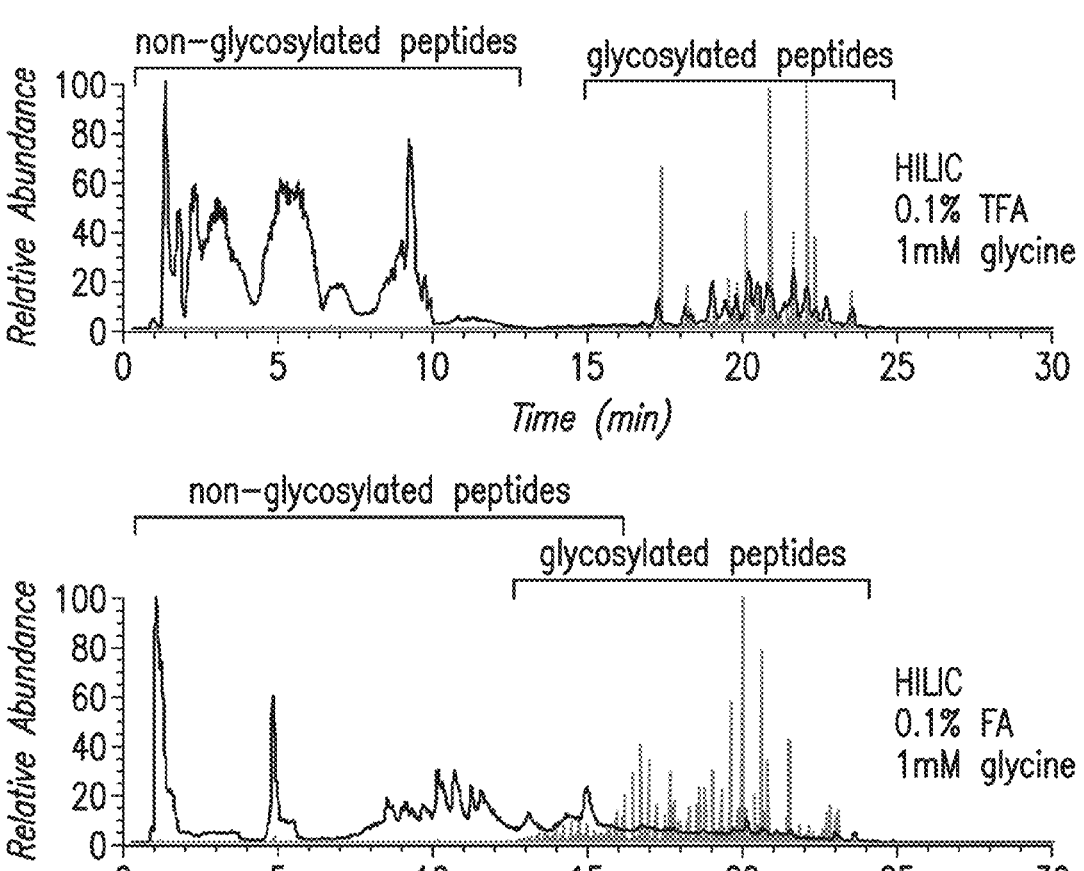
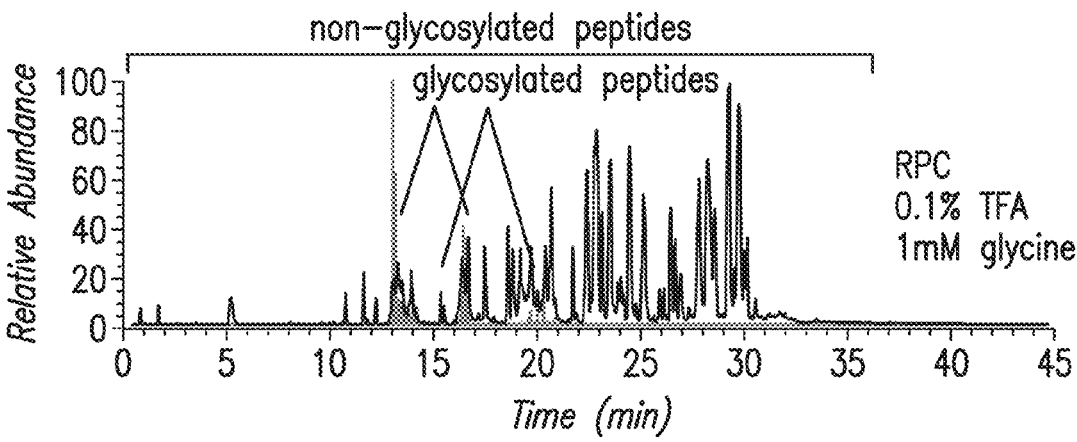
FIG.44D

Site 4ᵃ    XXXXXNXTXK
SEQ ID NO: 36

Site 4ᵇ    KXXXXXNXTXK
SEQ ID NO: 37

Site 5    XXXXNXTXXXK
SEQ ID NO: 38

Site 3    XXXNXTXR
SEQ ID NO: 39

Site 2ᵃ    NXTXXR
SEQ ID NO: 40

Site 2ᵇ    KNXTXXR
SEQ ID NO: 41

Site 1    EEQYNSTYR
SEQ ID NO: 35

Retention Time (min)

USE OF AMINO ACIDS TO ENHANCE SIGNAL IN MASS SPECTRAL ANALYSES

CROSS-REFERENCE TO RELATED APPLICATIONS

This application is a continuation of U.S. application Ser. No. 17/143,890, filed Jan. 7, 2021, which claims the benefit under 35 USC § 119(e) of US Provisional Application Nos. 62/958,366, filed Jan. 8, 2020; and 63/053,836, filed Jul. 20, 2020, each of which is incorporated herein by reference in its entirety for all purposes.

REFERENCE TO A SEQUENCE LISTING

This application incorporates by reference a computer readable Sequence Listing in ST.26 XML format, titled 10675US02_Sequence, created on Sep. 7, 2023 and containing 53,586 bytes.

FIELD OF THE INVENTION

The present invention pertains to mass spectral analyses, and relates to methods of enhancing mass spectrometry signal by use of amino acids, such as glycine, or modified amino acids.

BACKGROUND

Liquid chromatography-mass spectrometry (LC-MS) is used in the characterization of biomolecules including peptide and protein therapeutics. Although LC-MS is a powerful technology for characterization of recombinant proteins and post-translational and protein modifications, such as disulfide bonds, glycosylation and phosphorylation, separation and sensitivity has been found to be insufficient. For example, glycosylation can be characterized at the peptide level by analyzing glycopeptides generated from a tryptic digestion of an antibody. However, glycopeptides possessing heterogeneous glycoforms are often not well separated by reverse phase-based liquid chromatography (RPLC), which is traditionally used for peptide mapping. In addition, online mass spectrometry (MS) induced in-source fragmentation of the sugar chain in glycopeptides can produce truncated glycoform artifacts, which compromise the accurate quantification of the relative abundance of the different glycoforms using MS.

BRIEF SUMMARY OF THE INVENTION

In one aspect, the present invention provides a method of enhancing a mass spectral signal, comprising: contacting a sample to a separation column under conditions that permit sample components to bind to the substrate; applying a first mobile phase gradient to the separation column, wherein the first mobile phase gradient comprises trifluoroacetic acid (TFA) and a small molecule additive (e.g., an amino acid), formic acid (FA) and a small molecule additive (e.g., an amino acid), or ammonium formate and a small molecule additive (e.g., an amino acid); applying a second mobile phase gradient to the separation column, wherein the second mobile phase gradient comprises TFA in acetonitrile (ACN) and a small molecule additive (e.g., an amino acid), formic acid (FA) in acetonitrile (ACN) and a small molecule additive (e.g., an amino acid), or ammonium formate in water and acetonitrile (ACN) and a small molecule additive (e.g., an amino acid); and performing mass spectrometric analysis on eluted sample components.

In some embodiments, the small molecule additive in the first mobile phase is glycine.

In some embodiments, the small molecule additive in the first mobile phase is glycine and the concentration is between about 1 mM to about 2 mM glycine.

In some embodiments, the glycine concentration in the first mobile phase is about 1 mM.

In some embodiments, the glycine concentration in the first mobile phase is about 2 mM.

In some embodiments, the small molecule additive in the second mobile phase is glycine.

In some embodiments, the small molecule additive in the second mobile phase is glycine and the concentration is between about 1 mM to about 2 mM glycine.

In some embodiments, the glycine concentration in the second mobile phase is about 1 mM.

In some embodiments, the glycine concentration in the second mobile phase is about 2 mM.

In some embodiments, the TFA concentration in the first mobile phase is about 0.05% to TFA in $H_2O$ or the FA concentration in the first mobile phase is about 0.1% FA.

In some embodiments, the TFA concentration in the second mobile phase comprises about 0.05% TFA in 80% ACN and 20% $H_2O$ or about 0.1% TFA in 80% ACN and 20% $H_2O$.

In some embodiments, the ammonium formate concentration in the first mobile phases is mM, pH is 4.4

In some embodiments, the second mobile phase comprises 15% 50 mM ammonium formate, pH 4.4 in $H_2O$ and 85% ACN.

In some embodiments, the sample comprises peptides, nucleotides or glycans.

In some embodiments, the peptides are glycopeptides.

In some embodiments, the glycopeptides are obtained from a monoclonal antibody.

In some embodiments, the monoclonal antibody is of isotype IgG1, IgG2, IgG3, IgG4, or mixed isotype.

In some embodiments, the method further comprises preparing the sample prior to contacting the sample to a separation column under conditions that permit sample components to bind to the substrate.

In some embodiments, preparing the sample comprises: contacting a sample with a denaturing and reducing solution under conditions that permit sample denaturation and reduction; contacting denatured and reduced sample with an alkylating solution under conditions that permit sample alkylation; contacting alkylated sample with a digest solution under conditions that permit sample digestion; and contacting digested sample with a quenching solution under conditions that stop sample digestion.

In some embodiments, preparing the sample comprises: releasing glycans from samples using enzymes or chemical reaction; labeling released glycans with fluorescence labels or reducing released glycans using reducing agents.

In some embodiments, the sample is a monoclonal antibody and the digest solution comprises a protease.

In some embodiments, the protease comprises trypsin.

In some embodiments, the separation column is a liquid chromatography (LC) separation column.

In some embodiments, LC separation column comprises a hydrophilic interaction (HILIC) liquid chromatography column.

In some embodiments, performing mass spectrometric analysis on eluted sample components comprises applying electrospray ionization to generate charged ions from the eluted sample components and measuring the generated charge ions.

In some embodiments, the method enhances the mass spectral signal as indicated by about 5 to 14-fold on average and/or an approximately about 2 to 1000-fold increase in high charge state species (e.g., $z \geq 3$).

In some embodiments, the spectral signal increase by approximately 14-fold and/or approximately 1000-fold increase in high charge state species.

In some embodiments, the sample contains a glycopeptide or a glycan, and the mass spectral signal obtained on the eluted sample components is enhanced by from 2-fold to 50-fold relative to a mass spectral signal obtained on a control sample in the absence of the small molecule additive. In some cases, the glycopeptide is an O-glycan containing glycopeptide. In some cases, the glycopeptide is an N-glycan containing glycopeptide. In some cases, the glycan is a O-glycan. In some cases, the glycan is a N-glycan. In some cases, the O-glycan or the N-glycan is linked to a label, optionally procainamide, 2-aminobenzande or RapiFluor. In any of these embodiments, the small molecule additive may be glycine.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges and all values falling within such ranges are encompassed within the scope of the present disclosure. Each of the values discussed above or herein may be expressed with a variation of 1%, 5%, 10% or 20%. For example, a concentration of mM may be expressed as 10 mM±0.1 mM (1% variation), 10 mM±0.5 mM (5% variation), 10 mM±1 mM (10% variation) or 10 mM±2 mM (20% variation). Other embodiments will become apparent from a review of the ensuing detailed description.

```
                                        (SEQ ID NO: 3)
ALEWLADIWWDDK, (SEQ ID NO: 4)
ALPAPIEK, (SEQ ID NO: 34)
DIQMTQSPSTLSASVGDR, (SEQ ID NO: 5)
DMIFNFYFDVWGQGTTVTVSSASTK,
```

-continued (SEQ ID NO: 6)
DSTYSLSSTLTLSK, (SEQ ID NO: 7)
DTLMISR, (SEQ ID NO: 8)
EPQVYTLPPSR, (SEQ ID NO: 9)
ESGPALVKPTQTLTLTCTFSGFSLSTAGMSVGWIR, (SEQ ID NO: 10)
FNWYVDGVEVHNAK, (SEQ ID NO: 11)
FSGSGSGTEFTLTISSLQPDDFATYYCFQGSGYPFTFGGGTK, (SEQ ID NO: 12)
GFYPSDIAVEWESNGQPENNYK, (SEQ ID NO: 13)
GPSVFPLAPSSK, (SEQ ID NO: 14)
HYNPSLK, (SEQ ID NO: 15)
LASGVPSR, (SEQ ID NO: 16)
LLIYDTSK, (SEQ ID NO: 17)
NQVSLTCLVK, (SEQ ID NO: 18)
NQVVLK, (SEQ ID NO: 19)
QVTLR (SEQ ID NO: 20)
SGTASVVCLLNNFYPR, (SEQ ID NO: 21)
SLSLSPG, (SEQ ID NO: 22)
STSGGTAALGCLVK, (SEQ ID NO: 23)
THTCPPCPAPELLGGPSVFLFPPKPK, (SEQ ID NO: 24)
TPEVTCVVVDVSHEDPEVK, (SEQ ID NO: 25)
TTPPVLDSDGSFFLYSK, (SEQ ID NO: 26)
TVAAPSVFIFPPPSDEQLK, (SEQ ID NO: 27)
VDNALQSGNSQESVTEQDSK, (SEQ ID NO: 28)
VGYMHWYQQKPGK, (SEQ ID NO: 29)
VTITCSASSR, (SEQ ID NO: 30)
VTNMDPADTATYYCAR, (SEQ ID NO: 31)
VVSVLTVLHQDWLNGK, (SEQ ID NO: 32)
VYACEVTHQGLSSPVTK, -continued and (SEQ ID NO: 33)
WQQGNVFSCSVMHEALHNHYTQK.

Figure 11:
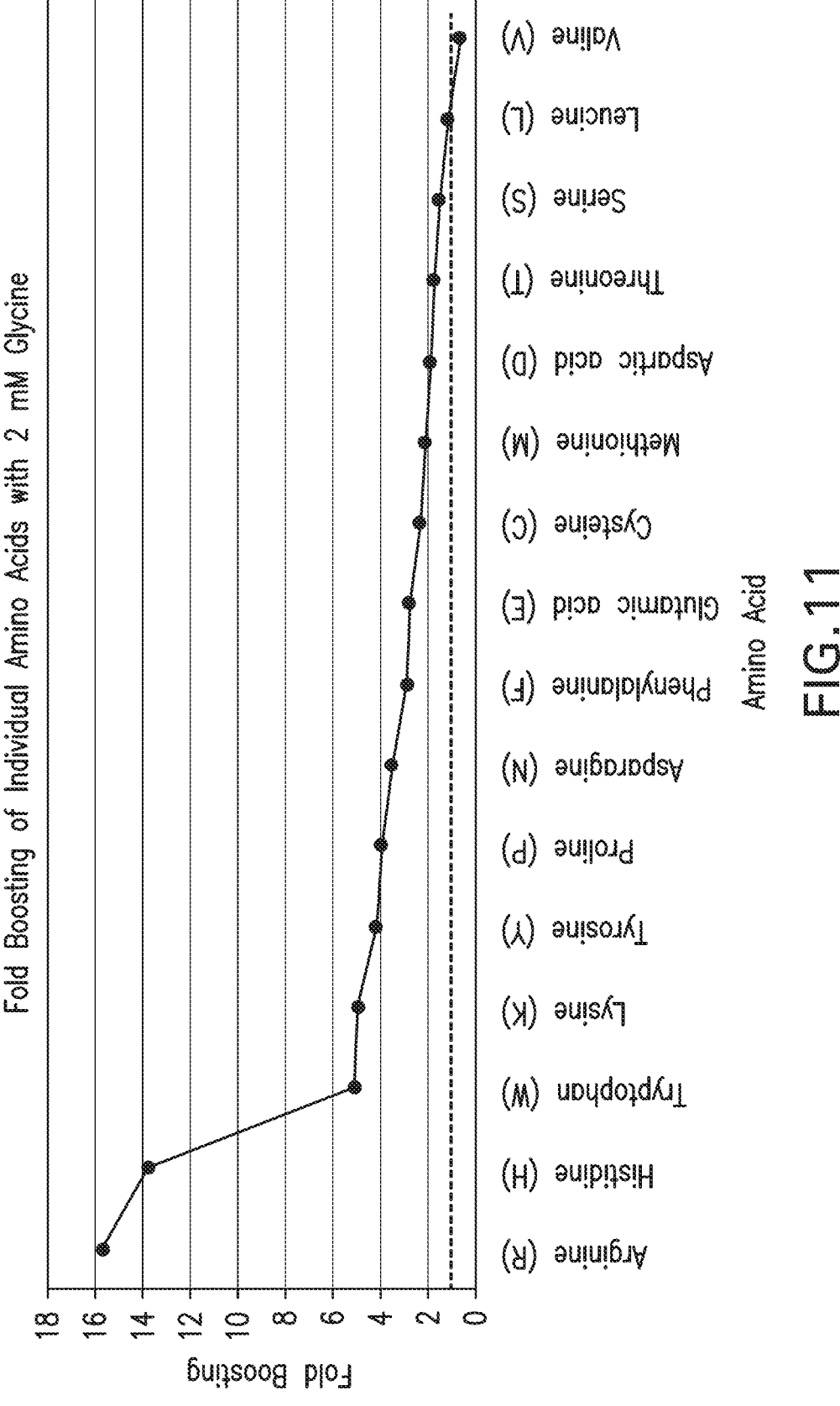

FIG. 11 shows fold boosting of individual amino acids with 2 mM glycine.

Figure 12:
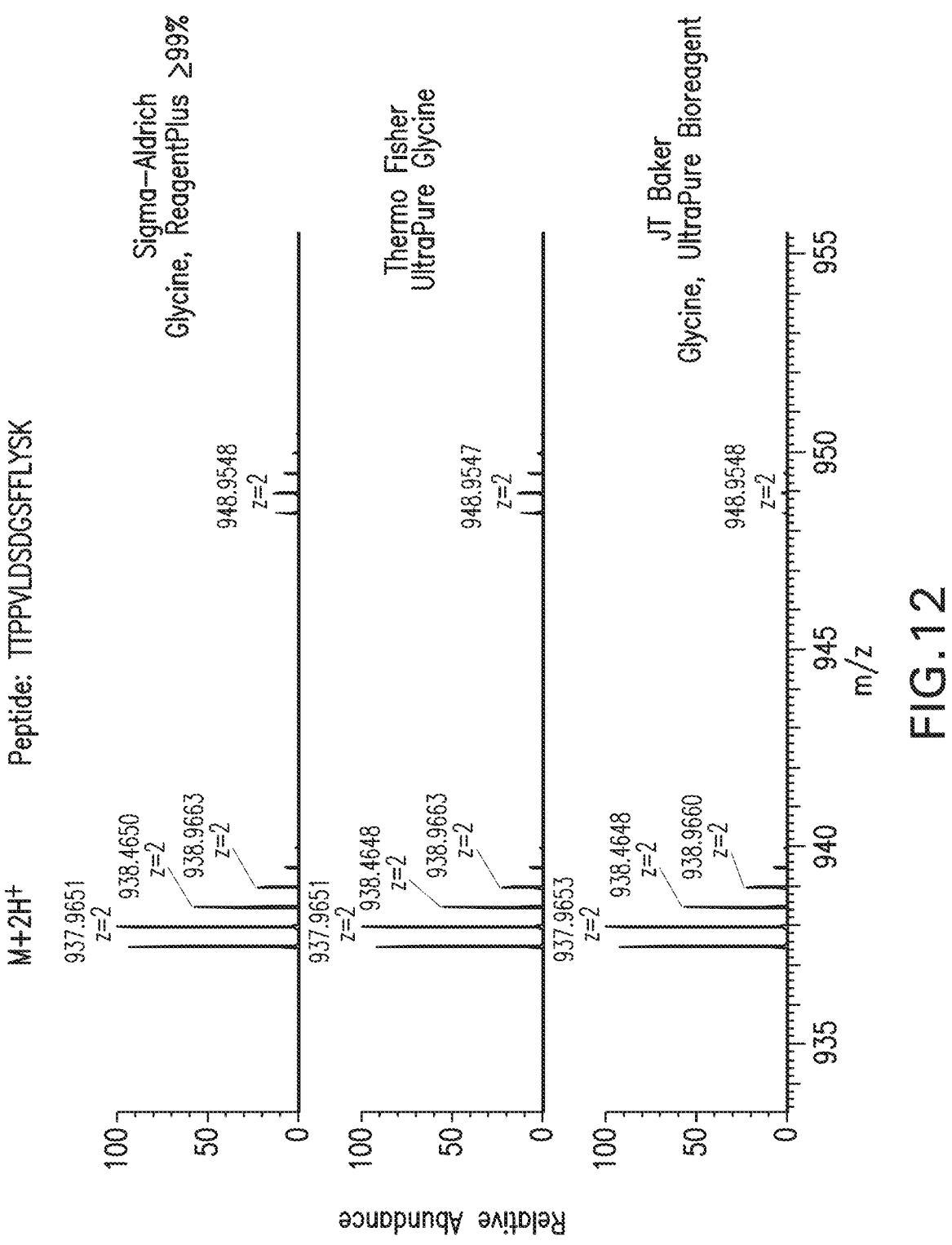

FIG. 12 shows the effect of trace sodium in commercial glycine formulations on TTPPVLDSDGSFFLYSK (SEQ ID NO: 25) peptide.

Figure 13:
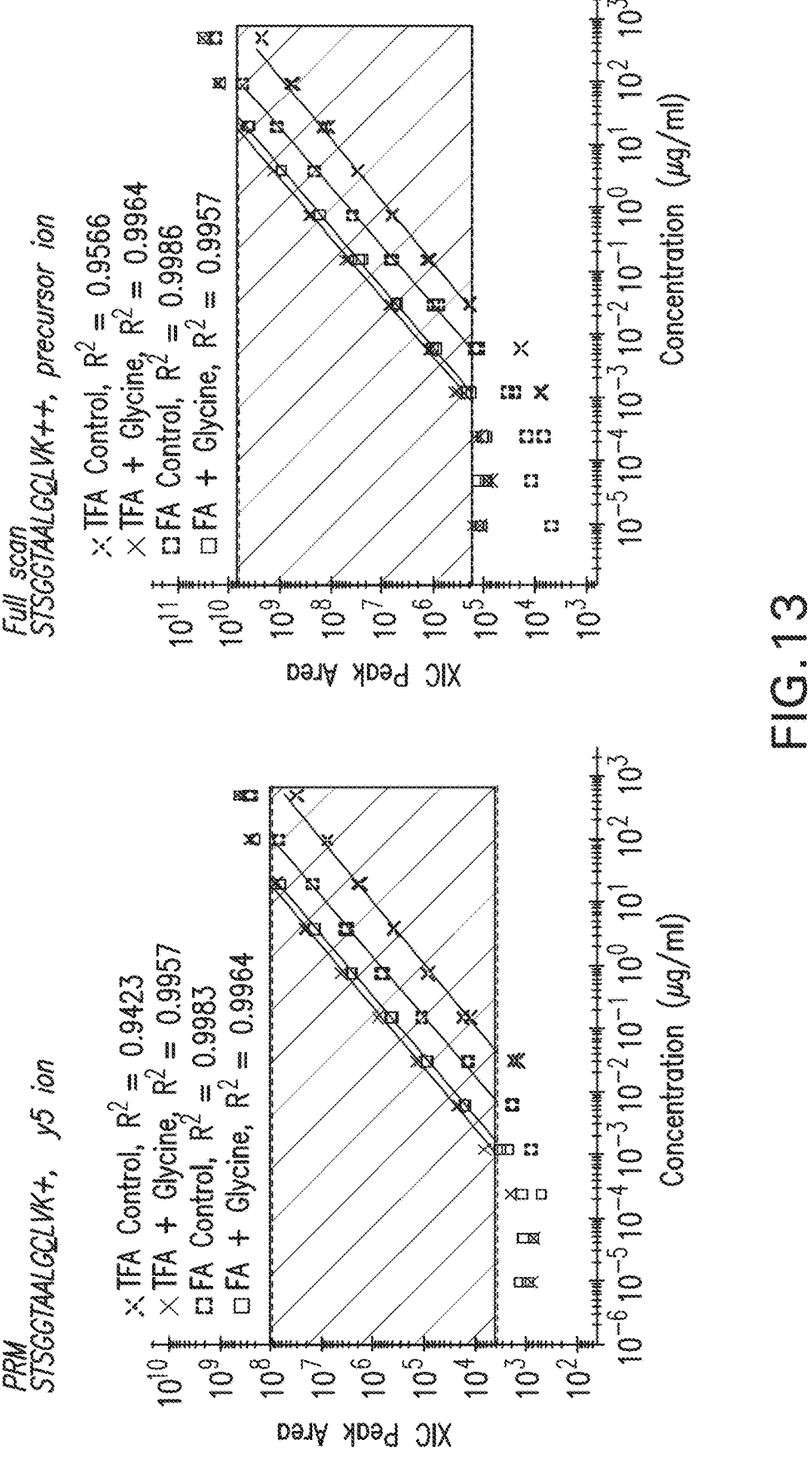

FIG. 13 provides a comparison between quantification of STSGGTAALGCLVK (SEQ ID NO: 22) peptide using PRM and full scan.

Figure 14:
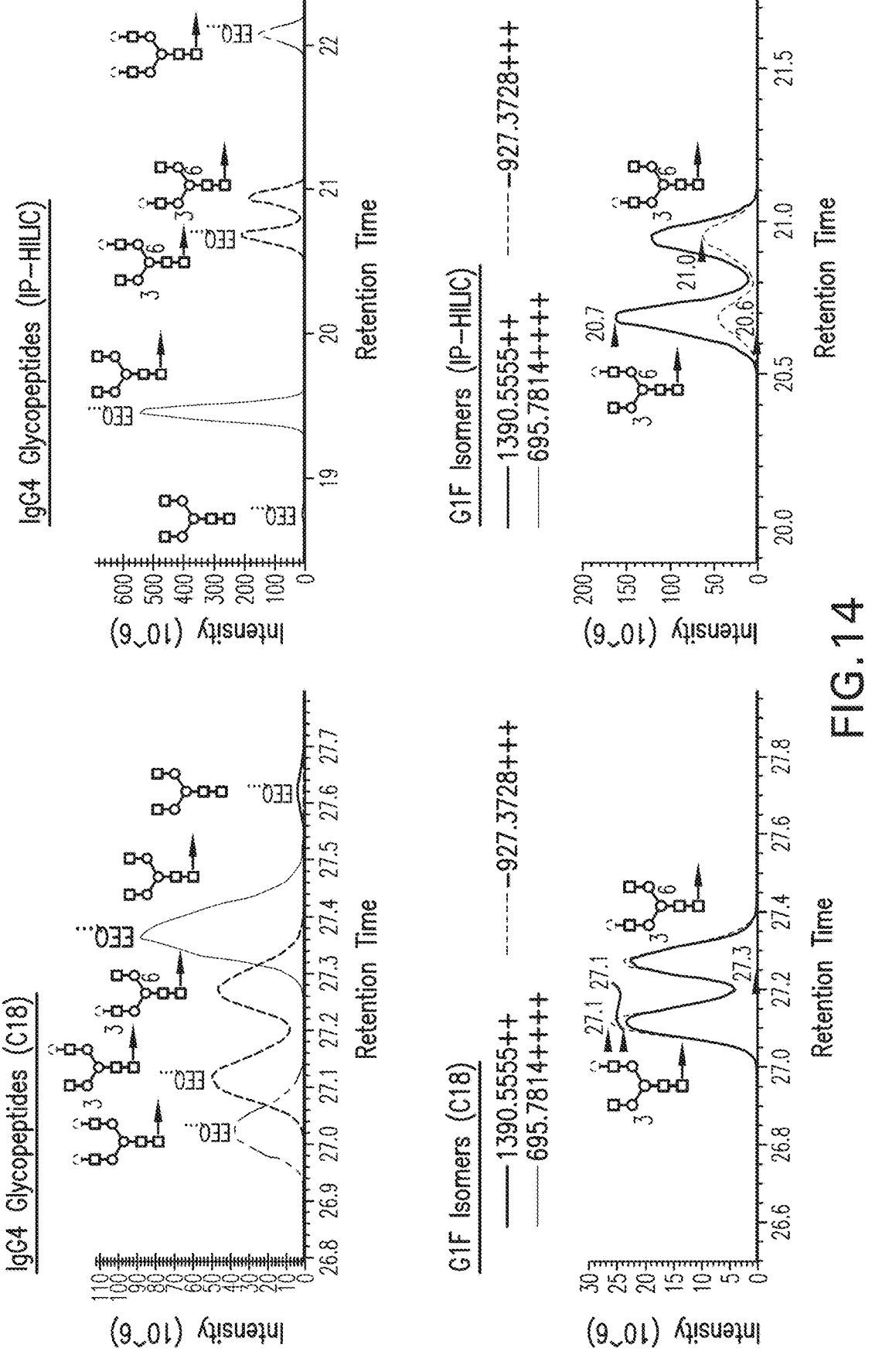

FIG. 14 illustrates some advantages of HILIC based liquid chromatography over reverse phase for glycopeptide analysis of a 9-residue peptide.

Figure 15:
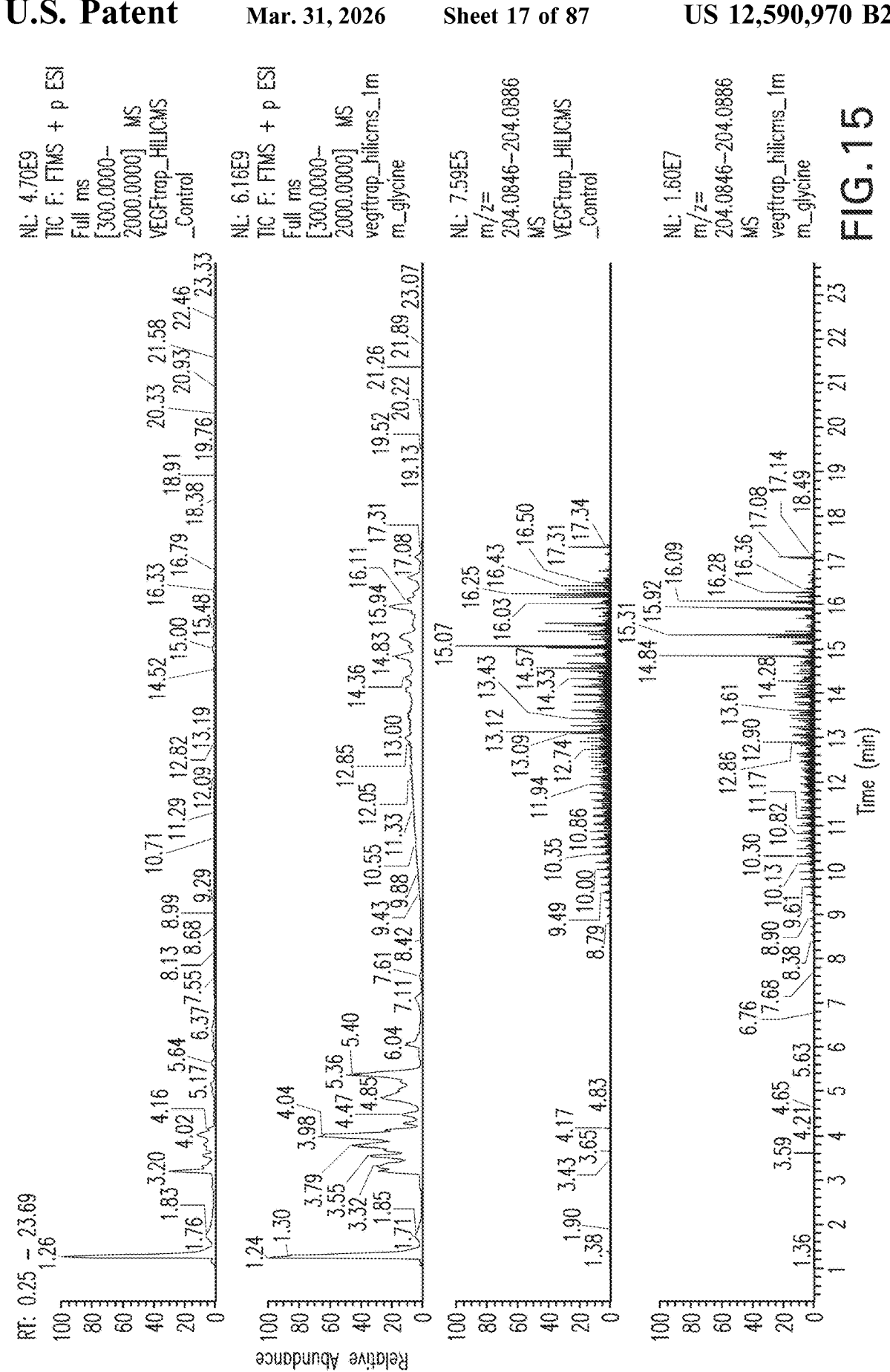

FIG. 15 illustrates signal boost observed in glycine-added buffer for both MS1 and MS2.

Figure 16:
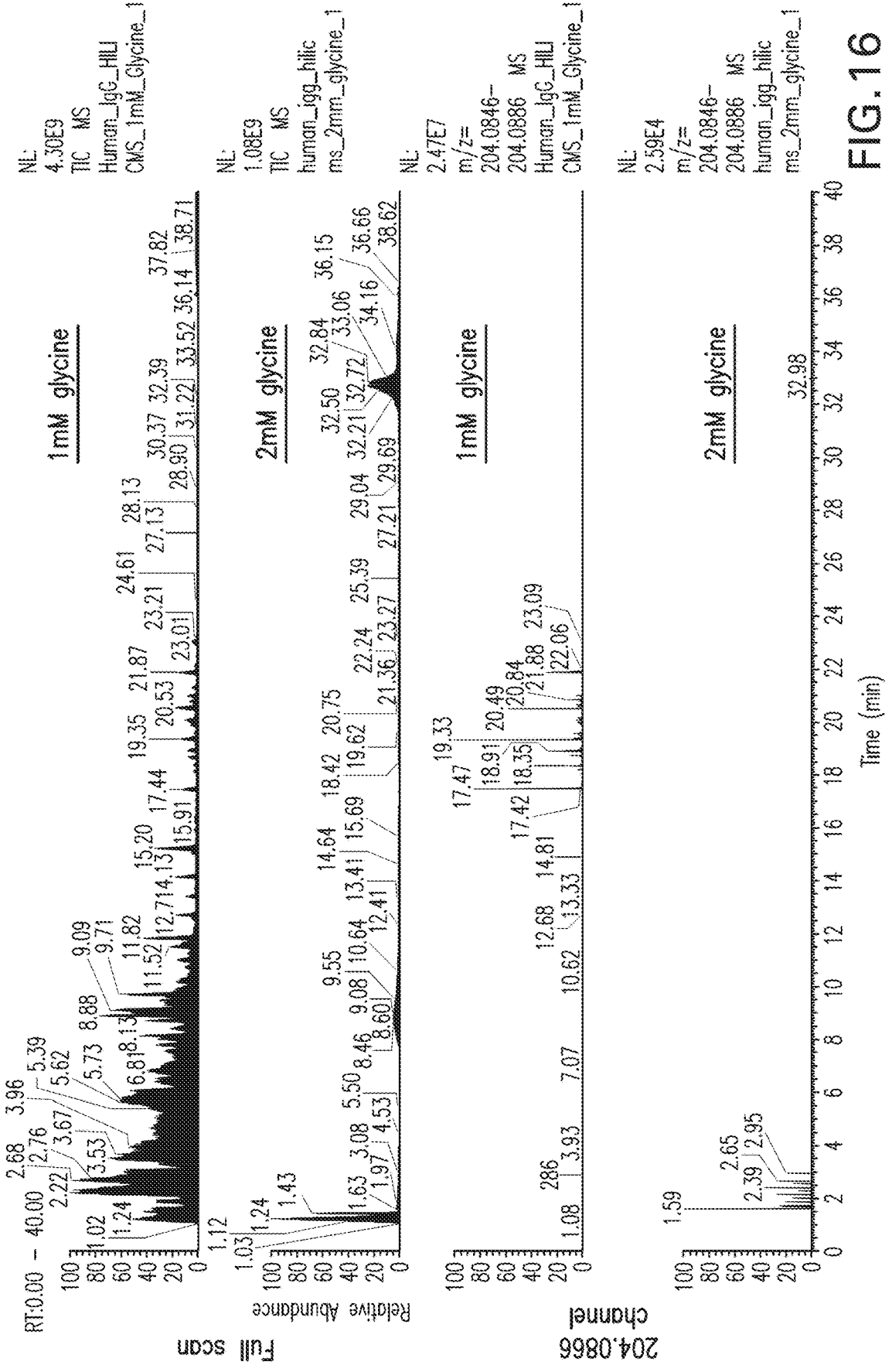

FIG. 16 illustrates 2 mM glycine prevents binding.

Figure 17:
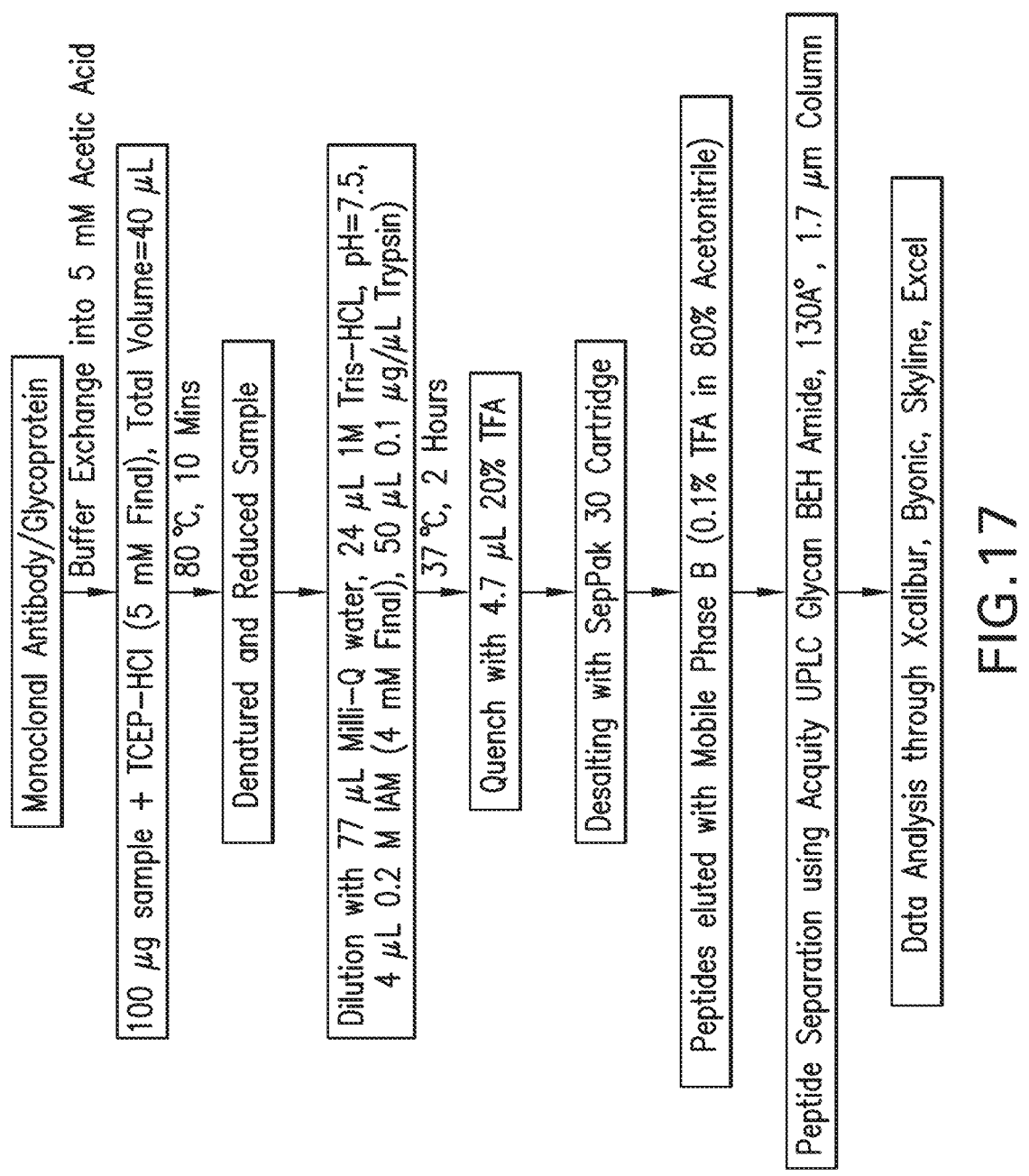

FIG. 17 is exemplary sample preparation workflow schematic for glycopeptide analysis through IP-HILIC based LC.

Figure 18:
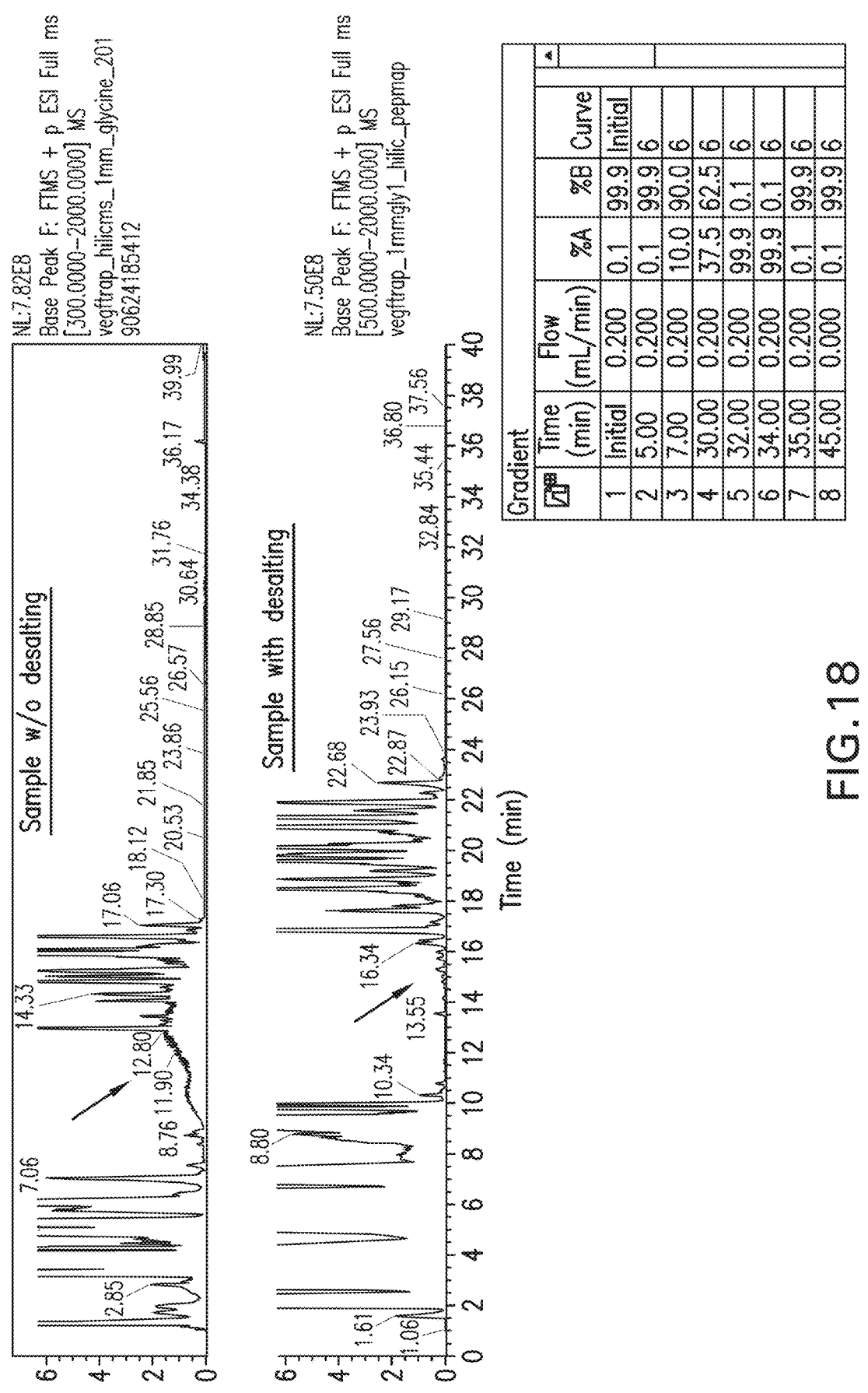

FIG. 18 shows the effect of desalting in which desalting with SepPak 30 cartridge eliminated elevated baseline (see arrow).

FIGS. 19 and 20 provide tables illustrating the effect of glycine on peak area.

FIGS. 21A and 21B show peak area of all glycoforms in evaluated mAbs.

Figure 22:
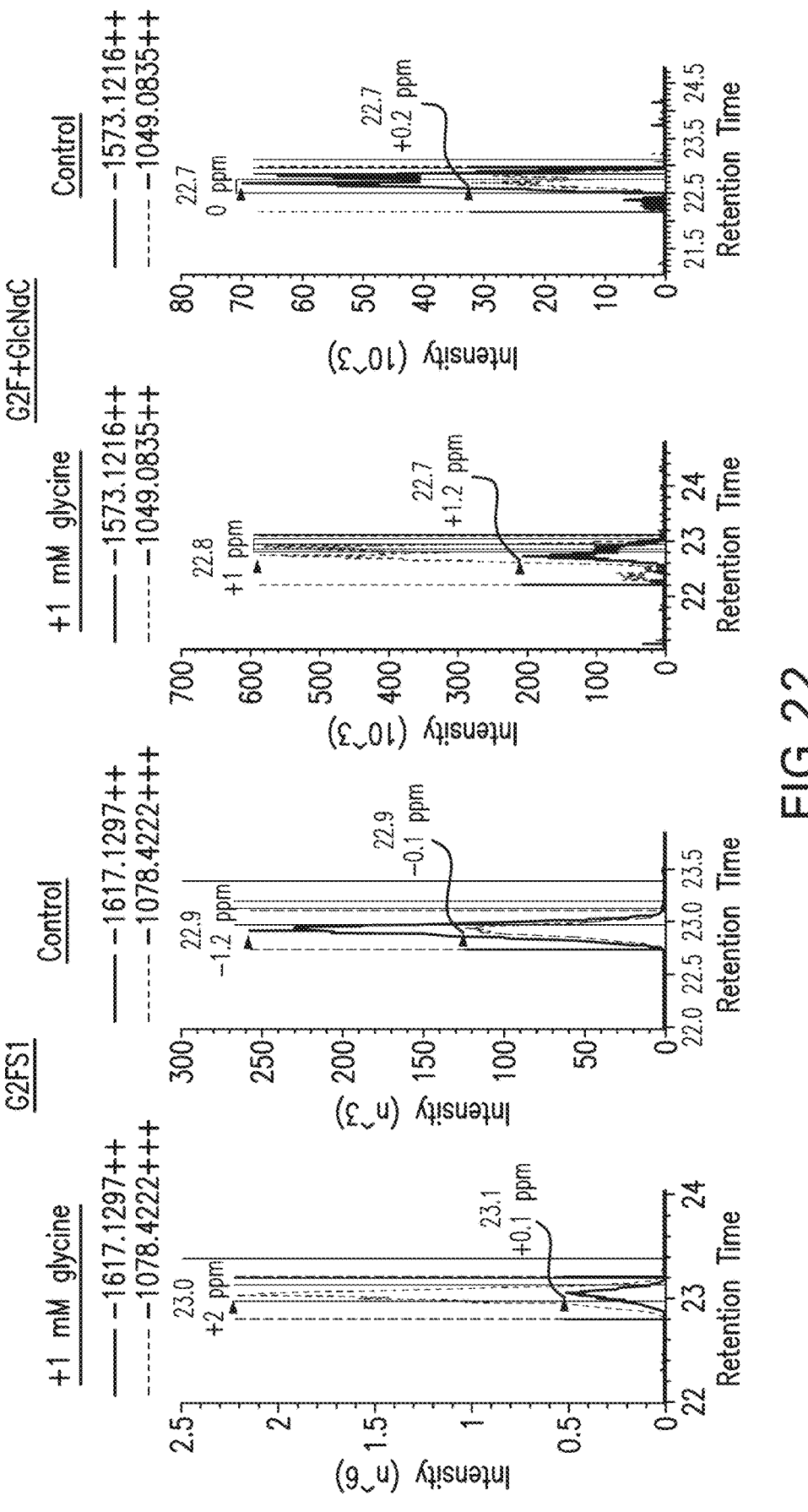

FIG. 22 shows enhanced fragmentation capacity by charge state shift in the presence of 1 mM glycine of a 9-residue peptide.

Figure 23:
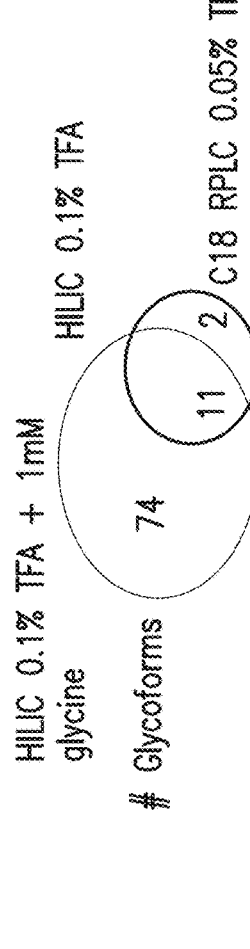

FIG. 23 shows glycine increased the number of peptide spectrum matches (PSM) and glycoforms in VEGF TRAP.

Figure 24:
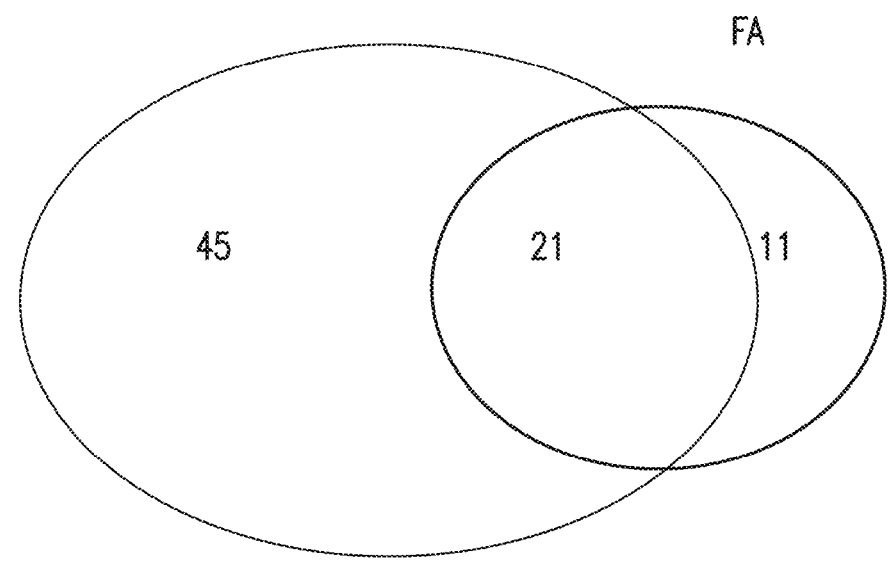

FIG. 24 illustrates the number of sequence variants identified when using TFA+glycine as compared to FA following Byologic validation.

Figure 25:
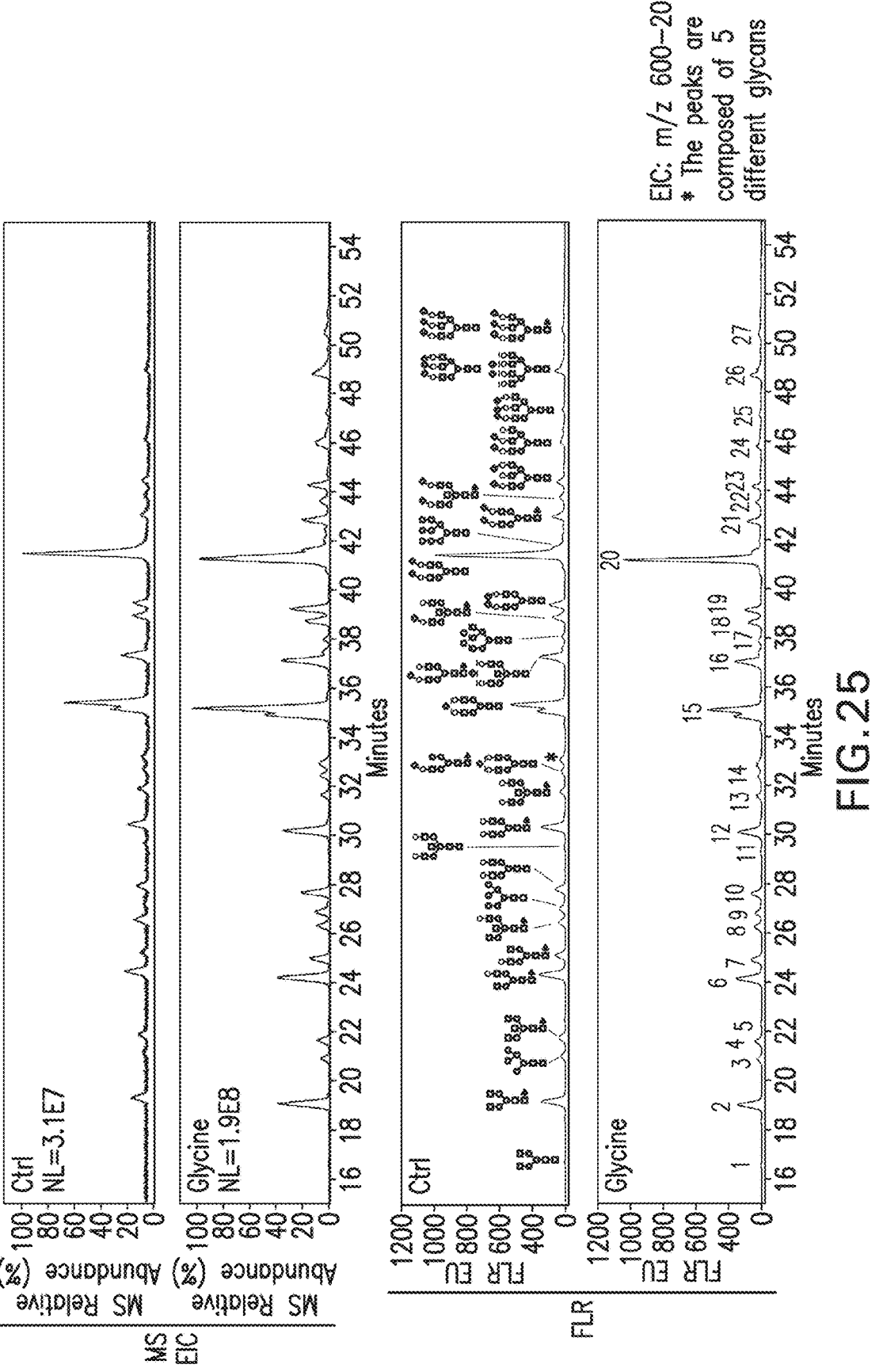

FIG. 25 illustrates the glycine boost effect on PROCA-labeled serum N-glycans in ammonium formate mobile phases. Shown is a mass spectrometry (MS) extracted ion chromatograph (EIC) and fluorescence (FLR) chromatogram traces of PROCA labeled N-glycans from human serum analyzed by HILIC using ammonium formate containing mobile phases (control) and the same mobile phases with additional 1 mM glycine (Glycine).

Figure 26B:
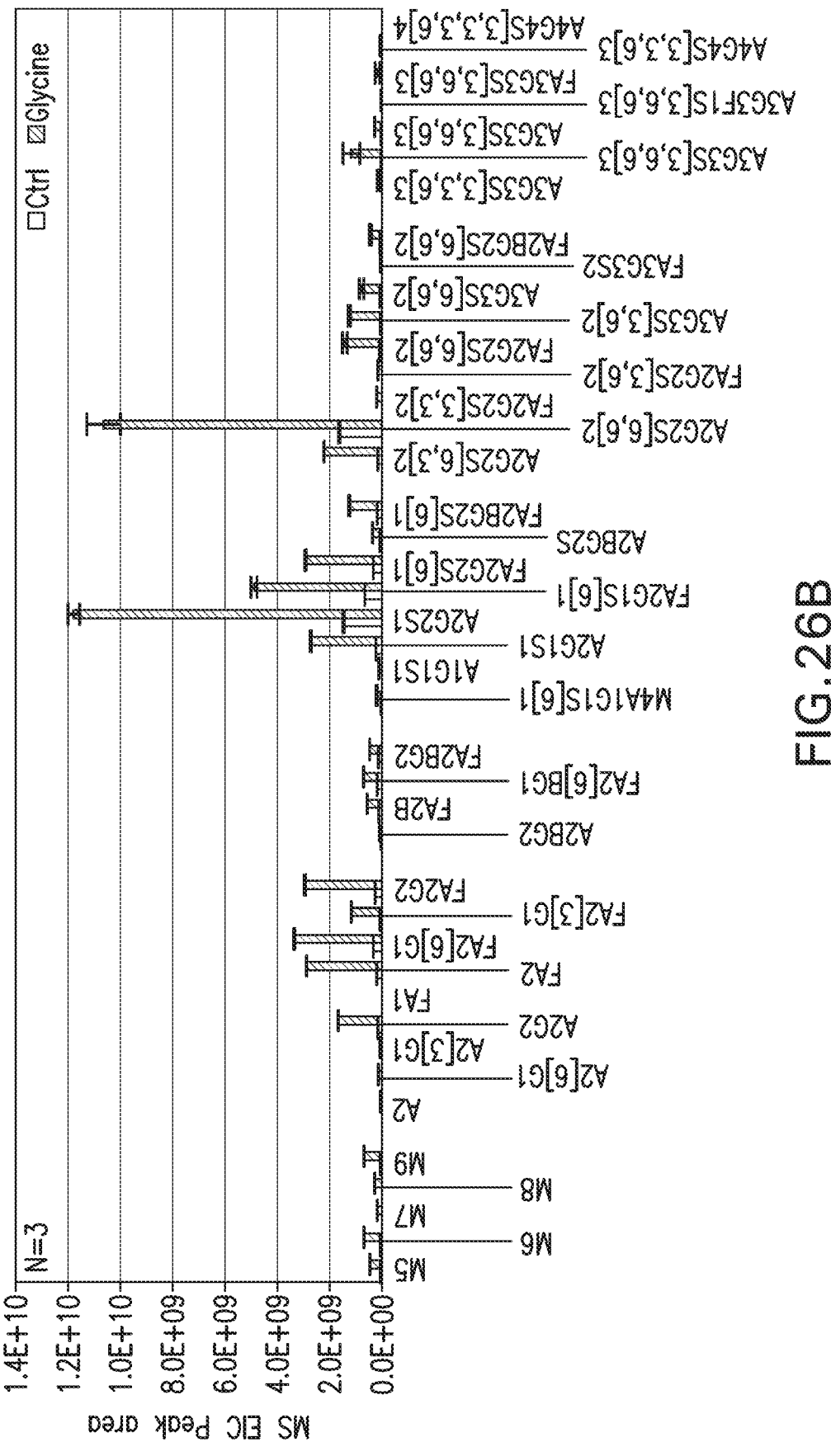
Figure 26C:
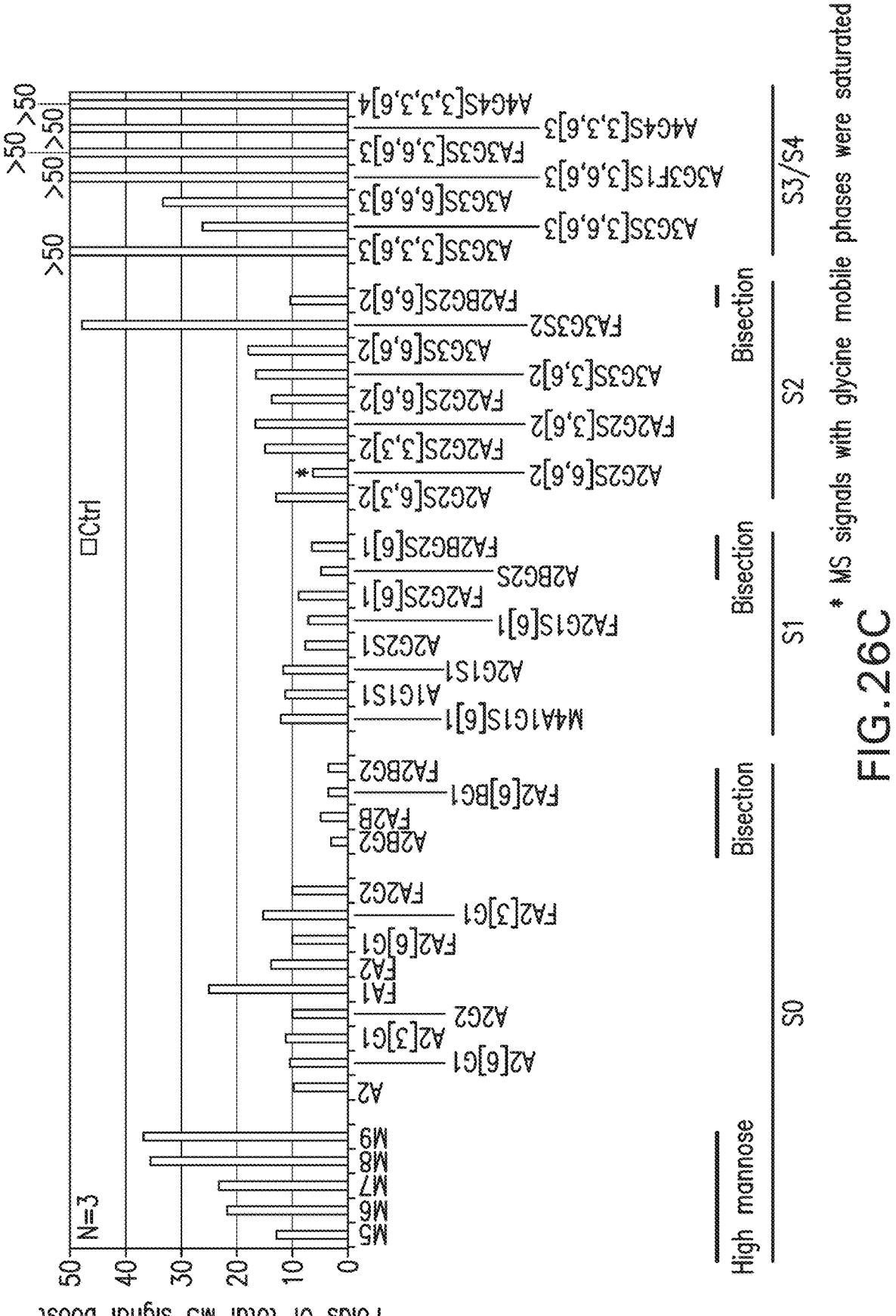

FIGS. 26A, 26B, and 26C illustrate total MS signals of PROCA-labeled N-glycans in ammonium formate mobile phases. FIGS. 26A and 26C show the folds of MS signal enhancement for PROCA labeled serum N-glycans by inclusion of 1 mM glycine in ammonium formate mobile phases. FIG. 26B shows the MS EIC peak areas of PROCA labeled serum N-glycans in ammonium formate-containing mobile phases (control) and the same mobile phases with additional 1 mM glycine (Glycine).

Figure 27:
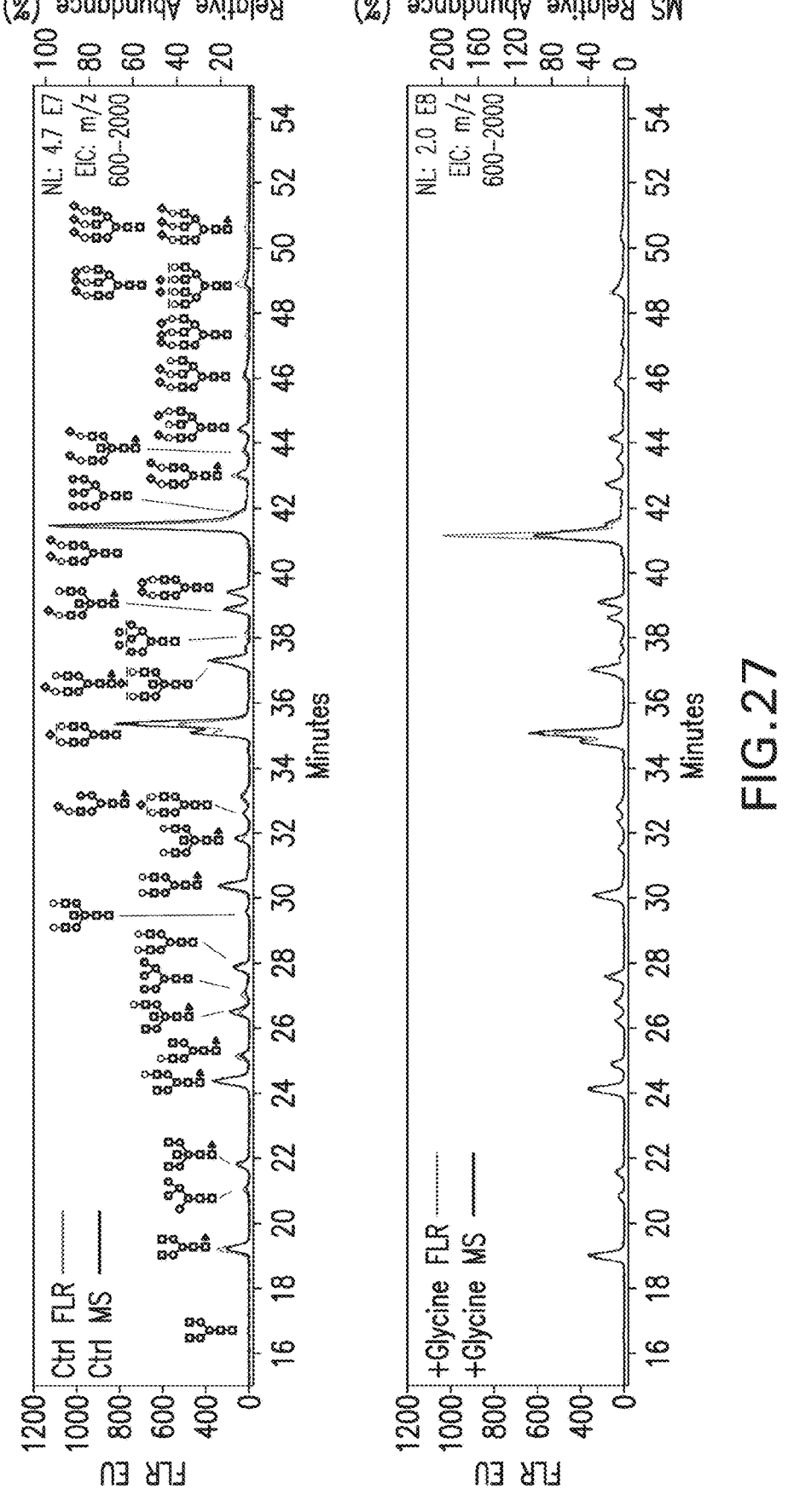

FIG. 27 illustrates that mass chromatograms with glycine-containing mobile phases better resembles FLR chromatogram than that in control mobile phases. Shown are the overlayed mass EIC and FLR chromatogram traces of PROCA labeled N-glycans from human serum analyzed by HILIC using ammonium formate-containing mobile phases (control) and the same mobile phases with additional 1 mM glycine (Glycine).

Figure 28B:
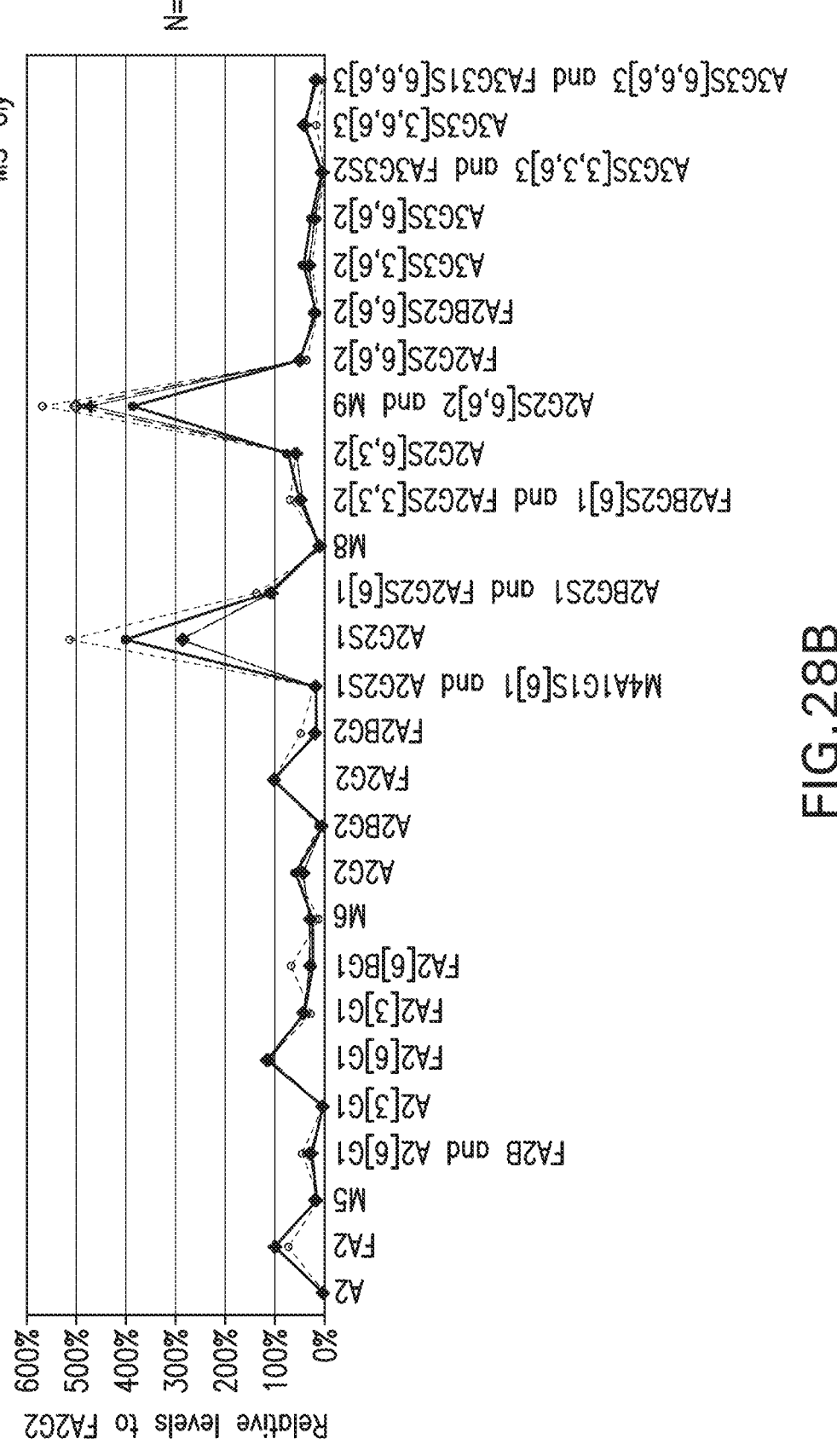
Figure 28C:
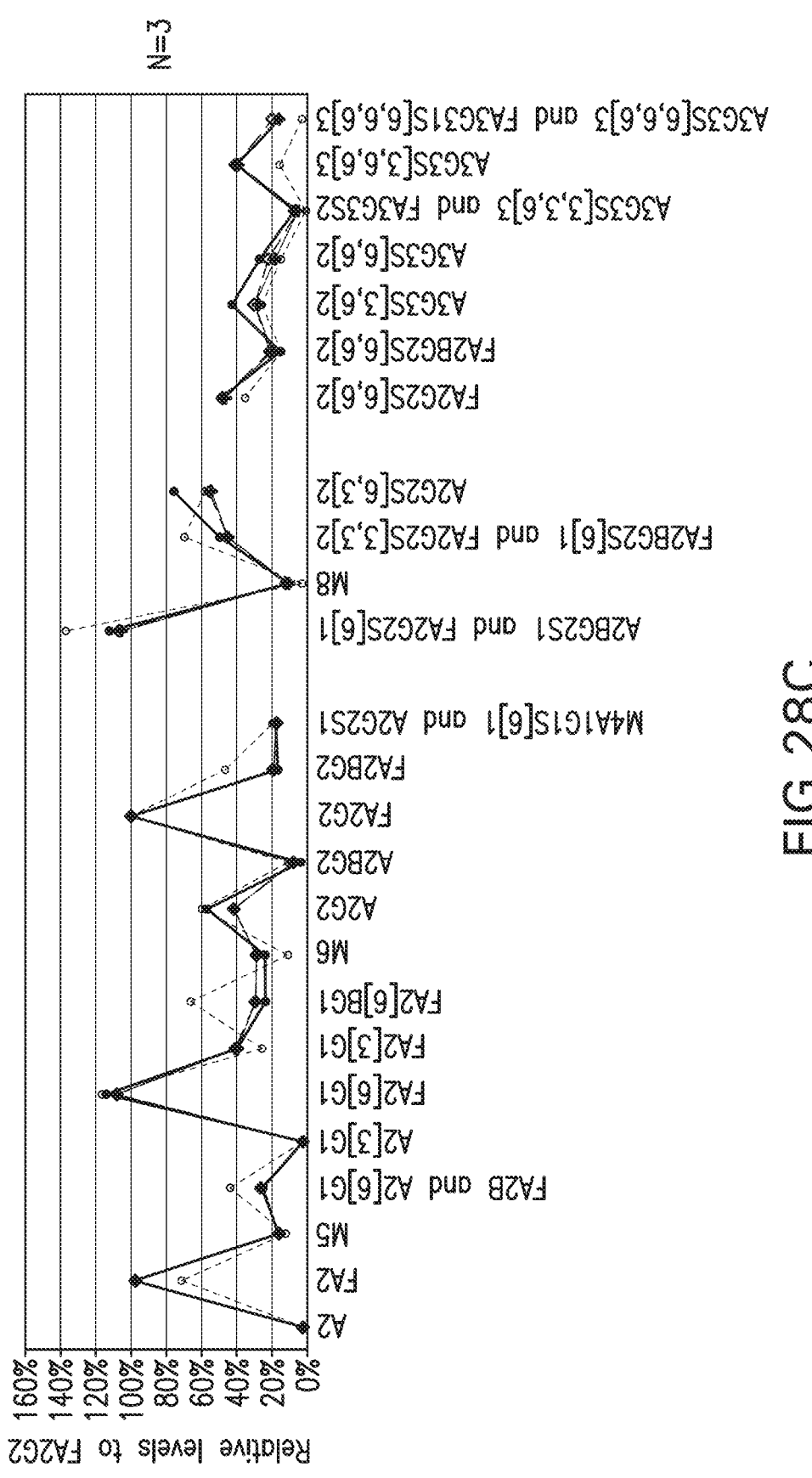

FIGS. 28A, 28B, and 28C illustrate a comparison of PROCA labeled serum N-glycan MS peak intensities with and without glycine in ammonium formate mobile phases. Shown are the relative levels of PROCA-labeled N-glycans based on FLR or MS EIC peak areas normalized to those of FA2G2 analyzed by HILIC using ammonium formate-containing mobile phases (control) and the same mobile phases with additional 1 mM glycine (Glycine).

Figure 29:
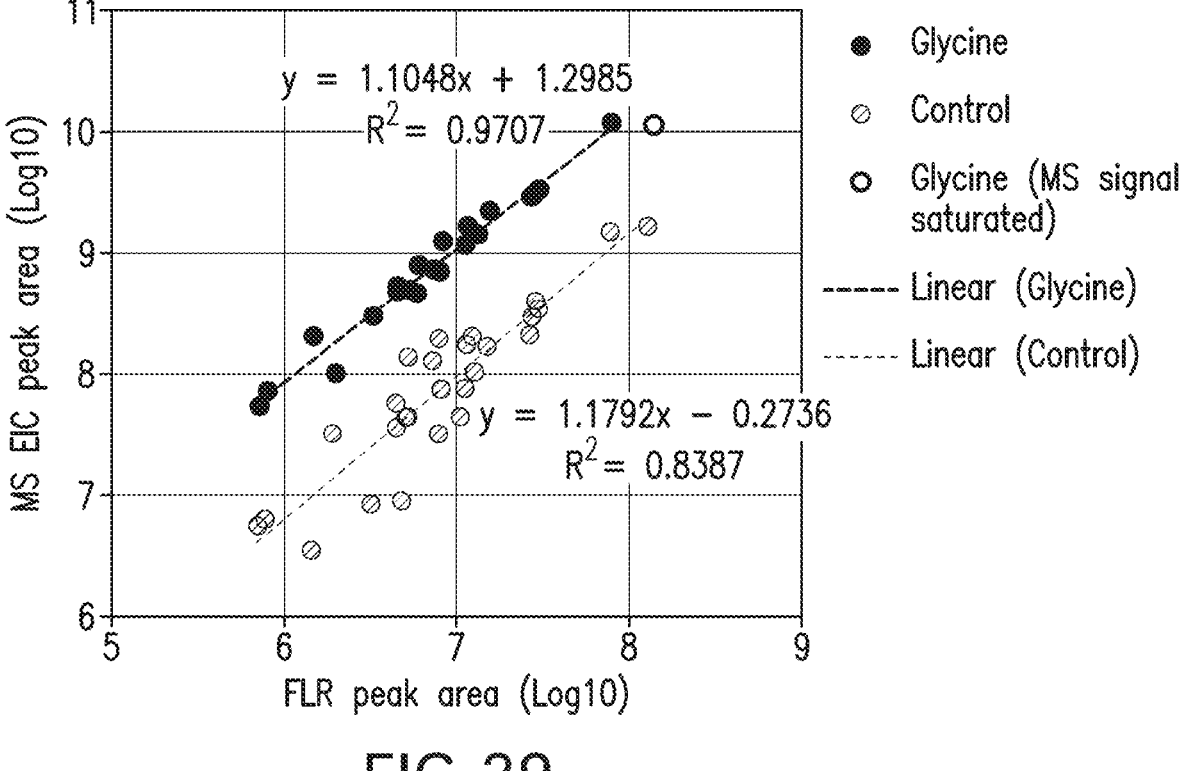

FIG. 29 illustrates that MS peak areas of PROCA labeled glycans are more proportional to the FLR peak areas in ammonium formate mobile phases with glycine. Shown is the scatter plot of serum N-glycan EIC peak areas versus FLR peak areas (logarithm scale) for analysis using ammonium formate mobile phases without (control) and with (glycine) 1 mM glycine additive. The equations and R square values of linear regression for each condition are shown. The smaller R square value for the glycine condition compared to that for the control condition demonstrates PROCA labeled N-glycans can be more accurately quantified by MS with glycine addition to mobile phases.

Figure 30B:
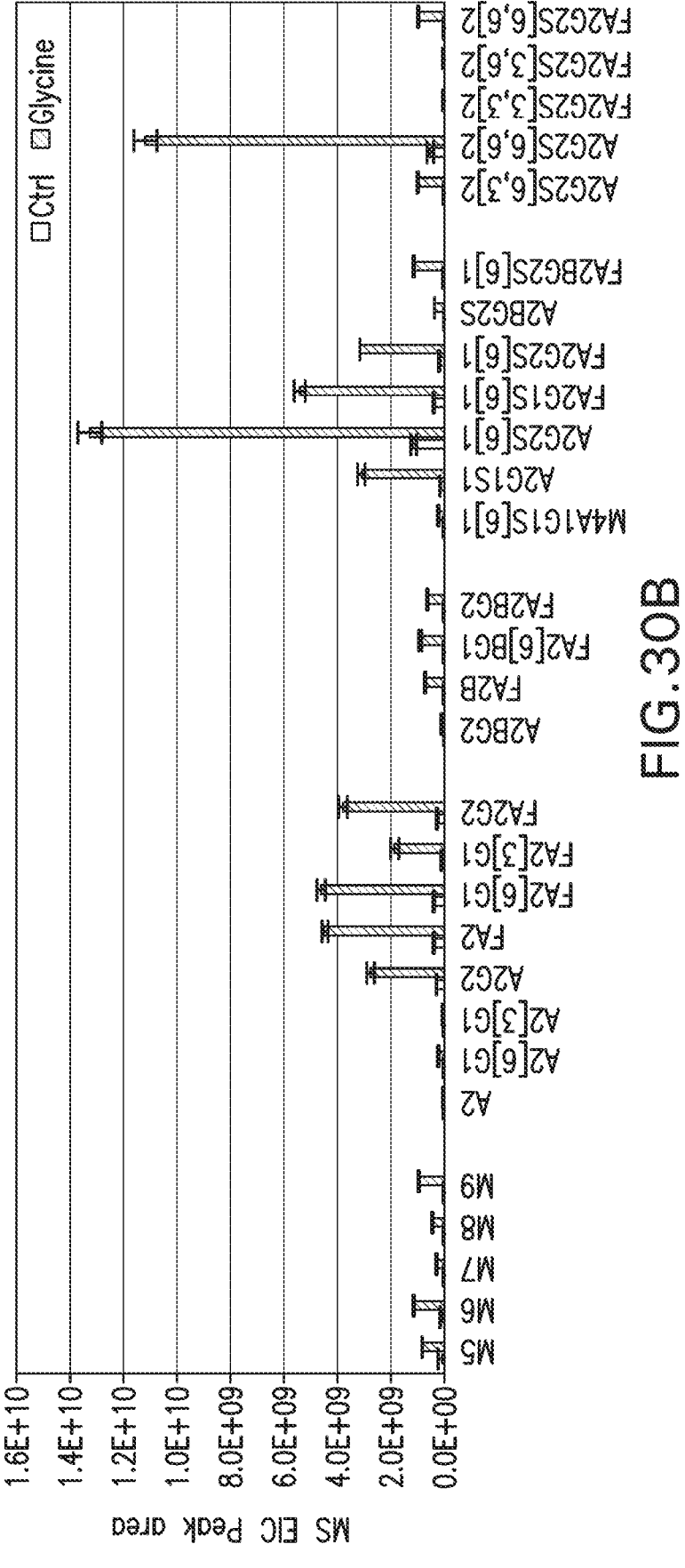
Figure 30C:
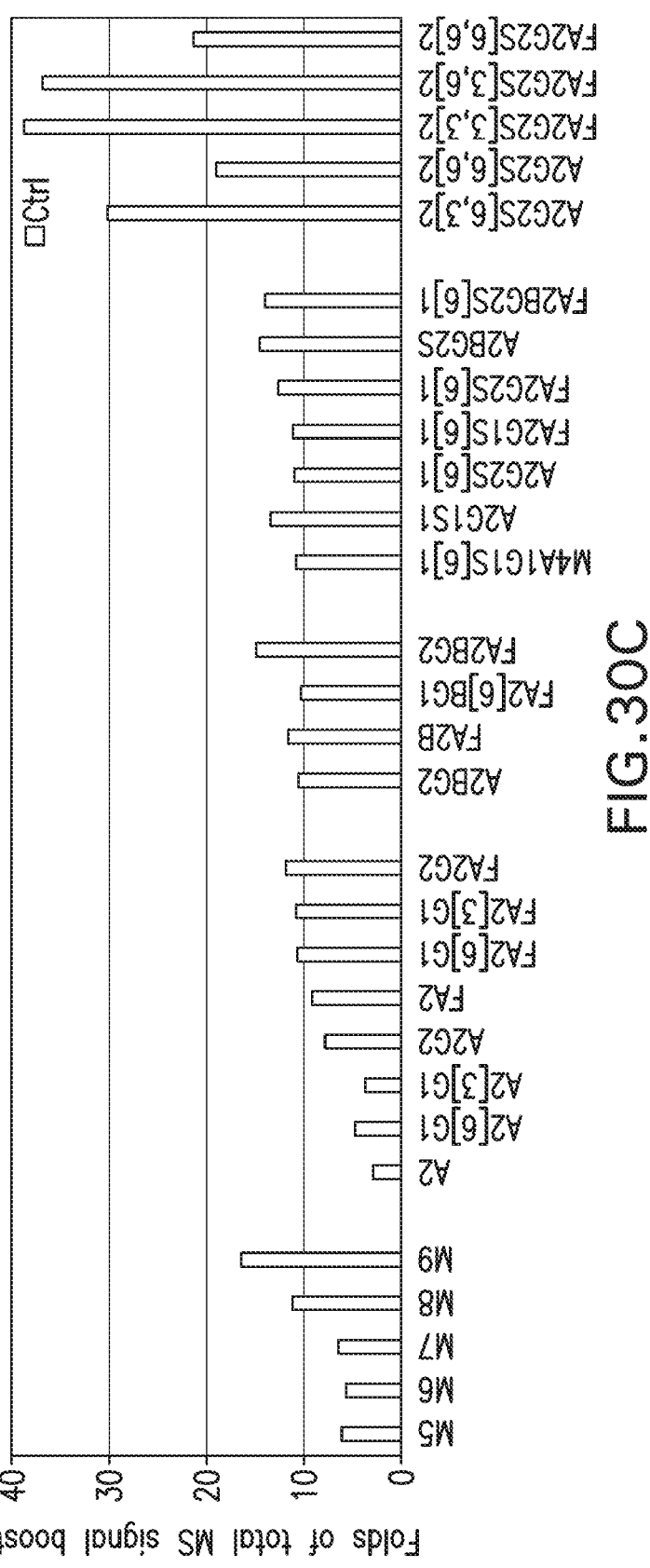

FIGS. 30A, 30B, and 30C illustrate MS signal boost of PROCA labeled N-glycans by glycine in formic acid mobile phases. FIG. 30A and FIG. 30C show the folds of MS signal enhancement for PROCA labeled serum N-glycans by including 1 mM glycine in 0.1% FA mobile phases analyzed by HILIC. FIG. 30B shows the MS EIC peak areas of PROCA labeled serum N-glycans in 0.1% FA mobile phases (Ctrl) and the same mobile phases with additional 1 mM glycine (Glycine).

Figure 31B:
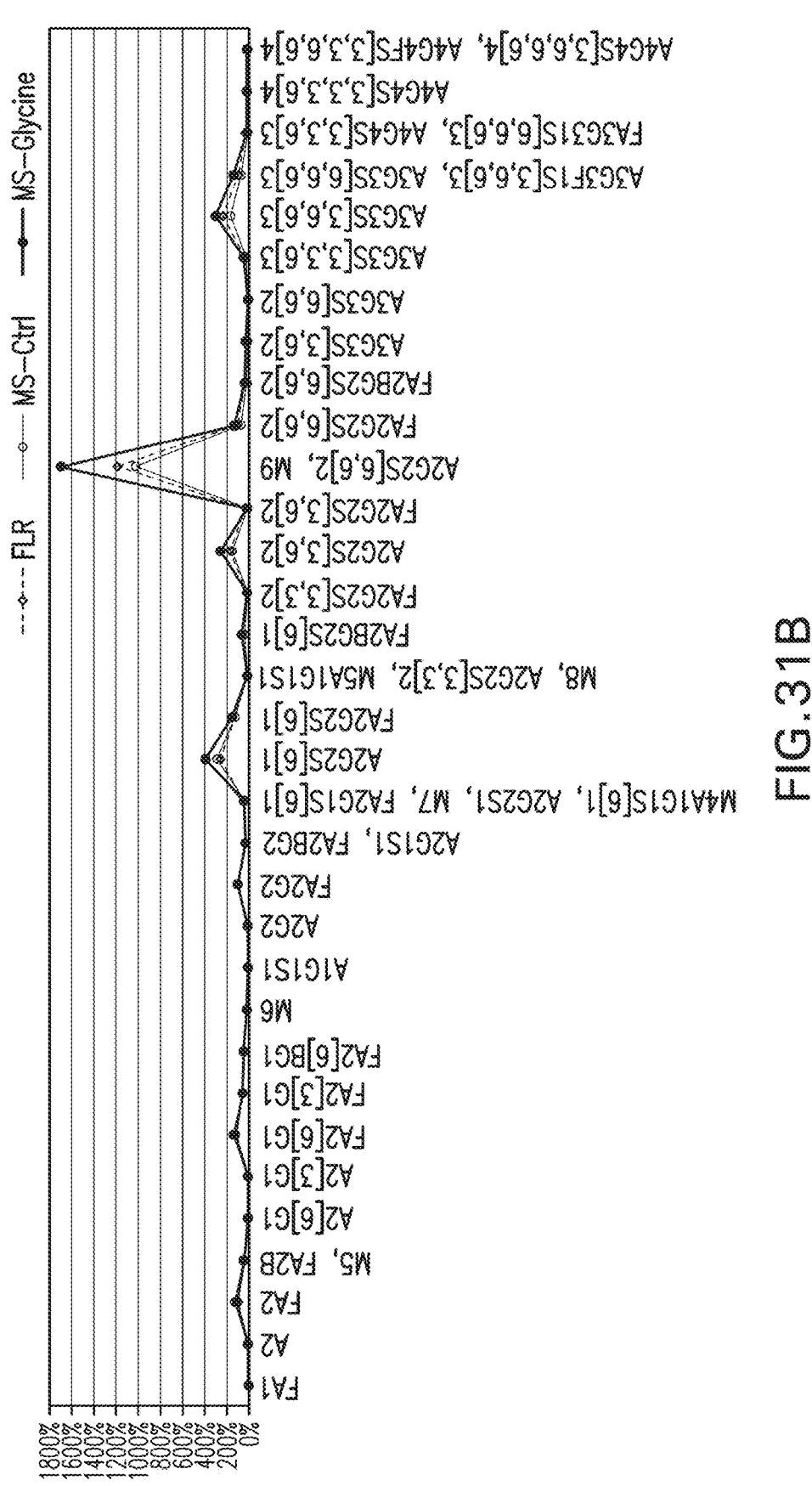
Figure 31C:
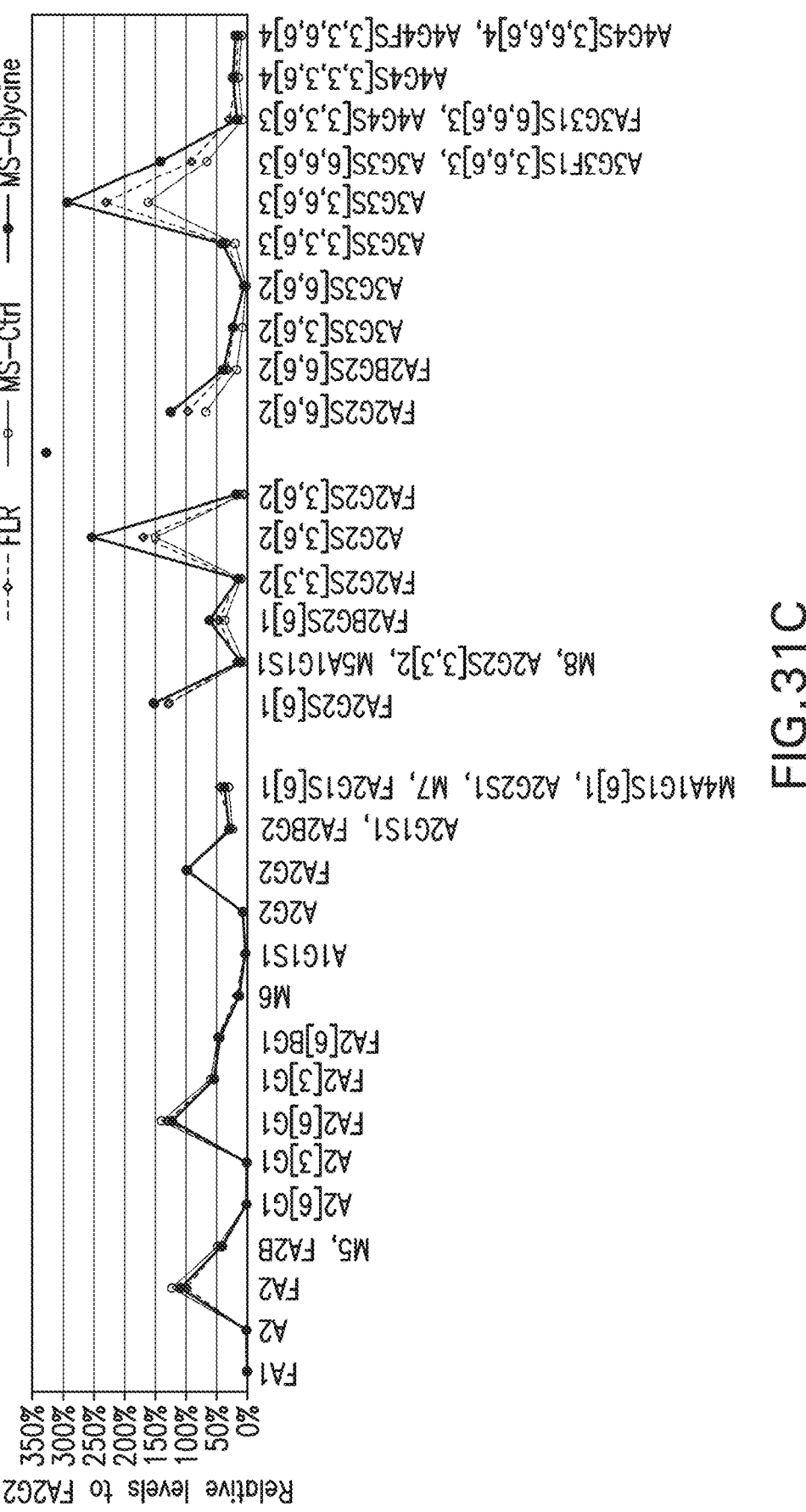

FIGS. 31A, 31B, and 31C illustrate comparison of Rapi-Fluor labeled plasma N-glycan MS peak intensities with and without glycine in ammonium formate mobile phases. Shown are the relative levels of RapiFluor-labeled N-glycans based on FLR or MS EIC peak areas normalized to those of FA2G2 analyzed by HILIC using ammonium formate containing mobile phases (Ctrl) and the same mobile phases with additional 1 mM glycine (Glycine). FIG. 31A also shows the folds of MS signal enhancement and charge state shift for PROCA labeled serum N-glycans by glycine additive.

FIG. 32 illustrates comparison of reduced serum N-glycan MS peak intensities with and without glycine in ammonium formate mobile phases. Depicted is a table showing the MS signal change and the average charge states of reduced serum N-glycans analyzed by HILIC using ammonium formate containing mobile phases (Ctrl) and the same mobile phases with additional 1 mM glycine (Glycine).

FIG. 33 illustrates LC-FLR-MS conditions for analysis of labeled or reduced N-glycans.

Figure 34:
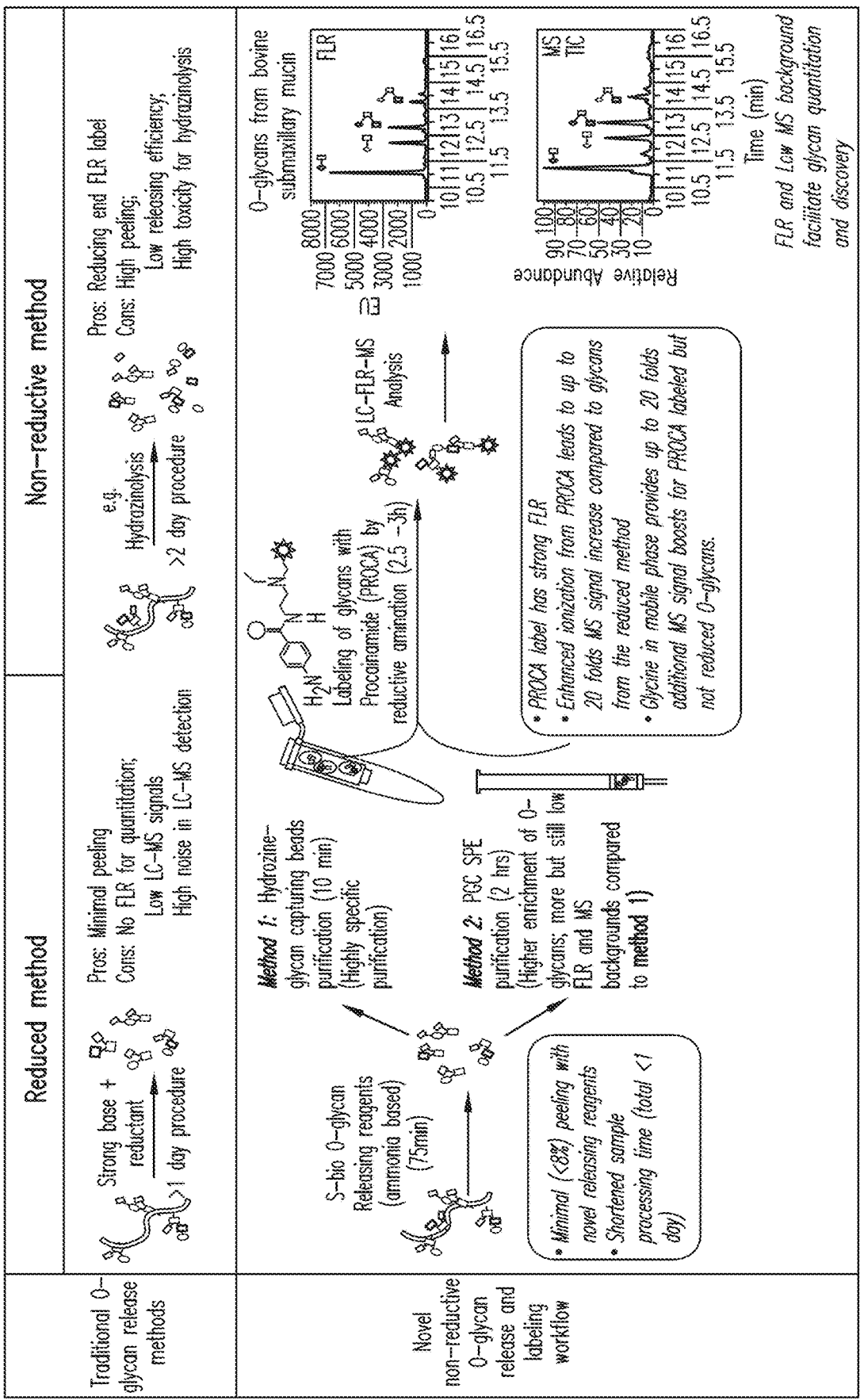

FIG. 34 shows an exemplary method for O-glycan preparation and analysis by LC-MS and FLR detection.

Figure 35:
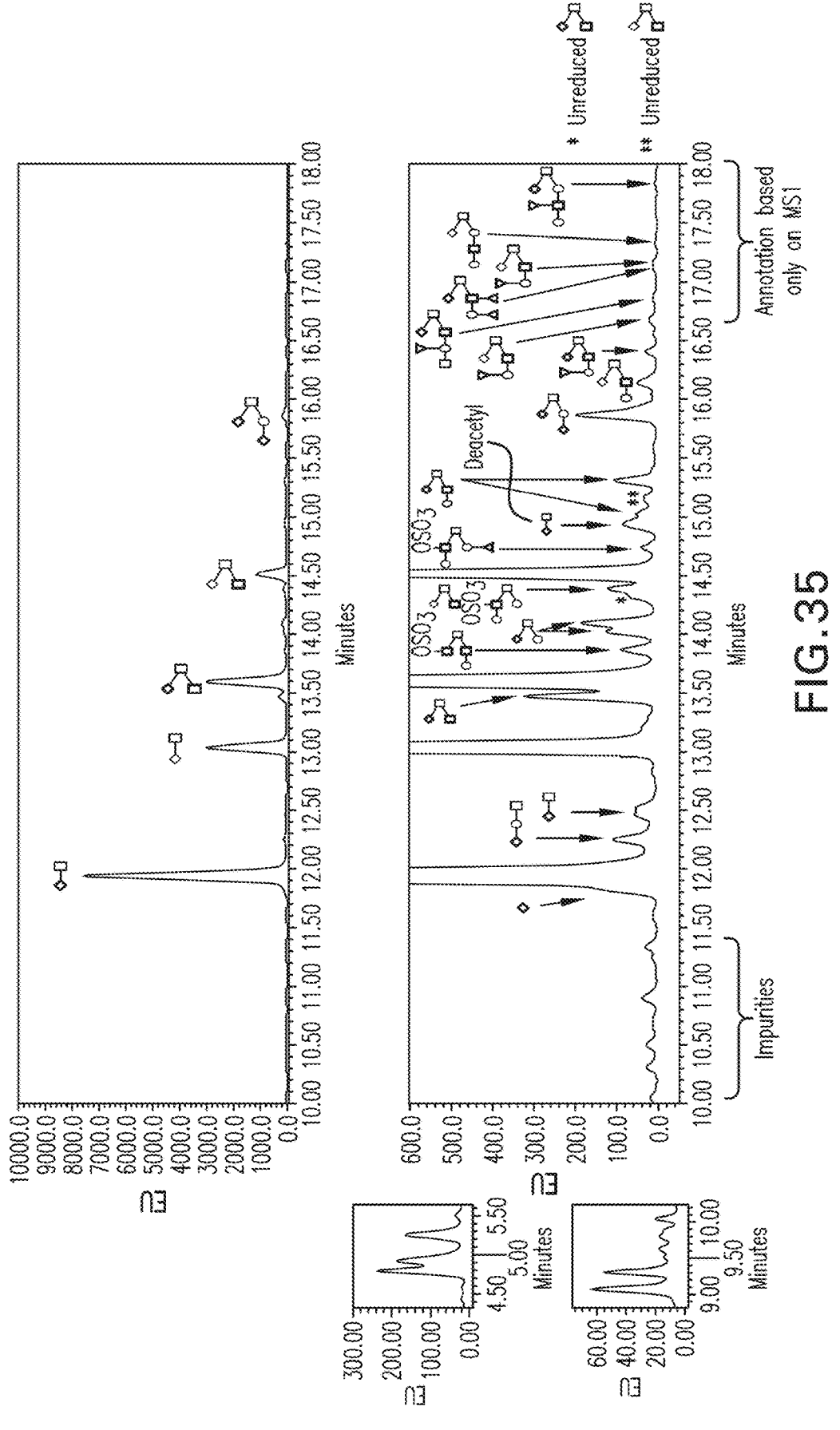

FIG. 35 shows PROCA labeled O-glycans from bovine submaxillary mucin (BSM) 2 µg on column, fluorescence and optimized reductive amination.

Figure 36:
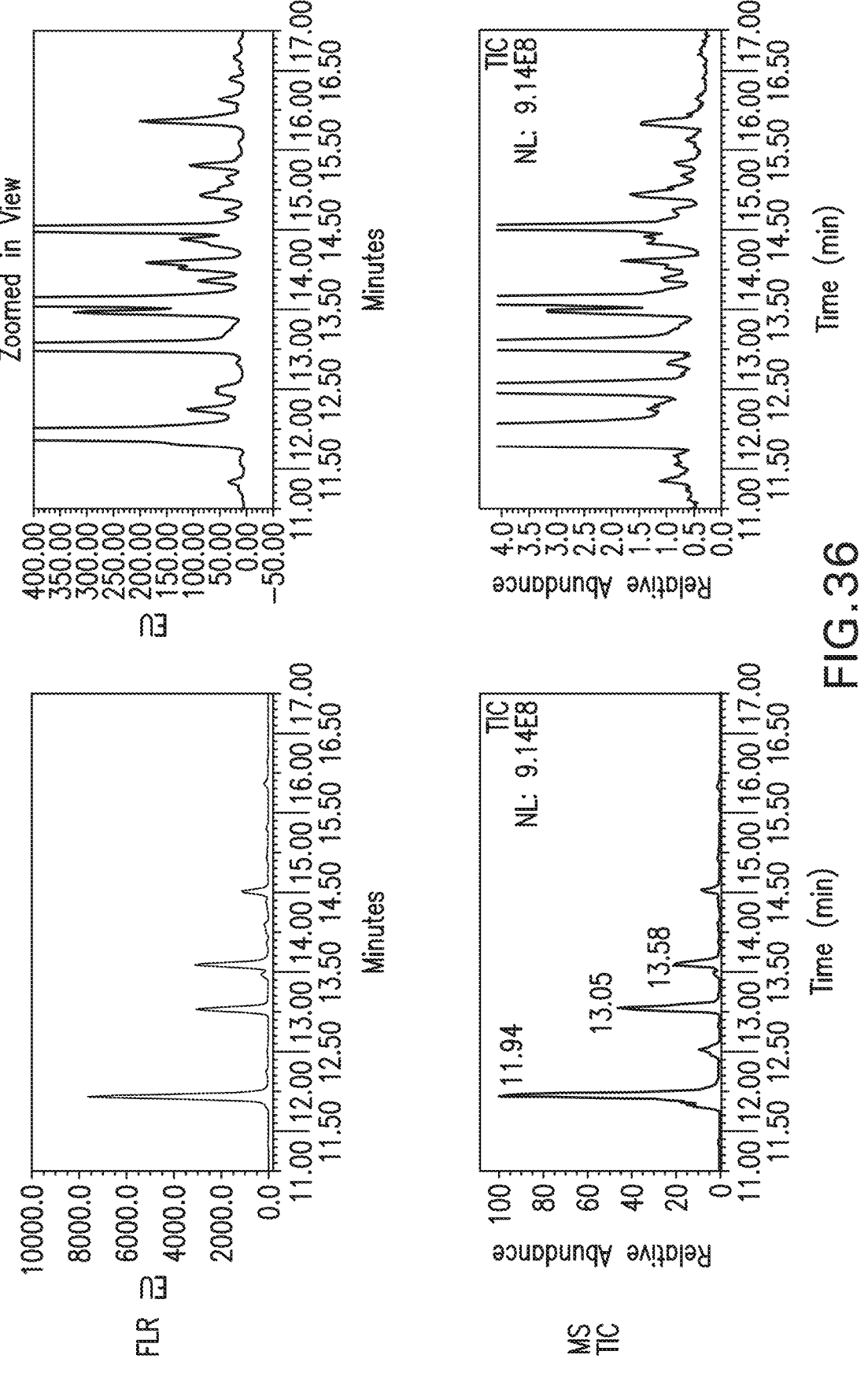

FIG. 36 demonstrates that the PROCA-labeled O-glycan FL and MS TIC profiles are highly comparable.

Figures 37A, 37B:
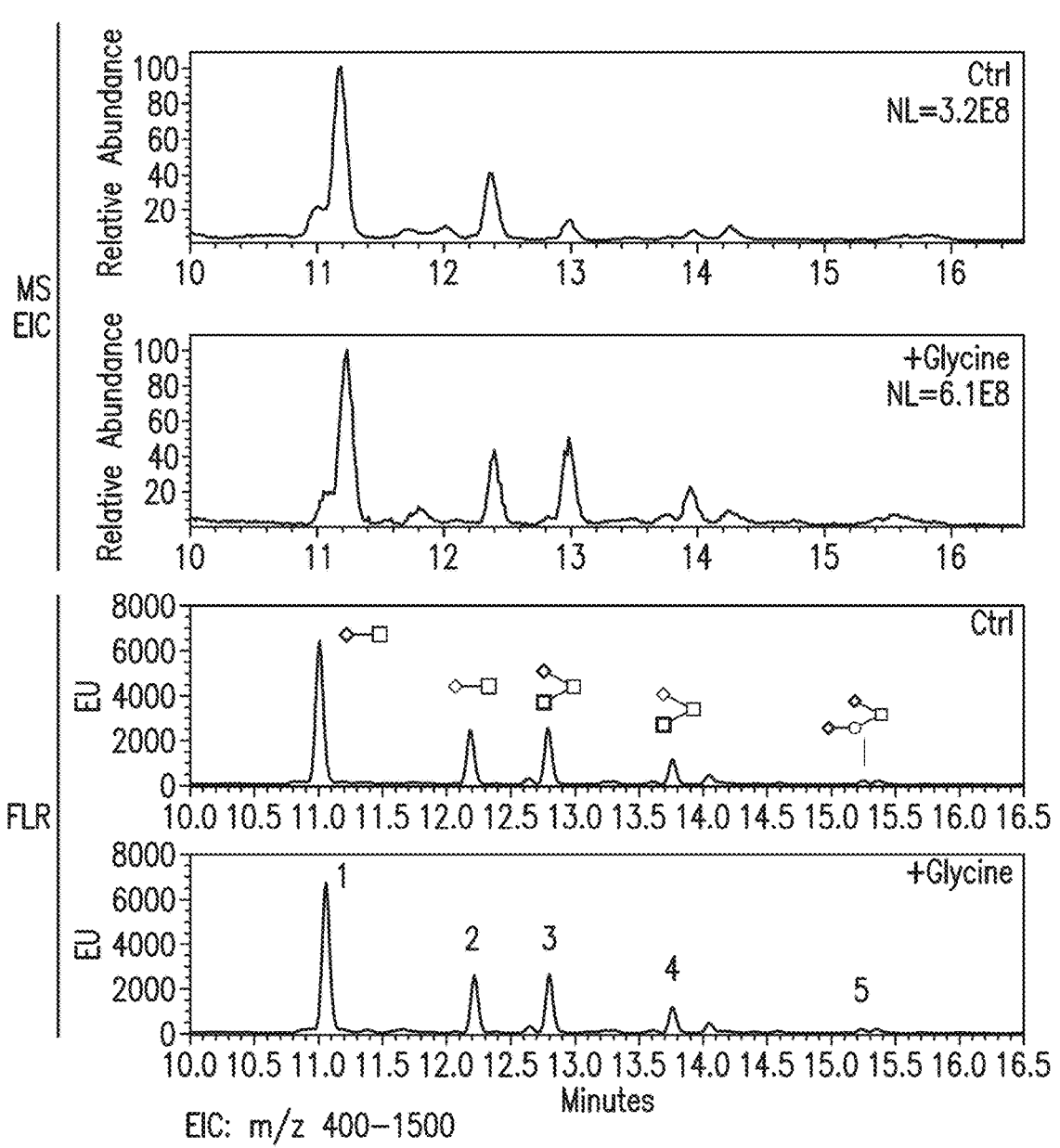

FIGS. 37A and 37B illustrate a comparison of PROCA-labeled bovine submaxillary mucin (BSM) O-glycan MS peak intensities with and without glycine in ammonium formate mobile phases. FIG. 37A shows the MS EIC and FLR chromatogram traces of PROCA labeled 0-glycans from BSM analyzed by HILIC using ammonium formate-containing mobile phases (control) and the same mobile phases with additional 1 mM glycine (Glycine). FIG. 37B shows a comparison of O-glycans FLR and MS peak intensities (normalized to those of HexNAc1NeuAc1) with and without glycine in mobile phases.

FIGS. 38A, 38B, and 38C illustrates glycine boost effects on BSM O-glycans without or with various labels. FIG. 38A shows glycine boost effect on PROCA-labeled BSM O-glycans.

FIG. 38B shows glycine boost effect on 2AB-labeled BSM O-glycans. FIG. 38C shows glycine boost effect on reduced BSM O-glycans.

FIG. 39 shows exemplary LC-FLR-MS conditions for analysis of labeled or reduced 0-glycans.

Figure 40:
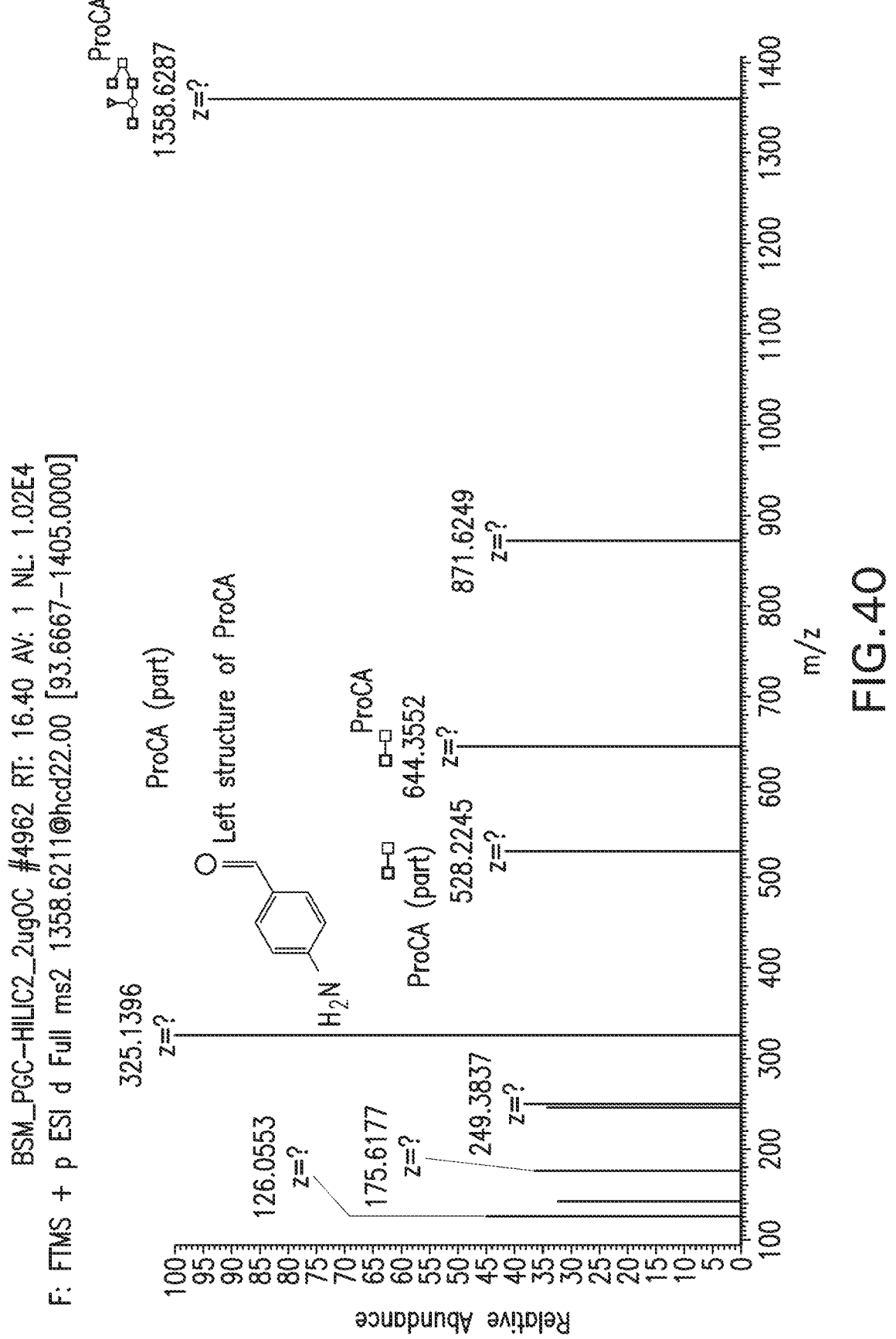
Figure 41:
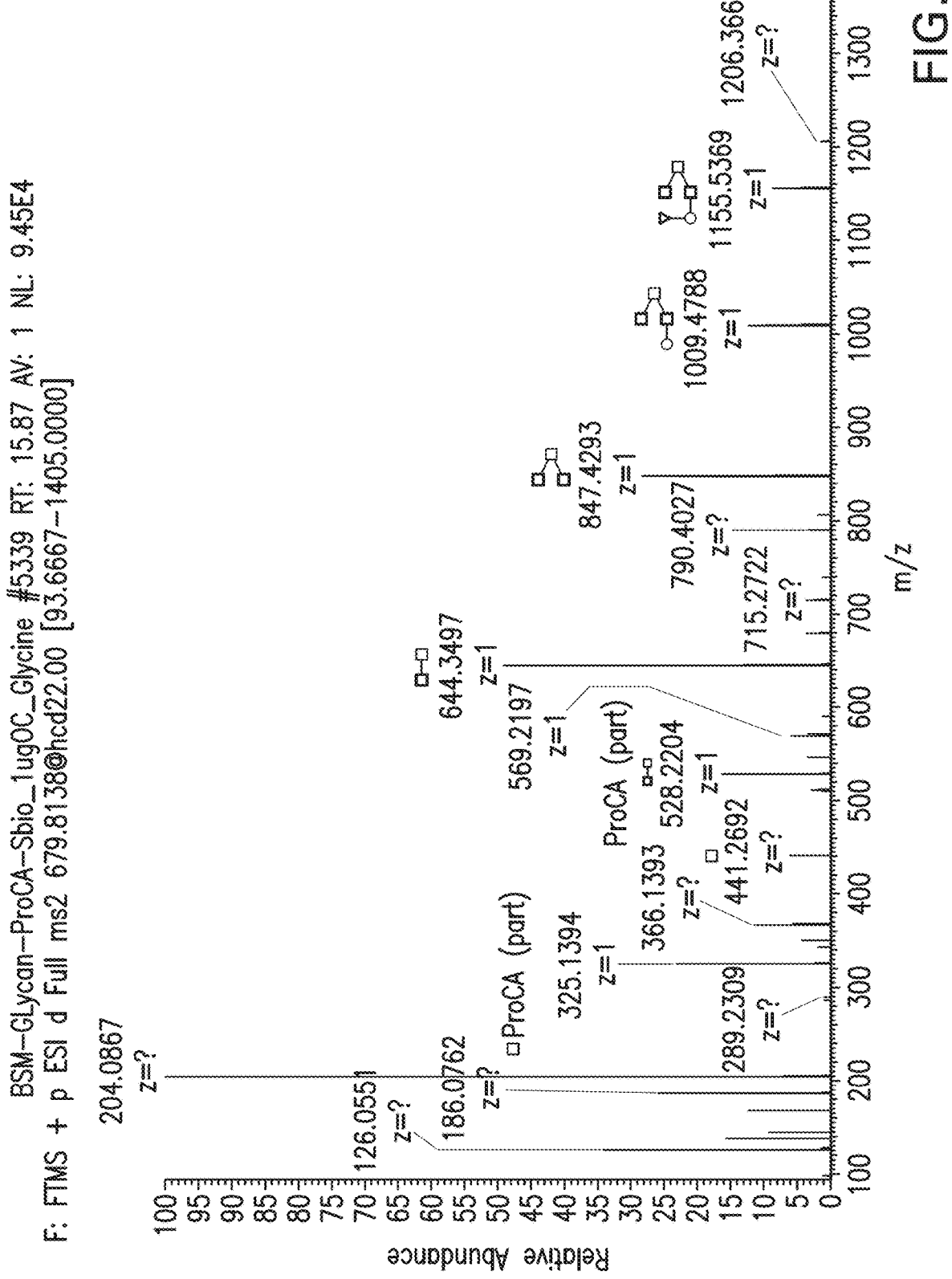

FIGS. 40 and 41 illustrate the effect of glycine on MS2 confirmation of O-glycan structure that has very low level when using beads purification.

Figure 42A:
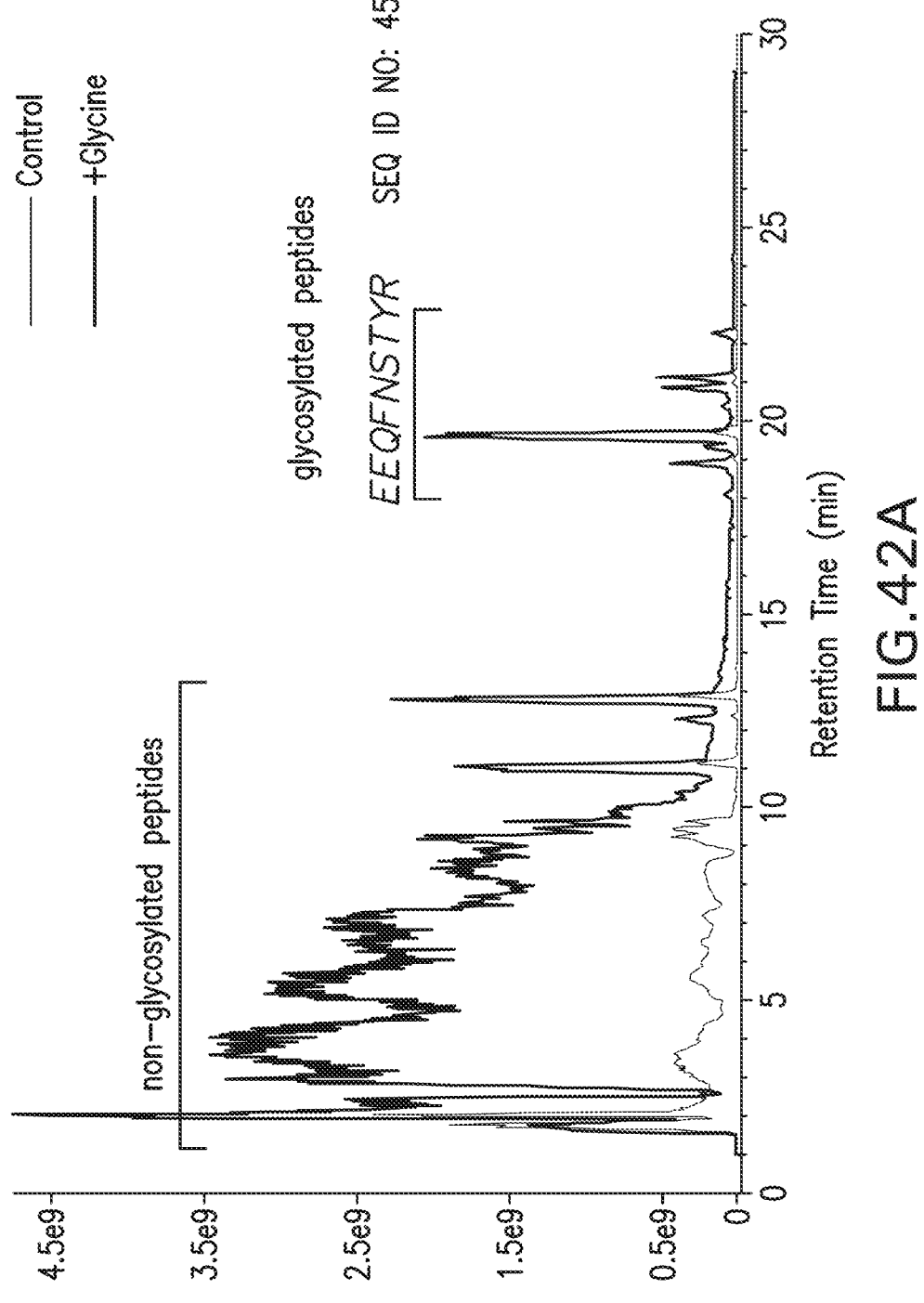

FIG. 42A shows TIC profiles of a typical IgG4 under optimized IP-HILIC condition in the presence of glycine additive and without glycine.

Figure 42B:
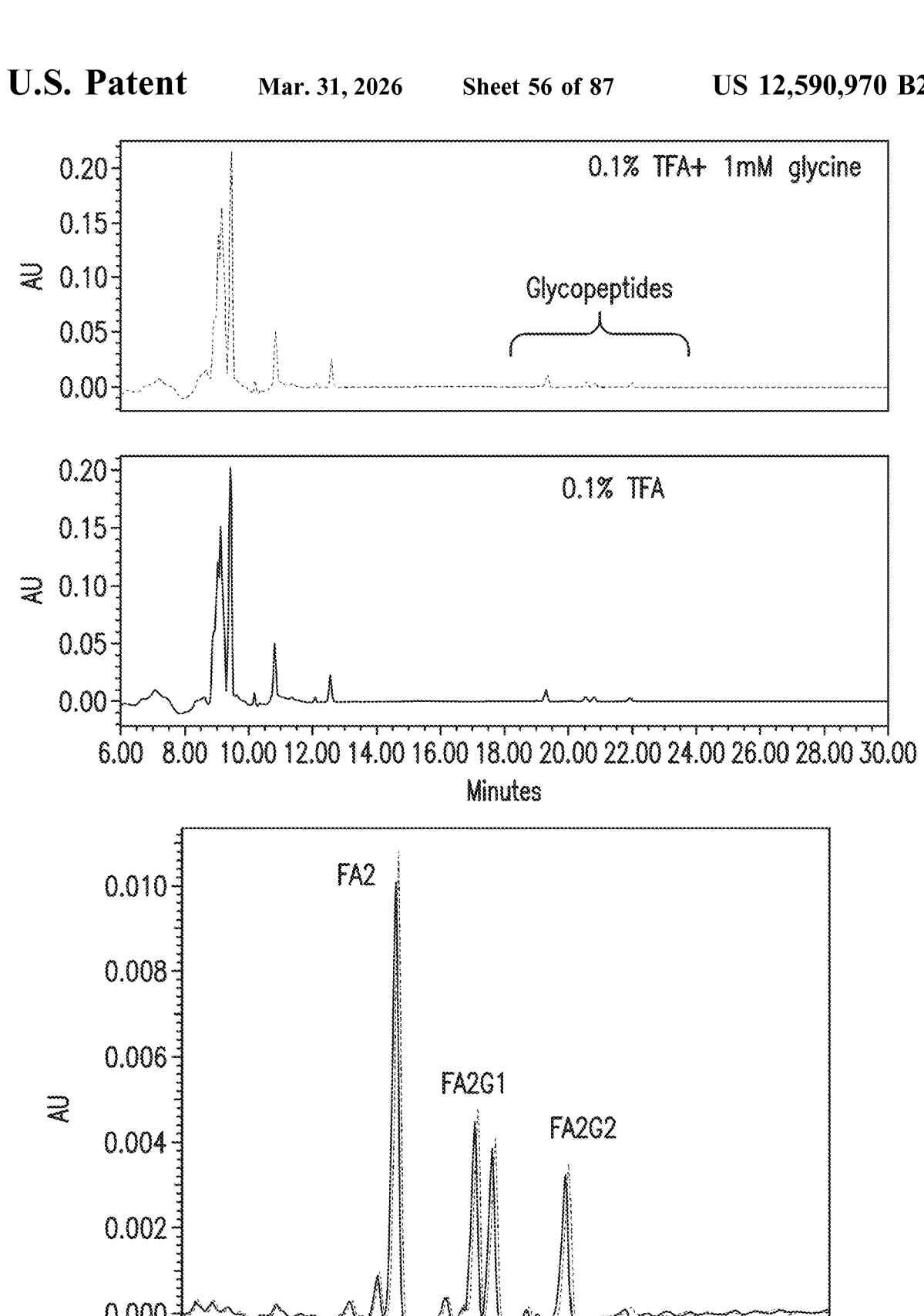

FIG. 42B shows UV chromatogram traces of mAb1 tryptic digest for IP-HILIC-MS analysis using the mobile phase containing 1 mM glycine and control conditions.

FIGS. 42C-1, 42C-2, and 42C-3 shows a comparison between the separation of isoforms (left) and multiple glycoforms (right) using different lengths of linear gradient for IP-HILIC-MS.

Figures 1, 42C:
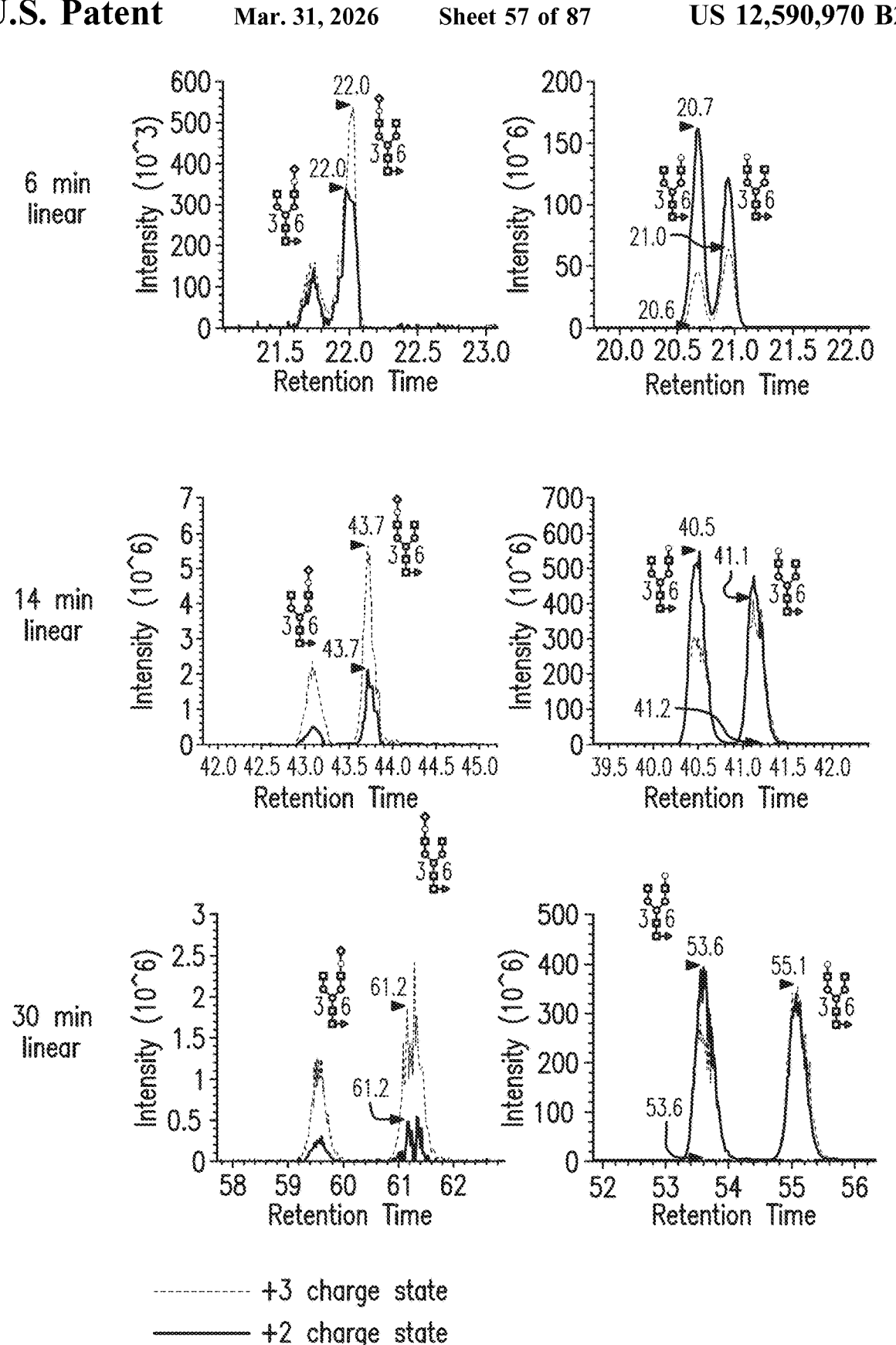
FIG. 1C shows the heavy chain (SEQ ID NO: 1) and light chain (SEQ ID NO: 2) of NISTmAb.
Figure 42D:
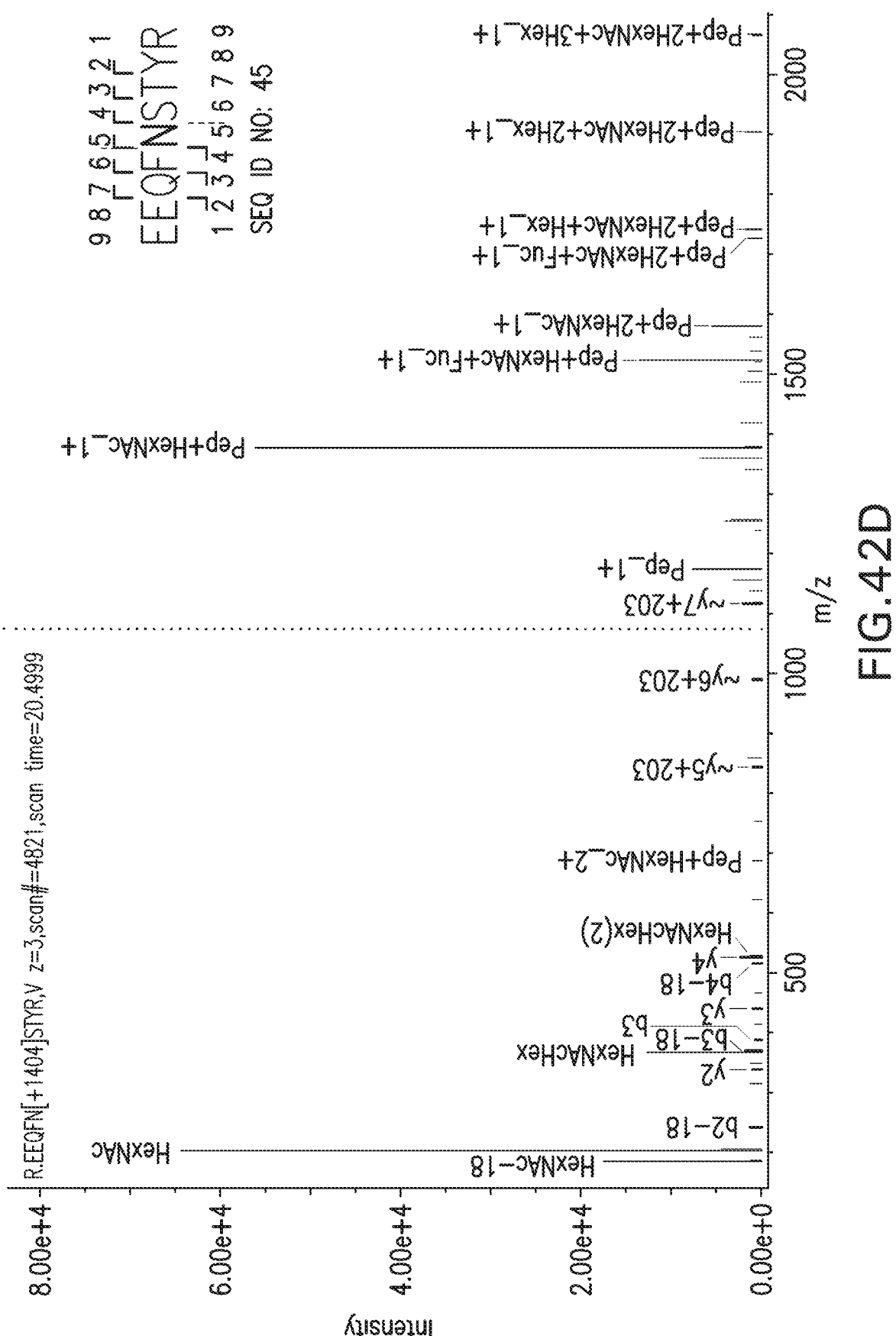
Figure 42E:
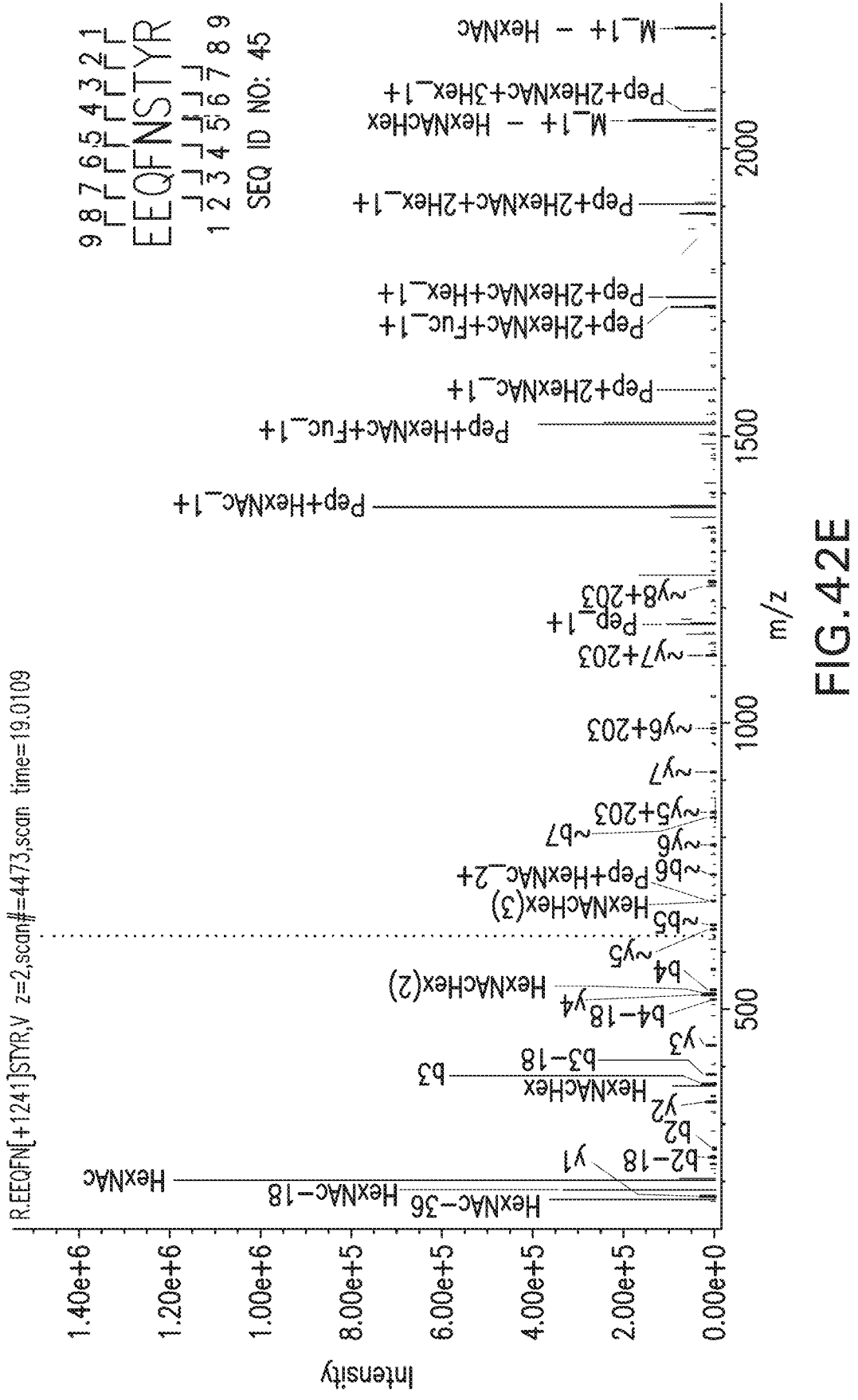

FIGS. 42D and 42E show examples of tandem mass spectra of glycopeptides from IgG4. The spectra with the highest score within all PSMs for the glycopeptides are shown.

Figure 42F:
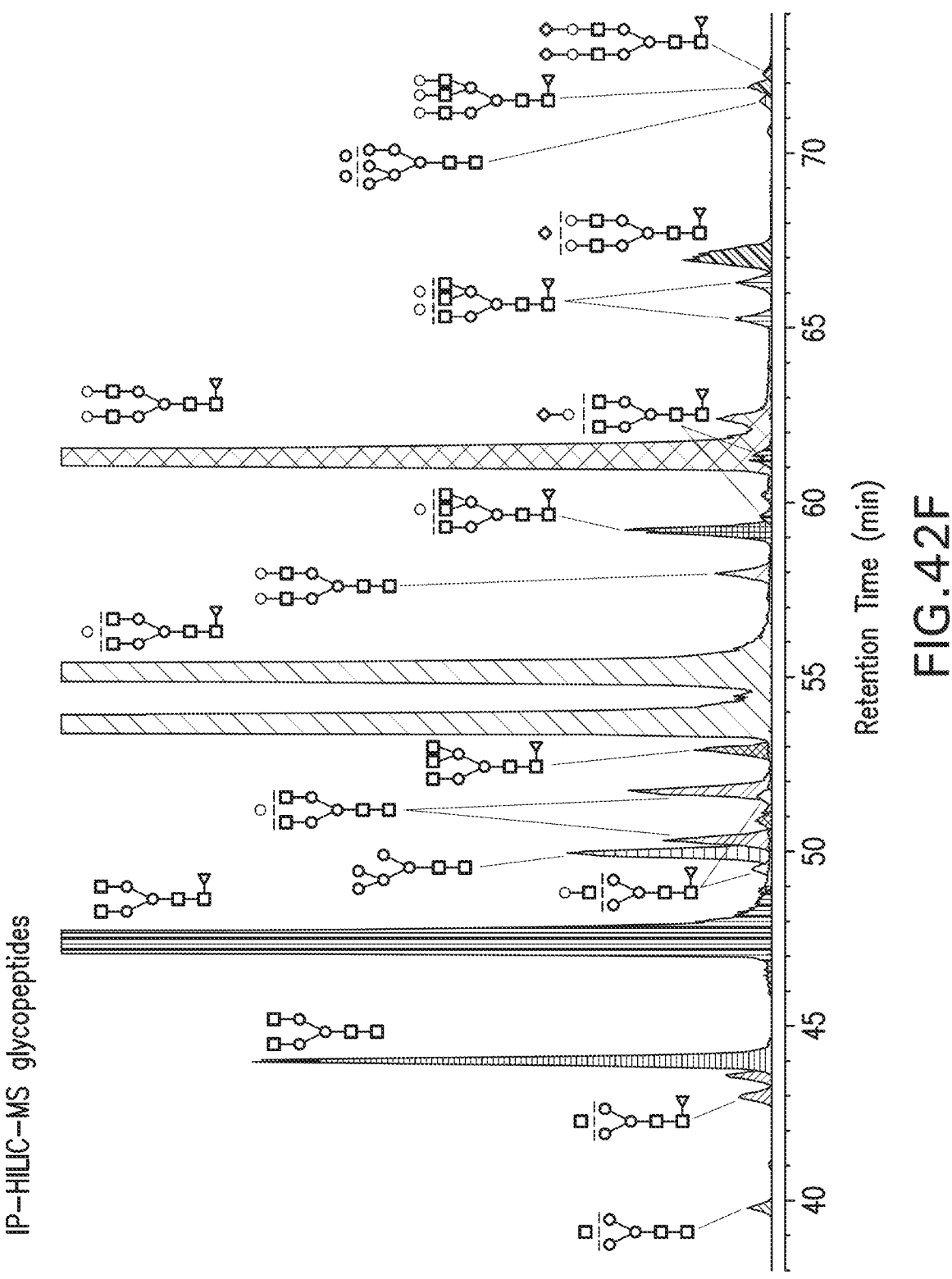

FIG. 42F shows EIC peaks of glycopeptides for mAb2 analyzed using IP-HILIC-MS. The cartons represent glycan structures using harmonized symbol nomenclature for glycans (SNFG): square, N-acetylglucosamine; triangle, fucose; circle, mannose; circle, galactose; diamond, N-acetylneuraminic acid.

Figure 42G:
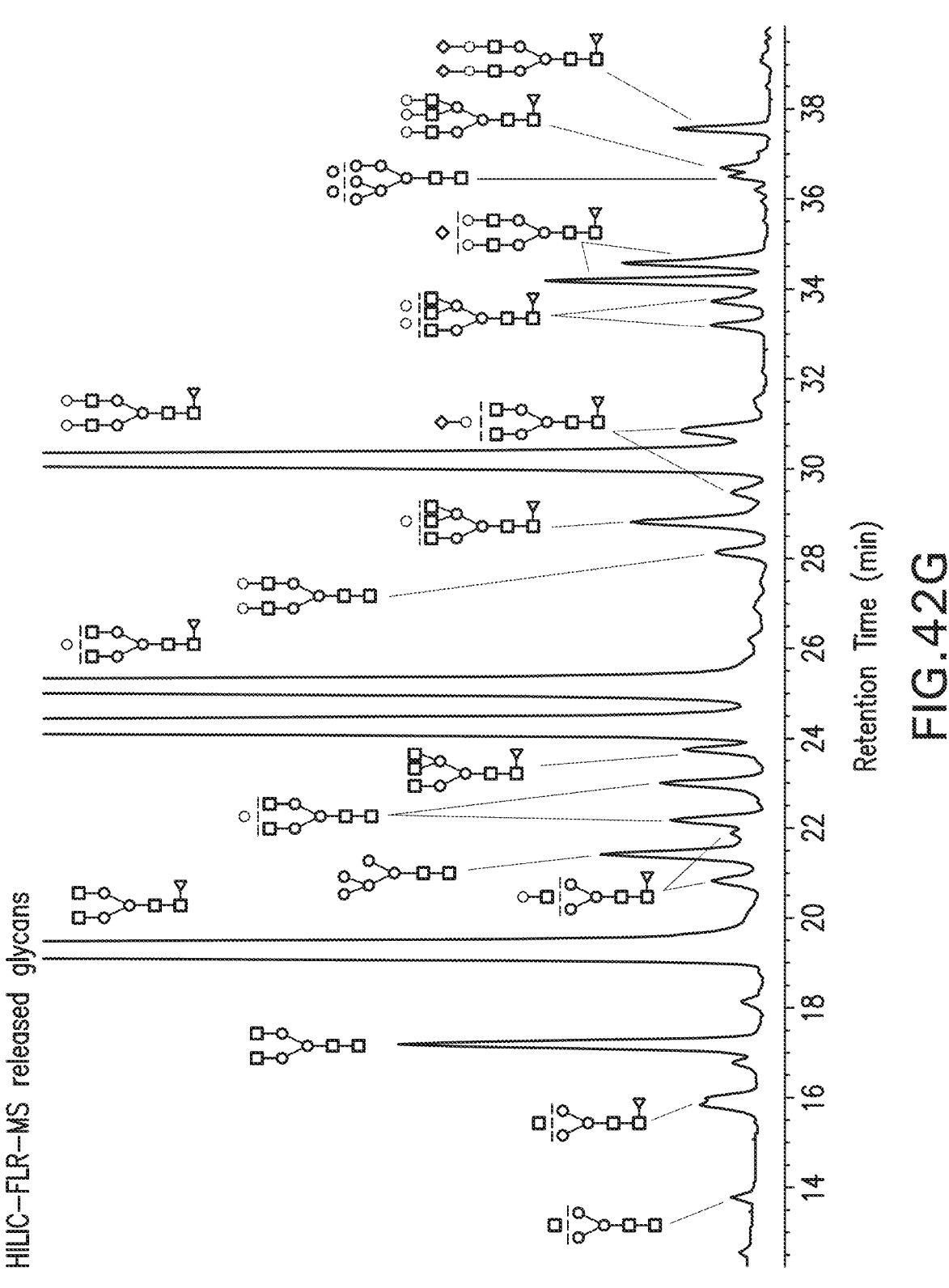

FIG. 42G shows EIC peaks of released glycans from mAb2 analyzed using HILIC-FLR-MS at pH 5.5.

Figures 1, 42H:
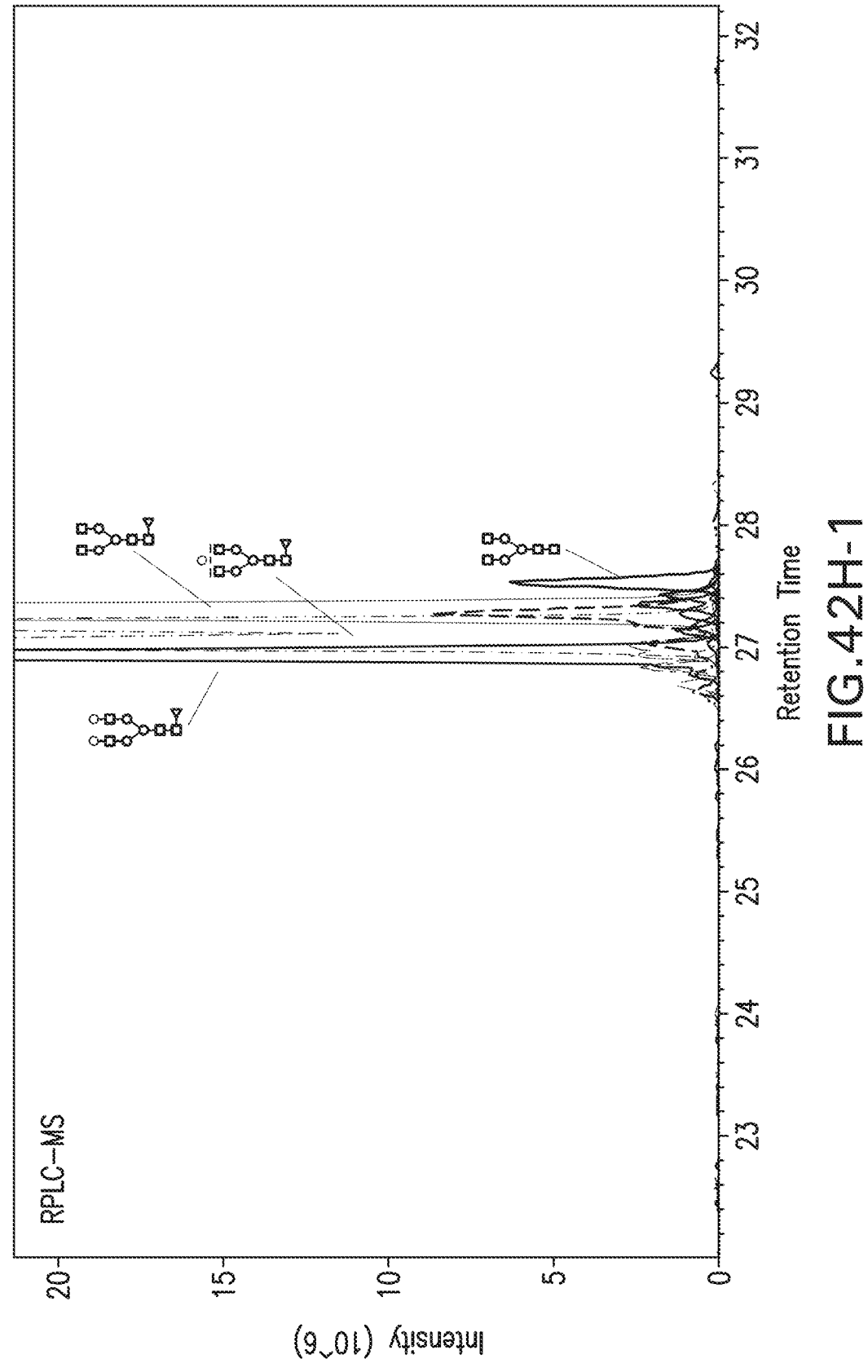
Figure 42H:
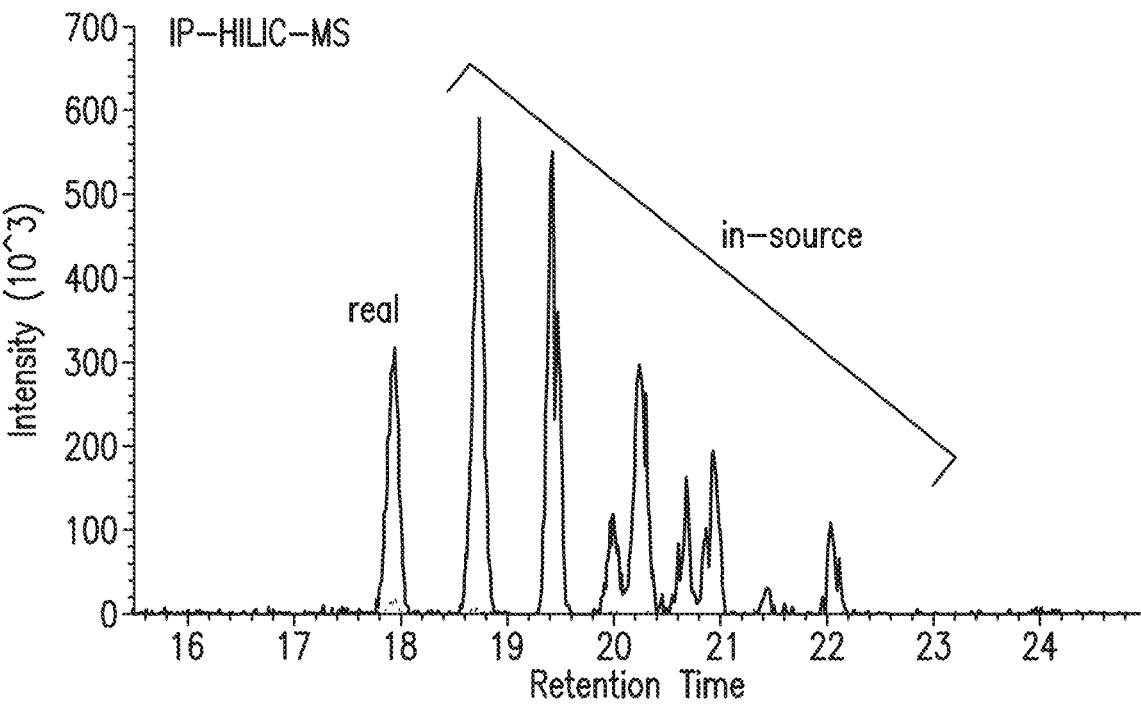
Figure 2:
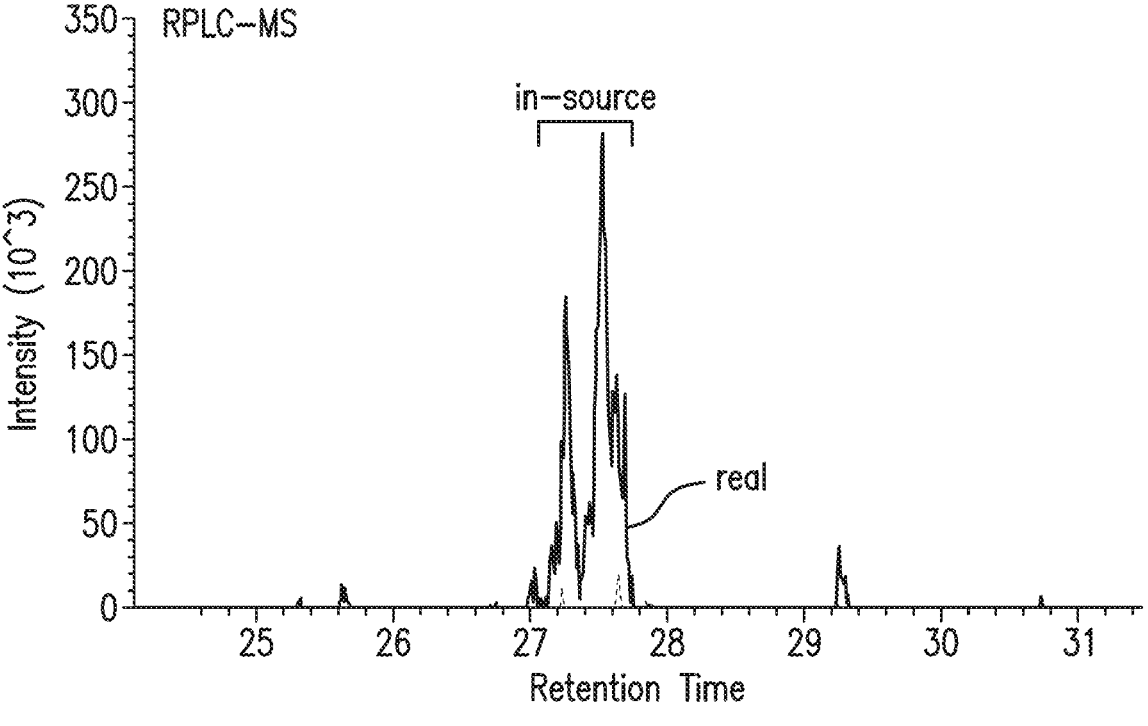
FIG. 2 provides the chemical structures for glycine derivatives.

FIGS. 42H-1 and 42H-2 shows RPLC-MS of tryptic peptides from IgG4 using 80 min gradient. All glycoforms elute in a single cluster (right panel); and an efficient glycoform separation in IP-HILIC-MS excludes the artificial glycoforms generated from the in-source fragmentation (left panel).

Figure 43A:
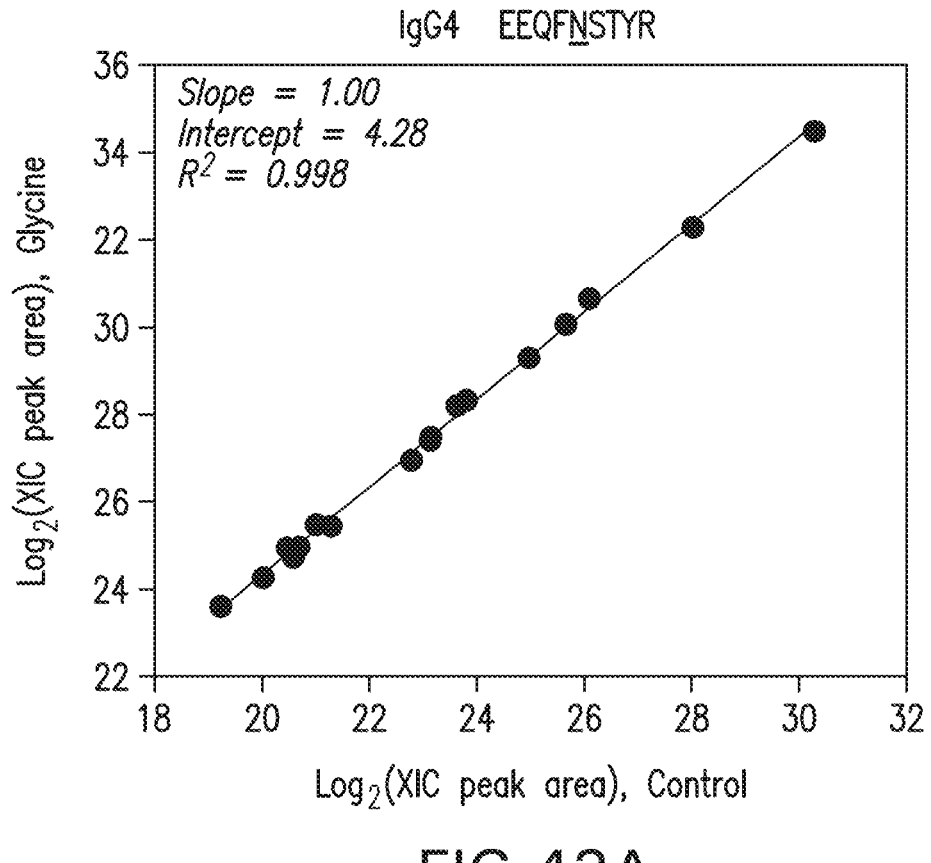
Figure 43B:
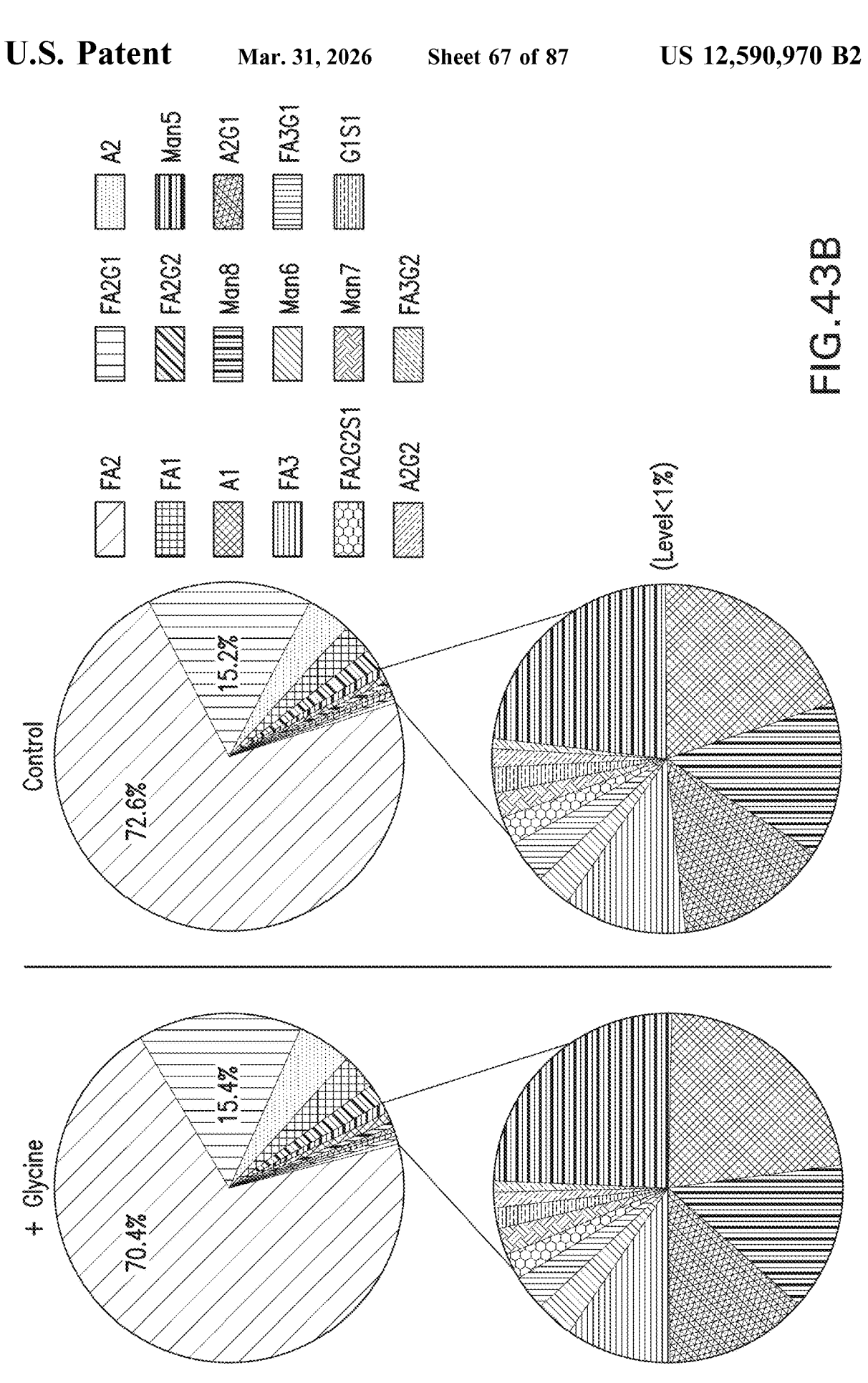
Figures 2, 43D:
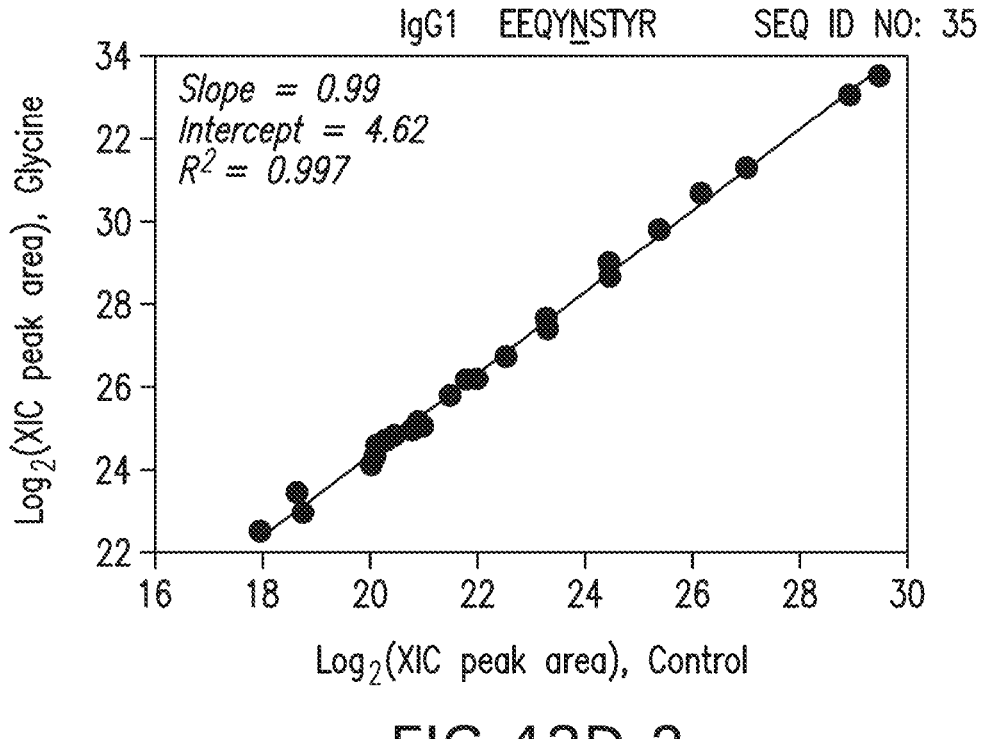
Figures 3, 43D:
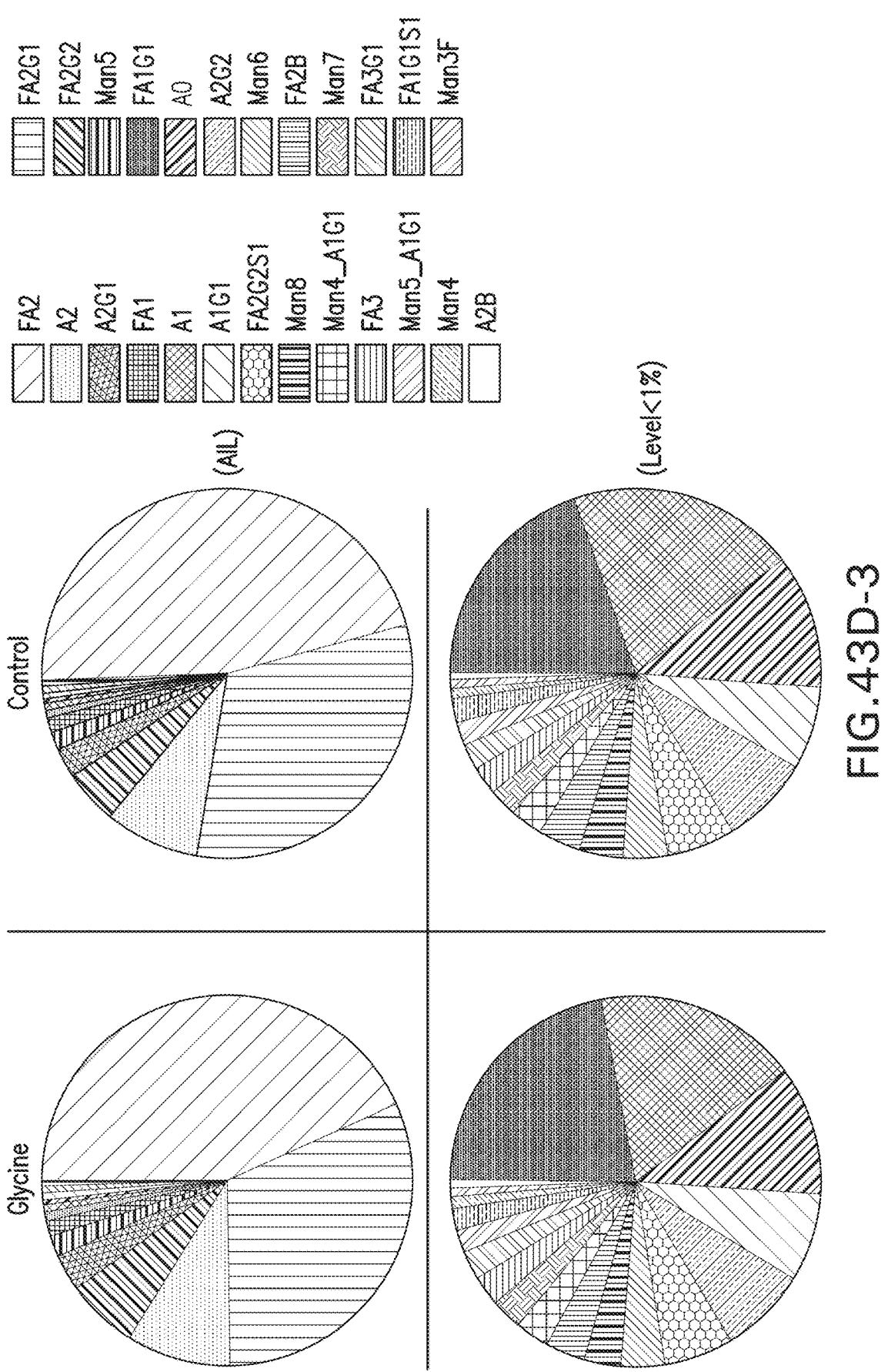

FIGS. 43A and 43B show all glycoforms of mAb1 at the Fc glycosylation site N297 quantified based on IP-HILIC-MS runs with and without glycine, shown as FIG. 35A absolute EIC peak areas and FIG. 35B relative abundance for each individual glycan.

FIG. 43C shows a table of measured EIC peak area and relative quantitation for individual glycoforms from mAb1 (IgG4).

FIGS. 43D-1, 43D-2, and 43D-3 shows glycopeptide analysis for mAb5 (IgG1)-TIC chromatogram; Elution profile of the most abundant 10 glycoforms analyzed using IP-HILIC-MS; Elution profile of the most abundant 10 glycoforms analyzed using RPLC-MS; Glycine-assisted ESI signal boosting for each individual glycoforms; and Relative percentage of each identified glycoform.

FIG. 43E shows a table of measured EIC peak area and relative quantitation for individual glycoforms from mAb5 (IgG1). *The fold change is dramatically increased when the peak areas of glycoforms in control sample are low due to poor detection.

Figure 43F:
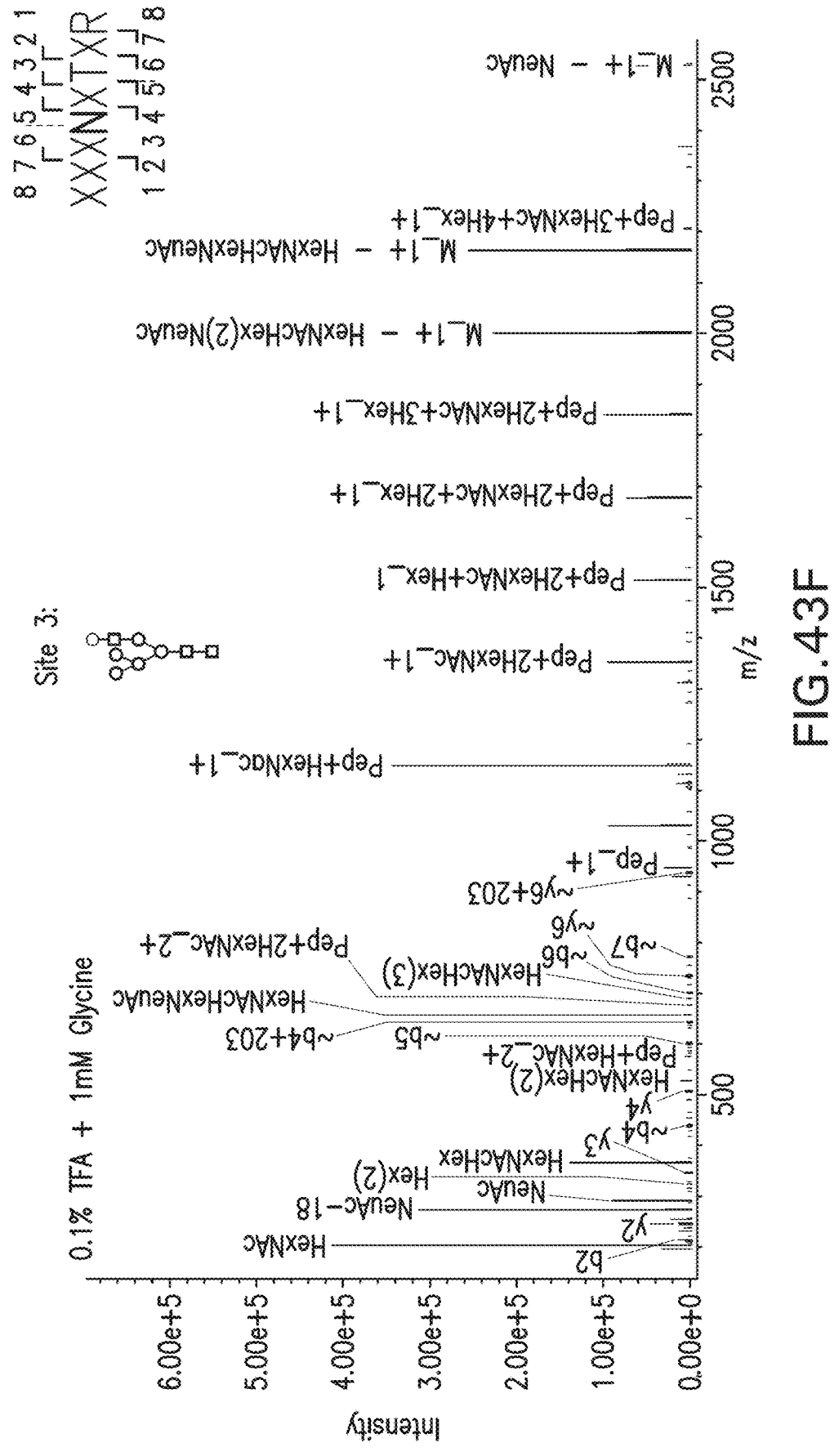
Figure 43G:
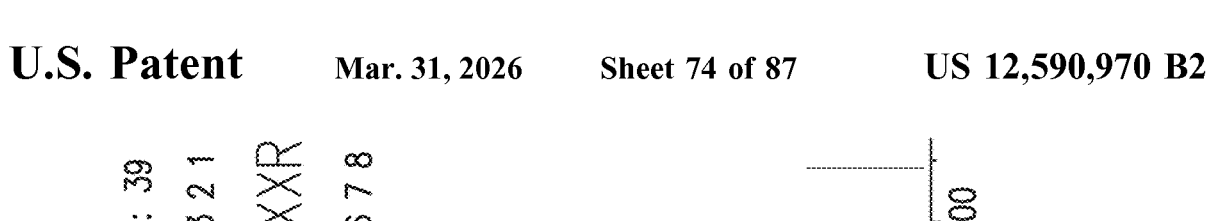

FIGS. 43F and 43G show examples of tandem mass spectra from tryptic peptides from fP1 analyzed by IP-HILIC-MS using the mobile phases containing 0.1% TFA (FIG. 35G) or 0.1% TFA+1 mM glycine as signal booster (FIG. 35F). Both spectra have the highest score ranked within all PSMs for this glycopeptide.

Figure 44A:
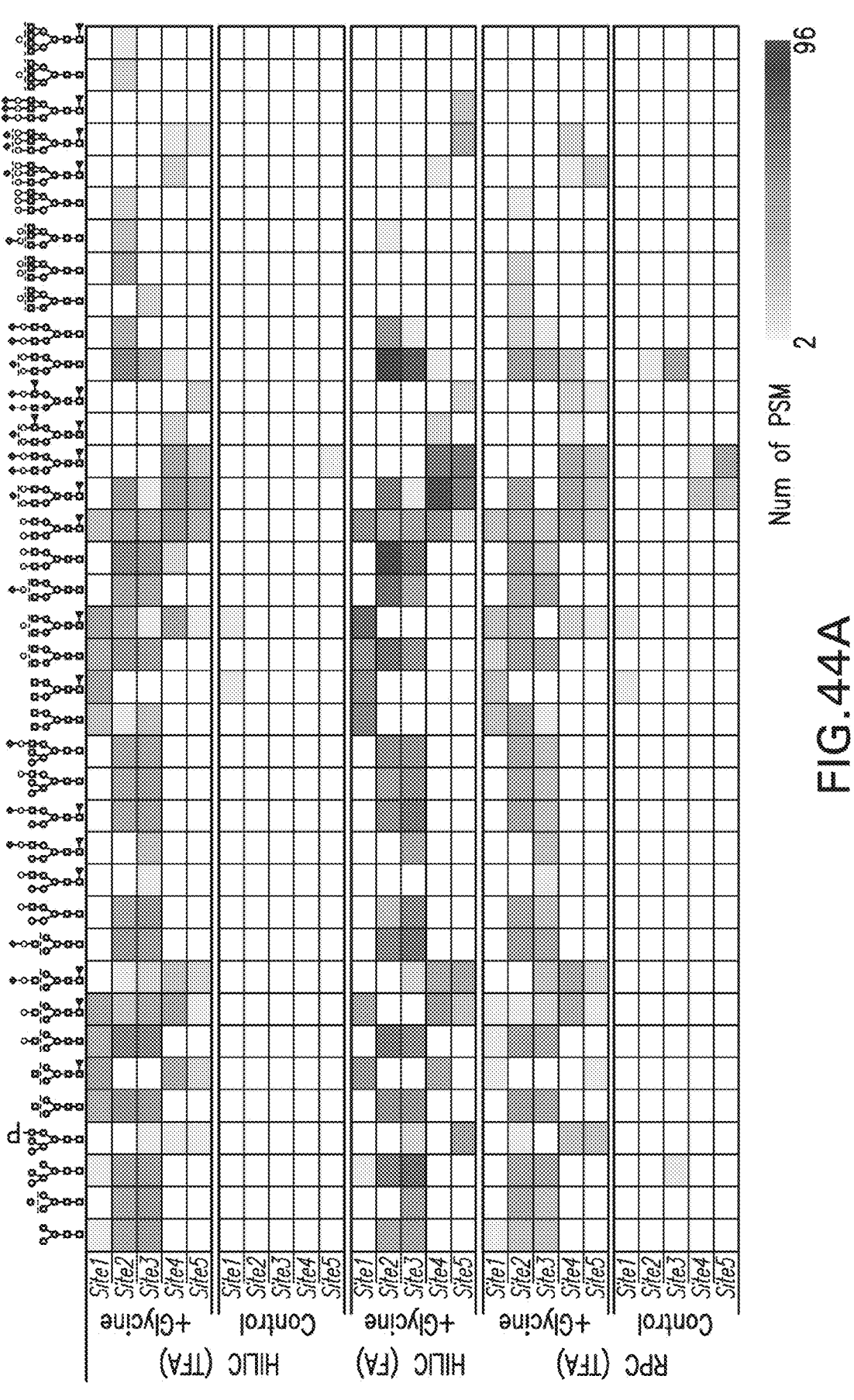
Figure 44B:
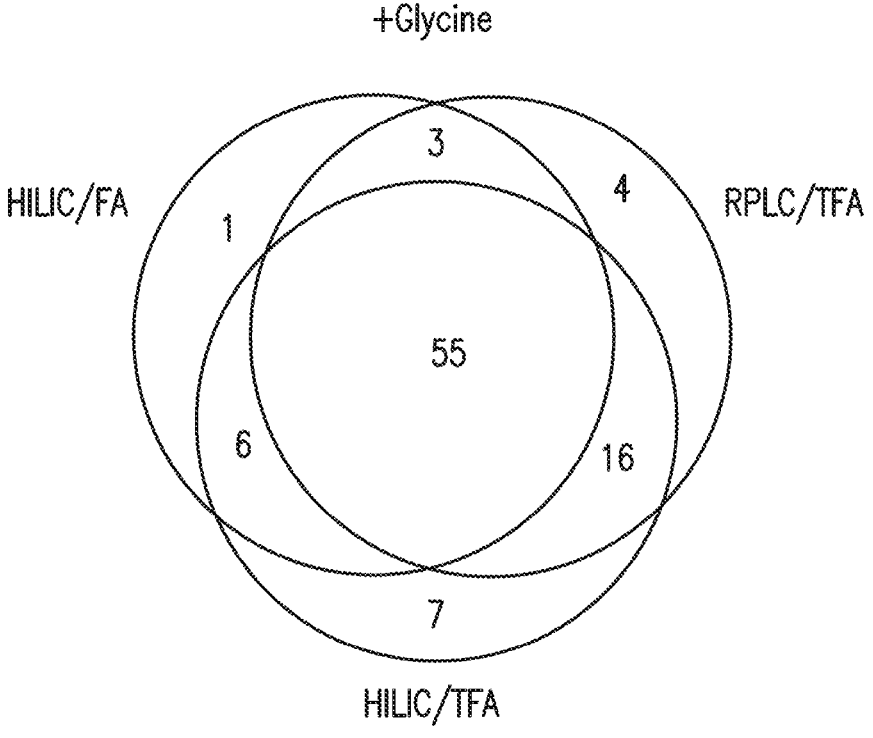

FIGS. 44A and 44B show comparison of glycopeptide identification for Fc-domain fusion protein fP1 among different separation methods, IP-HILIC with TFA, HILIC with FA and RPLC with TFA. 1 mM of glycine is applied for all experiments to eliminate the impact of ion suppression during MS detection. FIG. 36A shows complete site-specific glycosylation maps. FIG. 36B shows summarized numbers of identified glycopeptides in different methods.

Figure 44C:
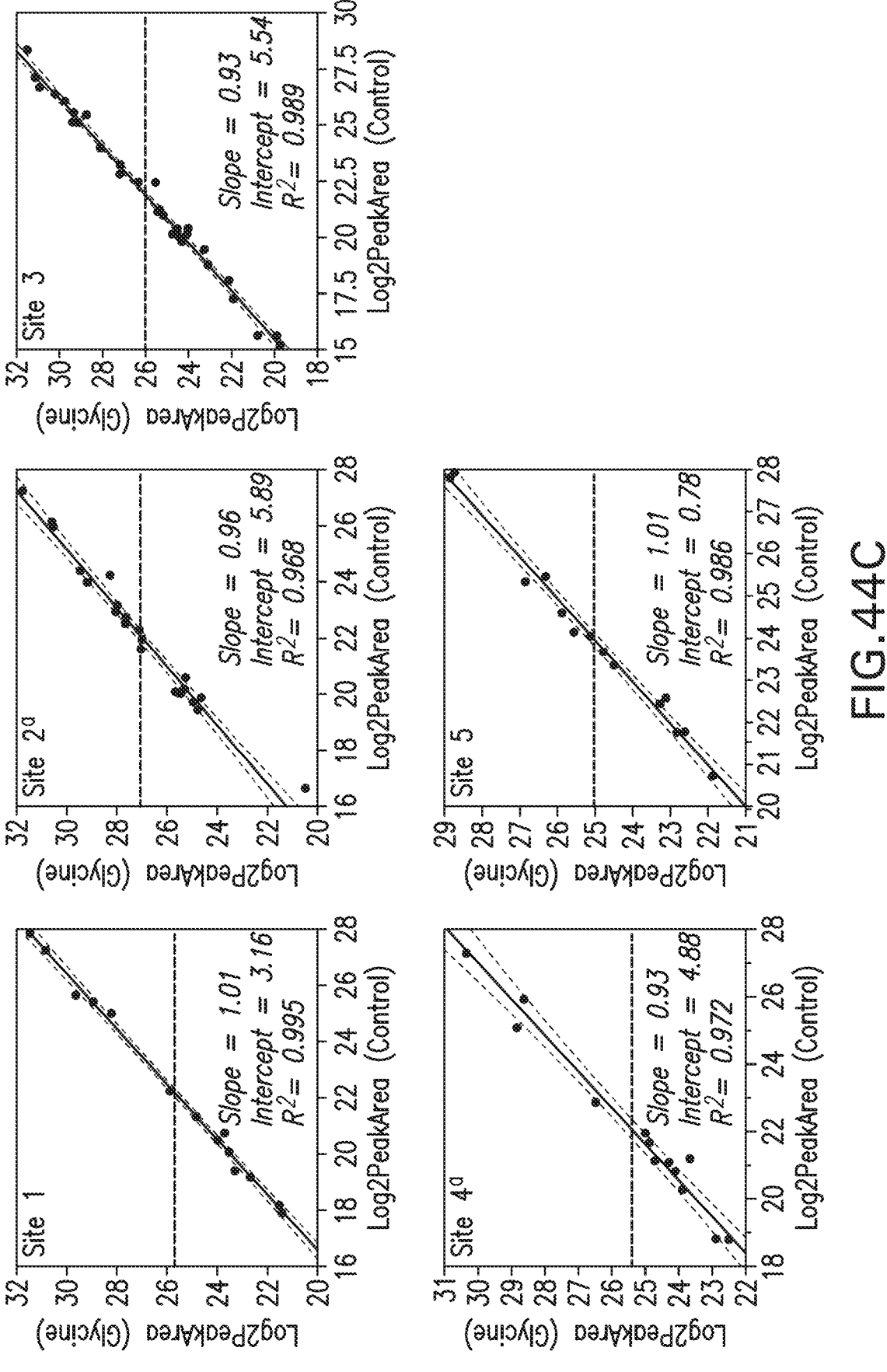

FIG. 44C shows glycine-based signal fold changes for different glycosite containing peptides.

FIG. 44D shows Oxonium ion extraction (yellow trace) and TIC (other traces) profiles of digested fP1 analyzed by IP-HILIC-MS with TFA (top panel), HILIC-MS with FA (middle panel) and RPLC-MS with TFA (bottom panel).

Figure 45A:
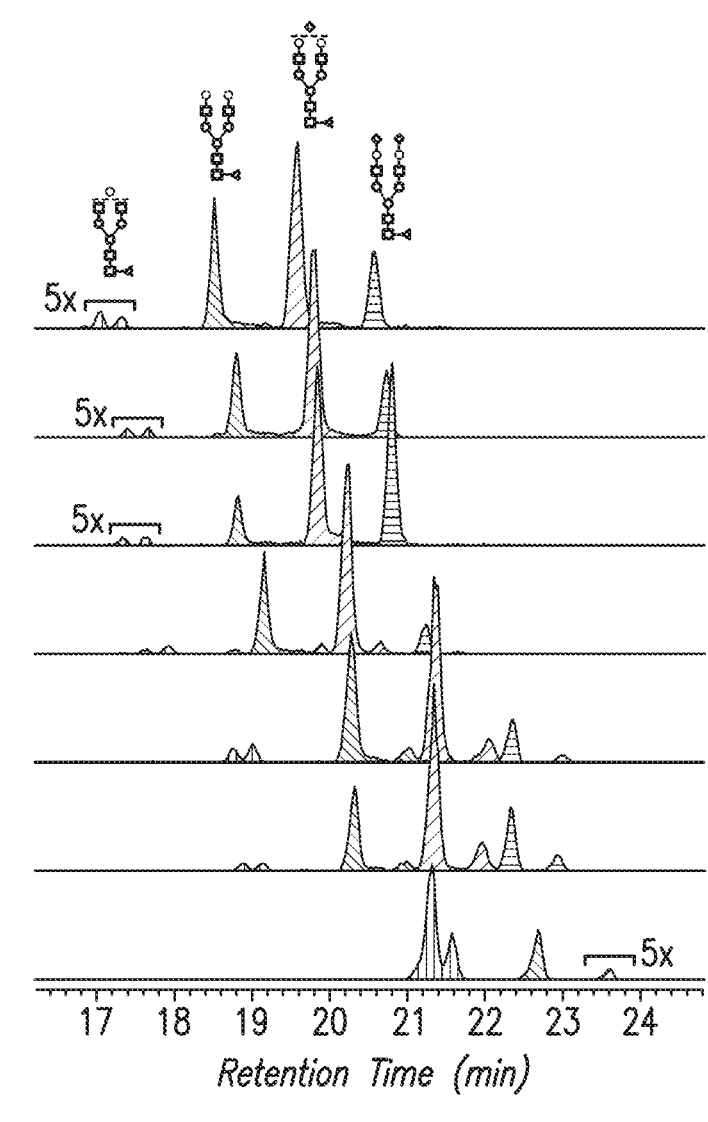

FIG. 45A shows EIC peaks of four representative glycoforms in 7 glycosite-containing peptides from fP1. The color on the peptide sequence indicates amino acids potentially contributing to the hydrophilicity, shown as polar residues containing hydroxyl, amide or primary amine group (orange) and strong polar residues containing guanidino group (red), and glycosylated asparagine (blue).

Figure 45B:
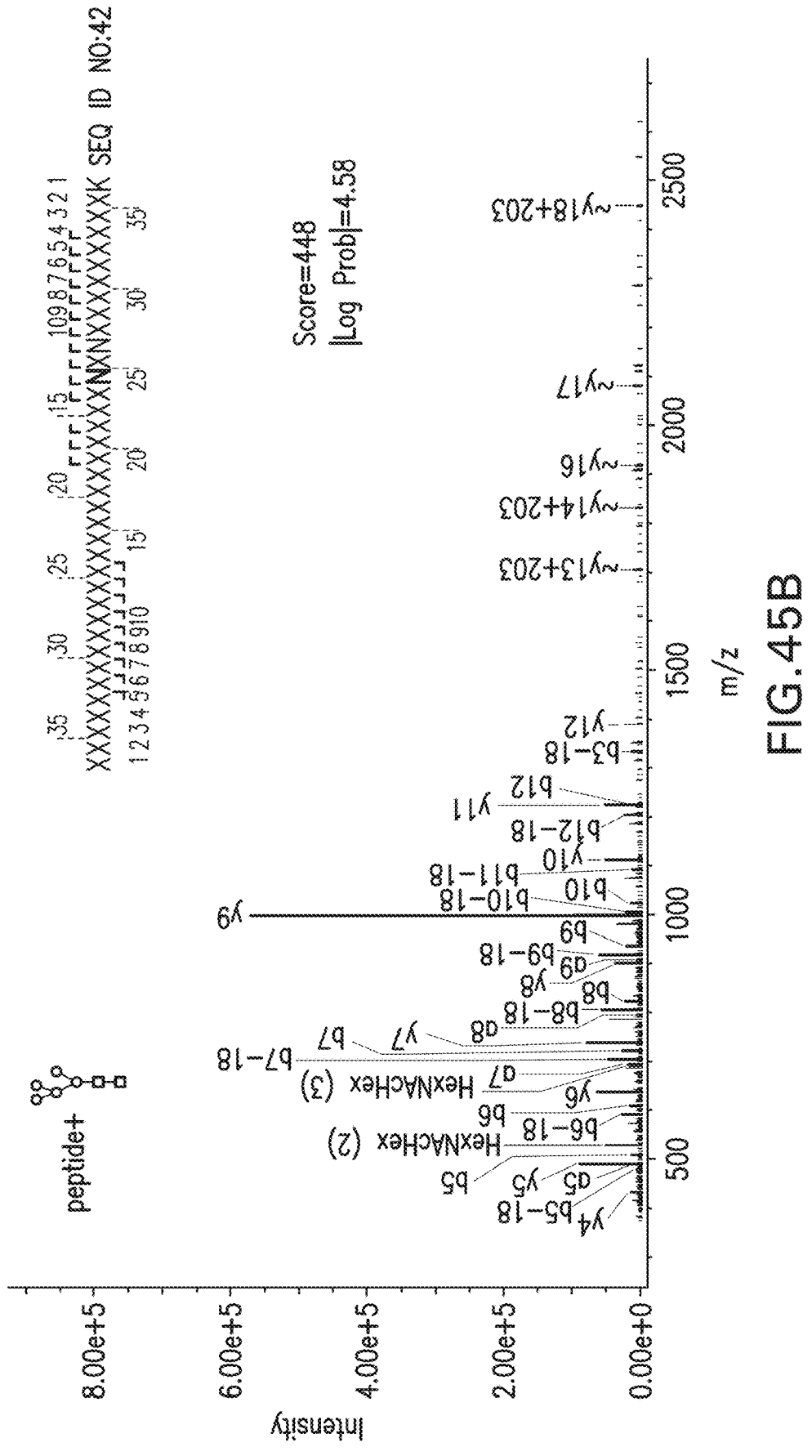
Figure 45C:
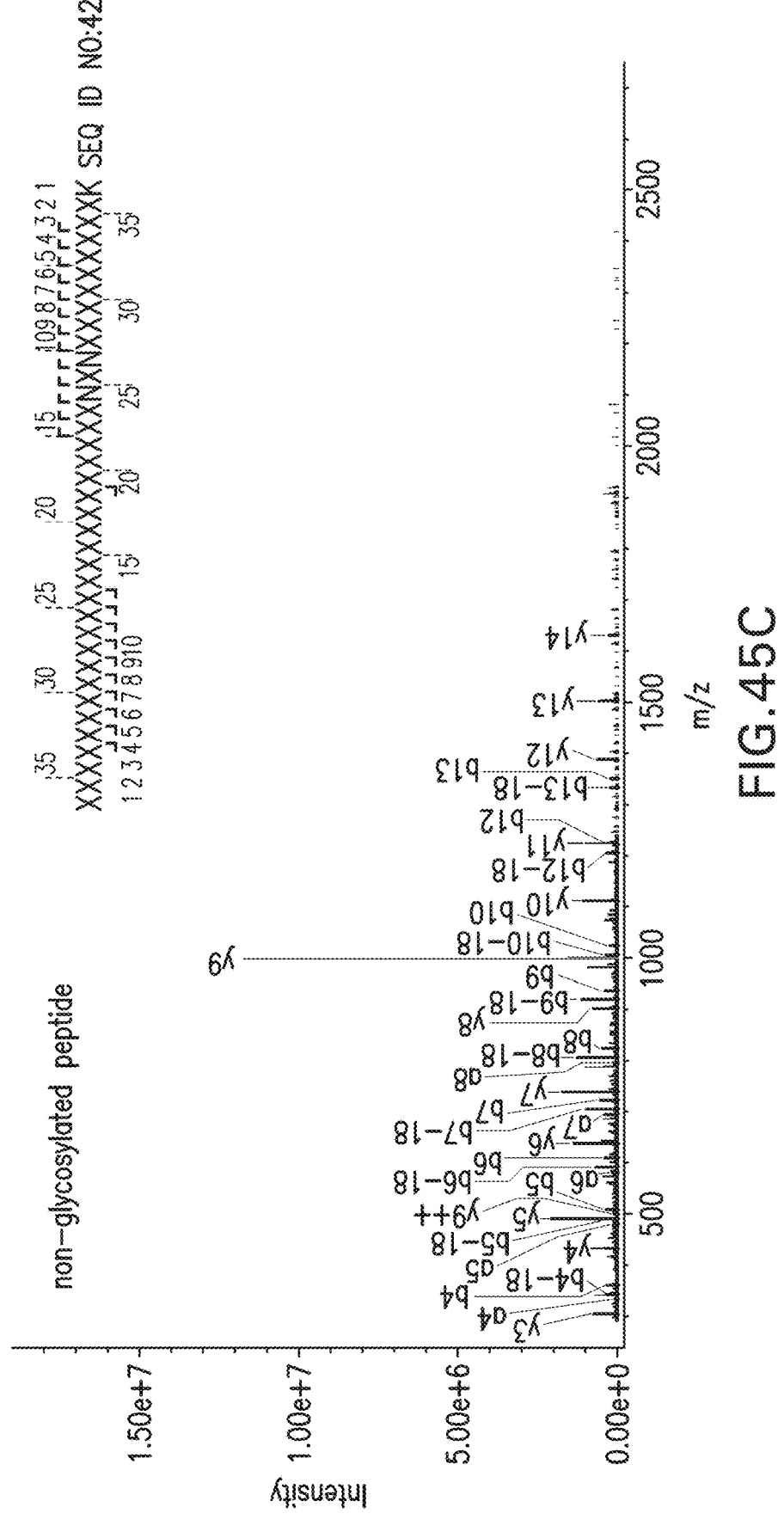

FIGS. 45B and 45C show tandem mass spectra of glycopeptide at the non-canonical N-glycosylation site and the unoccupied peptide identified in mAb3.

Figure 45D:
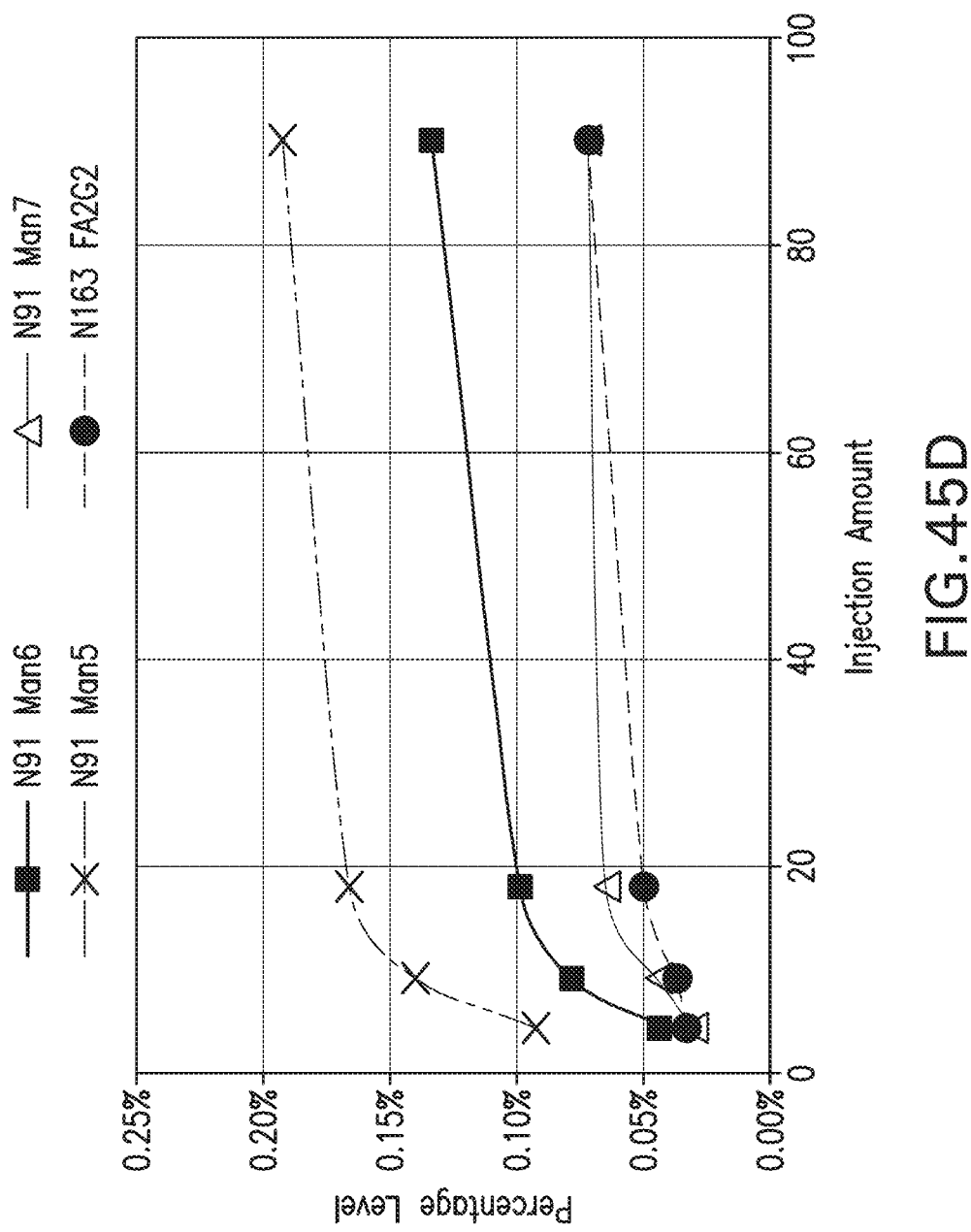

FIG. 45D shows the relative percentage of low abundance N-glycosylation at non-canonical site of mAb3 analyzed using IP-HILIC-MS.

Figure 45E:
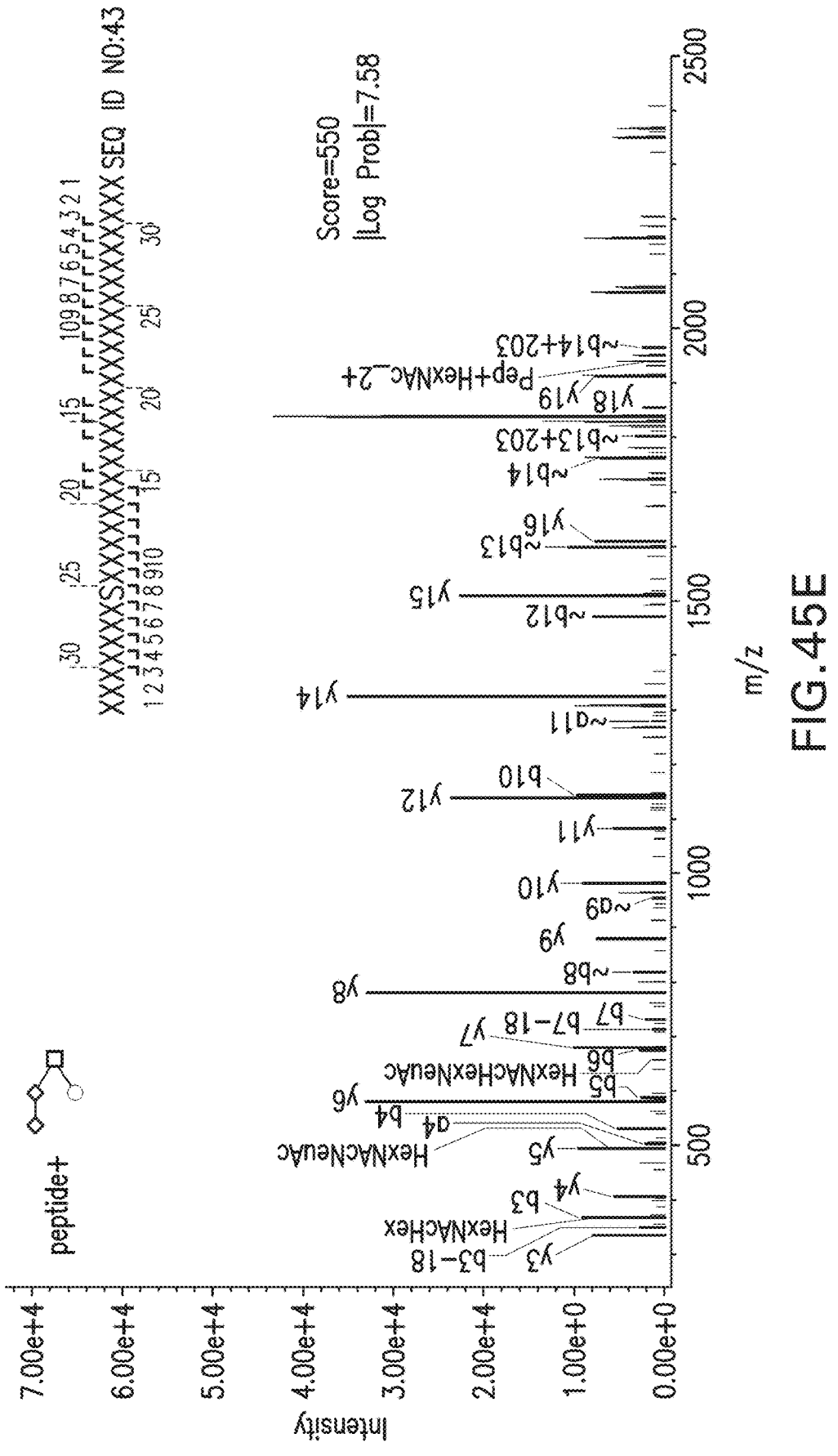
Figure 45F:
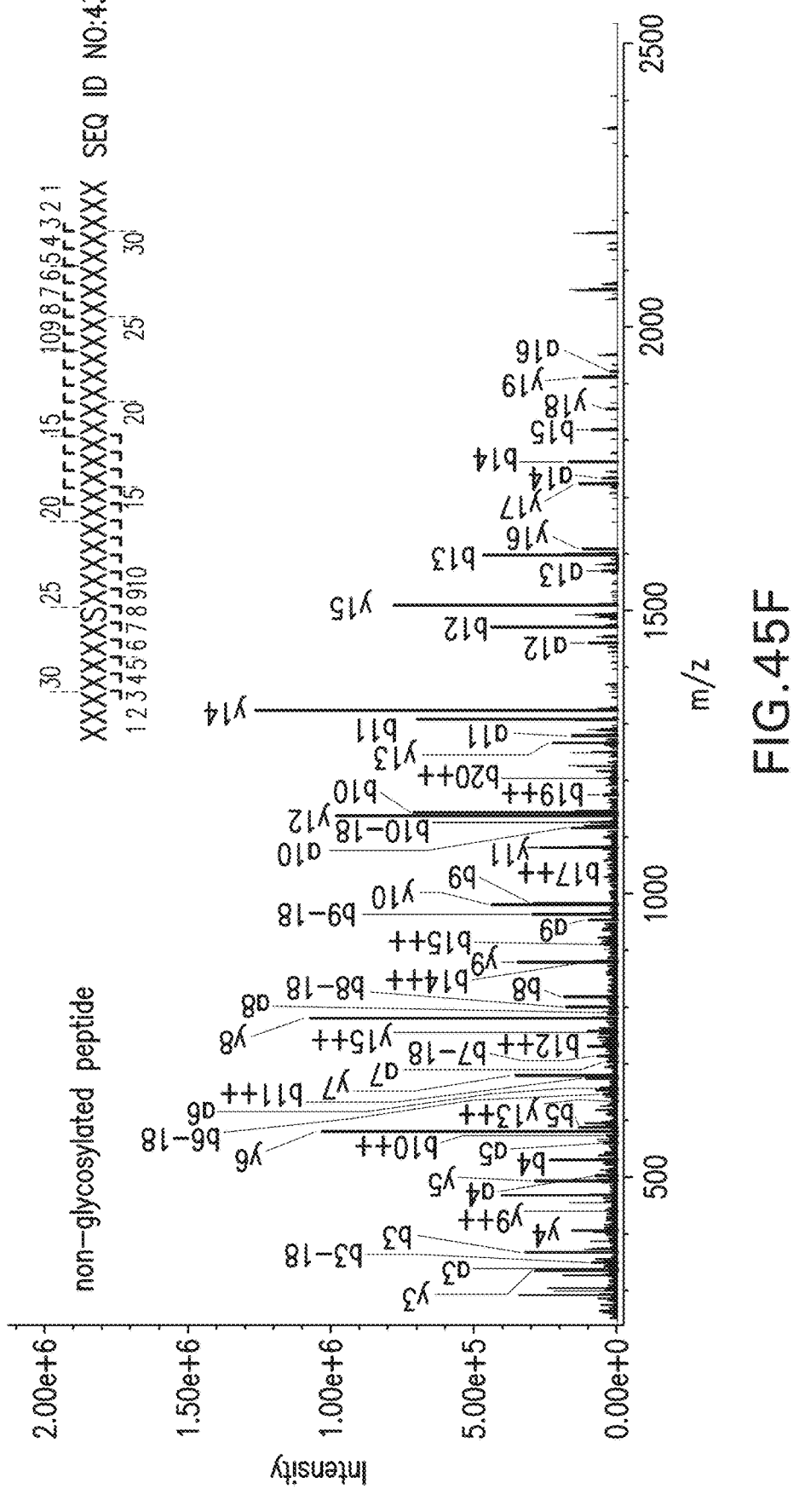

FIGS. 45E and 45F show tandem mass spectra of O-linked glycopeptide and the unoccupied peptide identified in mAb4.

FIGS. 46A, 46B, 46C, and 46D show EIC for low abundance non-canonical N-glycosylated peptides and base peak chromatogram (BPC) for mAb3 acquired under (A)(C) RPLC-MS with glycine and (B)(D) IP-HILIC-MS with 4.5 μg sample injection. The MS peak intensity has been normalized using the highest peak. Peak numbers 1~4 represent Man5, Man6, Man7 at N91 and FA2G2 at N163, respectively.

Figure 46A:
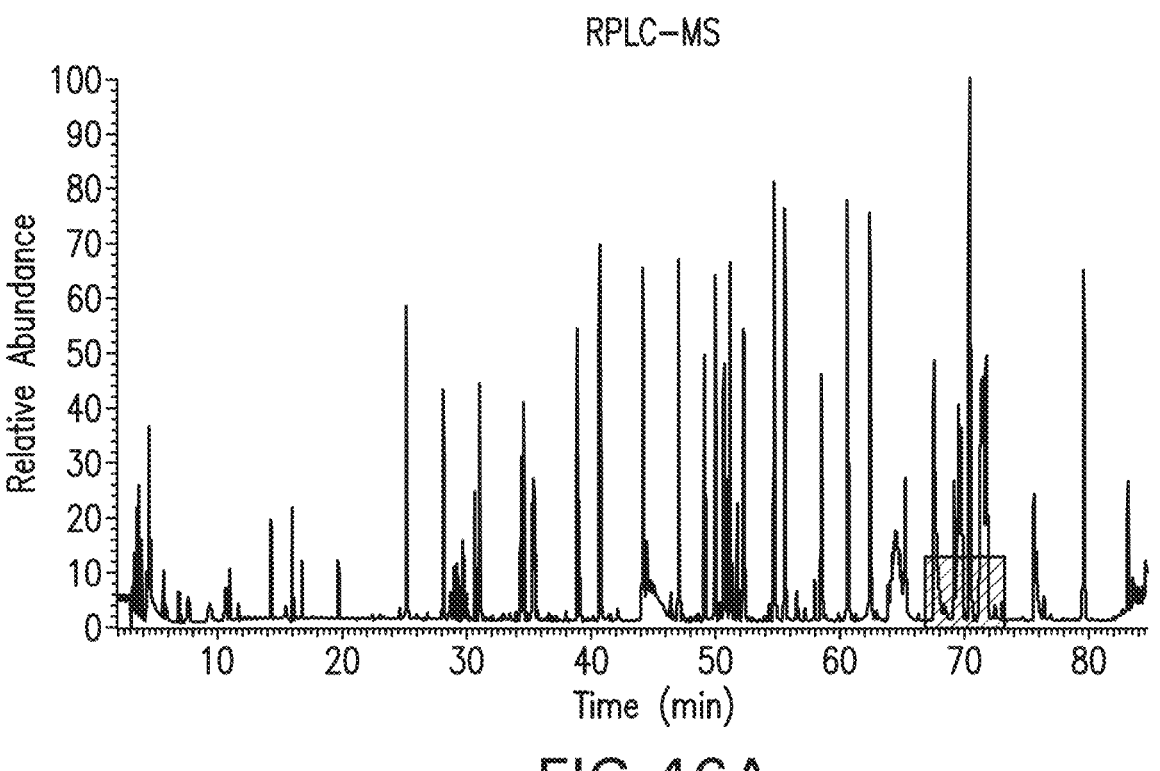
Figure 46B:
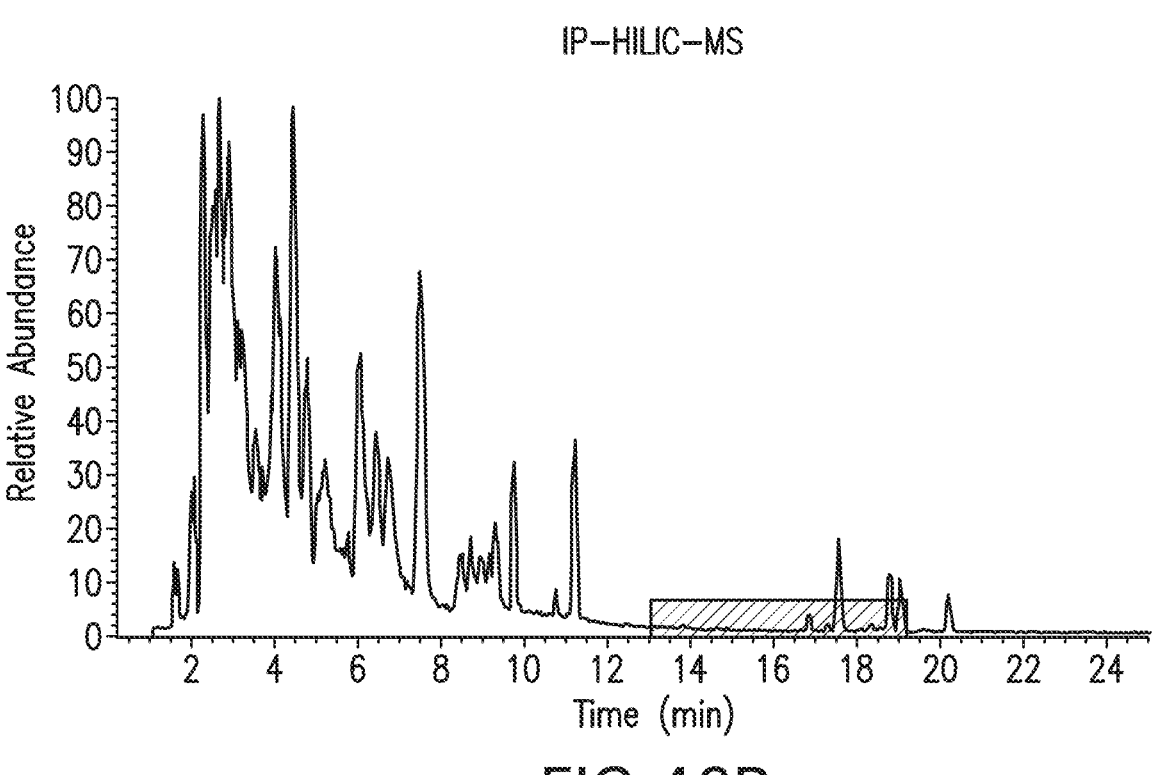
Figure 46C:
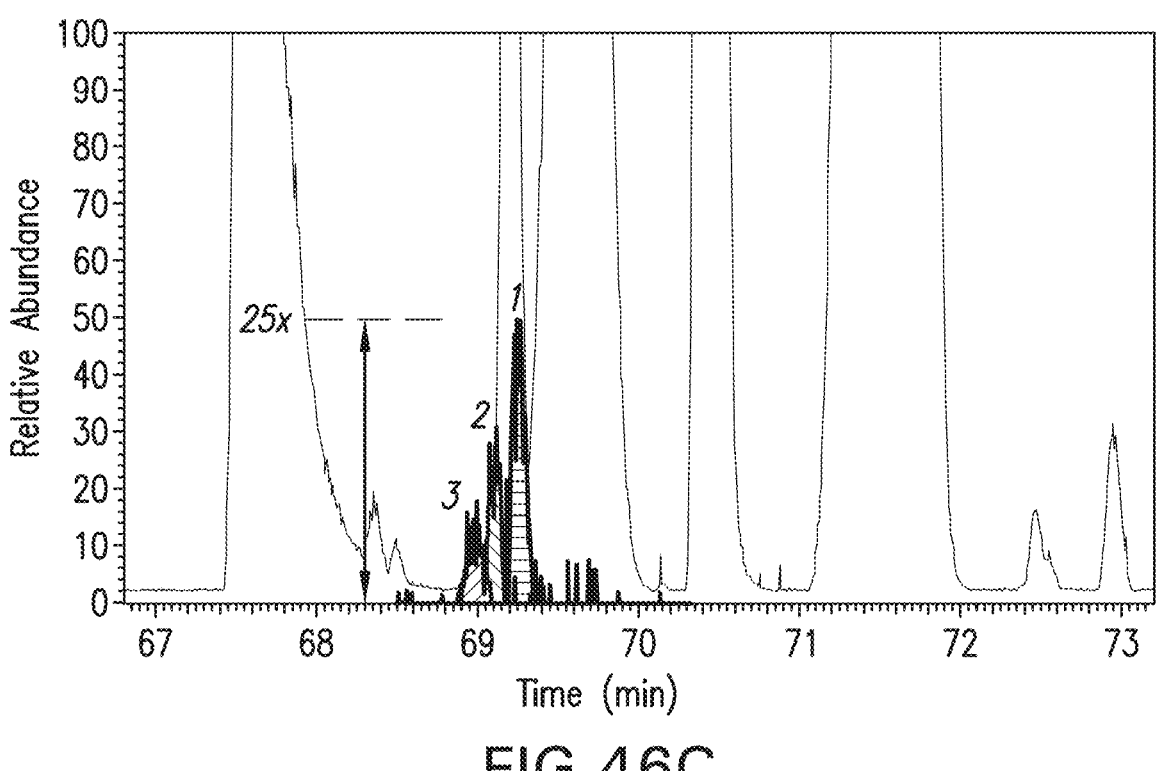
Figure 46D:
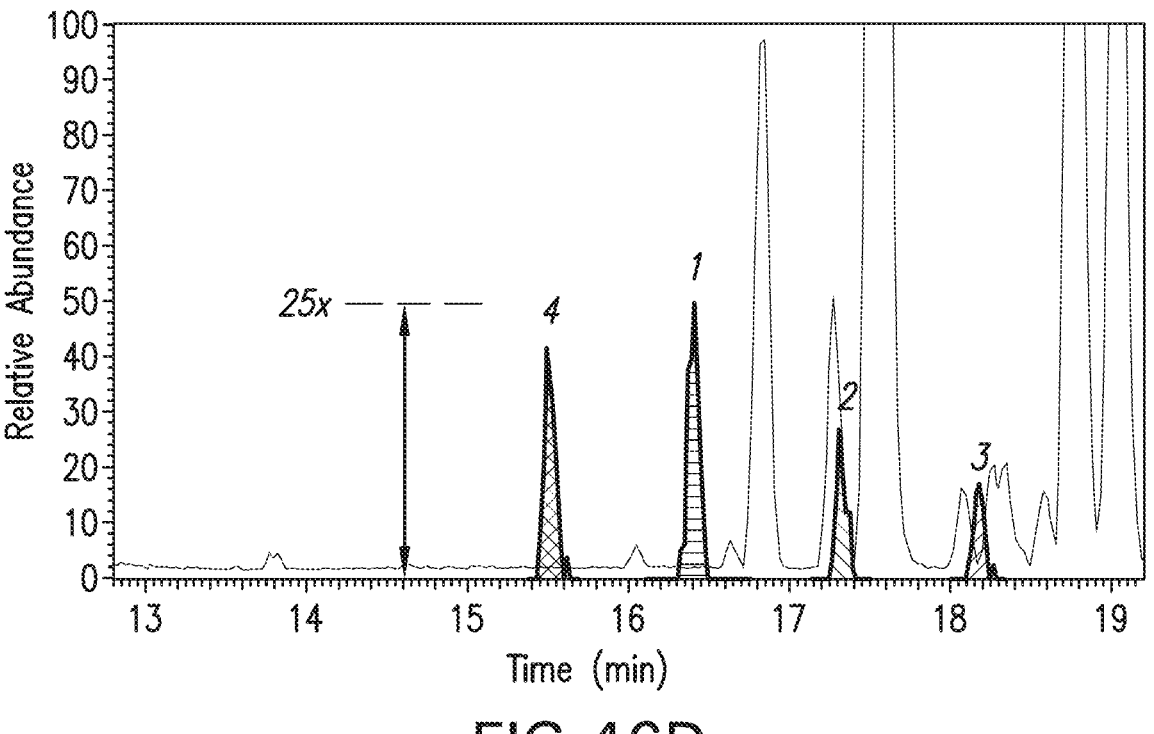
Figure 46E:
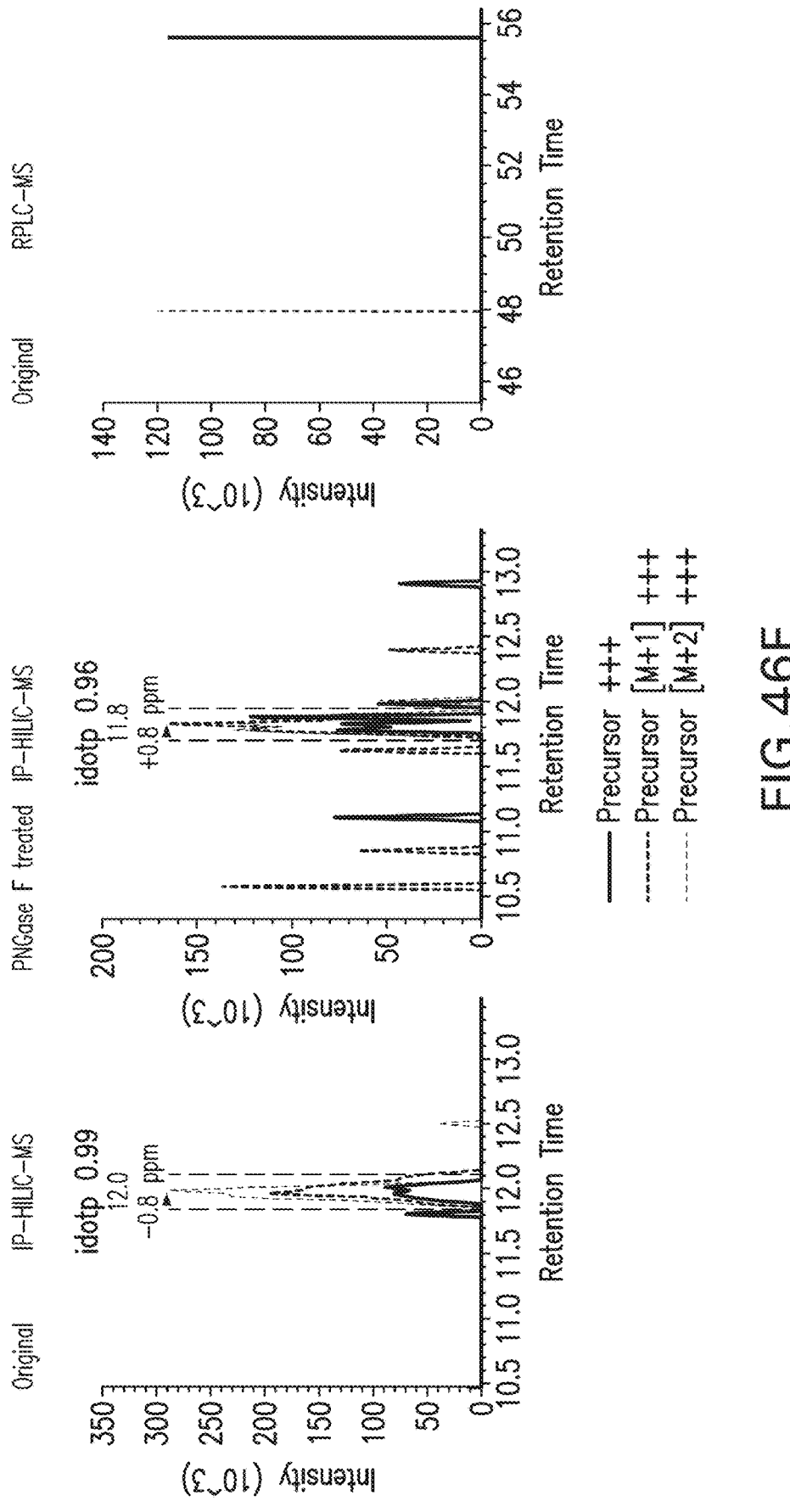

FIG. 46E shows MS1 extraction of the identified O-linked glycopeptide in mAb4.

DETAILED DESCRIPTION OF THE INVENTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

ACN: Acetonitrile
ESI-MS: Electrospray Ionization Mass Spectrometry

FA: Formic Acid
FLR: Fluorescent Detection
HC: Heavy Chain
HESI: Heated Electrospray Ionization
HILIC: Hydrophilic Interaction Liquid Chromatography
IP-HILIC: Ion-pairing Hydrophilic Interaction Chromatography
IgG: Immunoglobulin G
LC: Light Chain
LC-MS: Liquid Chromatography-Mass Spectrometry
mAb: Monoclonal Antibody
MPA: Mobile Phase A
MPB: Mobile Phase B
MS: Mass Spectrometry
MW: Molecular Weight
PROCA: Procainamide
2-AB: 2-aminobenzamide
PTMs: Post-translational Modifications
RPLC: Reversed Phase Liquid Chromatography
RPLC-MS/MS: Reversed Phase Liquid Chromatography Tandem Mass Spectrometry
SPE: Solid Phase Extraction
TFA: Trifluoroacetic Acid
UV: Ultraviolet

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527(Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989). Methods for generating human antibodies in transgenic mice are also known in the art. For example, using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to a desired antigen are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term as used herein, "glycopeptide/glycoprotein" is a modified peptide/protein, during or after their synthesis, with covalently bonded carbohydrates or glycan. In certain embodiments, a glycopeptide is obtained from a monoclonal antibody, for example, from a protease digest of a monoclonal antibody.

The term as used herein, "glycan" is a compound comprising one or more of sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein, such as a monoclonal antibody, is an important character to identify its function or cellular location. For example, a specific monoclonal antibody is modified with specific glycan moiety.

The term "hydrophilic interaction chromatography" or HILIC is intended to include a process employing a hydrophilic stationary phase and a hydrophobic organic mobile phase in which hydrophilic compounds are retained longer than hydrophobic compounds. In certain embodiments, the process utilizes a water-miscible solvent mobile phase.

The term "sample," as used herein, refers to a mixture of molecules that comprises at least an analyte molecule, e.g., glycopeptide, such as obtained from a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., glycoprotein). Examples include, but are not limited to, solid phase extraction, solid phase micro extraction, electrophoresis, mass spectrometry, e.g., ESI-MS, SPE HILIC, or MALDI-MS, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling," as used herein, refers to any of various methods of analysis which are used in combination to provide the content, composition, or characteristic ratio of glycopeptides in a sample.

"Electrospray Ionization Mass Spectrometry" or "ESI-MS" is technique used in mass spectrometry to produce ions using an electrospray in which a high voltage is applied to a liquid to create an aerosol. For example, in electrospray, the ions are created from proteins in solution which allows fragile molecules to be ionized intact which may preserve non-covalent interactions. Electrospray ionization is the ion source of choice to couple liquid chromatography with mass spectrometry (LC-MS). The analysis can be performed online, by feeding the liquid eluting from the LC column directly to an electrospray, or offline, by collecting fractions to be later analyzed in a classical nanoelectrospray-mass spectrometry setup. LC-MS can be used to characterize proteins including quantifying biomarkers, analyzing sequence variants and identifying and quantifying glycopeptides.

"Contacting," as used herein, includes bringing together at least two substances in solution or solid phase.

General Description

Thus, there is a need for protein characterization methods with increased sensitivity. The disclosed invention meets that need.

Disclosed herein is a new method of LC-MS based protein characterization that increases mass spec detection sensitivity. This new method is based upon studies reported herein wherein the inventors made the surprising discovery that the inclusion of a small molecule additive (e.g., an amino acid or modified amino acid) in the mobile phase solutions during liquid chromatography resulted in significant boosting of mass spectral signal as compared to the signal generated in the absence of such small molecule additives. The inventors also found that the presence of such additive, for example an amino acid (e.g., glycine), did not affect the retention and chromatographic resolution of peptides and glycans on the LC column when added into the mobile phase buffers. Moreover, the effects of the additives, e.g., an amino acid such as glycine, on signal boosting, charge state shifting and PTM quantitation of peptides and glycans were reproducible. Further, TFA and glycine buffer was found to improve lower limit of quantification (LLOQ) in the protein quantitation, identify glycopeptides more confidently without affecting the relative quantitation compared to the regular TFA buffer in the IP-HILIC-LC-MS method, and identify more sequence variants while generating complementary information compared to the FA buffer regularly used for sequence variants analysis. Thus, the disclosed discovery has a very broad range of applications on LC-MS based protein characterization via improving the mass spec detection sensitivity. In some embodiments, the disclosed methods can be used for biomarker quantitation, sequence variants analysis and/or peptide, such as glycopeptide, and/or glycan identification and quantitation by LC-MS.

In some embodiments, the method includes contacting a sample to a separation column under conditions that permit sample components to bind to the substrate; applying a mobile gradient to the separation column, wherein the mobile gradient buffer comprises a small molecule additive (e.g., an amino acid) and TFA, FA, ammonium formate or and/or ACN; and performing mass spectrometric analysis on eluted sample components.

The mobile phase used may include buffers with and without ion pairing agents, e.g., acetonitrile and water. Ion pairing agents include formate, acetate, TFA and salts. Gradients of the buffers can be used, e.g., if two buffers are used, the concentration or percentage of the first buffer can decrease while the concentration or percentage of the second buffer increases over the course of the chromatography run. For example, the percentage of the first buffer can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% over the course of the chromatography run. As another example, the percentage of the second buffer can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% over the course of the same run. Optionally, the concentration or percentage of the first and second buffer can return to their starting values at the end of the chromatography run. As an example, the percentage of the first buffer can change in five steps from 85% to 63% to 59% to 10% to 85%; while the percentage of the second buffer in the same steps changes from 15% to 37% to 41% to 90% to 15%. The percentages can change gradually as a linear gradient or in a non-linear (e.g., stepwise) fashion. For example, the gradient can be multiphasic, e.g., biphasic, triphasic, etc. In some embodiments, the methods described herein use a decreasing acetonitrile buffer gradient which corresponds to increasing polarity of the mobile phase without the use of ion pairing agents.

In some embodiments, applying a mobile gradient to the separation column includes applying a first mobile gradient buffer to the separation column, wherein the first mobile phase buffer includes TFA and a small molecule additive (e.g., an amino acid), FA and a small molecule additive (e.g., an amino acid) or ammonium formate and a small molecule additive (e.g., an amino acid) and applying a second mobile gradient to the separation column, wherein the second mobile phase buffer comprises TFA in ACN and a small molecule additive (e.g., an amino acid), FA in ACN and a small molecule additive (e.g., an amino acid), or ammonium formate in water/ACN and a small molecule additive.

In various embodiments, the small molecule additive is selected from glycine, alanine, serine, valine, N-acetyl glycine, methionine, β-alanine, aspartic acid, or N-methyl glycine. In some cases, the amino acid is selected from glycine, alanine, serine or valine. In some embodiments, the amino acid is alanine. In some embodiments, the amino acid is serine. In some embodiments, the amino acid is valine. In some embodiments, the amino acid in the first mobile phase buffer is glycine. In some embodiments, the amino acid in the second mobile phase buffer is glycine. In some embodiments, the amino acid in the first and second mobile phase buffers is glycine. In some embodiments, the small molecule additive (e.g., the amino acid) in the first and/or second mobile phase buffer is one of the small molecules (e.g., modified amino acids) or other amino acids identified above or herein.

The concentration of the small molecule additive (e.g., amino acid) in the mobile phase buffer is about 0.5 mM to about 5 mM, such as between about 0.5 mM to about 3 mM, about 1 mM and about 2 mM, including 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, 2.0 mM, 2.1 mM, 2.2 mM, 2.3 mM, 2.4 mM, 2.5 mM, 2.6 mM, 2.7 mM, 2.8 mM, 2.9 mM, 3.0 mM, 3.1 mM, 3.2 mM, 3.3 mM, 3.4 mM, 3.5 mM, 3.6 mM, 3.7 mM, 3.8 mM, 3.9 mM, 4.0 mM, 4.1 mM, 4.2 mM, 4.3 mM, 4.4 mM, 4.5 mM, 4.6 mM, 4.7 mM, 4.8 mM, 4.9 mM, or 5.0 mM. In some embodiments, the small molecule additive (e.g., amino acid) is less than 5 mM. In some embodiments, the small molecule additive is glycine at a concentration of less than 5 mM. In some embodiments, the amino acid in the first mobile phase buffer is glycine and the concentration is between about 1 to about 2 mM glycine. In some embodiments, the amino acid in the second mobile phase buffer is glycine and the concentration is between about 1 to about 2 mM glycine. In some embodiments, the glycine concentration in the first mobile phase buffer is about 1 mM. In some embodiments, the glycine concentration in the first mobile phase buffer is about 2 mM. In some embodiments, the amino acid in the second mobile phase buffer is glycine and the concentration is between about 1 to about 2 mM glycine. In some embodiments, the glycine concentration in the second mobile phase buffer is about 1 mM. In some embodiments, the glycine concentration in the second mobile phase buffer is about 2 mM. In some embodiments, the amino acid in the first and second mobile phase buffer is glycine and the concentration is between about 1 to about 2 mM glycine.

In some embodiments, the TFA concentration in the first mobile phase is about 0.03% to TFA in $H_2O$, such as about 0.03% to 0.1% or the FA is about 0.05% to about 0.15% in $H_2O$, such as about 0.1% FA. In some embodiments, the TFA concentration is about 0.05% to about TFA in $H_2O$ or the FA concentration in the first mobile phase is about 0.1% FA. For example, the TFA concentration is about 0.03%, 0.04%, 0.05%, 0.06%, 0.07%, 0.08%, 0.09%, or 0.1% in $H_2O$. In some embodiments, the TFA concentration in the second mobile phase comprises about TFA in 80% ACN and 20% $H_2O$ or about 0.1% TFA in 80% ACN and 20% $H_2O$. In some embodiments, the concentration of ACN in the second mobile phase is about 60% to 100%, such as between 80% and 100%, including 60%, 65%, 70%, 75%, 80%, 85%, 90%, 95% or 100%.

In some embodiments, the ammonium formate concentration in the first mobile phases is mM in $H_2O$. In some embodiments, the second mobile phase is 15% 50 mM in $H_2O$ and 85% ACN.

In some embodiments, the sample comprises peptides, nucleotides or glycans. For example, the sample can include glycopeptides, such as glycopeptides obtained from a monoclonal antibody. In some embodiments, the monoclonal antibody is of isotype IgG1, IgG2, IgG3, IgG4, or mixed isotype.

In some embodiments, the method includes preparing the sample prior to contacting the sample to a separation column under conditions that permit sample components to bind to the substrate. In some embodiments, sample preparation includes contacting a sample with a denaturing and reducing solution under conditions that permit sample denaturation and reduction; contacting denatured and reduced sample with an alkylating solution under conditions that permit sample alkylation; contacting alkylated sample with a digest solution under conditions that permit sample digestion; and contacting digested sample with a quenching solution under conditions that stop sample digestion.

In some embodiments, preparing the sample comprises: releasing glycans from samples using enzymes or chemical reaction; labeling released glycans with fluorescence labels or reducing released glycans using reducing agents.

In some embodiments, the N-glycans can be released from glycoproteins using PNGase F. In some embodiments, the O-glycans be released from glycoprotein by basic chemicals. The released N-glycans can react with RapiFluor fluorescent label. The released N-glycans and O-glycans can be reduced by sodium borohydride or can be linked to PROCA or 2-AB by incubating with acetic acid and sodium cyanoborohydride.

In some embodiments, the sample is a monoclonal antibody and the digest solution comprises one or more proteases, such as trypsin. In some examples, the method is used for characterizing/analyzing glycopeptides, such as glycopeptides obtained from a monoclonal antibody, such as an antibody that has been digested with one or more proteases. In some embodiments, an antibody in a sample can be treated and prepared by reduction, enzymatic degradation, denaturation or fragmentation prior to contacting the resulting sample to a substrate. For example, the methods can be used to characterize the glycosylation of proteins, e.g., monoclonal antibody (mAb) therapeutics, by means of fragment, and peptide-level LC-MS, such as HILIC-MS analyses. In certain embodiments, the samples at any intervening step may be concentrated, diluted, desalted or the like.

The glycopeptide is obtained from glycosylated protein, such as a monoclonal antibody. The glycosylated monoclonal antibody may be prepared by reduction, enzymatic digestion, denaturation, fragmentation, chemical cleavage and a combination thereof. The methods disclosed herein are applicable to any antibody isotype, such as IgG1, IgG2, IgG3, IgG4, or of mixed isotype. Reduction is to reduce disulfide bonds into two thiols in a 3-dimensional protein, such as monoclonal antibody. Reduction can be performed by heat-denaturing, adding a surfactant, or adding a denaturing agent, e.g., guanidine HCl (6M), in the presence of a reducing agent, e.g. TCEP-HCl. Enzymatic degradation is a digestion of the protein with a protease, e.g., trypsin or Achromobacter protease I (Lys-C). In addition, the glycoprotein can be denatured by heat or chemicals, or a combination thereof. Fragmentation involves cleaving protein portions of a single or multi-subunit protein, such as a monoclonal antibody, with physical, biological or chemical methods.

In some embodiments, the separation column is a liquid chromatography (LC) separation column. Liquid chromatography, including HPLC, can be used to analyze structures, such as peptides, including glycopeptides. Various forms of liquid chromatography can be used to study these structures, including anion-exchange chromatography, reversed-phase HPLC, size-exclusion chromatography, high-performance anion-exchange chromatography, and normal phase (NP) chromatography, including NP-HPLC (see, e.g., Alpert et al., J. Chromatogr. A 676:191-202 (1994)). Hydrophilic interaction chromatography (HILIC) is a variant of NP-HPLC that can be performed with partially aqueous mobile phases, permitting normal-phase separation of peptides, carbohydrates, nucleic acids, and many proteins. The elution order for HILIC is least polar to most polar, the opposite of that in reversed-phase HPLC. HPLC can be performed, e.g., on an HPLC system from Waters (e.g., Waters 2695 Alliance HPLC system), Agilent, Perkin Elmer, Gilson, etc.

NP-HPLC, preferably HILIC, is a particularly useful form of HPLC that can be used in the methods described herein. NP-HPLC separates analytes based on polar interactions between the analytes and the stationary phase (e.g., substrate). The polar analyte associates with and is retained by the polar stationary phase. Adsorption strengths increase with increase in analyte polarity, and the interaction between the polar analyte and the polar stationary phase (relative to the mobile phase) increases the elution time. Use of more polar solvents in the mobile phase will decrease the retention time of the analytes while more hydrophobic solvents tend to increase retention times.

Various types of substrates can be used with NP-HPLC, e.g., for column chromatography, including silica, amino, amide, cellulose, cyclodextrin and polystyrene substrates. Examples of useful substrates, e.g., that can be used in column chromatography, include: polySulfoethyl Aspartamide (e.g., from PolyLC), a sulfobetaine substrate, e.g., ZIC®-HILIC (e.g., from SeQuant), POROS® HS (e.g., from Applied Biosystems), POROS® S (e.g., from Applied Biosystems), PolyHydroethyl Aspartamide (e.g., from PolyLC), Zorbax 300 SCX (e.g., from Agilent), PolyGLYCOPLEX® (e.g., from PolyLC), Amide-80 (e.g., from Tosohaas), TSK GEL® Amide-80 (e.g., from Tosohaas), Polyhydroxyethyl A (e.g., from PolyLC), Glyco-Sep-N (e.g., from Oxford GlycoSciences), and Atlantis HILIC (e.g., from Waters). In some embodiments, the disclosed methods include columns that utilize one or more of the following functional groups: carbamoyl groups, sulfopropyl groups, sulfoethyl groups (e.g., poly (2-sulfoethyl aspartamide)), hydroxyethyl groups (e.g., poly (2-hydroxyethyl aspartamide)) and aromatic sulfonic acid groups.

The column temperature can be maintained at a constant temperature throughout the chromatography run, e.g., using a commercial column heater. In some embodiments, the column is maintained at a temperature between about 18° C. to about 70° C., e.g., about 30° C. to about 60° C., about 40° C. to about 50° C., e.g., at about 20° C., about 25° C., about 30° C., about 35° C., about 40° C., about 45° C., about 50° C., about 55° C., about 60° C., about 65° C., or about 70° C. In some embodiments, the column temperature is about 40° C.

The flow rate of the mobile phase can be between about 0 to about 100 ml/min. For analytical proposes, flow rates typically range from 0 to 10 ml/min, for preparative HPLC, flow rates in excess of 100 ml/min can be used. For example, the flow rate can be about 0.5, about 1, about 1.5, about 2, about 2.5, about 3, about 3.5, about 4, about 4.5, or about 5 ml/min. Substituting a column having the same packing, the same length, but a smaller diameter requires a reduction in the flow rate in order to retain the same retention time and resolution for peaks as seen with a column of wider diameter. In some embodiments, a flow rate equivalent to about 1 ml/min in a 4.6×100 mm, 5 μm column is used.

In some embodiments, the run time can be between about 15 to about 240 minutes, e.g., about 20 to about 70 min, about 30 to about 60 min, about 40 to about 90 min, about 50 min to about 100 min, about 60 to about 120 min, about 50 to about 80 min.

The NP-HPLC can be adjusted to be performed on a nanoscale, e.g., using columns with an inner diameter of about 75 μm (see, e.g., Wuhrer et al., Anal. Chem. 76:833-838 (2004); Wuhrer et al., Internat. J. Mass. Spec. 232:51-57 (2004)).

In certain embodiments, the separation column is a hydrophilic interaction (HILIC) separation column and the molecules, such as glycopeptides, are subsequently eluted from the HILIC separation column, for example using a mobile phase gradient to resolve the individual species of glycopeptides, thereby purifying and or separating glycopeptides in the sample. In certain examples, the eluted glycopeptides from the HILIC are separated into one or more fractions. Such fractions can be used for subsequent analysis, such as MS analysis. In certain embodiments, the methods include identifying the molecules, such as glycopeptides and/or glycan present in one or more of the fractions. In certain embodiments, the glycan is an N-glycan or O-glycan. In some embodiments, the methods further comprise detecting the glycopeptide, for example using the UV signal from the peptide portion of the glycopeptide. This may be done for fractions of a sample and allows the selection of specific fractions for further analysis, for example mass spec (MS) analysis. In some embodiments, the methods comprise detecting the glycans using the FLR signals from the fluorescent labels linked to the glycans.

In some embodiments, performing mass spectrometric analysis on eluted sample components includes applying electrospray ionization to generate charged ions from the eluted sample components and measuring the generated charge ions.

In application of mass spectrometry for the analysis of biomolecules, the molecules are transferred from the liquid or solid phases to gas phase and to vacuum phase. Since many biomolecules are both large and fragile (proteins being a prime example), two of the most effective methods for their transfer to the vacuum phase are matrix-assisted laser desorption ionization (MALDI) or electrospray ionization (ESI). In general, ESI is more sensitive, while MALDI is faster. Significantly, some peptides ionize better in MALDI mode than ESI, and vice versa (Genome Technology, June 220, p 52). ESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the capillary into an electrospray nozzle, e.g., the capillary functions as the sample loader. In another embodiment, the capillary itself functions as both the extraction device and the electrospray nozzle. In some embodiments, the method enhances the mass spectral signal as indicated by about 2 to 27-fold, such as 5 to 14-fold on average and/or an approximately about 2 to 1000-fold increase in high charge state species (e.g., $z \geq 3$). In some embodiments, at glycine 1 mM, when sample loading amount is 10 ug, the fold change is around 5. In some embodiments, the spectral signal increase by approximately 14-fold and/or approximately 1000-fold increase in high charge state species. It is contemplated that glycine fold boosting can be dependent on sample loading amount and glycine concentration. For example, higher glycine concentration generates higher boosting for different sample loading amount than lower glycine concentration and the boosting overall increases with the decrease of the sample loading amount. There is a certain point below which no significant change (<10%) in the fold boosting with the loading amount can be observed (as demonstrated in FIGS. 1A, 1B and 2).

In some embodiments, other ionization modes are used e.g., turbospray ionization mass spectrometry, nanospray ionization mass spectrometry, thermospray ionization mass spectrometry, sonic spray ionization mass spectrometry, SELDI-MS and MALDI-MS. In general, an advantage of these methods is that they allow for the "just-in-time" purification of sample and direct introduction into the ionizing environment. It is to be noted that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt.

In some embodiments, the substrate is prepared for the addition of the sample by washing, e.g. a prewashing step. In some embodiments, the substrate is washed prior to contact with a glycopeptide sample. In various embodiments, the substrate is contacted with a sample containing biomolecules, such as glycopeptides, for enrichment. With regard to the sample solution, it will include the biomolecules, such as glycopeptides, dissolved in a solvent in which the biomolecules, such as glycopeptides, are soluble, and in which the biomolecules, such as glycopeptides, will bind to the substrate. Preferably, the binding is strong, resulting in the binding of a substantial portion of the biomolecules, such as a substantial portion, including greater than 50% of the biomolecules, such as greater than 50% of glycopeptides. In some cases, substantially all, greater than 95% of the biomolecules, such as glycopeptides, will be bound. In various embodiments, the solvent is an aqueous solution, typically containing a buffer, salt, and/or surfactants to solubilize and stabilize the biomolecules, such as glycopeptides. In some embodiments, the biomolecule sample, such as a glycopeptide sample, is a solution of with a low pH below about 6.5, such as below about 6.5, 6.0, 5.5, 5.0, 4.5, 4.0, 3.5 or 3.0.

In one particular embodiment, a method of enhancing mass spectral signal includes denaturing and reducing a monoclonal antibody. For example, a monoclonal antibody can be denatured and reduced with acetic acid, such as 5 mM acetic acid, in the presence of TCEP-HCl with heat for a sufficient time for the denaturation and reduction to occur, such as 80° C. for 10 minutes. After denaturation and reduction, the sample is alkylated. In some examples, the sample is first diluted and then alkylated. For example, the same can be diluted with 100 mM Tris-HCl (pH 7.5) containing 8 M urea and then alkylated with iodoacetamide for 30 minutes in the dark at room temperature. Following alkylation, the sample is further diluted to reduce the urea concentration, such diluted with 100 mM Tri-HCl (pH 7.5) to reduce the urea concentration to less than 1 M. The sample is then digested with a protease. For example, the sample is treated with trypsin at an enzyme to substrate ratio of 1:20 (w/w) at 37° C. for 4 hours. At the desired time, digestion is stopped, such as be quenching the sample with TFA, such as 10% TFA. The digested sample is then subjected to online LC-MS analysis. For example, the tryptic digest (reduced/alkylated) sample is loaded at a sufficient concentration (e.g., 0.25 μg) and the mobile phase gradient A (MP-A) includes TFA in $H_2O$ with 1 to 2 mM glycine, such as TFA in $H_2O$ with 2 mM glycine, followed by the mobile phase gradient B of TFA in ACN with 1 to 2 mM glycine, such as 0.05% TFA in 80% ACN and 20% $H_2O$ with 2 mM glycine.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: New Method for ESI-MS Signal Boosting with Glycine Additive

Tryptic digest of NISTmAb: 100 μg NISTmAb was denatured and reduced in 5 mM acetic acid in the presence of 5 mM TCEP-HCl at 80° C. for 10 minutes. After denaturation and reduction, the sample was diluted with 100 mM Tris-HCl (pH 7.5) containing 8 M urea and alkylated with iodoacetamide for 30 minutes in the dark at room temperature. Following alkylation, the sample was further diluted with 100 mM Tri-HCl (pH 7.5) to reduce the urea concentration to less than 1 M. The sample was incubated with trypsin at an enzyme to substrate ratio of 1:20 (w/w) at 37° C. for 4 hours. The digested sample was quenched by addition of 10% TFA to stop trypsin digestion and then subjected to online LC-MS analysis. NISTmAb Tryptic digest (reduced/alkylated) was loaded at different amounts of 0.05-10 μg, MP-A: 0.05% TFA, 0.0625-5 mM glycine in $H_2O$, MP-B: 0.05% TFA, 0.0625-5 mM glycine in 80% ACN and 20% $H_2O$ where the column was ACQUITY UPLC Peptide BEH C18, 130 Å, 1.7 μm, 2.1 mm×150 mm (Waters) and LC conditions were 0.25 mL/min, 40° C. column temperature.

Figure 3:
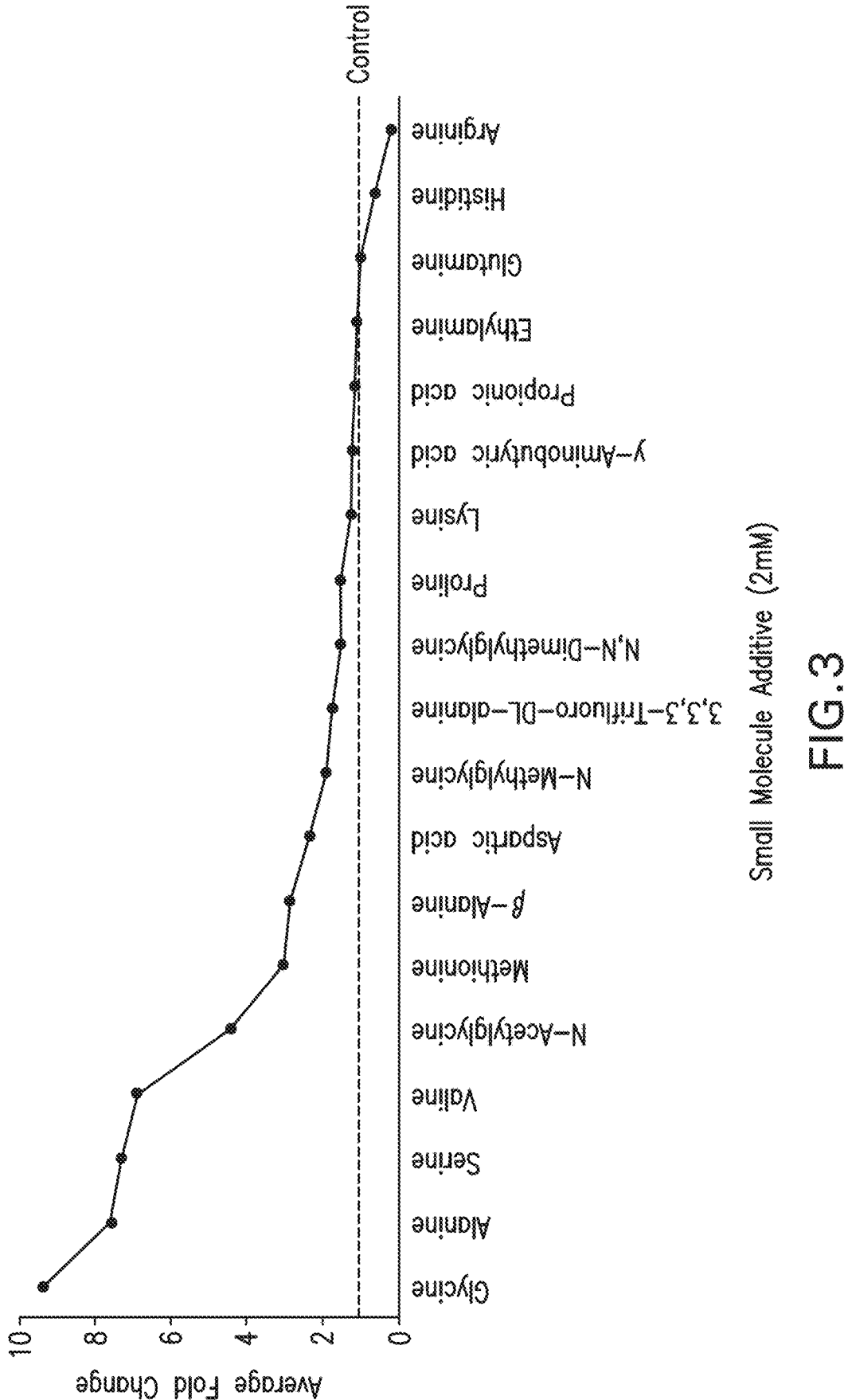
FIG. 3 shows the average MS1 fold boosting of NISTmAb tryptic peptides by reagent (2 mM).

To investigate different small molecule reagents on the MS boosting (as illustrated in FIG. 3), NISTmAb Tryptic digest (reduced/alkylated) was loaded at a concentration of 0.25 μg, MP-A: 0.05% TFA in $H_2O$, MP-B: 0.045% TFA in ACN where the column was ACQUITY UPLC Peptide BEH C18, 130 Å, 1.7 μm, 2.1 mm×150 mm (Waters) and LC conditions were 0.25 mL/min, 40° C. column temperature, syringe pump was used to deliver 125 mM different small molecule solutions in 50:50 $H_2O$/ACN at 10 μL/min to mix with eluent from LC column and the final small molecule concentration was approximately 5 mM.

Table 1 provides % A and % B at the various time points.

TABLE 1

| Time (min) | % A | % B |
|---|---|---|
| 0 | 99.9 | 0.1 |
| 5 | 99.9 | 0.1 |
| 47 | 65.0 | 35.0 |
| 48 | 0.1 | 99.9 |
| 54 | 0.1 | 99.9 |
| 55 | 99.9 | 0.1 |
| 60 | 99.9 | 0.1 |

Figure 1A:
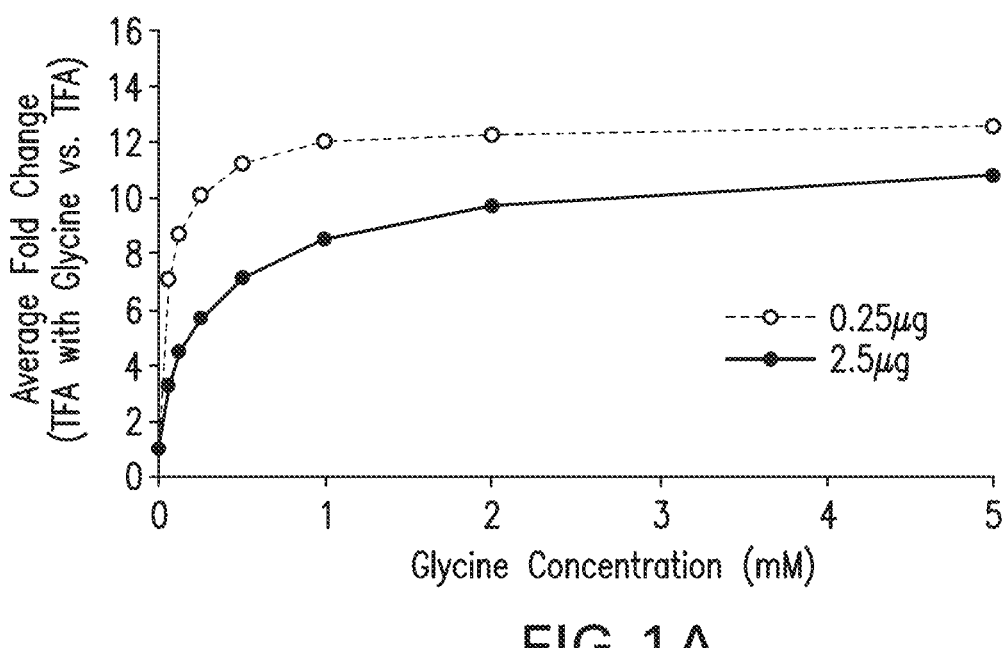
FIGS. 1A and 1B show the effect of glycine at various concentrations on MS boosting and effect of various sample loading amounts on MS boosting.
Figure 1B:
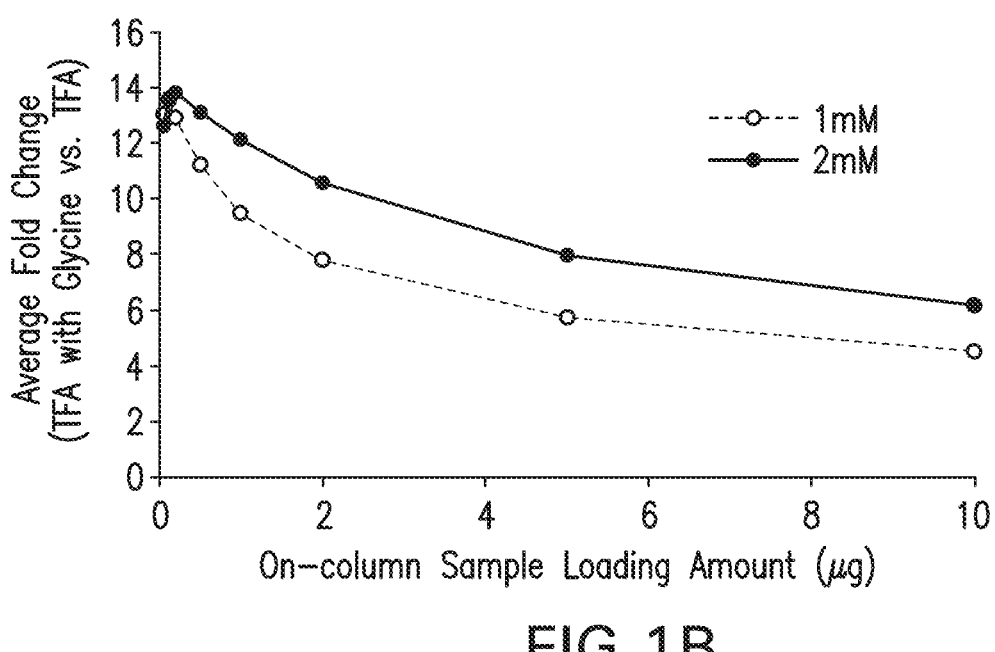

FIGS. 1A and 1B illustrate the effect of glycine at various concentrations on MS boosting and the effect of various sample loading amounts on MS boosting. FIGS. 1A and 1B were generated by direct adding glycine into TFA mobile phase bottles (MPA: 0.05% TFA in water and glycine; MPB: 0.05% TFA in 80% ACN and 20% water and glycine), not by post-column syringe pump configuration. In FIG. 1A, a clear dependence of glycine boosting on the sample loading amount is illustrated. Higher glycine concentration for the higher loading amount was needed to obtain the same fold boosting as the lower glycine concentration for the lower loading amount.

FIG. 1B shows increasing the sample loading amount overall decreased the boosting power of glycine on the responses of the peptides. Glycine at 2 mM exhibited higher boosting than at 1 mM for different sample loading amounts. Also, as the decrease of the sample loading amount, the increase tendency of fold boosting gradually slowed down. The minimal change (<10%) in the fold boosting with the loading amount was observed when sample loading amounts were below 0.2 and 0.5 μg at glycine concentrations of 1 and 2 mM, respectively.

Although the reduced fold boosting was observed with increasing sample loading amount, the mass spectrometry responses (i.e., EIC peak areas of the peptides) were still higher at higher loading amount than at the lower loading amount even with higher fold boosting.

Figure 4:
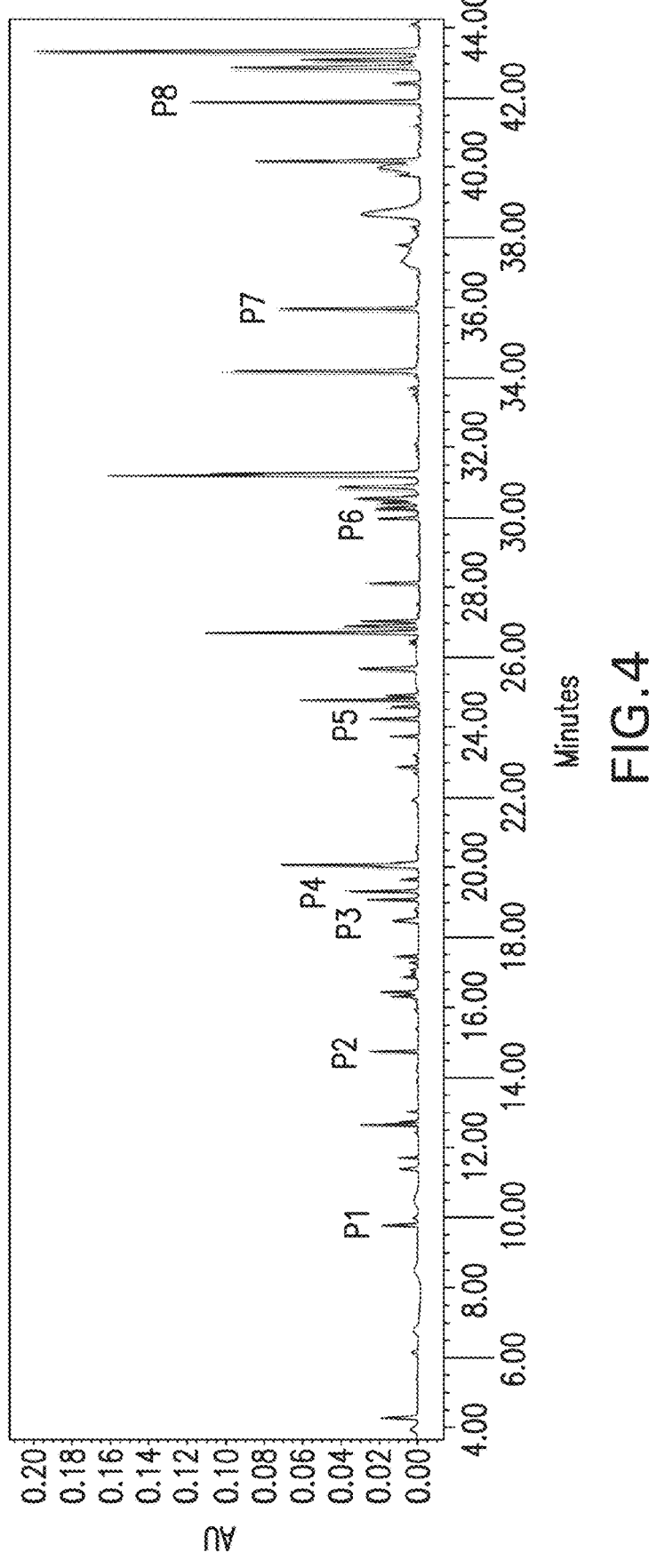
FIG. 4 shows a minimal change in chromatographic separation of peptides after adding glycine to TFA buffers.
Figure 6:
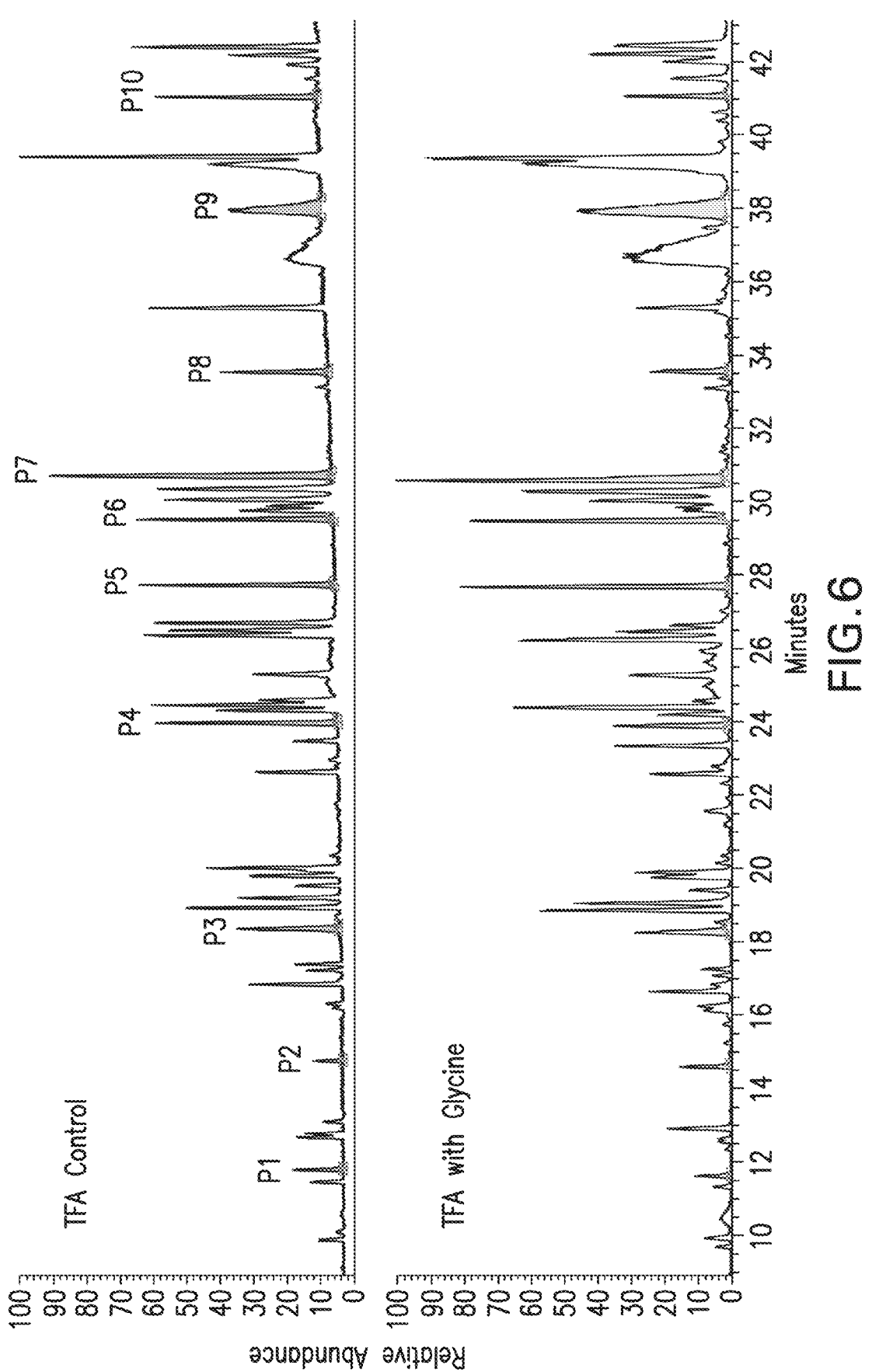
FIG. 6 shows the signal-to-noise ratio observed with TFA control and TFA in the presence of glycine, with 2.5 µg loading of NISTmAb digest.

FIG. 2 provides the chemical structures of ten amino acids based upon different chemical properties of their side chains including alanine and valine (hydrophobic side chain), serine (hydrophilic side chain), proline (cyclic side chain), methionine (sulfur-containing side chain), glutamine (amide-containing side chain), glutamic acid (acidic side chain), lysine and arginine (basic side chain) and histidine (aromatic side chain) as well as several glycine variants derived from modifying glycine on amine group (e.g., N, N-dimethylglycine, N-acetylglycine, N-methylglycine and propionic acid), side chain (e.g., 3,3,3-trifluoro-DL-alanine) or carboxyl group (e.g., ethylamine) or inserting glycine with additional carbon atoms to extend the distance between amine and carboxyl groups (e.g., β-alanine and γ-aminobutyric acid). FIG. 3 is a graph illustrating the average MS1 fold boosting of NISTmAb tryptic peptides by different small molecule reagents (2 mM). As illustrated by FIG. 3, glycine showed the highest average boosting. Glycine is also the molecule with the lowest molecular weight. FIG. 4 is a tracing illustrating a minimal change in chromatographic separation of peptides after adding glycine to TFA buffers. The conditions for the studies were 2.5 μg loading of NISTmAb tryptic digest (reduced/alkylated); MP-A: TFA in $H_2O$ with or without 2 mM glycine, MP-B: 0.05% TFA in 80% ACN and 20% $H_2O$ with or without 2 mM glycine, column was Acquity UPLC Peptide BEH C18, 130 Å, 1.7 μm, 2.1 mm×150 mm (Waters with LC conditions of 0.25 mL/min, 40° C. column temperature. Note MP-B was changed from the conventional condition of 0.05% TFA in ACN to 0.05% TFA in 80% ACN and 20% $H_2O$ because of the solubility issue of 2 mM glycine in 100% ACN. Table 2 below shows the UPLC performance metrics for 8 representative peptide peaks (P1-P8) selected in the UV chromatogram (see FIG. 4) across the whole LC gradient, exhibiting highly comparable UPLC performance metrics between two mobile phase systems with retention time differences <0.06 min, peak width % differences <1.4% and peak area % differences <1.9%. Peak width—the corresponding width of the base of the peak obtained by drawing the tangent lines at 50% peak height; Table 3 provides the % A and % B at the various time points.

even more than 10-fold. The mean boost was 13.2× and % relative standard deviation (RSD) was less than 5% for all peptides. FIG. 6 is a total ion current (TIC) plot illustrating the signal-to-noise ratio observed with TFA control and TFA in the presence of glycine, with 2.5 μg loading of NISTmAb. Ten representative tryptic peptides with different retention times across the whole LC gradient were selected to compare their signal-to-noise ratios in the total ion chromatograms between TFA mobile phases with and without glycine additive. The signal-to-noise ratios were indeed boosted with glycine additive for those ten tryptic peptides. Similar to peptide-dependent response boosting, selected peptides also showed different signal-to-noise ratio boosting with a wide range up to more than one order of magnitude. Glycine additive boosted the mass spectrometry responses of tryptic peptides, however no boosting was observed for the background noise stemming from small molecule contaminants generated from the ambient environment during electrospray ionization. This boosting feature could lead to the improved signal-to-noise ratios of tryptic peptides while the absolute responses were boosted.

TABLE 4

| | | Signal-to-noise Ratio | | |
| Representative Peak | Retention Time (min) | TFA Control | TFA with Glycine | Fold Increase |
|---|---|---|---|---|
| P1 | 11.7 | 4 | 23 | 5.8 |
| P2 | 14.7 | 3 | 33 | 11.0 |
| P3 | 18.3 | 9 | 62 | 6.9 |
| P4 | 23.9 | 16 | 74 | 4.6 |

TABLE 2

| | TFA Control | | | TFA with Glycine | | | Comparison Statistics | | |
| Representative Peak | Retention Time (min) | Peak Width (min) | Peak Area | Retention Time (min) | Peak Width (min) | Peak Area | Retention Time Diff (min) | Peak Width % Diff | Peak Area % Diff |
|---|---|---|---|---|---|---|---|---|---|
| P1 | 9.78 | 0.08 | 59679 | 9.76 | 0.09 | 59188 | 0.02 | 0.2% | 0.8% |
| P2 | 14.75 | 0.07 | 64700 | 14.72 | 0.07 | 64335 | 0.03 | 0.3% | 0.6% |
| P3 | 19.08 | 0.07 | 66250 | 19.05 | 0.07 | 66202 | 0.03 | 0.6% | 0.1% |
| P4 | 19.32 | 0.08 | 103940 | 19.29 | 0.08 | 103120 | 0.03 | 0.0% | 0.8% |
| P5 | 24.25 | 0.10 | 95242 | 24.21 | 0.10 | 94117 | 0.04 | 0.2% | 1.2% |
| P6 | 29.99 | 0.08 | 64337 | 29.93 | 0.08 | 65571 | 0.06 | 1.4% | 1.9% |
| P7 | 35.98 | 0.09 | 235272 | 35.92 | 0.09 | 235951 | 0.06 | 0.1% | 0.3% |
| P8 | 41.89 | 0.09 | 393689 | 41.85 | 0.09 | 395706 | 0.04 | 0.2% | 0.5% |

TABLE 3

| Time (min) | % A | % B |
|---|---|---|
| 0 | 99.9 | 0.1 |
| 5 | 99.9 | 0.1 |
| 47 | 50.0 | 50.0 |
| 48 | 0.1 | 99.9 |
| 54 | 0.1 | 99.9 |
| 55 | 99.9 | 0.1 |
| 60 | 99.9 | 0.1 |

Figure 5:
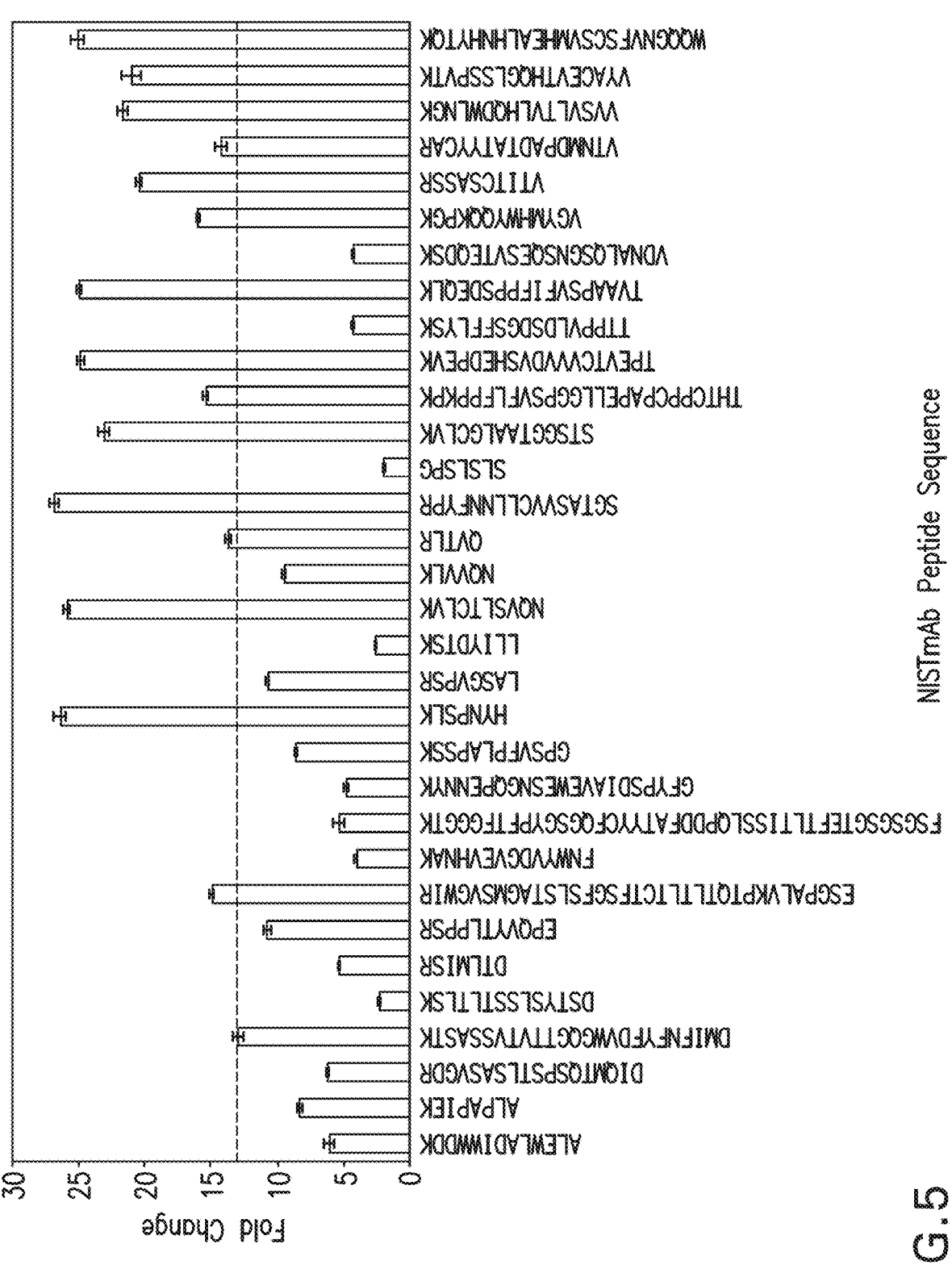
FIG. 5 shows the reproducibility of boosting by 2 mM glycine in TFA buffers with 0.25 µg loading NISTmAb. The following peptides are shown in FIG. 5: ALEWLADI-VWVDDK (SEQ ID NO: 3), ALPAPIEK (SEQ ID NO: 4), DIQMTQSPSTLSASVGDR (SEQ ID NO: 34), DMIFNFYFDVWGQGTTVTVSSASTK (SEQ ID NO: 5), DSTYSLSSTLTLSK (SEQ ID NO: 6), DTLMISR (SEQ ID NO: 7), EPQVYTLPPSR (SEQ ID NO: 8), ESGPALVKPTQTLTLTCTFSGFSLSTAGMSVGWIR (SEQ ID NO: 9), FNVVYVDGVEVHNAK (SEQ ID NO: 10), FSGSGSGTEFTLTISSLQPDDFA-TYYCFQGSGYPFTFGGGTK (SEQ ID NO: 11), GFYPS-DIAVEWESNGQPENNYK (SEQ ID NO: 12), GPSVF-PLAPSSK (SEQ ID NO: 13), HYNPSLK (SEQ ID NO: 14), LASGVPSR (SEQ ID NO: 15), LLIYDTSK (SEQ ID NO: 16), NQVSLTCLVK (SEQ ID NO: 17), NQVVLK (SEQ ID NO: 18), QVTLR (SEQ ID NO: 19) SGTASVVCLLNNFYPR (SEQ ID NO: 20), SLSLSPG (SEQ ID NO: 21), STSGGTAALGCLVK (SEQ ID NO: 22), THTCPPCPAPELLGGPSVFLFPPKPK (SEQ ID NO: 23), TPEVTCVVVDVSHEDPEVK (SEQ ID NO: 24), TTPPVLDSDGSFFLYSK (SEQ ID NO: 25), TVAAPSVFIFPPSDEQLK (SEQ ID NO: 26), VDNALQSGNSQESVTEQDSK (SEQ ID NO: 27), VGYMHVVYQQKPGK (SEQ ID NO: 28), VTITCSASSR (SEQ ID NO: 29), VTNMDPADTATYYCAR (SEQ ID NO: 30), VVSVLTVLHQDWLNGK (SEQ ID NO: 31), VYACEVTHQGLSSPVTK (SEQ ID NO: 32), and WQQGNVFSCSVMHEALHNHYTQK (SEQ ID NO: 33).

FIG. 5 is a bar graph illustrating the reproducibility of boosting by 2 mM glycine in TFA buffers with 0.25 μg loading NISTmAb with 10 replicates of each sample. A peptide-dependent response boosting was observed, and the fold boosting of different tryptic peptides was across a wide range of 2-27 folds with approximately 13.2 folds on average. Most of the peptides exhibited the response boosting of at least 5-fold with more than half of the peptides showing TABLE 4-continued

| | | Signal-to-noise Ratio | | |
| Representative Peak | Retention Time (min) | TFA Control | TFA with Glycine | Fold Increase |
|---|---|---|---|---|
| P5 | 27.7 | 17 | 174 | 10.2 |
| P6 | 29.5 | 17 | 167 | 9.8 |
| P7 | 30.6 | 25 | 214 | 8.6 |
| P8 | 33.5 | 10 | 51 | 5.1 |
| P9 | 37.9 | 8 | 97 | 12.1 |
| P10 | 41.1 | 14 | 68 | 4.9 |

Figure 7:
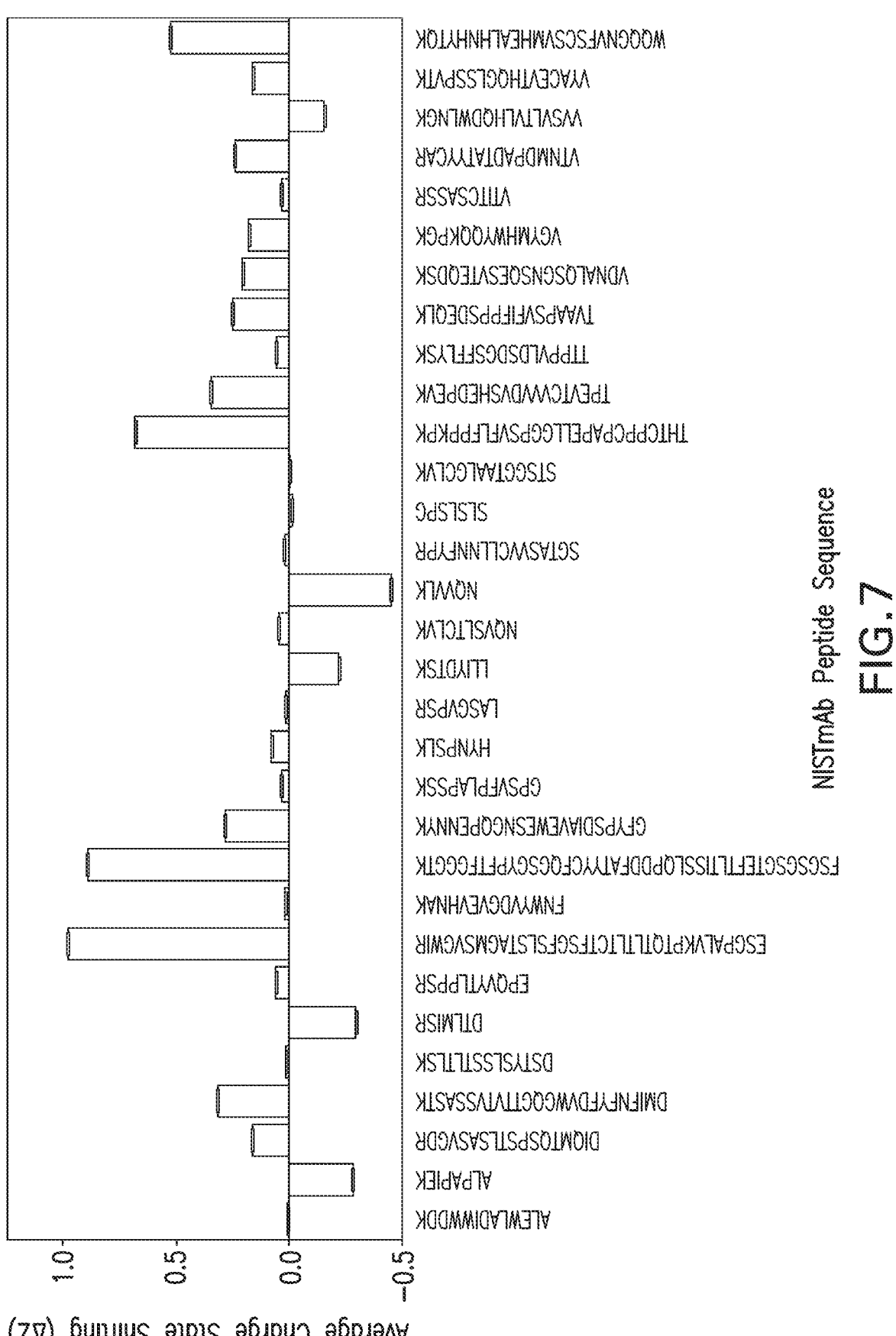
FIGS. 7, 8A and 8B show charge state shifting with glycine present. The following peptides are shown in FIG. 7: ALEWLADIVWVDDK (SEQ ID NO: 3), ALPAPIEK (SEQ ID NO: 4), DIQMTQSPSTLSASVGDR (SEQ ID NO: 34), DMIFNFYFDVWGQGTTVTVSSASTK (SEQ ID NO: DSTYSLSSTLTLSK (SEQ ID NO: 6), DTLMISR (SEQ ID NO: 7), EPQVYTLPPSR (SEQ ID NO: 8), ESGPALVKPTQTLTLTCTFSGFSLSTAGMSVGWIR (SEQ ID NO: 9), FNVVYVDGVEVHNAK (SEQ ID NO: 10), FSGSGSGTEFTLTISSLQPDDFA-TYYCFQGSGYPFTFGGGTK (SEQ ID NO: 11), GFYPS-DIAVEWESNGQPENNYK (SEQ ID NO: 12), GPSVF-PLAPSSK (SEQ ID NO: 13), HYNPSLK (SEQ ID NO: 14), LASGVPSR (SEQ ID NO: 15), LLIYDTSK (SEQ ID NO: 16), NQVSLTCLVK (SEQ ID NO: 17), NQVVLK (SEQ ID NO: 18), QVTLR (SEQ ID NO: 19) SGTASVVCLLNNFYPR (SEQ ID NO: 20), SLSLSPG (SEQ ID NO: 21), STSGGTAALGCLVK (SEQ ID NO: 22), THTCPPCPAPELLGGPSVFLFPPKPK (SEQ ID NO: 23), TPEVTCVVVDVSHEDPEVK (SEQ ID NO: 24), TTPPVLDSDGSFFLYSK (SEQ ID NO: 25), TVAAPSVFIFPPSDEQLK (SEQ ID NO: 26), VDNALQSGNSQESVTEQDSK (SEQ ID NO: 27), VGYMHVVYQQKPGK (SEQ ID NO: 28), VTITCSASSR (SEQ ID NO: 29), VTNMDPADTATYYCAR (SEQ ID NO: 30), VVSVLTVLHQDWLNGK (SEQ ID NO: 31), VYACEVTHQGLSSPVTK (SEQ ID NO: 32), and WQQGNVFSCSVMHEALHNHYTQK (SEQ ID NO: 33). Studies performed using a peptide with the amino acid sequence of SEQ ID NO: 9 is shown in FIG. 8A, and a peptide with residues of SEQ ID NO: 18 in FIG. 8B.
Figure 8A:
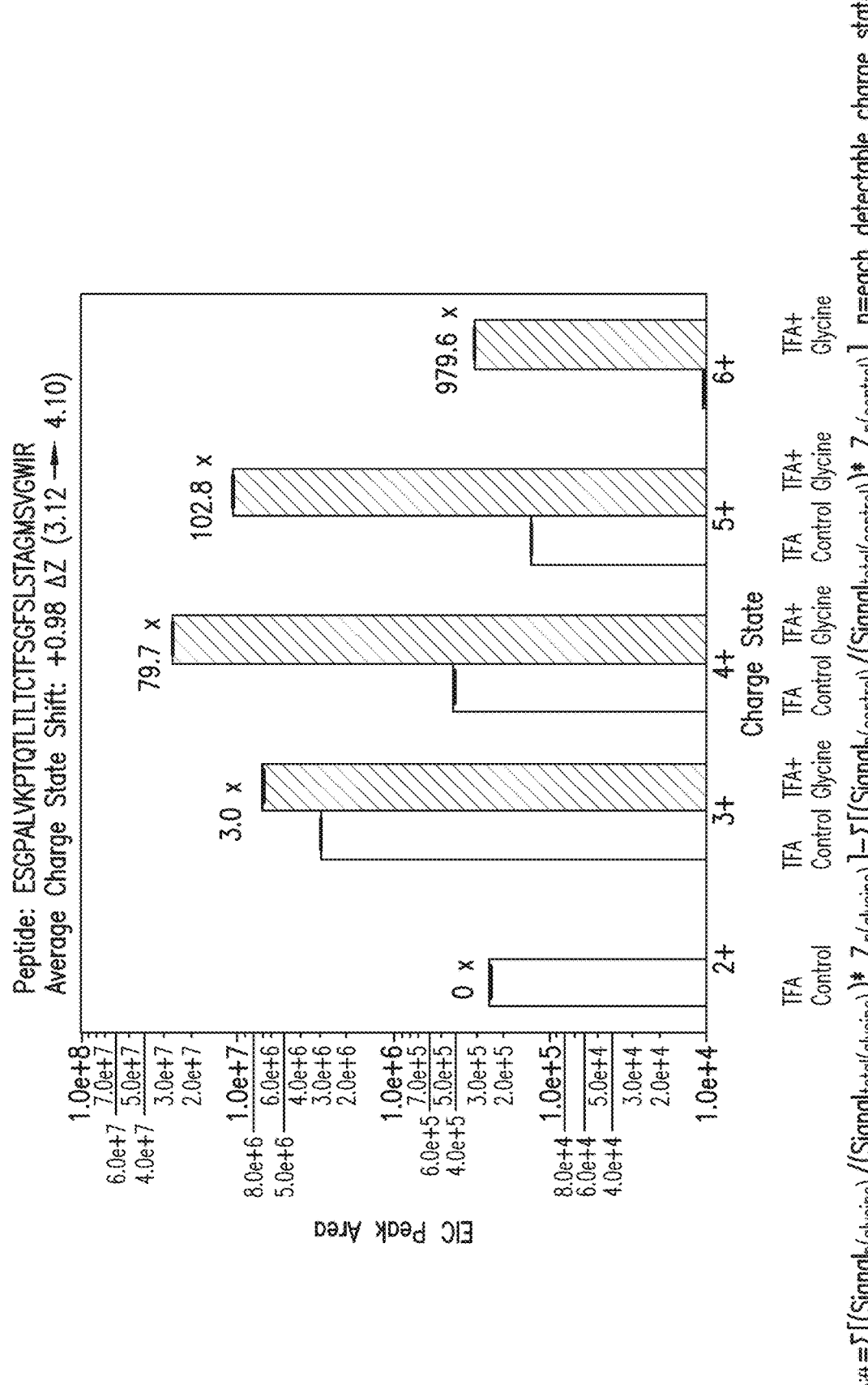
Figure 8B:
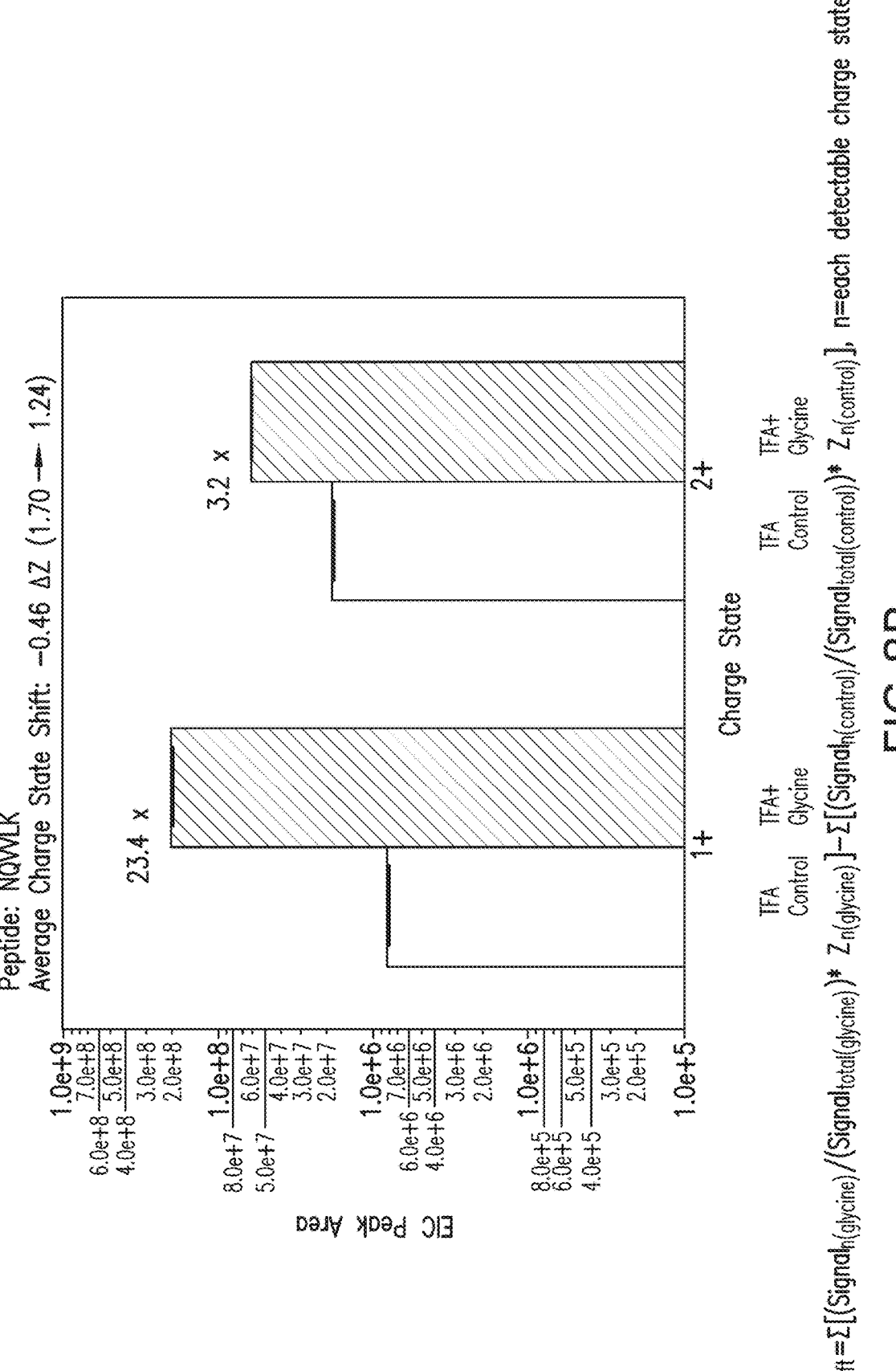
Figure 9:
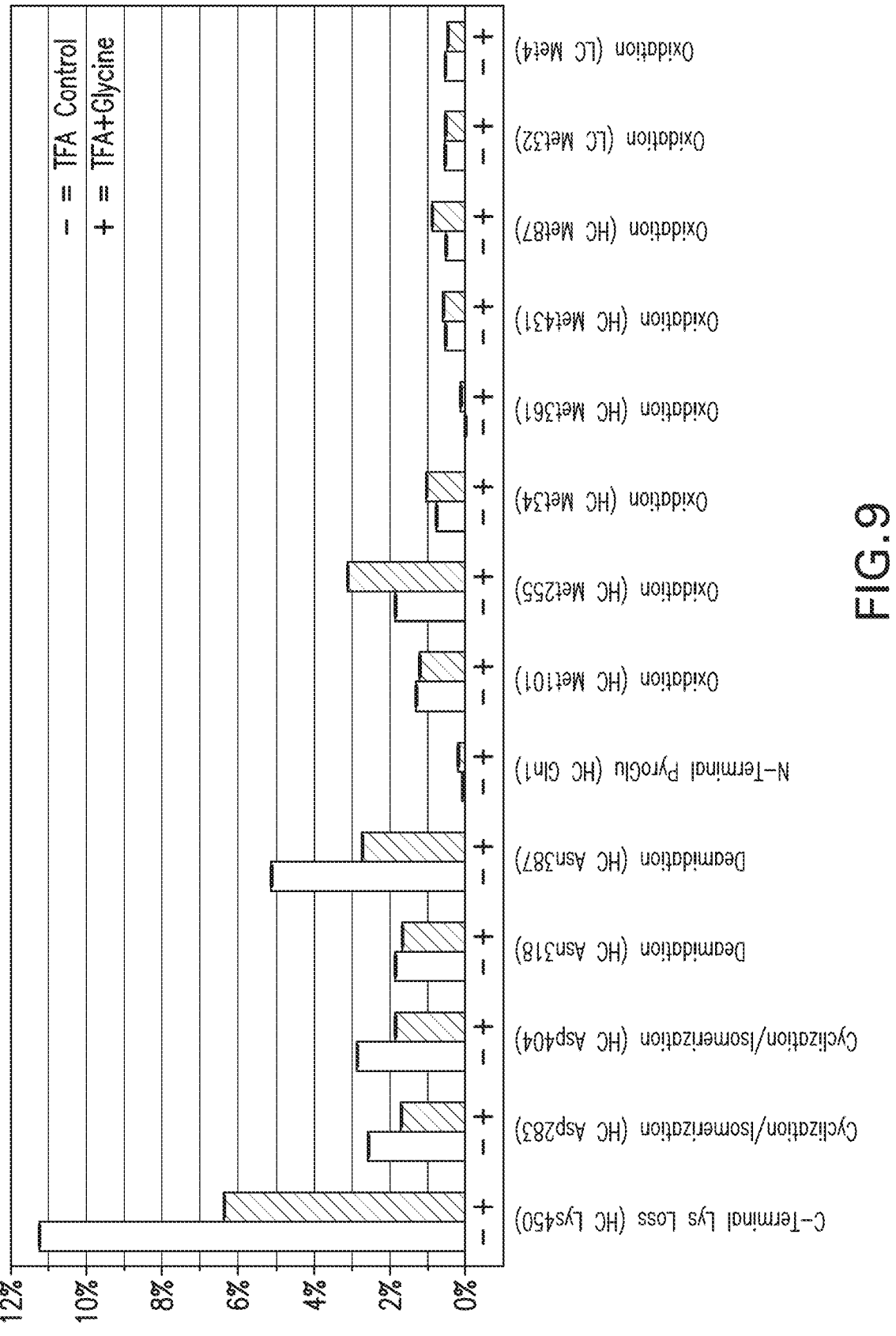
FIG. 9 shows PTM % quantitation in the presence and absence of 2 mM glycine (TFA buffers, 0.25 µg NISTmAb loading).
Figure 10:
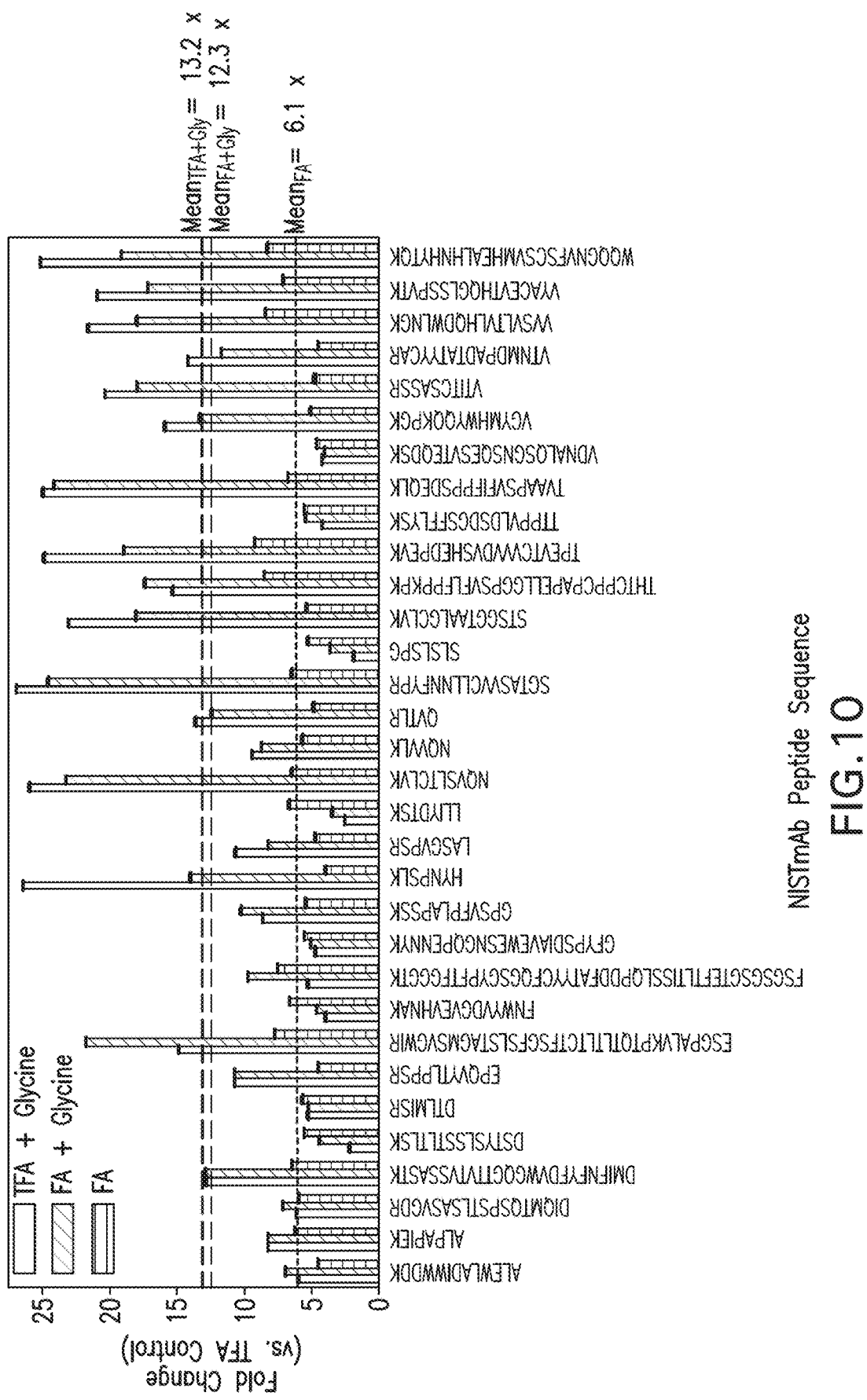
FIG. 10 shows fold boosting by the presence of glycine with TFA or FA or FA alone versus TFA control. Peptides with the following residues are shown in FIG. 10.

FIGS. 7, 8A and 8B bar graphs illustrating charge state shifting with glycine present. % RSD was less than 0.4% for all peptides; 10 replicates. The average charge state shifting was peptide dependent, and both upward shifting and downward shifting were observed. FIG. 9 is a bar graph illustrating PTM % quantitation in the presence and absence of 2 mM glycine (TFA buffers, 0.25 μg NISTmAb loading), 10 replicates. FIG. 10 is a bar graph illustrating fold in boosting by the presence of glycine with TFA or FA or FA alone versus TFA control, 3 replicates. As shown in FIG. 10, TFA in the presence of 2 mM glycine resulted in a 13.2× boost as compared to 12.3× boost observed with FA in the presence of 2 mM glycine or 6.1× with FA.

FIG. 11 is a graph illustrating fold boosting of individual amino acids with 2 mM glycine (Colum: Discovery HS F5-3, 15 cm×2.1 mm, 3 μm (Supelco); 1 nmol loading of each amino acid). FIG. 12 illustrates the effect of trace sodium in commercial glycine formulations.

ESI-MS Signal Boosting with Glycine Additive for Protein Quantitation was evaluated. FIG. 13 provides a comparison between quantification of STSGGTAALGCLVK peptide (SEQ ID NO: 22) using PRM and Full scan. The same response linear range across three orders of magnitude was observed for TFA and FA with glycine mobile phases with the similar regression slope to TFA and FA control mobile phases, indicating the consistent response boosting of glycine additive in a broad protein concentration. Due to the response boosting of glycine additive in TFA and FA mobile phases the response linear range also reached to a lower protein concentration compared to TFA and FA control mobile phases. This feature might open up an opportunity to consider glycine-based mobile phases as alternatives to quantify low-abundant proteins in the complex matrices with increased sensitivity.

Example 2: ESI-MS Signal Boosting with Glycine Additive: IP-HILIC-MS-Based Glycopeptide Identification and Quantitation FIG. 14 illustrates the advantages of HILIC based liquid chromatography over reverse phase for glycopeptide analysis. Peptides were prepared by either reduced or non-reduced peptide mapping methods routinely performed. As illustrated in FIG. 14, better separation of glycopeptides was obtained in HILIC whereas clustering of glycopeptides was observed in reverse phase. For example, increased separation of isomers, such as G1F, was seen with IP-HILIC versus reverse phase. Moreover, glycopeptide elution order on HILIC column was correlated with the size of glycans attached to the peptide making it easy to differentiate the artifacts generated by in-source fragmentation of large glycans from real peak (non-overlapping distinct elution time).

FIG. 15 illustrates signal boost was observed in glycine-added buffer for both MS1 and MS2. Sample was trypsin digested pooled VEGF trap IND lots, column: Waters BEH-Amide and Mobile Phase: A: 0.1% TFA and B: 80% ACN+0.1% TFA. FIG. 16 illustrates high concentration of glycine prevented binding.

FIG. 17 provides an exemplary sample preparation workflow schematic for glycopeptide analysis through HILIC based LC. FIG. 18 illustrates the effect of desalting in which desalting with SepPak 30 cartridge eliminated elevated baseline (see arrow). Eluting peptides with mobile phase B (0.1% TFA in 80% acetonitrile) eliminated drying step after desalting thereby saving time and increasing the efficiency of the process. Studies also revealed that metal adducts could be reduced by using polyethylene solvent container (such as a polyethylene bottle from Belart) during the mobile phases compared to glass bottle. A 2.7× intensity boost and 1.7× intensity boost were observed when using plastic bottle as compared to a glass bottle during the mobile phases. It is believed that the plastic bottle decreased heterogeneity caused by sodium and thus, MS signal was boosted. Additionally, solvent bottles soaked overnight in 60% isopropyl alcohol removed leachable impurities/hardening agents. FIGS. 19 and 20 provide tables illustrating the effect of glycine. FIG. 19 shows that glycine increased the peak area of all glycoforms by 20-fold in IGG1 (*glycoforms in this table were only identified based on tandem MS, in either run;  for the glycoforms that do not have tandem MS data, thus the peak was determine based on the precursor mass and retention time identified in other runs (shown in column labeled Peptide 1_Control). FIG. 20** provides peak area of all glycoforms in an IGG4 molecule (*glycoforms in this table were only identified based on tandem MS, in either run; for the glycoforms that do not have tandem MS data, the peak was determine based on the precursor mass and retention time identified in other runs (shown in column labeled Peptide 2 Control; *the fold change of the glycoform that has the abundance below the LLOQ in control run will give overestimated number (shown in the brackets)). FIG. 21 provides peak area of all glycoforms in evaluated mAbs. The relative distribution of all glycoforms remained the same in the presence of glycine. FIG. 22 illustrates enhanced fragmentation capacity by charge state shift in the presence of 1 mM glycine. Major charge state of glycopeptide shifted from +2 to +3, the latter is prone to fragmentation easily. Signal boost with added glycine (1 mM) for VEGF TRAP was observed. Glycine increased the number of peptide spectrum matches (PSM) and glycoforms in VEGF TRAP (see FIG. 23).

Example 3: ESI-MS Signal Boosting with Glycine Additive: Sequence Variants Analysis This example demonstrates the ability of glycine in TFA to increase the number of sequence variants. Number of sequence variants identified when using TFA+glycine as compared to FA following Byologic validation are illustrated in FIG. 24.

Example 4: ESI-MS Signal Boosting with Glycine Additive: Glycan Analysis

Upon released from glycoproteins, N-glycans can be labeled with various fluorescent tags which often also enhance MS response. Labeled or reduced N-glycans can be analyzed by HILIC with mobile phases containing salts e.g. ammonium formate. Glycine, 1 mM in mobile phases, was found to boost MS signals of PROCA labeled N-glycans from human serum (3-over 50 folds) (refer to FIG. 25 and FIGS. 26A-26C). Glycine had stronger effect on high mannose and large acidic N-glycans (>10 folds). Using ammonium formate mobile phases without glycine, the MS profile of PROCA labeled N-glycans showed some difference from FLR profile which is widely used for glycan quantitation (refer to FIG. 27 and FIGS. 28A-28C). High mannose and large N-glycans with three sialic acids had relatively lower MS signals whereas bisecting N-glycans had relatively higher MS signals by comparing MS and FLR profiles. By adding glycine in mobile phases, the MS signals were not only higher but also more comparable to FLR (refer to FIG. 27 and FIGS. 28A-C). FIG. 29 shows the scatter plot of serum N-glycan with PROCA label EIC peak areas versus FLR peak areas (logarithm scale) in control and glycine containing condition. The smaller R square value of linear regression for the glycine condition compared to that for the control condition demonstrates that glycine can improve accuracy of N-glycan quantitation using MS signals. Strong signal boosting effect by glycine on PROCA labeled N-glycans can also be observed using mobile phases containing 0.1% FA (3-38 folds) (refer to FIGS. 30A-30C). Glycine also showed moderate signal boost effect on RapiFluor labeled N-glycans and small reduced N-glycans (1-3 folds) using ammonium formate mobile phases (refer to FIGS. 31A-31C and FIG. 32). Inhibitory effect on larger reduced N-glycans was observed (FIG. 32). Relative levels of large RapiFluor labeled N-glycans based on MS peak areas and FLR peak areas were more comparable using glycine condition compared to that under control condition (FIG. 32). FIG. 33 provides exemplary LC-FLR-MS conditions for analysis of N-glycans.

Unlike N-glycans, there is no satisfactory O-glycan releasing method due to the lack of releasing enzyme and challenges in releasing efficacy and O-glycan reducing end decomposition through chemical release. FIG. 34 provides an exemplary method for O-glycan preparation and analysis by LC-MS and fluorescence (FLR) detection.

FIG. 35 illustrates the result of PROCA labeled O-glycans from bovine submaxillary mucin (BSM) 2 μg on column, fluorescence and optimized reductive amination. FIG. 36 demonstrates that the PROCA-labeled O-glycan FL and MS TIC profiles are highly comparable. PROCA labeled O-glycans released from BSM run on HILIC (equals to 2 μg on column). Low MS background was observed. Glycine, 1 mM in mobile phases, was found to boost effect on PROCA labeled BSM O-glycans purified from beads (2 μg on column, FIGS. 37A-B). FIGS. 37A-37B provides the results from comparing O-glycans FLR and MS peak intensities with and without glycine in mobile phases. Compared to FLR, PROCA signals drop significantly with the increase of glycan size. Glycine compensated this effect and made the MS signals more comparable to FLR intensities (FIGS. 37A-37B). Glycine had moderate boosting effect (1-3 folds) for small (1-2 sugar rings)—O-glycans-(refer to FIGS. 38A-38C). Glycine had strong boosting effects for larger and/or acidic glycans (3-over 35 folds) labeled with PROCA (refer to FIG. 38A). The effects were strong for those carrying two sialic acids (>35 folds). Glycine was observed to have a moderate boosting effect for 2AB labeled BSM O-glycans (<3 folds) (refer to FIG. 38B). MS-signals of small reduced can be boosted by glycine up to 12 folds (Refer to FIG. 38C). However, inhibitory effect on larger reduced O-glycans was observed. FIG. 39 provides exemplary LC-FLR-MS conditions for analysis of PROCA labeled or reduced O-glycans. FIG. 40 illustrates that singly charged glycan provides poor MS2 in the absence of glycine. FIG. 41 illustrates that doubly charged ions from glycine-boosted sample provides greatly enhanced MS2 information.

Example 5: Glycine Additive in Trifluoroacetic Acid-Containing Mobile Phases Facilitates Site-Specific Glycosylation Profiling of Biopharmaceuticals by Ion-Pairing Hydrophilic Interaction Chromatography Mass Spectrometry Many biotherapeutics such as monoclonal antibodies (mAb) and Fc-domain fusion proteins contain heterogeneous glycan contents at one or multiple glycosylation site(s). Site-specific glycan profile characterization was critical for monitoring the quality of these molecules during different stages of drug development. Ion-pairing hydrophilic interaction chromatography (IP-HILIC) as an orthogonal separation method to reversed-phase liquid chromatography (RPLC) can achieve better separation between individual glycoforms as well as identification of glycopeptides from the non-glycosylated peptides. However, an online IP-HILIC coupled to mass spectrometry detection may suffer from the suppression of mass spectrometry signal during electrospray ionization due to the trifluoroacetic acid (TFA) commonly used as an ion-pairing agent. In this example, reported is an optimized condition for IP-HILIC-MS where glycine is added in the TFA-containing mobile phases to enhance the MS detection sensitivity for glyco-peptides up to approximately 50-fold by eliminating the ion-suppression effect of an ion-pairing agent while still retaining excellent separation capacity. It is demonstrated that with enhanced detection sensitivity IP-HILIC-MS can identify an increased number of site-specific N-linked glycans for IgG1 and IgG4 mAbs as well as a Fc-domain fusion protein (containing five N-glycosylation sites) and achieve comparable quantitative results compared to the traditional method by using RPLC mass spectrometry (RPLC-MS). It is also demonstrated that IP-HILIC-MS can be used to identify low level O-glycosylation and non-consensus N-glycosylation on mAbs without any enrichment prior to LC-MS analysis.

I. Introduction

Glycosylation is a critical quality attribute of biotherapeutics including monoclonal antibodies (mAb) and Fc-domain (fragment crystallization domain) fusion proteins. The Fc domain glycosylation profile at the conserved asparagine-297 site is strongly associated with effector functions such as antibody-dependent cellular cytotoxicity (ADCC) and complement-dependent cytotoxicity (CDC), which can impact the drug efficacy in oncology therapy. Although Fc N-glycosylation is not directly involved in interaction with the targets, N- or O-linked glycans at a non-canonical site that is often located in the Fab (antigen-binding fragment) region of a mAb or functional domains of a Fc-domain fusion protein may have a negative impact on the binding affinity to the targets. Glycosylation in biotherapeutics is also correlated with pharmacokinetic and pharmacodynamics profiles and other molecular properties such as charge heterogeneity, stability, and immunogenicity. Because glycosylation of mAb or Fc-domain fusion proteins often exhibit versatile profiles in different protein expression systems, manufacturing processes, and protein sequences, a comprehensive characterization of the site-specific glycan profile includes a series of pivotal tasks including demonstration of glycan profile comparability amongst different sample lots, or investigation of the root cause for glycosylation-related issues during nonclinical development of biopharmaceuticals.

N-linked glycosylation profiling can be carried out by sequentially releasing the glycans from proteins via exoglycosidase treatment, labeling the reduced termini with fluorescence reagents and analyzing the released glycan mixture using hydrophilic interaction chromatography coupled to fluorescence and mass spectrometry detection (HILIC-FLR-MS), however it cannot provide information on the site-specific glycosylation if the protein contains multiple glycosylation sites. Instead, a direct analysis of intact glycopeptides can reveal site-specific glycosylation profiles for both N- and O-linked glycans. In a typical workflow of glycopeptide identification, protein is digested with protease and analyzed using reversed-phase chromatography (RPLC) coupled to mass spectrometry. It is an approach used for characterization of biopharmaceuticals to confirm the protein amino acid sequence and provide site-specific quantitation upon post-translational and chemical modifications including glycosylation (often referred to as "peptide mapping"). Relative abundances of individual glycans can be quantified based on the peak areas of extracted ion chromatograms (EIC) of corresponding glycopeptides. However, RPLC-based glycopeptide separation mainly relies on the amino acid sequence as glycan compositions have little contribution to the hydrophobicity difference, which may result in the following: (1) glycoforms from the peptide with the same amino acid sequence are eluted as a cluster of peaks whose retention times are close to each other; (2) glycopeptides may not be well-distinguished from other non-glycosylated peptides if their peptide sequences have similar hydrophobicity. For instance, the MS signal of a low abundance glycopeptide from an atypical N- or O-linked glycosylation site can be considerably suppressed in the presence of co-eluting high abundance interference species from other glycopeptides or non-glycosylated peptides due to limit of MS detection dynamic range and column loading capacity.

In contrast with RPLC, HILIC implements an effective separation for glycans of different compositions and structural isomers. HILIC coupled to mass spectrometry has been used for analyzing N-glycans released from single biotherapeutics or glycomics analysis in different types of complex samples. Intact glycopeptide analysis using HILIC-MS that was performed under a mild acidic condition were also reported for antibodies and other glycoproteins, which exhibited an excellent separation for different glycoforms including glycan isomers. Glycopeptides can be better separated from non-glycosylated peptides by simply altering the HILIC mobile phases with addition of 0.1% TFA, which provides an acidic environment (pH approximately 2) and a strong ion-paring property (TFA anion). Under this condition, the charged groups across the peptides can be neutralized, highly reducing the hydrophilicity of non-glycosylated peptides, while the glycopeptides are less affected as glycans are rich with uncharged polar moieties such as hydroxyl groups. Although ion-paring HILIC (IP-HILIC) separation has become a standard technique for offline glycopeptide enrichment in myriad glycoproteomic studies, it is rare to directly couple IP-HILIC with MS detection for glycopeptide identification due to an adverse signal suppression caused by the ion-pairing agent TFA, which may cause a 5- to 10-fold reduction in MS signal compared with formic acid at the same concentration. Therefore, recovering unwanted ion suppression is key for extending the application scope in a TFA-involved IP-HILIC-MS approach.

Numerous efforts to mitigate the TFA-related MS signal suppression were made in the past decades, ranging from introducing a post-column "fix solution" to substituting TFA with other "weaker ion-paring" agents. A method was discovered by direct addition of glycine to the TFA-containing mobile phases, resulting in significant improvement of approximately 1 order of magnitude for signal-to-noise ratios (S/N) in the peptide mapping of mAbs using a reserved-phase C18 column. Although the glycine additive was introduced prior to the column, it did not affect the performance of peptide separation on the C18 column. In the present example, it is demonstrated that this solution can also be applied to IP-HILIC-MS, which allows one to build up a highly sensitive and sustainable platform for unbiased site-specific glycosylation profiling for monoclonal antibodies or Fc-domain fusion proteins. Also disclosed is a unique example that this platform can selectively enhance the possibility to identify extremely low-abundance O-linked and non-consensus N-linked glycosylation in the Fab region of mAbs, without extra offline enrichment prior to LC-MS analysis.

II. Materials and Experiments

Chemicals and Materials

Four IgG4 monoclonal antibodies (mAb1, mAb2, mAb3, mAb4), an IgG1 monoclonal antibody (mAb5) and an Fc-domain fusion protein (fP1) were produced at Regeneron (Tarrytown, NY). Ultrapure Glycine (J.T. Baker brand), trifluoroacetic acid (sequencing grade), formic acid (sequencing grade) and acetonitrile (LC-MS grade) were purchased from Thermo Fisher Scientific (Waltham, MA). Ammonium formate (99%) was purchased from Acros Organics™. PNGase F was purchased from New England Biolabs (Ipswich, MA). GlycoWorks™ rapid deglycosylation kit was purchased from Waters (Milford, MA). Ultrapure water was generated by Milli-Q System (Millipore, Burlington, MA). All other chemicals were purchased from Sigma-Aldrich (St. Louis, MO) unless otherwise noted.

Trypsin Digestion

To prepare protein digests, monoclonal antibodies were denatured and reduced in solution containing 5 mM acetic acid and 5 mM tris (2-carboxyethyl phosphine hydrochloride) by heating at 80° C. for 10 minutes. Each sample was then neutralized into 100 mM Tris buffer, pH 8.0, containing 15 mM iodoacetamide, followed by trypsin digestion at an enzyme-to-substrate ratio of 1:20 (w/w) at 37° C. in the dark for 2 hours. For the Fc-domain fusion protein, the protein was reduced and denatured in the presence of 8 M of guanidine-HCl and 5 mM dithiothreitol by heating at 80° C. for 10 minutes, followed by alkylation with 15 mM iodoacetamide. Sample was buffer-exchanged to 100 mM Tris, pH 8.0, using NAP-5 Sephadex 5-25 column (GE Healthcare, Chicago, IL) and then digested under the same digestion condition as monoclonal antibodies. Digested peptides were further cleaned up through Sep-Pak C18 cartridges (Waters) following the vendor-provided protocol. Samples were dried under vacuum and reconstituted into 80% ACN (for HILIC-MS) or water (for RPLC-MS).

LC-MS Analysis of Glycopeptides

All LC-MS experiments were performed using an Acquity UPLC I-Class System (Waters) coupled to a Q-Exactive Plus Hybrid Quadrupole-Orbitrap Mass Spectrometer equipped with a heated electrospray ionization (HESI) source (Thermo Fisher Scientific). To minimize the formation of alkali adducts, all samples were transferred into polypropylene vials made for injection, mobile phase solutions were prepared and stored in polyethylene bottles and the LC lines were thoroughly cleaned in advance. Mobile phase A (MPA) is a pure aqueous phase containing 100% water (v/v), TFA or FA (v/v) and 1 mM glycine. Mobile phase B (MPB) was composed of 80% acetonitrile (v/v), 20% water (v/v), 0.1% TFA or FA (v/v) and 1 mM glycine. The glycine-free version of MPA and MPB were also made using the exact same recipe with equivalent amount of water instead of adding glycine.

Prior to the first sample injection after switching mobile phases between the glycine-in and glycine-free version, LC system was conditioned for at least 1 hour and the intensity of MS peak for protonated glycine at 76.07 m/z was monitored (scan range 50-750 m/z) for quality control purpose, stable MS signals were expected to reach normalized intensity at $1e^6$ and $1e^9$ for the mobile phases without and with glycine, respectively.

For HILIC-MS analysis, 6 μg (or larger amount if annotated) of desalted tryptic digested peptides was loaded onto a Waters Acquity UPLC Glycan BEH Amide column (130 Å, 1.7 μm, 2.1 mm×150 mm). The flow was initiated with 99.9% MPB at 0.2 mL/min and glycan-containing peptides were eluted and separated when percentage of MPB was decreased from 90% to 62.5%. For RPLC-MS analysis, samples were loaded onto a Waters Acquity UPLC BEH C18 column (130 Å, 1.7 µm, 2.1 mm×150 mm). The setup of mobile phases for RPLC-MS analysis is completely identical to HILIC-MS, but oppositely, the flow began at 99.9% MPA, and peptides were eluted when percentage of MPB was increased from 0.1% to 40%. Full MS scans were collected from 500 to 2000 m/z to avoid the glycine signals, resolution=70,000, AGC target=1e$^6$, maximum IT=100 ms, sheath gas=40, aux gas=10, sweep gas=0, spray voltage=3.8 kV, capillary temperature=350° C., aux gas heater temperature=250° C., S-lens RF level=50. Five most abundant precursors were selected for data-dependent MS2 scan, where NCE was set to 27, resolution=17,500, AGC target=5e$^5$, maximum IT=250 ms.

Data Processing for Glycopeptide Identification

Glycopeptide identification was performed using Byonic software in Protein Metrics suite by searching the raw files against protein sequence and a build-in glycan database containing 132 human N-linked glycans or 70 common O-linked glycans. For non-consensus N-glycan search, the same N-glycosylation database was customized to eliminate the site restriction following vendor-provided technique note. The preliminary list of unique glycopeptides was generated by filtering against 1% FDR. The list of precursors as well as the original searching result as a spectra library were then imported into Skyline Daily software (University of Washington, WA) for a full scan-based final ID validation and quantification through an automatic feature extraction and peak integration.

HILIC LC-MS analysis of derivatized glycans

To prepare samples for released N-linked glycan analysis, protein was denatured and reduced in a solution containing 0.1% RapiGest™ SF (Waters) and 4.2 mM Tris (2-carboxyethyl phosphine hydrochloride (TCEP-HCl) by heating at 80° C. for 10 minutes. Each sample was then deglycosylated by addition of PNGase F at an enzyme-to-substrate ratio of 1:5 (w/w) and incubation at 45° C. for 25 minutes to release the oligosaccharides, followed by derivatization of released glycans with RapiFluor™-MS Reagent (Waters) fluorescent tag through incubation at for 25 minutes. The derivatized samples were diluted in a final solution containing 25% N,N-dimethylformamide and 53% acetonitrile (v/v).

Data acquisition were executed using an Acquity UPLC I-Class System (Waters) coupled to a Q-Exactive Plus Hybrid Quadrupole-Orbitrap Mass Spectrometer (Thermo Fisher Scientific). 1 µg of released and derivatized glycan was loaded onto an Acquity UPLC Glycan BEH Amide column (130 Å, 1.7 µm, 2.1 mm×150 mm) (Waters). Mobile phase A is a pure aqueous phase containing 50 mM ammonium formate in water, pH=4.4. Mobile phase B is a pure organic phase (100% acetonitrile). Gradient began from 25% mobile phase A followed by increasing percentage of mobile phase A up to 32.2% in order to elute all the derivatized glycans. MS parameters were set as follow: full scan m/z range=650-2000, ACG target=1e$^6$, maximum IT=100 ms, resolution=source temperature=350° C., spray voltage=4.0 kV, aux gas heater temperature=250° C., S-lens RF level=50. Five most abundant precursors were selected for data-dependent MS2 scan, where ACG target=1e$^5$, maximum IT=250 ms, Stepped NCE=13, 20, resolution=17,500.

The monosaccharide compositions of the glycans were assigned based on the experimental mass measured for each glycan; the structures of glycans were assigned based of the match of the MS/MS fragmentation spectra to the theoretical fragmentation patterns predicted by the glycan structures in the UniCarbKB database.

III. Results and Discussion

Identification and Relative Quantification of Glycoforms for Monoclonal Antibodies.

Trypsin digestion of an IgG4 molecule generates a peptide containing the conserved N-glycosylation site (EEQFN-STYR (SEQ ID NO: 45), referred to as N297) with variable glycans and along with ~50 non-glycosylated peptides. The presence of 1 mM of glycine in the mobile phase (pH=2.0) significantly recovers the overall MS signals for IgG4 digest (mAb1) without affecting the elution profile of IP-HILIC including the peak width and retention time, as shown in FIG. 42A. The UV chromatograms acquired from TFA mobile phases with and without glycine are also identical (FIG. 42B). Observation from either of these two conditions, the entire elution profile can be divided into two distant regions, containing the peaks from non-glycosylated peptides and glycopeptides, respectively. It is also noted that different glycopeptides on the HILIC column are much better separated compared to the non-glycosylated peptides. The non-glycosylated peptide region (1-13 minutes) of mAb1, for instance, does not exhibit any resolved features for the first 11 min and only shows a limited number of peaks between 10 min and 13.5 minutes (FIG. 42A), while all peaks in the glycopeptide region (18-25 minutes) are well-resolved due to the hydrophilic difference among glycans.

A similar chromatographic profile is observed for another IgG4 molecule (mAb2). The peak resolution in the glycopeptide region can be independently improved by elongating the linear gradient (92% to 73% of mobile phase B), as shown in FIG. 42C1-42C3. Recovered S/N in the presence of glycine also ensures the quality of tandem mass spectra (exemplified in FIGS. 42D and 42E), allowing glycopeptides to be assigned confidently without referring to other assays such as the released glycan analysis. Extracted ion chromatograms of the most abundant 18 glycoforms of mAb1 from the data acquired with the optimized gradient are evenly distributed within 40 min, as shown in FIG. 42F. Each EIC peak representing a different glycan composition has a highly predictable elution time. For instance, an additional galactose (Gal) always caused a 7-minute increment in the elution time, regardless of its glycan composition. It may be a fucosylated core structure with any number of branched N-acetylglucosamine (GlcNAc) or an afucosylated core structure. Besides the well-resolved separation of glycans with different compositions, a baseline separation was also observed for the structure isomers due to a Gal being connected through either of 1,3 or 1,6 linkage with branched GlcNAc (e.g. FA2G1, A2G1). Of note, the elution profile observed from the intact glycopeptides is highly consistent with the elution profile of released glycans acquired under the near neutral pH using the same HILIC column (FIG. 42G), except for two sialic acid-containing glycans FA2G2S1 and FA2G1S1, whose relative elution time are slightly affected most likely due to the protonation of carboxyl acid groups in the presence of TFA.

In contrast to the wide elution time range in IP-HILIC, EIC peaks of the same glycopeptides from an RPLC-MS dataset elute only within a 1.5-minute window, even though the entire linear range for gradient is 80 minutes (FIG. 42H1-42H2). Although such a deficiency in peak separation can be still used for glycopeptide identification because of the high scan rate and sensitivity in prevailing state-of-the-art mass spectrometers, an improved separation always gains advantages in terms of reducing dynamic range of the co-eluting peptides and achieving more accurate peak integration. In addition, the artificial glycopeptides generated during in-source fragmentation, which have the same retention time as the larger glycoforms they are generated from, can be readily ruled out from the same pre-existing glycopeptides using IP-HILIC due to their different retention times, while this might be challenging for RPLC due to its inadequate separation (FIG. 42H1-42H2).

The level of S/N enhancement of glycine may vary for different peptide sequences or different peptide-to-glycine molar ratios. For a given sequence (EEQFNSTYR; SEQ ID NO: 45), all glycopeptides exhibit a similar S/N improvement that is independent of the glycan compositions and the relative abundance of individual glycoforms, illustrated by an excellent linearity ($R^2$=0.998) of plotting EIC peak areas for individual glycoforms of mAb1 under the two conditions (FIG. 43A). The consistency in signal boosting results in highly comparable percentage levels for different glycoforms quantified under two conditions, as shown in FIGS. 43B and 43C. This result suggests that TFA mainly suppresses the signal by forming ion-paring between TFA anion and the primary amine, which can only be found in amino acids instead of the sugar chains.

An average S/N boosting for the glycopeptides in an IgG4 is approximately 19.4-fold, determined from the intercept of the plot in FIG. 43A. Glycopeptides from an IgG1 were also analyzed and similar features are observed regarding the chromatographic profile as well as the S/N boosting, regardless a single amino acid substitution in the peptide sequence (EEQYNSTYR; SEQ ID NO: 35). The results are summarized in FIGS. 43D1-43D3 and 43E.

Characterization of Site-Specific N-Glycosylation Profile of Fc-Domain Fusion Protein Containing Multiple Glycosylation Sites Fusion protein fP1 contains five N-glycosylation sites including one conserved Fc glycosylation site (Site 1) equivalent to N297 from the mAbs and four additional sites (Site 2-4) located in the functional domains. For an IP-HILIC-MS analysis of the digested peptides, enhanced signal-to-noise ratio in the presence of glycine is pivotal for improved glycopeptide identification, which relies on the yield of fragment ions in MS2 spectra (see FIGS. 43F and 43G for example of tandem mass spectra). To systematically evaluate how glycine additive improves the identification of site-specific glycopeptides for fP1, the searching results from two condition runs were combined and filtered using relatively stringent parameters (Score>150, |LogProb|>2, #PSM≥2), as shown in FIG. 44A (top two panels), exhibiting that both numbers of high confident PSM and identified glycopeptides are improved with a glycine additive. It is observed that glycosylation profiles are different for each site, which are also verified by relative quantification using EIC peak areas (Table 5).

TABLE 5

Measured EIC peak area and relative quantitation for individual glycoforms at each glycosite of Fc-domain fusion protein fP1.

| | | 0.1% TFA + 1 mM Glycine | | | | 0.1% TFA | | | | |
| | | Replicate 1 | | Replicate 2 | | Replicate 1 | | Replicate 2 | | Average |
| Location | Glycan Name | Peak area | Level | Peak area | Level | Peak area | Level | Peak area | Level | fold change |
|---|---|---|---|---|---|---|---|---|---|---|
| Site 1 | | | | | | | | | | |
| | HexNAc | 2.1E+06 | 0.03% | 8.5E+05 | 0.01% | 1.6E+05 | 0.03% | 1.5E+05 | 0.03% | 9.8 |
| | HexNAc(1) dHex(1) | 7.1E+06 | 0.11% | 5.6E+06 | 0.08% | 3.0E+05 | 0.05% | 2.6E+05 | 0.05% | 22.5 |
| | HexNAc(2) Hex(3) | 1.1E+07 | 0.16% | 9.9E+06 | 0.14% | 7.2E+05 | 0.13% | 6.7E+05 | 0.12% | 14.8 |
| | A1 | 9.5E+06 | 0.14% | 1.0E+07 | 0.15% | 7.1E+05 | 0.13% | 6.5E+05 | 0.12% | 14.6 |
| | A1G1 | 1.6E+07 | 0.23% | 1.8E+07 | 0.25% | 1.4E+06 | 0.25% | 1.5E+06 | 0.29% | 11.2 |
| | A2 | 5.2E+08 | 7.75% | 5.1E+08 | 7.37% | 4.6E+07 | 8.18% | 4.4E+07 | 8.09% | 11.5 |
| | A2G1 | 3.1E+08 | 4.63% | 3.1E+08 | 4.50% | 3.4E+07 | 6.05% | 3.4E+07 | 6.25% | 9.2 |
| | A2G2 | 6.2E+07 | 0.92% | 6.2E+07 | 0.90% | 5.2E+06 | 0.93% | 4.7E+06 | 0.88% | 12.5 |
| | FA1 | 1.3E+07 | 0.19% | 1.1E+07 | 0.16% | 1.2E+06 | 0.22% | 9.6E+05 | 0.18% | 11.1 |
| | FA1G1S1 | 6.6E+06 | 0.10% | 6.9E+06 | 0.10% | 6.0E+05 | 0.11% | 5.8E+05 | 0.11% | 11.4 |
| | FA2 | 1.9E+09 | 28.13% | 1.9E+09 | 28.07% | 1.6E+08 | 28.76% | 1.6E+08 | 29.53% | 12.0 |
| | FA2G1 | 2.9E+09 | 42.99% | 3.0E+09 | 43.70% | 2.5E+08 | 44.67% | 2.3E+08 | 43.29% | 12.2 |
| | FA2G2 | 8.4E+08 | 12.44% | 8.4E+08 | 12.13% | 5.2E+07 | 9.32% | 5.3E+07 | 9.80% | 16.0 |
| | FA2G2_Man4 | 3.0E+06 | 0.04% | 2.6E+06 | 0.04% | 2.4E+05 | 0.04% | 2.5E+05 | 0.05% | 11.5 |
| | FA2G2S1 | 3.1E+07 | 0.47% | 2.7E+07 | 0.39% | 2.1E+06 | 0.38% | 2.1E+06 | 0.38% | 13.9 |
| | Man5 | 1.2E+07 | 0.18% | 1.5E+07 | 0.21% | 1.8E+06 | 0.32% | 1.7E+06 | 0.32% | 7.7 |
| | Man8 | 3.2E+06 | 0.05% | 2.8E+06 | 0.04% | 3.1E+05 | 0.05% | 2.9E+05 | 0.05% | 10.1 |
| Site 2 | | | | | | | | | | |
| | HexNAc(2) Hex(3) | 7.3E+07 | 0.53% | 6.7E+07 | 0.47% | 1.7E+06 | 0.25% | 1.5E+06 | 0.24% | 43.7 |
| | A1 | 6.6E+07 | 0.48% | 6.6E+07 | 0.46% | 1.6E+06 | 0.24% | 1.6E+06 | 0.24% | 41.4 |
| | A1G1 | 1.8E+08 | 1.26% | 1.7E+08 | 1.20% | 4.4E+06 | 0.66% | 4.2E+06 | 0.65% | 40.3 |
| | A1G1S1 | 2.7E+08 | 1.92% | 2.8E+08 | 1.98% | 1.0E+07 | 1.56% | 1.0E+07 | 1.60% | 26.5 |
| | A2 | 7.5E+07 | 0.54% | 7.3E+07 | 0.51% | 2.0E+06 | 0.30% | 1.9E+06 | 0.30% | 37.7 |
| | A2G1 | 8.2E+08 | 5.93% | 8.1E+08 | 5.67% | 2.7E+07 | 3.98% | 2.5E+07 | 3.96% | 31.3 |
| | A2G1S1 | 3.9E+08 | 2.81% | 4.0E+08 | 2.84% | 2.9E+07 | 4.30% | 2.7E+07 | 4.28% | 14.1 |
| | A2G2 | 2.2E+09 | 15.80% | 2.2E+09 | 15.57% | 1.2E+08 | 18.19% | 1.2E+08 | 18.24% | 18.5 |
| | A2G2S1 | 4.4E+09 | 31.90% | 4.7E+09 | 33.13% | 2.5E+08 | 36.78% | 2.3E+08 | 36.55% | 19.0 |
| | A2G2S2 | 1.8E+09 | 12.72% | 1.8E+09 | 12.52% | 9.6E+07 | 14.43% | 9.3E+07 | 14.47% | 18.7 |

TABLE 5-continued

Measured EIC peak area and relative quantitation for individual
glycoforms at each glycosite of Fc-domain fusion protein fP1.

| | | 0.1% TFA + 1 mM Glycine | | | | 0.1% TFA | | | | |
| | | Replicate 1 | | Replicate 2 | | Replicate 1 | | Replicate 2 | | Average |
| Location | Glycan Name | Peak area | Level | Peak area | Level | Peak area | Level | Peak area | Level | fold change |
|---|---|---|---|---|---|---|---|---|---|---|
| | A3G1/A2BG1 | 1.4E+07 | 0.10% | 1.4E+07 | 0.10% | 4.3E+05 | 0.06% | 3.8E+05 | 0.06% | 35.7 |
| | A3G2/A2BG2 | 4.6E+07 | 0.33% | 4.8E+07 | 0.34% | 1.5E+06 | 0.23% | 1.3E+06 | 0.21% | 32.6 |
| | A3G3 | 5.1E+07 | 0.37% | 5.1E+07 | 0.36% | 1.4E+06 | 0.21% | 1.5E+06 | 0.23% | 35.1 |
| | FA2G1 | 5.9E+07 | 0.42% | 6.1E+07 | 0.43% | 2.0E+06 | 0.30% | 2.1E+06 | 0.33% | 29.4 |
| | FA2G2 | 3.0E+08 | 2.15% | 3.0E+08 | 2.09% | 1.1E+07 | 1.58% | 1.1E+07 | 1.64% | 28.2 |
| | FA2G2S1 | 7.1E+08 | 5.13% | 7.5E+08 | 5.29% | 2.6E+07 | 3.92% | 2.4E+07 | 3.78% | 29.0 |
| | FA2G2S2 | 1.9E+08 | 1.37% | 1.9E+08 | 1.32% | 7.2E+06 | 1.08% | 7.1E+06 | 1.11% | 26.4 |
| | Man4_A1G1 | 1.7E+08 | 1.26% | 1.9E+08 | 1.31% | 5.9E+06 | 0.88% | 6.1E+06 | 0.95% | 30.1 |
| | Man5_A1G1 | 1.9E+08 | 1.37% | 2.0E+08 | 1.38% | 8.1E+06 | 1.22% | 7.9E+06 | 1.24% | 24.0 |
| | Man5_A1G1S1 | 3.5E+08 | 2.53% | 3.5E+08 | 2.44% | 1.2E+07 | 1.82% | 1.2E+07 | 1.90% | 28.7 |
| | Man4_A1G1S1 | 3.4E+08 | 2.47% | 3.5E+08 | 2.49% | 1.6E+07 | 2.33% | 1.5E+07 | 2.41% | 22.5 |
| | Man4 | 4.1E+07 | 0.29% | 4.1E+07 | 0.29% | 1.1E+06 | 0.16% | 1.0E+06 | 0.16% | 39.0 |
| | Man5 | 1.1E+09 | 8.02% | 1.1E+09 | 7.52% | 3.5E+07 | 5.31% | 3.4E+07 | 5.24% | 31.6 |
| | Man6 + Phosphate | 1.8E+07 | 0.13% | 2.0E+07 | 0.14% | 9.8E+05 | 0.15% | 9.6E+05 | 0.15% | 19.6 |
| Site 3 | | | | | | | | | | |
| | HexNAc(2) Hex(3) | 4.8E+07 | 0.35% | 1.2E+07 | 0.09% | 2.4E+06 | 0.24% | 2.2E+06 | 0.22% | 13.1 |
| | A1 | 2.2E+07 | 0.16% | 1.3E+07 | 0.10% | 1.2E+06 | 0.12% | 1.1E+06 | 0.11% | 15.1 |
| | A1G1S1 | 7.0E+08 | 5.09% | 6.7E+08 | 4.84% | 3.7E+07 | 3.59% | 3.5E+07 | 3.55% | 18.9 |
| | A2 | 8.9E+06 | 0.07% | 9.2E+06 | 0.07% | 4.6E+05 | 0.04% | 4.3E+05 | 0.04% | 20.2 |
| | A2G1 | 1.6E+08 | 1.14% | 1.5E+08 | 1.10% | 7.5E+06 | 0.73% | 7.2E+06 | 0.73% | 20.9 |
| | A2G1S1 | 1.6E+08 | 1.16% | 1.5E+08 | 1.07% | 9.8E+06 | 0.96% | 9.5E+06 | 0.96% | 15.9 |
| | A2G2 | 2.4E+09 | 17.52% | 2.3E+09 | 16.85% | 1.5E+08 | 14.45% | 1.4E+08 | 14.36% | 16.2 |
| | A2G2S1 | 3.0E+09 | 21.88% | 3.1E+09 | 22.45% | 3.4E+08 | 33.54% | 3.3E+08 | 33.59% | 9.0 |
| | A2G2S2 | 4.5E+08 | 3.28% | 4.7E+08 | 3.38% | 4.5E+07 | 4.36% | 4.5E+07 | 4.57% | 10.2 |
| | A3G1/A2BG1 | 2.3E+07 | 0.17% | 2.2E+07 | 0.16% | 1.1E+06 | 0.11% | 9.9E+05 | 0.10% | 21.4 |
| | A3G3 | 3.2E+06 | 0.02% | 3.4E+06 | 0.02% | 2.2E+05 | 0.02% | 2.0E+05 | 0.02% | 15.8 |
| | FA1G1 | 2.1E+07 | 0.15% | 2.1E+07 | 0.15% | 9.5E+05 | 0.09% | 9.1E+05 | 0.09% | 22.5 |
| | FA1G1_Man4 | 3.9E+07 | 0.28% | 3.8E+07 | 0.28% | 2.1E+06 | 0.21% | 2.0E+06 | 0.20% | 18.7 |
| | FA1G1S1 | 4.5E+07 | 0.33% | 4.1E+07 | 0.30% | 2.5E+06 | 0.24% | 2.4E+06 | 0.24% | 17.6 |
| | FA1G1S1_Man4 | 4.9E+07 | 0.36% | 4.9E+07 | 0.36% | 5.9E+06 | 0.57% | 5.5E+06 | 0.55% | 8.6 |
| | FA2G1 | 2.8E+07 | 0.21% | 2.8E+07 | 0.20% | 1.2E+06 | 0.12% | 1.1E+06 | 0.11% | 24.2 |
| | FA2G2 | 2.7E+08 | 2.01% | 3.0E+08 | 2.18% | 1.6E+07 | 1.59% | 1.6E+07 | 1.64% | 17.7 |
| | FA2G2S1 | 6.6E+08 | 4.82% | 7.0E+08 | 5.07% | 4.9E+07 | 4.74% | 4.8E+07 | 4.84% | 14.0 |
| | FA2G2S2 | 8.4E+07 | 0.61% | 8.9E+07 | 0.64% | 5.8E+06 | 0.56% | 5.5E+06 | 0.56% | 15.3 |
| | FA3G1 | 1.8E+06 | 0.01% | 1.8E+06 | 0.01% | 5.2E+04 | 0.01% | 5.0E+04 | 0.01% | 35.3 |
| | Man4 | 2.5E+07 | 0.18% | 2.3E+07 | 0.17% | 1.4E+06 | 0.14% | 1.3E+06 | 0.14% | 17.5 |
| | Man5 | 2.0E+09 | 14.93% | 2.0E+09 | 14.88% | 1.1E+08 | 10.72% | 1.0E+08 | 10.46% | 19.2 |
| | Man7 | 9.2E+06 | 0.07% | 1.1E+07 | 0.08% | 7.6E+05 | 0.07% | 6.9E+05 | 0.07% | 13.8 |
| | Man4_A1G1 | 7.1E+08 | 5.23% | 6.9E+08 | 5.02% | 3.7E+07 | 3.61% | 3.4E+07 | 3.48% | 19.7 |
| | Man4_A1G1S1 | 1.2E+09 | 9.05% | 1.3E+09 | 9.16% | 9.0E+07 | 8.77% | 8.5E+07 | 8.66% | 14.2 |
| | Man5_A1G1 | 5.8E+08 | 4.22% | 6.2E+08 | 4.49% | 3.5E+07 | 3.42% | 3.6E+07 | 3.60% | 16.9 |
| | Man5_A1G1S1 | 9.0E+08 | 6.58% | 9.3E+08 | 6.73% | 7.0E+07 | 6.84% | 6.8E+07 | 6.93% | 13.2 |
| | Man6 + Phosphate | 1.7E+07 | 0.12% | 1.7E+07 | 0.13% | 1.4E+06 | 0.14% | 1.3E+06 | 0.14% | 12.3 |
| Site 4 | | | | | | | | | | |
| | A2G2 | 1.2E+07 | 0.29% | 1.1E+07 | 0.28% | 7.9E+05 | 0.15% | 7.3E+05 | 0.14% | 15.1 |
| | A2G2S1 | 4.1E+07 | 1.03% | 4.2E+07 | 1.03% | 3.7E+06 | 0.69% | 3.6E+06 | 0.71% | 11.3 |
| | FA1 | 8.3E+06 | 0.21% | 8.4E+06 | 0.21% | 3.8E+05 | 0.07% | 3.4E+05 | 0.07% | 23.4 |
| | FA1G1 | 2.2E+07 | 0.55% | 2.2E+07 | 0.55% | 1.1E+06 | 0.21% | 1.0E+06 | 0.20% | 20.9 |
| | FA1G1S1 | 3.8E+07 | 0.96% | 4.0E+07 | 0.99% | 4.0E+06 | 0.76% | 4.0E+06 | 0.78% | 9.8 |
| | FA2G1 | 2.6E+07 | 0.66% | 2.5E+07 | 0.62% | 2.0E+06 | 0.38% | 1.9E+06 | 0.38% | 13.1 |
| | FA2G2 | 8.4E+08 | 21.14% | 8.2E+08 | 20.44% | 6.9E+07 | 13.01% | 6.6E+07 | 12.91% | 12.3 |
| | FA2G2S1 | 2.0E+09 | 50.26% | 2.0E+09 | 50.51% | 3.0E+08 | 57.18% | 2.9E+08 | 56.42% | 6.8 |
| | FA2G2S2 | 6.7E+08 | 16.92% | 7.0E+08 | 17.47% | 1.1E+08 | 21.09% | 1.1E+08 | 21.98% | 6.1 |
| | FA2FG2S1 | 3.1E+07 | 0.77% | 3.1E+07 | 0.77% | 3.3E+06 | 0.62% | 3.4E+06 | 0.66% | 9.3 |
| | FA2FG2S2 | 1.8E+07 | 0.45% | 1.8E+07 | 0.45% | 1.7E+06 | 0.32% | 1.7E+06 | 0.34% | 10.6 |
| | FA3G3S1 | 1.6E+08 | 4.02% | 1.6E+08 | 3.95% | 1.2E+07 | 2.24% | 1.2E+07 | 2.32% | 13.5 |
| | FA3G3S2 | 7.3E+07 | 1.82% | 7.3E+07 | 1.80% | 8.2E+06 | 1.55% | 7.5E+06 | 1.47% | 9.2 |
| | FA3G3S3 | 1.3E+07 | 0.32% | 1.3E+07 | 0.33% | 1.5E+06 | 0.28% | 1.6E+06 | 0.32% | 8.4 |
| | Man6 + Phosphate | 2.2E+07 | 0.56% | 2.4E+07 | 0.59% | 7.7E+06 | 1.45% | 6.7E+06 | 1.32% | 3.2 |
| Site 5 | | | | | | | | | | |
| | FA1 | 7.4E+06 | 0.54% | 7.5E+06 | 0.55% | 3.7E+06 | 0.53% | 3.4E+06 | 0.52% | 2.1 |
| | FA1G1 | 2.9E+07 | 2.13% | 2.8E+07 | 2.08% | 1.4E+07 | 2.03% | 1.3E+07 | 1.91% | 2.2 |
| | FA1G1S1 | 3.7E+07 | 2.70% | 3.6E+07 | 2.64% | 1.8E+07 | 2.61% | 1.6E+07 | 2.50% | 2.1 |

TABLE 5-continued

Measured EIC peak area and relative quantitation for individual
glycoforms at each glycosite of Fc-domain fusion protein fP1.

| | | 0.1% TFA + 1 mM Glycine | | | | 0.1% TFA | | | | |
| | | Replicate 1 | | Replicate 2 | | Replicate 1 | | Replicate 2 | | Average |
| Location | Glycan Name | Peak area | Level | Peak area | Level | Peak area | Level | Peak area | Level | fold change |
|---|---|---|---|---|---|---|---|---|---|---|
| | FA2G1 | 3.3E+06 | 0.24% | 3.4E+06 | 0.25% | 1.1E+06 | 0.15% | 1.0E+06 | 0.16% | 3.2 |
| | FA2G2 | 1.2E+08 | 8.87% | 1.2E+08 | 8.83% | 4.2E+07 | 6.11% | 4.2E+07 | 6.37% | 2.9 |
| | FA2G2S1 | 4.9E+08 | 35.51% | 4.8E+08 | 35.21% | 2.4E+08 | 34.75% | 2.2E+08 | 34.11% | 2.1 |
| | FA2G2S2 | 4.5E+08 | 32.55% | 4.5E+08 | 32.80% | 2.6E+08 | 37.71% | 2.5E+08 | 37.65% | 1.8 |
| | FA2FG2S1 | 1.1E+07 | 0.79% | 7.4E+06 | 0.55% | 6.1E+06 | 0.88% | 6.4E+06 | 0.97% | 1.5 |
| | FA2FG2S2 | 9.0E+06 | 0.66% | 8.2E+06 | 0.60% | 4.2E+06 | 0.60% | 5.0E+06 | 0.76% | 1.9 |
| | FA3G3S1 | 4.7E+07 | 3.46% | 5.1E+07 | 3.78% | 1.8E+07 | 2.63% | 1.9E+07 | 2.83% | 2.7 |
| | FA3G3S2 | 5.8E+07 | 4.23% | 6.0E+07 | 4.41% | 2.2E+07 | 3.21% | 2.1E+07 | 3.25% | 2.7 |
| | FA3G3S3 | 2.5E+07 | 1.79% | 2.3E+07 | 1.68% | 1.0E+07 | 1.50% | 1.1E+07 | 1.66% | 2.2 |
| | FA4G4S2 | 6.8E+06 | 0.50% | 6.0E+06 | 0.44% | 3.6E+06 | 0.52% | 3.6E+06 | 0.54% | 1.8 |
| | Man6 + Phosphate | 8.3E+07 | 6.05% | 8.4E+07 | 6.18% | 4.7E+07 | 6.77% | 4.5E+07 | 6.79% | 1.8 |

Similar to mAbs, the signal boosting is highly consistent for all glycoforms from the same glycosylation site (FIG. 44C), resulting in comparable relative percentages of individual glycoforms quantified with and without glycine additive (Table 5). It is also noticeable that signal boosting varies for glycopeptides containing different glycosites, ranging from 2-fold (at Site 5) to (at Site 2). It indicates that the level of TFA-based signal suppression or glycine-based TFA mitigation considerably varies for different peptide sequences.

Besides the adequate signal-to-noise ratio, a sufficient LC separation is also advantageous for site-specific glycosylation identification in a highly glycosylated protein. All glycopeptide peaks can be well distinguished from non-glycosylated peptides by IP-HILIC separation, revealed by the EIC peak of oxonium signature ion(s) in the MS2 spectra from glycopeptides (FIG. 44D). To examine how these glycopeptides separate from each other, EIC Peaks of four representative glycoforms (FA2G1, FA2G2, FA2G2S1 and FA2G2S2) are extracted for all seven glycosite-containing peptides, as seven peak "envelopes" shown in FIG. 45A. The elution profile within one envelope is highly comparable to the one within other envelopes, including elution order of glycoforms and retention time difference between each peak. And the retention time difference between two envelopes of glycopeptides is only correlated with the amino acid sequence, which is probably attributed to the frequency of polar residues, as suggested in several models for prediction of peptide retention in HILIC. Descriptively, the sequence of peptide at Site 4 (XXXXXNXTXK, SEQ ID NO: 36) possesses five polar residues out of 10 total amino acids, giving a 50% frequency of occurrence. The sequence of another peptide covering the same glycosite but containing an additional N-termini lysine residue (noted as Site 4[b]) has slightly higher percentage of polar residues (54.4%) and therefore the envelope of the glycopeptides at Site 4b elutes later than Site 4[a]. And the elution time of Site 4[b] is identical to the glycopeptide envelopes at Site 5 because both of these peptides contain 54.4% polar residues despite of different combination of amino acids. The envelope at Site 3 with only 50% polar residue elutes later than the last two envelopes, possibly due to the presence of C-terminal arginine (instead of lysine) in the peptide sequence, where the guanidino group may have larger contribution to the overall polarity. The same trend is also observed for all other three envelopes, whose peptide sequences contain C-terminal arginine and have high polar residue frequency. The Fc domain glycopeptides (Site 1) elutes at the end because of extremely high hydrophilicity determined by the peptide sequence consisting of all polar residues. Although the two acidic amino acids (Glu) in this peptide stay as the neutralized carboxylic acid form, they can still strongly bind to the neutral amide group of the stationary phase. In summary, glycopeptides can be separated upon both glycan structure and amino acid sequence; and the space between two glycoform peaks from one glycosite is filled with the peaks from other glycosites. Therefore, majority of glycopeptides in fP1 can be evenly distributed across a broad range of elution time, which allows the precursors to be effectively selected for MS2 scans during a data-dependent acquisition.

Such features observed in IP-HILIC separation using TFA may not be recapitulated when using a weaker acid without strong ion-pairing property such as formic acid. First, HILIC/FA-based separation may lead to an incomplete separation of non-glycosylated peptides from the glycopeptides; and the same extracted representative peaks showed other early-eluting sub-populations indicating the heterogeneous hydrophilicity of different glycopeptides due to lack of ion-paring reagent (FIG. 44D). Compared with HILIC/TFA separation, this deficiency in LC performance of HILIC/FA leads to less identification of glycopeptides as shown in the third panel of FIG. 44A and the Venn graph in FIG. 44B, although addition of glycine can still achieve about signal boosting in average and the identified glycopeptides have higher number of PSM compared to the TFA dataset. A HILIC performance in FA-containing mobile phases might be obtained using other HILIC stationary materials which could further improve glycopeptide identification when combining HILIC/FA with glycine additives. RPLC/TFA using a C18 column holds an orthogonal resolving power to separate glycopeptides from multiple sites. The glycopeptides from multiple sites are well-separated from each other as different clusters (FIG. 36D). Although they are not fully isolated from other non-glycosylated peptides, there are rarely non-glycosylated peptides in this single glycoprotein fP1 that are eluted in these glycopeptide clusters, therefore identification of glycopeptides by RPLC-MS remains comparable with IP-HILIC-MS method (FIG. 44A, last two panels and FIG. 44B).

Discovering Low Abundant O-Glycosylation and Non-Canonical N-Glycosylation in Monoclonal Antibody Using IP-HILIC-MS.

Since IP-HILIC shows the capability of characterizing glycopeptides from multiple glycosites in fP1, it should also have a potential to identify glycopeptides from a non-canonical glycosite for mAbs. The sample injection amount was slightly increased in order to improve the detectability of low abundance glycopeptides, therefore obtaining high quality of tandem mass spectra. In the study of mAb3 from the early stage of drug development, several low abundance glycopeptides with different amino acid sequences are confidently identified including miss-cleaved N297-containing glycopeptides (such as TKPREEQFNSTYR; SEQ ID NO: 44) as well as glycopeptides containing non-canonical glycosites of N91 located in VL domain and N163 located in CH1 domain (see example of tandem mass spectra in FIGS. 45B and 45C). Unlike the canonical Fc N297 site, which is predominantly occupied by glycans with fucosylated biantennary complex structure, three high-mannose type glycans are identified at light chain N91 and only one glycan FA2G2 is identified at heavy chain N163, and both sites possess glycan occupancy as low as 0.4% and 0.07%, respectively. Although a large sample injection amount may gain the possibility of identification for these low abundance glycopeptides, there might be an underestimation of the abundance of aglycosylated peptides due to their signal saturation. A lower sample injection amount quantifies lower (and perhaps more accurate) levels of occupancy for each individual glycan (FIG. 45D). In another study, a low abundance mucin type O-linked glycan HexNAc(1)Hex(1)NeuAc(2) is identified at the VH domain in one arm for a bispecific antibody, mAb4, when searching against the most frequently occurring mammalian O-linked glycan database (see example of tandem mass spectra in FIGS. 45E and 45F), although the level of this glycopeptide is quantified to be less than 0.05%. The existence of these rare glycans on Fab region are also confirmed on the intact protein level using strong cation exchange chromatography coupled to native mass spectrometry and no other glycans on Fab region are discovered.

Although these rare glycans cannot be independently discovered using RPLC-MS, there are still not enough cases for statistically demonstrating the advantage of using IP-HILIC-MS to identify low abundance noncanonical N-glycans or O-glycans. Instead, an investigation on the low abundance glycopeptides may provide a prospective regarding the impact from potential interference. Detection of extremely low abundance (glyco)peptides is usually challenging in the presence of highly abundant co-eluting interference, especially for a data-dependent-based acquisition in an Orbitrap type mass spectrometer, because the C-trap can be quickly filled up by highly abundant ions and the low abundant ions may not be sufficiently accumulated within a shortened injection time and may not produce over-the-threshold signals to trigger tandem MS2 for identification. Even though both HILIC and RPLC cannot fully eliminate the interference signals, the major source of the interference and the level of impact might be different. For RPLC-MS, the non-glycosylated peptides are widely distributed across the entire gradient and can potentially be the cause of interference for any low abundance glycopeptides (FIG. 46A), while for IP-HILIC-MS, there is supposedly no interference from non-glycosylated peptides, of which the entire population has been compressed into early elution time due to the ion-pairing of TFA, and the only source of interference is from the highly abundant canonical Fc glycopeptides (FIG. 46B). It is hypothesized that this Fc glycopeptide interference should have a lower negative effect compared to the non-glycosylated interference in RPLC-MS for low abundance glycopeptide identification because (1) the number of Fc glycopeptides are much less than that of non-glycosylated peptides and (2) the intensity of Fc glycopeptides is usually the lowest among all peptides digested from mAbs. In fact, only the major two or three glycoforms such as FA2, FA2G1 and FA2G2 in mAb3 (relative abundance>10%), may be identified as true interference but the remaining Fc glycoforms are of minimal concern due to their lower abundance.

As shown in FIG. 46C, out of the representative 6-minute window (67-73 minutes) in RPLC, total 2.7 minutes have MS signals from high abundance peptides (67.5-68 minutes, 69-70 minutes, 70.4-70.6 minutes, and 71-72 minutes), creating a high risk of co-eluting with any low abundance glycopeptides. It is observed that the entire cluster of three high mannose glycoforms at HC N91 is co-eluted with a 250-fold intense peak (69.0-69.4 minutes). This situation may happen anywhere across the entire 80-minute chromatogram. In IP-HILIC, although there are two glycopeptides (Man6 and Man7) from N91 partially co-eluting with Fc glycopeptides, the intensities of interference from Fc glycopeptides are only 50-fold and 8-fold, respectively. Out of the entire 10-minute glycopeptide elution region (12-22 minutes), only one minute (sum of the peak width for three major glycoforms) possess strong interference peaks, which means that 90% of the region may not have severe interference for low abundance glycopeptides, including a "valley" region (12.5-16.5 minutes in FIG. 46B), where only the background noise and other low abundance glycopeptides are observed.

Similarly, the O-linked glycopeptide on VH domain of mAb4 is also eluted in the same region in IP-HILIC-MS, in contrast, the EIC peak fails to be extracted from the RPLC-MS dataset likely due to increasing number of non-glycosylated peptides for bispecific mAb (FIG. 46E). Since O-glycan usually contains fewer monosaccharide units compared to N-glycan, O-glycopeptides would be less hydrophilic and likely to elute earlier than N-glycopeptides. It is hypothesized that any other O-glycopeptides from a mAb are also eluted in the "valley" region with minimal interference signals from either non-glycosylated peptides or Fc-glycosylated peptides.

This reduced level of interference makes IP-HILIC-MS a unique approach for low abundance glycopeptide identification, which also highlights the irreplaceable role of TFA as an ion-paring reagent as well as glycine as a signal boosting reagent in this application. This approach may be used as an approach for a fast screening of rare glycosylation during early stage biopharmaceutical discovery, without requiring a second dimension of glycopeptide enrichment. The performance can be further optimized by using an elongated gradient. In addition, since majority of unpredictable molecule-dependent critical quality attributes (CQAs) may be located at the Fab domain rather than the Fc domain, the focus was on the isolated Fab region by a complete removal of the Fc domain as well as the Fc N-glycopeptide interference, further improving the detection sensitivity.

In this study, it was demonstrated that glycine can be added into the TFA-containing mobile phases to significantly solve the sensitivity deficiency in TFA-based IP-HILIC-MS without adversely impacting the LC performance of peptide separation. This method is based on a regular flow pump and shows excellent stability and robustness, allowing for site-specific glycosylation profiling for a myriad of different types of biotherapeutics and glycosylated functional proteins. For mAbs, IP-HILIC-MS generates an unbiased glycan profile at the intact glycopeptide level compared to the released glycan analysis, suggesting that this approach might become a supplemental or substitution for the released glycan assay in the standard protein characterization. In addition, IP-HILIC-MS may be compatible with an MRM or PRM-based method for glycopeptide quantification, in which a relatively small number of precursors need to be scheduled simultaneously because of the wide elution time range of glycopeptides. These targeted or non-targeted IP-HILIC-MS methods can be smoothly grafted into a multi-attribute monitoring workflow or a high-throughput analytical platform, which holds promise in advancing analytical science for biopharmaceuticals industry.

A glycine additive can be used in RPLC-MS or HILIC-MS with weak ion paring for boosting MS signal and increasing overall site-specific glycosylation identification. The disclosed results on the Fc-domain fusion protein demonstrate that the IP-HILIC-MS method can strongly compete with RPLC-MS method (with the same signal intensity) with respect to mapping glycosylation profiles from multiple glycosylation sites. Due to the fast scan rate and high dynamic range for current state-of-the-art mass spectrometers, the interference from non-glycosylated peptides could be well-tolerated in RPLC-MS. However, for the low occupied glycosites, such as the non-canonical sites in mAbs, IP-HILIC still shows an advantage in improving their detectability even if no additional enrichment steps are involved. It is also reasonable to assume that IP-HILIC-MS will work much better than RPLC-MS when being applied to samples that heavily containing non-glycosylated peptide background; and the linear gradient can be selectively elongated in the glycopeptide elution region in IP-HILIC to efficiently increase glycopeptide separation, which could be hardly realized in RPLC-MS. Therefore, a targeted or non-targeted method for a fast and easy glycoform screening in a glyco-proteome scale such as in human serum can be implemented with the IP-HILIC-MS (UPLC) platform. Other than the neutral HILIC stationary phase material it is reported in this study (amide), other charged stationary phases such as the zwitterionic materials, can be evaluated.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 6

| SEQ ID NO: | Sequences Excluded from ST.26-Formatted Sequence Listing | |
| --- | --- | --- |
| | Sequence | |
| 36 | XXXXXNXTXK, where X is any naturally occurring amino acid | |
| 38 | XXXXNXTXXXK, where X is any naturally occurring amino acid | |
| 39 | XXXNXTXR, where X is any naturally occurring amino acid | |
| 40 | NXTXXR, where X is any naturally occurring amino acid | |
| 42 | XXXXXXXXXXXXXXXXXXXXXXXXXXNXNXXXXXXXXXXK, where X is any naturally occurring amino acid | |
| 43 | XXXXXXXSXXXXXXXXXXXXXXXXXXXXXXXXXX, where X is any naturally occurring amino acid | |

SEQUENCE LISTING

```
Sequence total quantity: 45
SEQ ID NO: 1            moltype = AA  length = 450
FEATURE                 Location/Qualifiers
REGION                  1..450
                        note = NISTmAb heavy chain
source                  1..450
                        mol_type = protein
                        organism = synthetic construct
SEQUENCE: 1
QVTLRESGPA LVKPTQTLTL TCTFSGFSLS TAGMSVGWIR QPPGKALEWL ADIWWDDKKH  60
YNPSLKDRLT ISKDTSKNQV VLKVTNMDPA DTATYYCARD MIFNFYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 2            moltype = AA  length = 213
FEATURE                 Location/Qualifiers
REGION                  1..213
                        note = NISTmAb light chain
source                  1..213
                        mol_type = protein
                        organism = synthetic construct
SEQUENCE: 2
```

```
DIQMTQSPST LSASVGDRVT ITCSASSRVG YMHWYQQKPG KAPKLLIYDT SKLASGVPSR      60
FSGSGSGTEF TLTISSLQPD DFATYYCFQG SGYPFTFGGG TKVEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 3            moltype = AA   length = 13
FEATURE                 Location/Qualifiers
REGION                  1..13
                        note = peptide of NISTmAB, heavy chain
source                  1..13
                        mol_type = protein
                        organism = synthetic construct
SEQUENCE: 3
ALEWLADIWW DDK                                                         13

SEQ ID NO: 4            moltype = AA   length = 8
FEATURE                 Location/Qualifiers
REGION                  1..8
                        note = peptide of NISTmAB
source                  1..8
                        mol_type = protein
                        organism = synthetic construct
SEQUENCE: 4
ALPAPIEK                                                                8

SEQ ID NO: 5            moltype = AA   length = 25
FEATURE                 Location/Qualifiers
REGION                  1..25
                        note = peptide of NISTmAB
source                  1..25
                        mol_type = protein
                        organism = synthetic construct
SEQUENCE: 5
DMIFNFYFDV WGQGTTVTVS SASTK                                            25

SEQ ID NO: 6            moltype = AA   length = 14
FEATURE                 Location/Qualifiers
REGION                  1..14
                        note = peptide of NISTmAB
source                  1..14
                        mol_type = protein
                        organism = synthetic construct
SEQUENCE: 6
DSTYSLSSTL TLSK                                                        14

SEQ ID NO: 7            moltype = AA   length = 7
FEATURE                 Location/Qualifiers
REGION                  1..7
                        note = peptide of NISTmAB
source                  1..7
                        mol_type = protein
                        organism = synthetic construct
SEQUENCE: 7
DTLMISR                                                                 7

SEQ ID NO: 8            moltype = AA   length = 11
FEATURE                 Location/Qualifiers
REGION                  1..11
                        note = peptide of NISTmAB
source                  1..11
                        mol_type = protein
                        organism = synthetic construct
SEQUENCE: 8
EPQVYTLPPS R                                                           11

SEQ ID NO: 9            moltype = AA   length = 35
FEATURE                 Location/Qualifiers
REGION                  1..35
                        note = peptide of NISTmAB
source                  1..35
                        mol_type = protein
                        organism = synthetic construct
SEQUENCE: 9
ESGPALVKPT QTLTLTCTFS GFSLSTAGMS VGWIR                                 35

SEQ ID NO: 10           moltype = AA   length = 14
FEATURE                 Location/Qualifiers
REGION                  1..14
                        note = peptide of NISTmAB
```

-continued

```
source                  1..14
                        mol_type = protein
                        organism = synthetic construct
SEQUENCE: 10
FNWYVDGVEV HNAK                                                  14

SEQ ID NO: 11           moltype = AA  length = 42
FEATURE                 Location/Qualifiers
REGION                  1..42
                        note = peptide of NISTmAB
source                  1..42
                        mol_type = protein
                        organism = synthetic construct
SEQUENCE: 11
FSGSGSGTEF TLTISSLQPD DFATYYCFQG SGYPFTFGGG TK                   42

SEQ ID NO: 12           moltype = AA  length = 22
FEATURE                 Location/Qualifiers
REGION                  1..22
                        note = peptide of NISTmAB
source                  1..22
                        mol_type = protein
                        organism = synthetic construct
SEQUENCE: 12
GFYPSDIAVE WESNGQPENN YK                                         22

SEQ ID NO: 13           moltype = AA  length = 12
FEATURE                 Location/Qualifiers
REGION                  1..12
                        note = peptide of NISTmAB
source                  1..12
                        mol_type = protein
                        organism = synthetic construct
SEQUENCE: 13
GPSVFPLAPS SK                                                    12

SEQ ID NO: 14           moltype = AA  length = 7
FEATURE                 Location/Qualifiers
REGION                  1..7
                        note = peptide of NISTmAB
source                  1..7
                        mol_type = protein
                        organism = synthetic construct
SEQUENCE: 14
HYNPSLK                                                          7

SEQ ID NO: 15           moltype = AA  length = 8
FEATURE                 Location/Qualifiers
REGION                  1..8
                        note = peptide of NISTmAB
source                  1..8
                        mol_type = protein
                        organism = synthetic construct
SEQUENCE: 15
LASGVPSR                                                         8

SEQ ID NO: 16           moltype = AA  length = 8
FEATURE                 Location/Qualifiers
REGION                  1..8
                        note = peptide of NISTmAB
source                  1..8
                        mol_type = protein
                        organism = synthetic construct
SEQUENCE: 16
LLIYDTSK                                                         8

SEQ ID NO: 17           moltype = AA  length = 10
FEATURE                 Location/Qualifiers
REGION                  1..10
                        note = peptide of NISTmAB
source                  1..10
                        mol_type = protein
                        organism = synthetic construct
SEQUENCE: 17
NQVSLTCLVK                                                       10

SEQ ID NO: 18           moltype = AA  length = 6
FEATURE                 Location/Qualifiers
REGION                  1..6
```

-continued

```
                         note = peptide of NISTmAB
source                   1..6
                         mol_type = protein
                         organism = synthetic construct
SEQUENCE: 18
NQVVLK                                                               6

SEQ ID NO: 19            moltype = AA  length = 5
FEATURE                  Location/Qualifiers
REGION                   1..5
                         note = peptide of NISTmAB
source                   1..5
                         mol_type = protein
                         organism = synthetic construct
SEQUENCE: 19
QVTLR                                                                5

SEQ ID NO: 20            moltype = AA  length = 16
FEATURE                  Location/Qualifiers
REGION                   1..16
                         note = peptide of NISTmAB
source                   1..16
                         mol_type = protein
                         organism = synthetic construct
SEQUENCE: 20
SGTASVVCLL NNFYPR                                                   16

SEQ ID NO: 21            moltype = AA  length = 7
FEATURE                  Location/Qualifiers
REGION                   1..7
                         note = peptide of NISTmAB
source                   1..7
                         mol_type = protein
                         organism = synthetic construct
SEQUENCE: 21
SLSLSPG                                                              7

SEQ ID NO: 22            moltype = AA  length = 14
FEATURE                  Location/Qualifiers
REGION                   1..14
                         note = peptide of NISTmAB
source                   1..14
                         mol_type = protein
                         organism = synthetic construct
SEQUENCE: 22
STSGGTAALG CLVK                                                     14

SEQ ID NO: 23            moltype = AA  length = 26
FEATURE                  Location/Qualifiers
REGION                   1..26
                         note = peptide of NISTmAB
source                   1..26
                         mol_type = protein
                         organism = synthetic construct
SEQUENCE: 23
THTCPPCPAP ELLGGPSVFL FPPKPK                                        26

SEQ ID NO: 24            moltype = AA  length = 19
FEATURE                  Location/Qualifiers
REGION                   1..19
                         note = peptide of NISTmAB
source                   1..19
                         mol_type = protein
                         organism = synthetic construct
SEQUENCE: 24
TPEVTCVVVD VSHEDPEVK                                                19

SEQ ID NO: 25            moltype = AA  length = 17
FEATURE                  Location/Qualifiers
REGION                   1..17
                         note = peptide of NISTmAB
source                   1..17
                         mol_type = protein
                         organism = synthetic construct
SEQUENCE: 25
TTPPVLDSDG SFFLYSK                                                  17

SEQ ID NO: 26            moltype = AA  length = 18
FEATURE                  Location/Qualifiers
```

-continued

```
REGION                 1..18
                       note = peptide of NISTmAB
source                 1..18
                       mol_type = protein
                       organism = synthetic construct
SEQUENCE: 26
TVAAPSVFIF PPSDEQLK                                                    18

SEQ ID NO: 27          moltype = AA  length = 20
FEATURE                Location/Qualifiers
REGION                 1..20
                       note = peptide of NISTmAB
source                 1..20
                       mol_type = protein
                       organism = synthetic construct
SEQUENCE: 27
VDNALQSGNS QESVTEQDSK                                                  20

SEQ ID NO: 28          moltype = AA  length = 13
FEATURE                Location/Qualifiers
REGION                 1..13
                       note = peptide of NISTmAB
source                 1..13
                       mol_type = protein
                       organism = synthetic construct
SEQUENCE: 28
VGYMHWYQQK PGK                                                         13

SEQ ID NO: 29          moltype = AA  length = 10
FEATURE                Location/Qualifiers
REGION                 1..10
                       note = peptide of NISTmAB
source                 1..10
                       mol_type = protein
                       organism = synthetic construct
SEQUENCE: 29
VTITCSASSR                                                             10

SEQ ID NO: 30          moltype = AA  length = 16
FEATURE                Location/Qualifiers
REGION                 1..16
                       note = peptide of NISTmAB
source                 1..16
                       mol_type = protein
                       organism = synthetic construct
SEQUENCE: 30
VTNMDPADTA TYYCAR                                                      16

SEQ ID NO: 31          moltype = AA  length = 16
FEATURE                Location/Qualifiers
REGION                 1..16
                       note = peptide of NISTmAB
source                 1..16
                       mol_type = protein
                       organism = synthetic construct
SEQUENCE: 31
VVSVLTVLHQ DWLNGK                                                      16

SEQ ID NO: 32          moltype = AA  length = 17
FEATURE                Location/Qualifiers
REGION                 1..17
                       note = peptide of NISTmAB
source                 1..17
                       mol_type = protein
                       organism = synthetic construct
SEQUENCE: 32
VYACEVTHQG LSSPVTK                                                     17

SEQ ID NO: 33          moltype = AA  length = 23
FEATURE                Location/Qualifiers
REGION                 1..23
                       note = peptide of NISTmAB
source                 1..23
                       mol_type = protein
                       organism = synthetic construct
SEQUENCE: 33
WQQGNVFSCS VMHEALHNHY TQK                                              23

SEQ ID NO: 34          moltype = AA  length = 18
```

```
FEATURE             Location/Qualifiers
REGION              1..18
                    note = peptide of NISTmAB
source              1..18
                    mol_type = protein
                    organism = synthetic construct
SEQUENCE: 34
DIQMTQSPST LSASVGDR                                           18

SEQ ID NO: 35       moltype = AA  length = 9
FEATURE             Location/Qualifiers
REGION              1..9
                    note = synthetic peptide sequence
source              1..9
                    mol_type = protein
                    organism = synthetic construct
SEQUENCE: 35
EEQYNSTYR                                                     9

SEQ ID NO: 36       moltype =   length =
SEQUENCE: 36
000

SEQ ID NO: 37       moltype = AA  length = 11
FEATURE             Location/Qualifiers
REGION              1..11
                    note = synthetic peptide
VARIANT             2..6
                    note = X can be any naturally occurring amino acid
VARIANT             8
                    note = X can be any naturally occurring amino acid
VARIANT             10
                    note = X can be any naturally occurring amino acid
source              1..11
                    mol_type = protein
                    organism = synthetic construct
SEQUENCE: 37
KXXXXXNXTX K                                                  11

SEQ ID NO: 38       moltype =   length =
SEQUENCE: 38
000

SEQ ID NO: 39       moltype =   length =
SEQUENCE: 39
000

SEQ ID NO: 40       moltype =   length =
SEQUENCE: 40
000

SEQ ID NO: 41       moltype = AA  length = 7
FEATURE             Location/Qualifiers
REGION              1..7
                    note = synthetic peptide
VARIANT             3
                    note = X can be any naturally occurring amino acid
VAR_SEQ             5..6
                    note = X can be any naturally occurring amino acid
source              1..7
                    mol_type = protein
                    organism = synthetic construct
SEQUENCE: 41
KNXTXXR                                                       7

SEQ ID NO: 42       moltype =   length =
SEQUENCE: 42
000

SEQ ID NO: 43       moltype =   length =
SEQUENCE: 43
000

SEQ ID NO: 44       moltype = AA  length = 13
FEATURE             Location/Qualifiers
REGION              1..13
                    note = synthetic peptide
source              1..13
                    mol_type = protein
```

-continued

```
                        organism = synthetic construct
SEQUENCE: 44
TKPREEQFNS TYR                                                     13

SEQ ID NO: 45          moltype = AA  length = 9
FEATURE                Location/Qualifiers
REGION                 1..9
                       note = synthetic peptide
source                 1..9
                       mol_type = protein
                       organism = synthetic construct
SEQUENCE: 45
EEQFNSTYR                                                          9
```

What is claimed is:

1. A method of enhancing a mass spectral signal, comprising:

contacting a sample to a separation column under conditions that permit sample components to bind to a substrate;

applying a first mobile phase gradient to the separation column, wherein the first mobile phase gradient comprises trifluoroacetic acid (TFA) and a small molecule additive or formic acid (FA) and a first small molecule additive, wherein the first small molecule additive is selected from glycine, alanine, serine, valine, N-acetyl glycine, methionine, β-alanine, aspartic acid, or N-methyl glycine;

applying a second mobile phase gradient to the separation column, wherein the second mobile phase gradient comprises TFA in acetonitrile (ACN) and a small molecule additive or FA in ACN and a second small molecule additive, wherein the second small molecule additive is selected from glycine, alanine, serine, valine, N-acetyl glycine, methionine, β-alanine, aspartic acid, or N-methyl glycine; and performing mass spectrometric analysis on eluted sample components, wherein separation between sample components on the separation column is not increased by addition of the small molecule additives in the mobile phase.

2. The method of claim 1, wherein the first or second small molecule additive concentration is between about 1 mM and about 2 mM.

3. The method of claim 1, wherein the first or second small molecule additive is glycine, and the glycine concentration is about 1 mM.

4. The method of claim 1, wherein the first or second small molecule additive is glycine, and the glycine concentration is about 2 mM.

5. The method of claim 1, wherein the TFA concentration in the first mobile phase is about 0.05% to 0.1% TFA in $H_2O$ or the FA concentration in the first mobile phase is about 0.1% FA.

6. The method of claim 1, wherein the TFA concentration in the second mobile phase comprises about 0.05% TFA in 80% ACN and 20% $H_2O$ or about 0.1% TFA in 80% ACN and 20% $H_2O$.

7. The method of claim 1, wherein the sample comprises peptides or nucleotides.

8. The method of claim 7, wherein the peptides are glycopeptides.

9. The method of claim 8, wherein the glycopeptides are obtained from a monoclonal antibody.

10. The method of claim 1, further comprising preparing the sample prior to contacting the sample to a separation column under conditions that permit sample components to bind to the substrate, wherein preparing the sample comprises:

contacting a sample with a denaturing and reducing solution under conditions that permit sample denaturation and reduction;

contacting denatured and reduced sample with an alkylating solution under conditions that permit sample alkylation;

contacting alkylated sample with a digest solution under conditions that permit sample digestion; and contacting digested sample with a quenching solution under conditions that stop sample digestion.

11. The method of claim 10, wherein the sample is a monoclonal antibody and the digest solution comprises a protease.

12. The method of claim 1, wherein the separation column is a liquid chromatography column, and wherein the liquid chromatography separation column comprises a hydrophilic interaction liquid chromatography column.

13. The method of claim 1, wherein performing mass spectrometric analysis on eluted sample components comprises applying electrospray ionization to generate charged ions from the eluted sample components and measuring the generated charge ions.

14. The method of claim 8, wherein the mass spectral signal obtained on the eluted sample components is enhanced by from 2-fold to 50-fold relative to a mass spectral signal obtained on a control sample in the absence of the first or second small molecule additive.

15. The method of claim 8, wherein the glycopeptide is an O-glycan containing glycopeptide or an N-glycan containing glycopeptide.

16. The method of claim 15, wherein O-glycan or N-glycan is linked to a label.

17. The method of claim 16, wherein the label is procainamide.

* * * * *